United States Patent
Ashkenazi et al.

(10) Patent No.: US 8,710,189 B2
(45) Date of Patent: Apr. 29, 2014

(54) ANTI-FGFR3 ANTIBODIES AND METHODS USING SAME

(71) Applicant: Genentech, Inc., South San Francisco, CA (US)

(72) Inventors: Avi Ashkenazi, San Mateo, CA (US); Jing Qing, San Francisco, CA (US); Christian Wiesmann, Bottmingen (CH); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/653,293

(22) Filed: Oct. 16, 2012

(65) Prior Publication Data

US 2013/0046078 A1 Feb. 21, 2013

Related U.S. Application Data

(62) Division of application No. 12/731,100, filed on Mar. 24, 2010, now Pat. No. 8,410,250.

(60) Provisional application No. 61/163,222, filed on Mar. 25, 2009.

(51) Int. Cl.
*C07K 16/00* (2006.01)
*C12P 21/08* (2006.01)

(52) U.S. Cl.
USPC .................. 530/387.1; 530/387.3; 530/388.1

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,929 A | 2/1982 | Morita et al. |
| 4,313,946 A | 2/1982 | Powell et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,683,195 A | 7/1987 | Mullis et al. |
| 4,683,203 A | 7/1987 | Anton et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 4,970,198 A | 11/1990 | Lee et al. |
| 4,975,278 A | 12/1990 | Senter et al. |
| 5,053,394 A | 10/1991 | Ellestad et al. |
| 5,079,233 A | 1/1992 | Lee |
| 5,122,469 A | 6/1992 | Mather et al. |
| 5,208,020 A | 5/1993 | Chari et al. |
| 5,264,365 A | 11/1993 | Georgiou et al. |
| 5,362,852 A | 11/1994 | Geoghegan |
| 5,416,064 A | 5/1995 | Chari et al. |
| 5,500,362 A | 3/1996 | Robinson et al. |
| 5,508,192 A | 4/1996 | Georgiou et al. |
| 5,571,894 A | 11/1996 | Wels et al. |
| 5,585,089 A | 12/1996 | Queen et al. |
| 5,587,458 A | 12/1996 | King et al. |
| 5,606,040 A | 2/1997 | McGahren et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter |
| 5,648,260 A | 7/1997 | Winter et al. |
| 5,663,149 A | 9/1997 | Pettit et al. |
| 5,693,762 A | 12/1997 | Queen et al. |
| 5,707,632 A | 1/1998 | Williams et al. |

(Continued)

FOREIGN PATENT DOCUMENTS

| EP | 0332435 B1 | 4/1992 |
| EP | 0332435 B2 | 4/1992 |

(Continued)

OTHER PUBLICATIONS

Abrahmsen et al., "Analysis of signals for secretion in the staphylococcal protein A gene" EMBO J 4:3901-3906 ( 1985).

Adams and Weiner, "Monoclonal antibody therapy of cancer" Nat. Biotechnol. 23(9):1147-1157 (Sep. 2005).

Adar et al., "Differential activation of cysteine-substitution mutants of fibroblast growth factor receptor 3 is determind by cysteine localization" J Bone Mineral Res. 17(5):860-868 ( 2002).

Agazie et al., "The phosphotyrosine phosphatase SHP2 is critical mediator of transformation induced by the oncogenic fibroblast growth factor receptor 3" Oncogene 22:6909-6918 ( 2003).

(Continued)

*Primary Examiner* — Hong Sang
(74) *Attorney, Agent, or Firm* — Stephanie Yonker

(57) ABSTRACT

The invention provides FGFR3 antibodies, and compositions comprising and methods of using these antibodies.

10 Claims, 35 Drawing Sheets

(56) References Cited

U.S. PATENT DOCUMENTS

| | | | |
|---|---|---|---|
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,821,337 A | 10/1998 | Carter et al. |
| 5,869,046 A | 2/1999 | Presta et al. |
| 5,869,245 A | 2/1999 | Yeung |
| 5,877,296 A | 3/1999 | Hamann et al. |
| 6,027,888 A | 2/2000 | Georgiou et al. |
| 6,083,715 A | 7/2000 | Georgiou et al. |
| 6,194,551 B1 | 2/2001 | Idusogie et al. |
| 6,306,591 B1 | 10/2001 | Cockett et al. |
| 6,737,056 B1 | 5/2004 | Presta |
| 6,849,255 B2 | 2/2005 | Gazit et al. |
| 7,135,311 B1 | 11/2006 | David et al. |
| 7,288,406 B2 | 10/2007 | Bogin et al. |
| 7,498,298 B2 | 3/2009 | Doronina et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0014024 A1 | 1/2004 | Yayon et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0116330 A1 | 6/2004 | Naito et al. |
| 2004/0132140 A1 | 7/2004 | Satoh et al. |
| 2005/0014934 A1 | 1/2005 | Hinton et al. |
| 2005/0123546 A1 | 6/2005 | Umana et al. |
| 2005/0147612 A1 | 7/2005 | Yayon et al. |
| 2005/0169933 A1 | 8/2005 | Steeves et al. |
| 2007/0092878 A1 | 4/2007 | Martinez et al. |
| 2007/0248605 A1 | 10/2007 | Hestir et al. |
| 2010/0003258 A1 | 1/2010 | Weng et al. |
| 2010/0047251 A1 | 2/2010 | Yayon et al. |
| 2010/0098696 A1 | 4/2010 | Sun et al. |
| 2010/0247531 A1 | 9/2010 | Ashkenazi et al. |
| 2010/0291114 A1 | 11/2010 | Wiesmann |

FOREIGN PATENT DOCUMENTS

| | | | |
|---|---|---|---|
| EP | 0545343 A1 | 11/1992 |
| EP | 0 404 097 B1 | 9/1996 |
| EP | 0425235 B1 | 9/1996 |
| EP | 1391213 A1 | 2/2004 |
| EP | 1611252 B1 | 7/2009 |
| EP | 1423428 B1 | 8/2009 |
| WO | 87/00195 A1 | 1/1987 |
| WO | 90/03430 A1 | 4/1990 |
| WO | 91/00360 A1 | 1/1991 |
| WO | 92/00373 A1 | 1/1992 |
| WO | 92/09690 A2 | 6/1992 |
| WO | 92/22764 A1 | 12/1992 |
| WO | 93/06213 A1 | 4/1993 |
| WO | 93/08829 A1 | 5/1993 |
| WO | 93/11161 A1 | 6/1993 |
| WO | 93/16185 A2 | 8/1993 |
| WO | 93/21232 A1 | 10/1993 |
| WO | 94/04690 A1 | 3/1994 |
| WO | 94/04690 R3 | 3/1994 |
| WO | 94/11026 A2 | 5/1994 |
| WO | 94/11026 A3 | 5/1994 |
| WO | 94/21813 A1 | 9/1994 |
| WO | 94/29351 A2 | 12/1994 |
| WO | 94/29351 A3 | 12/1994 |
| WO | 96/07321 A1 | 3/1996 |
| WO | 96/07754 A1 | 3/1996 |
| WO | 96/07754 R3 | 3/1996 |
| WO | 96/41620 A1 | 12/1996 |
| WO | 97/30087 A1 | 8/1997 |
| WO | 98/45479 A1 | 10/1998 |
| WO | 98/58964 A1 | 12/1998 |
| WO | 99/22764 A1 | 5/1999 |
| WO | 99/51642 A1 | 10/1999 |
| WO | 00/42072 A2 | 7/2000 |
| WO | 00/42072 A3 | 7/2000 |
| WO | 00/46343 A2 | 8/2000 |
| WO | 00/46343 A3 | 8/2000 |
| WO | 00/61739 A1 | 10/2000 |
| WO | 01/29246 A1 | 4/2001 |
| WO | 02/50246 A2 | 6/2002 |
| WO | 02/50246 A3 | 6/2002 |
| WO | 02/088172 A2 | 11/2002 |
| WO | 02/088172 A3 | 11/2002 |
| WO | 02/088172 R1 | 11/2002 |
| WO | 02/102973 A2 | 12/2002 |
| WO | 03/011878 A2 | 2/2003 |
| WO | 03/084570 A1 | 10/2003 |
| WO | 03/085119 A1 | 10/2003 |
| WO | 2004/056312 A2 | 7/2004 |
| WO | 2004/056312 A3 | 7/2004 |
| WO | 2005/035586 A1 | 4/2005 |
| WO | 2005/035778 A1 | 4/2005 |
| WO | 2005/053742 A1 | 6/2005 |
| WO | 2006/048877 A2 | 5/2006 |
| WO | 2006/048877 A3 | 5/2006 |
| WO | 2007/130697 | 11/2007 |
| WO | 2007/144893 A2 | 12/2007 |
| WO | 2007/144893 A3 | 12/2007 |
| WO | 2009/062690 A1 | 5/2009 |
| WO | 2009/137429 A1 | 11/2009 |
| WO | 2010/002862 A2 | 1/2010 |
| WO | 2010/002862 A3 | 1/2010 |
| WO | 2010/048026 A2 | 4/2010 |
| WO | 2010/048026 A3 | 4/2010 |
| WO | 2010/111367 A1 | 9/2010 |

OTHER PUBLICATIONS

Arie et al., "Chaperone function of FkpA, a heat shock prolyl isomerase, in the periplasm of *Escherichia coli*" Molec. Microb. 39(1):199-210 ( 2001).

Avivi et al., "A novel form of FGF receptor-3 using an alternative exon in the immunoglobulin domain III" FEBS Letters 330(3):249-252 (Sep. 1993).

Bai et al., "Mechanistic studies of AV370, a potent FGFR3 antagonistic antibody" Abstract (No. 3775) AACR Annual Meeting, Denver, CO, (Apr. 21, 2009).

Baldwin and Byers, "Monoclonal Antibodies in Cancer Treatment" Lancet 327(8481):603-605 (Mar. 15, 1986).

Barbas et al., "Assembly of combinatorial antibody libraries on phage surfaces: the gene III site" Proc. Natl. Acad. Sci. USA 88:7978-7982 (Sep. 1991).

Barbas et al., "In vitro evolution of a neutralizing human antibody to human immunodeficiency virus type 1 to enhance affinity and broaden strain cross-reactivity" Proc. Natl. Acad. Sci. USA 91:3809-3813 (Apr. 1994).

Barbas et al., "Semisynthetic combinatorial antibody libraries: a chemical solution to the diversity problem" Proc. Natl. Acad. Sci. USA 89:4457-4461 (May 1992).

Barnes and Sato, "Methods for growth of cultured cells in serum-free medium" Analytical Biochem. 102:255-270 ( 1980).

Bass et al., "Hormone Phage: An enrichment method for variant proteins with altered binding properties" Proteins: Structure, Function, and Genetics 8:309-314 ( 1990)

Bendig, Mary M., "Humanization of Rodent Monoclonal Antibodies by CDR Grafting" Methods: A Companion to Methods in Enzymology 8:83-93 (1995).

Bernard-Pierrot et al., "Oncogenic properties of the mutated forms of fibroblast growth factor receptor 3b" Carcinogenesis 27(4):740-747 ( 2006).

Boerner et al., "Production of antigen-specific human monoclonal antibodies from in vitro-primed human splenocytes" J Immunol. 147(1):86-95 (Jul. 1, 1991).

Bothmann and Pluckthun, "The periplasmic *Escherichia coli* peptidylprolyl cis,trans-isomerase FkpA" J Biol. Chem. 275(22):17100-17105 (Jul. 2, 2000).

(56) References Cited

OTHER PUBLICATIONS

Brennan et al., "Preparation of bispecific antibodies by chemical recombination of monoclonal immunoglobulin G\\subscript:1\\\ fragments" Science 229:81-83 (1985).
Brittis et al., "Fibroblast growth factor receptor function is required for the orderly projection of ganglion cell axons in the developing mammalian retina" Mol. Cell. Neurosci. 8:120-128 (1996).
Brodeur et al., "Mouse-human myeloma partners for the production of heterohybridomas" Monoclonal Antibody Productino Techniques and Applications, pp. 51-63 (New York: Marcel Dekker, Inc.), (1987).
Bruggemann et al., "Designer mice: the production of human antibody repertoires in transgenic animals" Year in Immunology 7:33-40 (1993).
Capel et al., "Heterogeneity of human IgG Fc receptors" Immunomethods 4:25-34 (1994).
Capellen et al., "Frequent activating mutations of FGFR3 in human bladder and cervix carcinomas" Nat. Genet. 23:18-20 (Sep. 1999).
Carlsson et al., "Protein thiolation and reversible protein-protein conjugation" Biochem J. 173:723-737 (1978).
Carter et al., "High level *Escherichia coli* expression and production of a bivalent humanized antibody fragment" Bio/Tech 10:163-167 (Feb. 1992).
Carter et al., "Humanization of an anti-p185\\\superscript:HER2\\\ antibody for human cancer therapy"Proc. Natl. Acad. Sci. USA 89:4285-4289 (May 1992).
Chang et al., "Immunohistochemistry accurately predicts FGFR3 aberrant expression and t(4;14) in multiple myeloma" Blood 106(1):353-355 (Jul. 1, 2005).
Chang, H., et al., "Immunohistochemistry accurately predicts FGFR3 aberrant expression and t(4;14) in multiple myeloma" Blood, 106:353-355 (Mar. 10, 2005).
Chari et al., "Immunoconjugates containing novel maytansinoids: promising anticancer drugs" Cancer Res. 52:127-131 (Jan. 1, 1992).
Chellaiah et al., "Fibroblast growth gactor teceptor (FGFR) 3. Alternative splicing in immunoglobulin-like domain III creates a receptor highly specific for acidic FGF/FGF-1" J Biol. Chem. 269(15):11620-11627 (Apr. 15, 1994).
Chen et al., "Chaperone Activity of DsbC" J Biol. Chem. 274(28):19601-19605 (Jul. 9, 1999).
Chen et al., "Constitutively activated FGFR3 mutants signal through PLCγ-dependent and -independent pathways for hematopoietic transformation" Blood 106(1):328-337 (2005).
Chen et al., "FGFR3 as a therapeutic target of the small molecule inhibitor PKC412 in hematopoietic malignancies" Oncogene 24:8259-8267 (2005).
Chesi et al., "Activated fibroblast growth factor receptor 3 is an oncogene that contributes to tumor progression in multiple myeloma" Blood 97(3):729-736 (2001).
Chesi et al., "Frequent translocation t(4;14)(p16.3;q32.3) in multiple myeloma is associated with increased expression and activating mutations of fibroblast growth receptor 3" Nat. Genet. 16:260-264 (Jul. 16, 1997).
Chothia and Lesk, "Canonical structures for the hypervariable regions of immunoglobulins" J. Mol. Biol. 196:901-917 (1987).
Clackson et al., "Making antibody fragments using phage display libraries" Nature 352:624-628 (Aug. 15, 1991).
Clynes et al., "Fc receptors are required in passive and active immunity to melanoma" Proc. Natl. Acad. Sci. USA 95:652-656 (Jan. 1998).
Colman P.M., "Effects of amino acid sequence changes on antibody-antigen interactions" Res Immunol 145:33-36 (1994).
Cortese et al., "Correlative gene expression and DNA methylation profiling in lung development nominate new biomarkers in lung" Intl. J Biochem. Cell Biol. 40:1494-1508 (2008).
Cotton et al., "Reactivity of cytosine and thymine in single-base-pair mismatches with hydroxylamine and osmium tetroxide and its applications to the study of mutations" Proc Natl Acad Sci USA 85:4397-4401 (Jun. 1988).
Cunningham and Wells, "High-resolution epitope mapping of hGH-receptor interactions by alanine-scanning mutagenesis" Science 24:1081-1085 (Jun. 2, 1989).
Daeron, "Fc Receptor Biology" Annu. Rev. Immunol. 15:203-234 (1997).
Dailey et al., "Mechanisms underlying differential responses to FGF signaling" Cytokine & Growth Factor Reviews 16:233-247 (2005).
Davies et al., "Mutations of the BRAF gene in human cancer" Nature 417:949-954 (2002).
d'Avis et al., "Constitutive activation of fibroblast growth factor receptor 3 by mutations responsible for the lethal skeletal dysplasia thanatophoric dysplasia type I" Cell Growth Differentiation 9:71-78 (Jan. 1998).
de Hass et al., "Fcγ receptors of phagocytes" J Lab. Clin. Med. 126(4):330-341 (1995).
Deevi et al., "Inhibiting FGFR3 for enhancing the cytotoxic effects of cisplatin on bladder cancer cells and possible mechanisms" AACR-NCI-EORTC International Conference: Molecular Targets and Cancer Therapeutics (San Francisco, CA Abstract B48), (Oct. 22-26, 2007).
Del Tito et al., "Automated fluorescent analysis procedure for enzymatic mutation detection" Clin. Chem. 44(4):731-739 (1998).
Delezoide et al., "Abnormal FGFR3 expression in cartilage of thanatophoric dysplasia fetuses" Hum. Mol. Genet. 6(11):1899-1906 (1997).
DiRenzo et al., "Receptor-Mediated Signaling 2: Poster Presentations Abstract #2080" Abstract 98th AACR Annual Meeting, Los Angeles, CA USA, pp. 1 (Apr. 16, 2007).
Doronina et al., "Development of potent monoclonal antibody auristatin conjugates for cancer therapy" Nat. Biotechnol. 21(7): 778-784 (Jul. 2003); (Erratum Nat. Biotechnol. 21(8): 941 (Aug. 2003)).
Duncan and Winter, "The binding site for Clq on IgG" Nature 322:738-740 (1988).
Dvorak et al., "Increased expression of fibroblast growth factor receptor 3 in CD34 + BCR-ABL_cells from patients with chronic myeloid leukemia" Leukemia 17:2418-2425 (2003).
Ellman, "Tissue sulfhydryl groups" Arch. Biochem. Biophys. 82:70-77 (1959).
Embleton et al., "In-cell PCT from mRNA: amplifying and linking the rearranged immunoglobulin heavy and light chain V-genes within single cells" Nucl. Acids Res. 20(15):3831-3837 (1992).
Emsley and Cowtan, "Coot: model-building tools for molecular graphics" Acta Cryst. D60:2126-2132 (2004).
Engels and Uhlmann, "Gene synthesis" Angew. Chem. Int. Ed. Engl. 28:716-734 (1989).
Eswarakumar et al., "Cellular signaling by fibroblast growth factor receptors" Cytokine & Growth Factor Reviews 16:139-149 (2005).
Fonseca et al., "Clinical and biologic implications of recurrent genomic aberrations in myeloma" Blood 101(11):4569-4575 (Jun. 1, 2003).
Fortin et al., "Distinct fibroblast growth factor (FGF)/FGF receptor signaling pairs initiate diverse cellular responses in the oligodendrocyte lineage" J Neuroscience 25(32):7470-7479 (Aug. 10, 2005).
Fraker and Speck, "Protein and cell membrane iodinations with a sparingly soluble chloroamide, 1,3,4,6-tetrachloro-3a,6a-diphenylglycoluril" Biochem Biophys Res Comm 80(4):849-857 (Feb. 28, 1978).
Gazzano-Santoro et al., "A non-radioactive complement-dependent cytotoxicity assay for anti-CD20 monoclonal antibody" J Immunol. Methods 202:163-171 (1997).
"Gemtuzumab Ozogamicin, Treatment of acute myeloid leukemia" Drugs of the Future :25(7):686-692 (2000).
Geoghegan and Stroh, "Site-directed conjugation of nonpeptide groups to peptides and proteins via periodate oxidation of a 2-amino alcohol. Application to modification at N-terminal serine" Bioconjugate Chem. 3:138-146 (1992).
Godfrey et al., "Quantitative mRNA expression analysis from formalin-fixed, paraffin-embedded tissues using 5' nuclease quantitative reverse transcription-polymerase chain reaction" J Mol. Diag. 2(2):84-91 (May 2000).

(56) References Cited

OTHER PUBLICATIONS

Gomez-Roman et al., "Fibroblast growth factor receptor 3 is overexpressed in urinary tract carcinomas and modulates the neoplastic cell growth" Clin. Cancer Res. 11:459-465 (Jan. 15, 2005).
Gong et al., "Importance of cellular microenvironment and circulatory dynamics in B cell immunotherapy" J Immunol 174:817-826 ( 2005).
Gozlan and Ben-An, "NMDA receptor redox sites: are they targets for selective neuronal protection" Trends Pharmacol. Sci. 16:368-374 ( 1995).
Graham et al., "Characteristics of a human cell line transformed by DNA from human adenovirus type 5" J. Gen. Virol. 36:59-72 ( 1977).
Gram et al., "In vitro selection and affinity maturation of antibodies from a naive combinatorial immunoglobulin library" Proc. Natl. Acad. Sci. USA 89:3576-3580 (Apr. 1992).
Grand et al., "Targeting FGFR3 in multiple myeloma: inhibition of t(4;14)-positive cells by SU5402 and PD173074" Leukemia 18:962-966 ( 2004).
Griffiths et al., "Human anti-self antibodies with high specificity from phage display libraries" EMBO J 12(2):725-734 ( 1993).
Grose and Dickson, "Fibroblast growth factor signaling in tumorigenesis" Cytokine & Growth Factor Reviews 16:179-186 ( 2005).
Gruber et al., "Efficient tumor cell lysis mediated by a bispecific single chain antibody expressed in *Escherichia coli*" J Immunol 152:5368-5374 ( 1994).
Guss et al., "Structure of the IgG-binding regions of streptococcal protein G" EMBO J 5(7):1567-1575 ( 1986).
Guttieri et al., "Cassette vectors for conversion of Fab fragments into full-length human IgG\\\subscript:1\\\ monoclonal antibodies by expression in stably transformed insect cells" Hybridoma and Hybridomics 22(3):135-145 ( 2003).
Guyer et al., "Immunoglobulin binding by mouse intestinal epithelial cell receptors" J Immunol. 117(2):587-593 (Aug. 1976).
Ham and McKeehan, "Media and Growth Requirements" Method Enzymol. 58:44-93 ( 1979).
Hara et al., "Overproduction of penicillin-binding protein 7 suppresses thermosensitive growth defect at low osmolarity due to an spr mutation of *Escherichia coli*" Microbial Drug Resistance 2(1):63-72 ( 1996).
Harris, "Production of humanized monoclonal antibodies for in vivo imaging and therapy" :Biochem. Soc. Trans. 23(4):1035-1038 (Nov. 1995).
Hauske et al., "Allosteric regulation of proteases" Chembiochem 9(18):2920-2928 (Dec. 15, 2008).
Hawkins et al., "Selection of phage antibodies by binding affinity mimicking affinity maturation" J. Mol. Biol. 226:889-896 ( 1992).
Hinman et al., "Preparation and characterization of monoclonal antibody conjugates of the calicheamicins: a novel and potent family of antitumor antibiotics" Cancer Res. 53:3336-3342 (Jul. 15, 1993).
Hogrefe et al., "A bacteriophage lambda vector for the cloning and expression of immunoglobulin Fab fragments on the surface of filamentous phage" Gene 128:119-126 ( 1993).
Holliger et al., "'Diabodies': Small bivalent and bispecific antibody fragments" P Natl Acad Sci USA 90:6444-6448 (Jul. 1993).
Hoogenboom and Winter, "By-passing immunisation human antibodies from synthetic repertoires of germline V\\\subscript:H\\\ gene segments rearranged in vitro" J. Mol. Biol. 227:381-388 ( 1992).
Hoogenboom et al., "Multi-subunit proteins on the surface of filamentous phage: methodologies for displaying antibody (Fab) heavy and light chains" Nucl. Acids Res. 19(15):4133-4137 ( 1991).
Hoogenboom et al., "Selecting and screening recombinant antibody libraries" Nature Biotech. 23(9):1105-1116 (Sep. 2005).
Hudziak et al., "p185\\\superscript:HER2\\\ monoclonal antibody has antiproliferative effects in vitro and sensitizes human breast tumor cells to tumor necrosis factor" Mol Cell Biol 9(3):1165-1172 (Mar. 1989).
Hurle and Gross, "Protein engineering techniques for antibody humanization" Curr. Opin. Biotechnol. 5:428-433 ( 1994).

Idusogie et al., "Mapping of the C1q binding site on Rituxan, a chimeric antibody with a human IgG1 Fc" J. Immunol. 164:4178-4184 ( 2000).
Jackson et al., "In vitro antibody maturation" J. Immunol. 154:3310-3319 ( 1995).
Jakobovits et al., "Analysis of homozygous mutant chimeric mice: deletion of the immunoglobulin heavy-chain joining region blocks B-cell development and antibody production" Proc. Natl. Acad. Sci. USA 90:2551-2555 (Mar. 1993).
Jakobovits et al., "Germ-line transmission and expression of a human-derived yeast artifical chromosome" Nature 362:255-258 (Mar. 18, 1993).
Jebar et al., "FGFR3 and Ras gene mutations are mutually exclusive genetic events in urothelial cell carcinoma" Oncogene 24:5218-5225 ( 2005).
Johnson and Williams, "Structural and functional diversity in the FGF receptor multigene family" Adv. Cancer Res. 60:1-41 ( 1993).
Johnston et al., "Fibroblast growth factor receptors (FGFRs) localize in different cellular Compartments" J Biol. Chem. 270(51):30643-30650 (Dec. 22, 1995).
Jones and Bendig, "Materials and Methods/Rapid PCT-cloning of full-length mouse immunoglobulin variable regions" Bio/Technology 9:88-89 (Jan. 1991).
Jones et al., "Replacing the complementarity-determining regions in a human antibody with those from a mouse" Nature 321:522-525 (May 1986).
Kan et al., "An essential heparin-binding domain in the fibroblast growth factor receptor kinase" Science 259:1918 ( 1993).
Keegan et al., "Isolation of an aditional member of the fibroblast growth factor receptor family, FGFR-3" Proc. Natl. Acad. Sci. USA 88:1095-1099 (Feb. 1991).
Kim et al., "Localization of the site of the murine IgG1 molecule that is involved in binding to the murine intestinal Fc receptor" Eur. J. Immunol. 24:2429-2434 ( 1994).
Knowles, "Novel therapeutic targets in bladder cancer: mutation and expression of FGF receptors" Future Oncol. 4(1):71-83 ( 2008).
Kohler and Milstein, "Continuous cultures of fused cells secreting antibody of predefined specificity" Nature 256:495-497 (Aug. 7, 1975).
Kostelny et al., "Formation of a bispecific antibody by the use of leucine zippers" J Immunol. 148:1547-1553 (Mar. 1, 1992).
Kozbor et al., "A human hybrid myeloma for production of human monoclonal antibodies" J Immunol. 133(6):3001-3005 (Dec. 1984).
Lee et al., "Bivalent antibody phage display mimics natural immunoglobulin" J. Immunol. Methods 284:119-132 ( 2004).
Lee et al., "High-affinity human antibodies from phage-displayed synthetic Fab libraries with a single framework scaffold" J. Mol. Biol. 340:1073-1093 ( 2004).
Legeai-Mallet et al., "Fibroblast growth factor receptor 3 mutations promote apoptosis but do not alter chondrocyte proliferation in thanatophoric dysplasia" J. Biol. Chem., 273(21):13007-13014 (May 22, 1998); (Erratum in J. Biol. Chem 273(30); 19358 (Jul. 24, 1998)).
Leung et al., "A method for random mutagenesis of a defined DNA segment using a modified polymerase chain reaction" Technique—A J Methods Cell and Molec. Biol. 1(1):11-15 ( 1989).
L'Hote and Knowles, "Cell responses to FGFR3 signalling: growth, differentiation and apoptosis" Exper. Cell Res. 304:417-431 ( 2005).
Li et al., "Activation of FGF receptors by mutations in the transmembrane domain" Oncogene 14:1937-1406 ( 1997).
Li et al., "An activating mutation of the myeloma associated oncogene fibroblast growth factor receptor 3 (FGFR3) has hematopoietic transforming potential in mice" Blood 92(10 SUPPL 1 (Part 1 of 2)) (Nov. 15, 1998).
Li et al., "The myeloma-associated oncogene fibroblast growth factor receptor 3 is transforming in hematopietic cells" Blood 97(8):2413-2419 (Apr. 15, 2001).
Li, Yan, "Study of signal transduction mediated via fibroblast growth factor receptor (FGFRs) by using mutant receptors" Dissertation (Abstract), ( 1997).
Liang et al., "Baculovirus expression cassette vectors for rapid production of complete human IgG from phage display selected antibody fragments" J. Immunol. 247:119-130 ( 2001).

(56) References Cited

OTHER PUBLICATIONS

Liang et al., "Function blocking antibodies to neuropilin-1 generated from a designed human synthetic antibody phage library" J. Mol. Biol. 266:815-829 ( 2007).
Lindmark et al., "Binding of immunoglobulins to protein A and immunoglobulin levels in mammalian sera" J Immunol. Methods 62:1-13 ( 1983).
Liu et al., "Eradication of large colon tumor xenografts by targeted delivery of maytansinoids" Proc. Natl. Acad. Sci. USA 93:8618-8623 (Aug. 1996).
Lode et al., "Targeted therapy with a novel enediyene antibiotic calicheamicin $\theta^{I}_{1}$ effectively suppresses growth and dissemination of liver metastases in a syngeneic model of murine neuroblastoma" Cancer Res. 58:2925-2928 (Jul. 15, 1998).
Mandler et al., "Immunoconjugates of geldanamycin and Anti-HER2 monoclonal antibodies: antiproliferative activity on human breast carcinoma cell lines" J. National Cancer Institute 92:19:1573-1581 (Oct. 4, 2000).
Mandler et al., "Modifications in synthesis strategy improved the yield and efficacy of geldanamycin-herceptin immunoconjugates" Bioconjugate Chem. 13:786-791 ( 2002).
Mandler et al., "Synthesis and evaluation of antiproliferative activity of a Geldanamycin-Herceptin198$^{TM}$ immunoconjugate" Bioorg. Med. Chem. Lett. 10:1025-1028 ( 2000).
Marks et al., "By-passing immunization, Human antibodies from V-gene libraries displayed on phage" J. Mol. Biol. 222:581-597 ( 1997).
Marks et al., "By-passing immunization: building high affinity human antibodies by chain shuffling" Bio/Technology 10:779-783 (Jul. 1992).
Martinez-Torrecuadrada et al., "Antitumor activity of fibroblast growth factor receptor 3-specific immunotoxins in a xenograft mouse model of bladder carcinoma is mediated by apoptosis" Mol. Cancer Ther. 7(4):862-873 (Apr. 2008).
Martinez-Torrecuadrada et al., "Targeting the extracellular domain of fibroblast growth factor receptor 3 with human single-chain Fv antibodies inhibits bladder carcinoma cell line proliferation" Clin. Cancer Res. 11(17):6280-6290 (Sep. 1, 2005).
Masui et al., "Growth inhibition of human tumor cells in athymic mice by anti-epidermal growth factor receptor monoclonal antibodies" Cancer Res. 44:1002-1007 (Mar. 1984).
Mather et al., "Culture of testicular cells in hormone-supplemented serum-free medium" Ann. NY Acad. Sci. 383:44-68 ( 1982).
Mather, J. P., "Establishment and characterization of two distinct mouse testicular epithelial cell lines" Biol. Reproduction 23:243-252 ( 1980).
Matsuda et al., "Structure and physical map of 64 variable segments in the 3'0.8-megabase region of the human immunoglobulin heavy-chain locus" Nat. Genet. 3:88-94 (Jan. 1993).
McCoy et al., "Likelihood-enhanced fast translation functions" Acta Cryst. D61:458-464 ( 2005).
Meyer et al., "The cytoplasmic tyrosine kinase Pyk2 as a novel effector of fibroblast growth factor receptor 3 activation" J Biol. Chem. 279(27):28450-28457 (Jul. 2, 2004).
Milstein and Cuello, "Hybrid hybridomas and their use in immunohistochemistry" Nature 305:537-540 (Oct. 6, 1983).
Mohammadi et al., "Structural basis for fibroblast growth factor receptor activation" Cytokine & Growth Factor Reviews 16: 107-137 ( 2005).
Moreau et al., "Recurrent 14q32 translocations determine the prognosis of multiple myeloma, especially in patients receiving intensive chemotherapy" Blood 100(5):1579-1583 (Sep. 1, 2002).
Morimoto and Inouye, "Single-step purification of F(ab')$_2$ fragments of mouse monoclonal antibodies (immunoglobulins G1) by hydrophobic interaction high performance liquid chromatography using TSKgel phenyl-5PW" J. Biochem. Biophys. Meth. 24:107-117 ( 1992).
Morrison et al., "Chimeric human antibody molecules: mouse antigen-binding domains with human constant region domains" Proc. Natl. Acad. Sci. USA 81:6851-6855 (Nov. 1984).
Munson and Rodbard, "Ligand: A versatile computerized approach for characterization of ligand-binding systems" Anal. Biochem. 107-220-239 ( 1980).
Murshudov et al., "Refinement of macromolecular structures by the maximum-likelihod method" Acta Cyst. D53:240-255 ( 1997).
Myers et al., "Detection of single base substitutions by ribonuclease cleavage at mismatches in RNA:DNA duplexes" Science 230:1242-1246 (Dec. 13, 1985).
Naski et al., "Graded activation of fibroblast growth factor receptor 3 by mutations causing achondroplasia and thanatophoric dysplasia" Nat. Genet. 13:233-237 (Jan. 1996).
Nicolaou et al., "Calicheamicin $\theta^{I}_{1}$ : a rationally designed molecule with extremely potent and selective DNA cleaving properties and apoptosis including activity" Agnew. Chem. Int. Ed. Engl. 33(2):183-186 ( 1994).
Niculescu-Duvaz and Springer, "Antibody-directed enzyme prodrug therapy (ADEPT): a review" Adv. Drug Deliv. Rev. 26:151-172 ( 1997).
Novack et al., "Detection of single base-pair mismatches in DNA by chemical modification followed by electrophoresis in 15% polyacrylamide gel" Proc. Natl. Acad. Sci. USA 83:586-590 (Feb. 1986).
Okazaki et al., "Fucose depletion from human IgG1 oligosaccharide enhances binding enthalpy and association rate between IgG1 and Fyc$\gamma$RIIIa" J. Mol. Biol. 336:1239-1249 ( 2004).
Olsen et al., "Insights into the molecular basis for fibroblast growth factor receptor autoinhibition and ligand-binding promiscuity" Proc. Natl. Acad. Sci. USA 101(4):935-940 (Jan. 27, 2004).
Opposition filed to EP 1 423 428 B (Opposition filed May 26, 2010 to EP 1 423 428 B May 26, 2010).
Orita et al., "Detection of polymorphisms of human DNA by gel electrophoresis as single-strand conformation polymorphisms" Proc. Natl. Acad. Sci. USA 86:2766-2770 (Apr. 1989).
Orita et al., "Rapid and sensitive detection of point mutations and DNA polymorphisms using the polymerase chain reaction" Genomics 5:874-879 ( 1989).
Orlandi et al., "Cloning immunoglobulin variable domains for expression by the polymerase chain reaction" Proc. Natl. Acad. Sci. USA 86:3833-3837 (May 1989).
Ornitz and Leder, "Ligand specificity and heparin dependence of fibroblast growth factor receptors 1 and 3" J Biol. Chem 267(23):16305-16311 (Aug. 15, 1992).
Orum et al., "Efficient method for constructing comprehensive murine Fab antibody libraries displayed on phage" Nucl. Acids Res. 21(19):4491-4498 ( 1993).
Otwinowski and Minor, "Processing of X-ray diffraction data collected in oscillation mode" Meth. Enzymol. 276:307-326 ( 1997).
Pai et al , "Inhibition of fibroblast growth factor 19 reduces tumor growth by modulating $\beta$-catenin signaling" Cancer Res. 68(13):5086-5095 (Jul. 1, 2008).
Pandit et al., "The fibroblast growth factor receptor, FGFR3, forms gradients of intact and degraded protein across the growth plate of developing bovine ribs" Biochem. J. 361 (Pt 2):231-241 (Jan. 15, 2002).
Partanen et al., "Putative tyrosine kinases expressed in K-562 human leukemia cells" Proc. Natl. Acad. Sci. USA 87(22):8913-8917 (Nov. 1990).
Paterson et al., "Preclinical studies of fibroblast growth factor receptor 3 as a therapeutic target in multiple myeloma" Br J Haematology 124:595-603 ( 2004).
Paul, William E. Fundamental Immunology, 3rd edition,: 292-295, ( 1993).
Pegram et al., "Inhibitory effects of combinations of HER-2/neu antibody and chemotherapeutic agents used for treatment of human breast cancers" Oncogene 12:2241-2251 ( 1999).
Pettit et al., "Antineoplastic agents 365. Dolastatin 10 SAR probes" Anti-Cancer Drug Design 13:243-277 ( 1998).

(56) References Cited

OTHER PUBLICATIONS

Pettit et al., "Dolastatins 24: synthesis of (–)-dolastatin 10.\\\subscript:1\\\ X-ray molecular structure of N,N-dimethylvalyl-valyl-dolaisoleuine tert-butyl ester" J. Chem. Soc., Perkins Trans. 1:859-863 ( 1996).

Pettit et al., "Specific activities of dolastatin 10 and peptide derivatives against cryptococcus neoformans" Antimicrob. Agents and Chemotherapy 42(11):2961-2965 (Nov. 1998).

Pettit et al., "The absolute configuration and synthesis of natural (–)-Dolastatin 10 \\\subscript:1\\\" J Am. Chem. Soc. 111:5463-5465 ( 1989).

Pettit et al., "The dolastatins; 18: stereospecific synthesis of dolaproine" Synthesis:719-725 (Jun. 1996).

Plotnikov et al., "Structural basis for FGF receptor dimerization and activation" Cell 98:641-650 (Sep. 3, 1999).

Plowright et al., "An activating mutation of the myeloma associated oncogene fibroblast growth factor receptor 3 (FGFR3) promotes interleukin-6 (IL-6) independence and upregulation of BCL-XL" Blood 92(10 SUPPL 1 (Part 1 of 2)):383A (Nov. 15, 1998).

Plowright et al., "Ectopic expression of fibroblast growth factor receptor 3 promotes myeloma cell proliferation and prevents apoptosis" Blood 95(3):992-998 (Feb. 1, 2000).

Pluckthun, A., "Mono- and bivalent antibody fragments produced in *Escherichia coli*: engineering, folding and antigen binding" Immunol. Reviews(130):151-188 ( 1992).

Pollett et al., "Overexpression of the myeloma-associated oncogene fibroblast growth factor receptor 3 confers dexamithasone resistance" Blood 100(10):3819-3821 (Nov. 15, 2002).

Presta et al., "Humanization of an antibody directed against IgE" J. Immunol. 151(5):2623-2632 (Sep. 1, 1993).

Presta, "Antibody engineering" Curr. Opin. Struct. Biol. 2:593-596 ( 1992).

Proba et al., "Functional antibody single-chain fragments from the cytoplasm of *Escherichia coli*: influence of thioredoxin reductase (TrxB)" Gene 159:203-207 ( 1995).

Product Sheets R&D System Santa Cruz Biotechnology, Inc. FGFR-3 (B-9):sc-13121 (downloaded Aug. 31, 2011).

Product Sheets R&D Systems, Human FGF R3 (IIIb) Antibody, Monoclonal Mouse IgG\\\subscript:1\\\ Clone #13311, MAB795 (downloaded Aug. 31, 2011).

Product Sheets R&D Systems, Human FGF R3(IIIb) Antibody, Monoclonal Mouse IgG\\\subscript:1\\\ Clone #136315, MAB1474 (downloaded Aug. 31, 2011).

Product Sheets R&D Systems, Human FGF R3 (IIIc) Antibody, Monoclonal Mouse IgG\\\subscript:1\\\ Clone #136312, MAB7662 (downloaded Aug. 31, 2011).

Product Sheets R&D Systems, Human FGF R3 Antibody, Monoclonal Mouse IgG\\\subscript:1\\\ Clone 190 136318, MAB7661 (downloaded Aug. 31, 2011).

Product Sheets R&D Systems, Monoclonal Anti-Mouse FGF R3 Antibody Clone #136812, MAB710 (downloaded Aug. 31, 2011).

Pytel et al., "Tyrosine kinase blockers: new hope for successful cancer therapy" Anti-Cancer Agents Med. Chem. 9(1):66-76 (Jan. 2009).

Qing et al., "Antibody-based targeting of FGFR3 in bladder carcinoma and t(4;14)-positive multiple myeloma in mice" J. Clin. Invest. 199(5):1216-1229 (May 2009).

Qiu et al., "Over-expression of fibroblast growth factor receptor 3 in human hepatocellular carinoma" World J Gastroenterol. 11(34):5266-5272 ( 2005).

Ramm and Plukthun, "The periplasmic *Escherichia coli* peptidylprolyl cis,trans-isomerase FkpA" J. Biol. Chem. 275(22):17106-17113 (Jun. 2, 2000).

Rauchenberger et al., "Human combinatorial Fab library yeilding specific and functional antibodies against the human fibroblast growth factor receptor 3" J Biol. Chem. 278(40):38194-38205 (Oct. 3, 2003).

Rauchenberger, R. et al., "Human combinatorial Fab library yeilding specific and functional antibodies against the human fibroblast growth factor receptor 3" The Journal of Biological Chemistry, 278(40):38194-38205 ( 2003).

Ravetch and Kinet, "Fc receptors" Annu. Rev. Immunol. 9:457-492 ( 1991).

Reply filed to Opposition to EP 1 423 428 on Mar. 11, 2011 (Reply to Opposition filed Mar. 11, 2011).

Riechmann et al., "Reshaping human antibodies for therapy" Nature 332:323-327 (Mar. 24, 1988).

Ripka et al., "Two chinese hamster ovary gylcosylation mutants affected in the conversion of GDP-mannose to GDP-fucose" Arch. Biochem. Biophys. 249(2):533-545 (Sep. 1986).

Ronchetti et al., "Deregulated FGFR3 mutants in multiple myeloma cell lines with t(4;14): comparative analysis of Y373C, K650E and thenovel G384D mutations" Oncogene 20:3553-3562 ( 2001).

Rowland et al., "Drug localisation and growth inhibition studies of vindesine-monoclonal anti-CEA conjugates in a human tumor xenograft" Cancer Immunol. Immunother. 21:183-187 ( 1986).

Ruano and Kidd, "Direct haplotyping of chromosomal segments from multiple heterozygotes via allele-specific PCR amplification" Nucl. Acids Res. 17(20):8392 ( 1989).

Rudikoff et al. Proc. Natl. Acad. Sci. USA, 79(6):1979-1983, (Mar. 1982).

Saiki et al., "Primer-directed enzymatic amplification of DNA with a thermostable DNA polymerase" Science 239:487-491 (Jan. 29, 1988).

Sastry et al., "Cloning of the immunological repertoire in *Escherichia coli* for generation of monoclonal catalytic antibodies: construction of a heavy chain variable region-specific cDNA library" Proc. Natl. Acad. Sci. USA 86:5728-5732 (Aug. 1989).

Schier et al., "Identification of functional and structural amino-acid residues by parsimonious mutagenesis" Gene 169:147-155 ( 1996).

Shalaby et al., "Development of humanized bispecific antibodies reactive with cytotoxic lymphocytes and tumor cell overexpression the HER2 protooncogene" J. Exp. Med 175:217-225 (Jan. 1992).

Shenk et al., "Biochemical method for mapping mutational alterations in DNA with S1 nuclease: the location of deletions and teperature-sensitive mutation in Simian virus 40" Proc. Natl. Acad. Sci. USA 72(3):989-993 (Mar. 1975).

Schields et al., "High resolution mapping of the binding site on human IgG1 for FcγRI, FcγRII, FcγRIII, and FcRn and design of IgG1 variantes with improved binding to the FcΞR" J Biol. Chem. 276(9):6591-6604 (Mar. 2, 2001).

Sidhu et al., "Phage-displayed antibody libraries of synthetic heavy chain complementarity determining regions" J. Mol. Biol. 338:299-310 ( 2004).

Siebenlist et al., "*E. coli* RNA polymerase interacts homologously with two different promoters" Cell 20:269-281 (Jun. 1980).

Simmons et al., "Expression of full-length immunoglobulins in *Escherichia coli*: rapid and efficient production of aglycosylated antibodies" J Immunol. Methods 263:133-147 ( 2002).

Sims et al. et al., "A Humanized CD18 Antibody Can Block Function without Cell Destruction" J. Immunol. 151(4):2296-2308 (Aug. 1993).

Skerra, A., "Bacterial expression of immunoglobulin fragments" Curr. Opin. Immunol. 5:256-262 (1993).

Specht et al., "Quantitative gene expression analysis in microdissected archival formalin-fixed and paraffin-embedded tumor tissue" Am. J Pathol. 158(2):419-429 (Feb. 2001).

Steger et al., "Localization of fibroblast growth factor 2 (FGF-2) protein and the receptors FGF4 1-4 in normal human seminiferous epithelium" Histoghem. Cell Biol. 111:57-62 ( 1998).

Suresh et al. et al., "Bispecific Monoclonal Antibodies from Hybrid Hybridomas" Method Enzymol. 121:210-228 ( 1986).

Suzuki et al., "βKlotho is required for fibroblast growth factor (FGF) 21 signaling through FGF receptor (FGFR) 1c and FGFR3c" Molec. Endocrin. 22(4):1006-1014 ( 2008).

Syrigos and Epenetos, "Antibody directed enzyme prodrug therapy (ADEPT): a review of the experimental and clinical considerations" Anticancer Res. 19:605-614 ( 1999).

(56) References Cited

OTHER PUBLICATIONS

Thorpe, "Antibody carriers of cytotoxic agents in cancer therapy: a review" Monoclonal Antibodies '84: Biological and Clinical Applications (A Pinchera, G. Doria, F. Dammacco and A. Bargellesi, eds. pp. 475-506 (1985)).

Tomlinson et al. et al., "The repertoire of human germline VH sequences reveals about fifty groups of VH segments with different hypervariable loops" J Mol. Biol. 227(3):776-798 (Oct. 5, 1992).

Tomlinson et al., "FGFR3 protein expression and its relationship to mutation status and prognostic variables in bladder cancer" J. Pathol. 213(91-98) ( 2007).

Tomlinson et al., "Knockdown by shRNA identifies S249C mutant FGFR3 as a potential therapeutic target in bladder cancer" Oncogene 26:5889-5899 ( 2007).

Traunecker et al., "Bispecific single chain molecules (Janusins) target cytotoxic lymphocytes on HIV infected cells" EMBO J 10(12):3655-3659 ( 1991).

Trudel et al., "CHIR-258, a novel, mulitargeted tyrosine kinase inhibitor for the potential treatment of t(4;14) multiple myeloma" Blood 105(7):2941-2948 (Apr. 1, 2005).

Trudel et al., "Inhibition of fibroblast growth factor receptor 3 induces differentiation and apoptosis in t(4;14) myeloma" Blood 103(9):3521-3528 ( 2004).

Trudel et al., "Targeting FGFR3 in t(4;14) multiple myeloma: preclinical studies of PRO-001, a novel anti-FGFR3 neuitralizing antibody" Blood 104(11 SUPPL 1):680A (Nov. 2004).

Trudel et al., "The in hibitory anti-FGFR3 antibody, PRO-001, is cytotoxic to t(4;14) multiple myeloma cells" Blood 107:4039-4046 ( 2006).

Tutt et al., "Trispecific F(ab')\\\subscript:3\\\ derivatives that use cooperative signalling via the TCR/CD3 complex and CD2 to activate and redirect resting cytotoxic T cells" J Immunol. 147(1):60-69 (Jul. 1, 1991).

Urlaub and Chasin, "Isolation of Chinese hamster cell mutants deficient in dihydrofolate reductase activity" Proc. Natl. Acad. Sci USA 77(7):4216-4220 (Jul. 1980).

van Rhijn et al., "Frequent FGFR3 mutations in utothelial papilloma" J. Pathol. 198:245-251 ( 2002).

Vaswani and Hamilton et al., "Humanized antibodies as potential therapeutic drugs" Ann. Allergy Asthma Immunol. 1:105-115 ( 1998).

Verhoeyen et al. et al., "Reshaping Human Antibodies: Grafting an Antilysozyme Activity" Science 239:1534-1536 (Mar. 1988).

Vitetta et al., "Redesigning Nature's Posions to Create Anti-Tumor Reagents" Science 238:1098-1104 ( 1987).

Wang et al., "Transcritpome analysis method for in vivo mechanism of action study: IMC-D11 and anti-FGFR3 +/− cisplatin in bladder cancer models" Eur. J. Cancer 6:12 SUPPL 63) (Oct. 2008).

Ward et al., "Binding activites of a repertoire of single immunoglobulin variable domains secreted from Escherichia coli" Nature 341:544-546 (Oct. 12, 1989).

Waterhouse et al., "Combinatorial infection and in vivo recombination: a strategy for making large phage antibody repertoires" Nucl. Acids Res. 21:2265-2266 ( 1993).

Williams and Winter, "Cloning and sequencing of human immunoglobulin V\\\subscript:λ\\\ gene segments" Eur. J Immunol. 23:1456-1461 ( 1993).

Williams et al., "Activation of the FGF receptor underlies neurite outgrowth stimulated by L1, N-Cam, and N-Cadherin" Neuron 13:583-594 (Sep. 1994).

Winter et al., "A method to detect and characterize point mutations in transcribed genes: amplification and overexpression of the mutant c-Ki-ras alllele in human tumor cells" Proc. Natl. Acad. Sci. USA 82:7575-7579 (Nov. 1985).

Winter et al., "Making antibodies by phage display technology" Annu. Rev. Immunol. 12:433-455 ( 1994).

Wiseman et al., "Ibritumomab tiuxetan radioimmunotherapy for patients with relapsed or refractory non-Hodgkin lymphoma and mild thrombocytopenia: a phase II multicenter trial" Blood 99(12):4336-4342 ( 2002).

Wiseman et al., "Phase I/II 90Y-Zevalin (yttrium-90 ibritumomab tiuxetan, IDEC-Y2B8) radioimmunotheraphy dosimetry results in relapsed or refractory non-Hodgkin's lymphoma" Eur. J Nucl. Med. 27(7):766-777 (Jul. 2000).

Witzig et al et al., "Randomized Controlled Trial of Yttrium-90—Labeled Ibritumomab Tiuxetan Radioimmunotheraphy Versus Rituximab Immunotherapy for Patients With Relapsed or Refractory Low-Grade, Follicular, or Transformed B-Cell Non-Hodgkin's Lymphoma" J Clin. Oncol. 20(10):2453-2463 (May 15, 2002).

Witzig et al., "Treatment with ibritumomab tiuxetan radioimmunotherapy in patients with rituximab-refractory follicular non-Hodgkin's lymphoma" J Clin. Oncol. 29(15):3263-3269 (Aug. 1, 2002).

Woenckhaus et al., "Smoker and cancer-related gene expression in bronchial epithelium and non-small-cell lung cancers" J. Pathol. 210:192-204 ( 2006).

Woyke et al., "In vitro activities and postantifungal effects of the potent dolastatin 10 derivative auristatin PHE" Antimicrob. Agents Chemother. 45(12):3580-3584 (Dec. 2001).

Wu and Wallace, "The ligation amplification reaction (LAR)—amplification of speffific DNA sequences using sequential rounds of template-dependent ligtation" Genomics 4:560-569 ( 1989).

Xin et al., "CHIR-258 is efficacious in a newly developed fibroblast growth factor receptor 3-expressing orthopic multiple myeloma model in mice" Clin. Cancer Res. 12(16):4908-4915 (Aug. 15, 2006).

Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol. Bioeng. 87(5):614-622 (Sep. 5, 2004).

Yaniv, "Enhancing elements for activation of eukaryotic promoters" Nature 297:17-18 (May 6, 1982).

Yelton et al., "Affinity maturation of the BR96 anti-carcinoma antibody by codon-based mutagenesis" J Immunol. 155:1994-2004 ( 1995).

Zammit et al., "Altered intracellular localization of fibroblast growth factor receptor 3 in human breast cancer" J Pathol. 194(1):24-34 (May 2001).

| Clone # | H1 | | | | | | | | | |
|---|---|---|---|---|---|---|---|---|---|---|
| | 26 | 27 | 28 | 29 | 30 | 31 | 32 | 33 | 34 | 35 |
| 184.6 | G | F | T | F | T | S | T | G | I | S |
| 184.6.1 | G | F | T | F | T | S | T | G | I | S |
| 184.6.58 | G | F | T | F | T | S | T | G | I | S |
| 184.6.62 | G | F | T | F | S | T | T | G | I | S |
| 184.6.21 | G | F | T | F | T | S | T | G | I | S |
| 184.6.49 | G | F | T | F | T | S | T | G | I | S |
| 184.6.51 | G | F | S | F | T | G | T | G | I | S |
| 184.6.52 | G | F | T | F | Y | T | T | G | I | S |
| 184.6.92 | G | F | S | F | W | S | T | G | I | S |
| 184.6.1.N54S | G | F | T | F | T | S | T | G | I | S |
| 184.6.1.N54G | G | F | T | F | T | S | T | G | I | S |
| 184.6.1.N54A | G | F | T | F | T | S | T | G | I | S |
| 184.6.1.N54Q | G | F | T | F | T | S | T | G | I | S |
| 184.6.58.N54S | G | F | T | F | T | S | T | G | I | S |
| 184.6.58.N54G | G | F | T | F | T | S | T | G | I | S |
| 184.6.58.N54A | G | F | T | F | T | S | T | G | I | S |
| 184.6.58.N54Q | G | F | T | F | T | S | T | G | I | S |
| 184.6.1.NS D30E | G | F | T | F | T | S | T | G | I | S |

| Clone # | H2 | | | | | | | | | | | | | | | | | |
|---|---|---|---|---|---|---|---|---|---|---|---|---|---|---|---|---|---|---|
| | 49 | 50 | 51 | 52 | 52a | 53 | 54 | 55 | 56 | 57 | 58 | 59 | 60 | 61 | 62 | 63 | 64 | 65 |
| 184.6 | G | R | I | Y | P | T | N | G | S | T | N | Y | A | D | S | V | K | G |
| 184.6.1 | G | R | I | Y | P | T | N | G | S | T | N | Y | A | D | S | V | K | G |
| 184.6.58 | G | R | I | Y | P | T | N | G | S | T | N | Y | A | D | S | V | K | G |
| 184.6.62 | G | R | I | Y | P | L | Y | G | S | T | H | Y | A | D | S | V | K | G |
| 184.6.21 | G | R | I | Y | P | Y | D | D | S | F | Y | Y | A | D | S | V | K | G |
| 184.6.49 | G | R | I | Y | P | T | N | G | S | T | N | Y | A | D | S | V | K | G |
| 184.6.51 | G | S | I | Y | P | Y | F | A | T | K | N | Y | A | D | S | V | K | G |
| 184.6.52 | G | R | I | Y | P | A | F | G | S | S | I | Y | A | D | S | V | K | G |
| 184.6.92 | G | R | I | Y | P | S | S | A | T | T | N | Y | A | D | S | V | K | G |
| 184.6.1.N54S | G | R | I | Y | P | T | S | G | S | T | N | Y | A | D | S | V | K | G |
| 184.6.1.N54G | G | R | I | Y | P | T | G | G | S | T | N | Y | A | D | S | V | K | G |
| 184.6.1.N54A | G | R | I | Y | P | T | A | G | S | T | N | Y | A | D | S | V | K | G |
| 184.6.1.N54Q | G | R | I | Y | P | T | Q | G | S | T | N | Y | A | D | S | V | K | G |
| 184.6.58.N54S | G | R | I | Y | P | T | S | G | S | T | N | Y | A | D | S | V | K | G |
| 184.6.58.N54G | G | R | I | Y | P | T | G | G | S | T | N | Y | A | D | S | V | K | G |
| 184.6.58.N54A | G | R | I | Y | P | T | A | G | S | T | N | Y | A | D | S | V | K | G |
| 184.6.58.N54Q | G | R | I | Y | P | T | Q | G | S | T | N | Y | A | D | S | V | K | G |
| 184.6.1.NS D30E | G | R | I | Y | P | T | S | G | S | T | N | Y | A | D | S | V | K | G |

*FIG. 1A*

| Clone # | H3 | | | | | | | | | | | | | | | | | | | |
|---|---|---|---|---|---|---|---|---|---|---|---|---|---|---|---|---|---|---|---|---|
| | 93 | 94 | 95 | 96 | 97 | 98 | 99 | 100 | A | B | C | D | | | | | | M | 101 | 102 |
| 184.6 | A | R | T | Y | G | I | Y | D | L | Y | V | D | Y | T | E | Y | V | M | D | Y |
| 184.6.1 | A | R | T | Y | G | I | Y | D | L | Y | V | D | Y | T | E | Y | V | M | D | Y |
| 184.6.58 | A | R | T | Y | G | I | Y | D | L | Y | V | D | Y | T | E | Y | V | M | D | Y |
| 184.6.62 | A | R | T | Y | G | I | Y | D | L | Y | V | D | Y | T | E | Y | V | M | D | Y |
| 184.6.21 | A | R | T | Y | G | I | Y | D | L | Y | V | D | Y | T | E | Y | V | M | D | Y |
| 184.6.49 | A | R | T | Y | G | I | Y | D | L | Y | V | D | Y | T | E | Y | V | M | D | Y |
| 184.6.51 | A | R | T | Y | G | I | Y | D | L | Y | V | D | Y | T | E | Y | V | M | D | Y |
| 184.6.52 | A | R | T | Y | G | I | Y | D | L | Y | V | D | Y | T | E | Y | V | M | D | Y |
| 184.6.92 | A | R | T | Y | G | I | Y | D | L | Y | V | D | Y | T | E | Y | V | M | D | Y |
| 184.6.1.N54S | A | R | T | Y | G | I | Y | D | L | Y | V | D | Y | T | E | Y | V | M | D | Y |
| 184.6.1.N54G | A | R | T | Y | G | I | Y | D | L | Y | V | D | Y | T | E | Y | V | M | D | Y |
| 184.6.1.N54A | A | R | T | Y | G | I | Y | D | L | Y | V | D | Y | T | E | Y | V | M | D | Y |
| 184.6.1.N54Q | A | R | T | Y | G | I | Y | D | L | Y | V | D | Y | T | E | Y | V | M | D | Y |
| 184.6.58.N54S | A | R | T | Y | G | I | Y | D | L | Y | V | D | Y | T | E | Y | V | M | D | Y |
| 184.6.58.N54G | A | R | T | Y | G | I | Y | D | L | Y | V | D | Y | T | E | Y | V | M | D | Y |
| 184.6.58.N54A | A | R | T | Y | G | I | Y | D | L | Y | V | D | Y | T | E | Y | V | M | D | Y |
| 184.6.58.N54Q | A | R | T | Y | G | I | Y | D | L | Y | V | D | Y | T | E | Y | V | M | D | Y |
| 184.6.1.NS D30E | A | R | T | Y | G | I | Y | D | L | Y | V | D | Y | T | E | Y | V | M | D | Y |

| Clone # | L1 | | | | | | | | | | |
|---|---|---|---|---|---|---|---|---|---|---|---|
| | 24 | 25 | 26 | 27 | 28 | 29 | 30 | 31 | 32 | 33 | 34 |
| 184.6 | R | A | S | Q | D | V | S | T | A | V | A |
| 184.6.1 | R | A | S | Q | D | V | D | T | S | L | A |
| 184.6.58 | R | A | S | Q | D | V | D | I | S | L | A |
| 184.6.62 | R | A | S | Q | D | V | S | T | A | V | A |
| 184.6.21 | R | A | S | Q | D | V | S | T | A | V | A |
| 184.6.49 | R | A | S | Q | V | I | D | I | S | L | A |
| 184.6.51 | R | A | S | Q | D | V | S | T | A | V | A |
| 184.6.52 | R | A | S | Q | D | V | S | T | A | V | A |
| 184.6.92 | R | A | S | Q | D | V | S | T | A | V | A |
| 184.6.1.N54S | R | A | S | Q | D | V | D | T | S | L | A |
| 184.6.1.N54G | R | A | S | Q | D | V | D | T | S | L | A |
| 184.6.1.N54A | R | A | S | Q | D | V | D | T | S | L | A |
| 184.6.1.N54Q | R | A | S | Q | D | V | D | T | S | L | A |
| 184.6.58.N54S | R | A | S | Q | V | V | D | T | S | L | A |
| 184.6.58.N54G | R | A | S | Q | V | V | D | T | S | L | A |
| 184.6.58.N54A | R | A | S | Q | V | V | D | T | S | L | A |
| 184.6.58.N54Q | R | A | S | Q | V | V | D | T | S | L | A |
| 184.6.1.NS D30E | R | A | S | Q | D | V | E | T | S | L | A |

*FIG. 1B*

| Clone # | L2 | | | | | | |
|---|---|---|---|---|---|---|---|
| | 50 | 51 | 52 | 53 | 54 | 55 | 56 |
| 184.6 | S | A | S | F | L | Y | S |
| 184.6.1 | S | A | S | F | L | Y | S |
| 184.6.58 | S | A | S | S | L | A | S |
| 184.6.62 | S | A | S | F | L | Y | S |
| 184.6.21 | S | A | S | F | L | Y | S |
| 184.6.49 | G | A | S | T | L | A | S |
| 184.6.51 | S | A | S | F | L | Y | S |
| 184.6.52 | S | A | S | F | L | Y | S |
| 184.6.92 | S | A | S | F | L | Y | S |
| 184.6.1.N54S | S | A | S | F | L | Y | S |
| 184.6.1.N54G | S | A | S | F | L | Y | S |
| 184.6.1.N54A | S | A | S | F | L | Y | S |
| 184.6.1.N54Q | S | A | S | F | L | Y | S |
| 184.6.58.N54S | S | A | S | S | L | A | S |
| 184.6.58.N54G | S | A | S | S | L | A | S |
| 184.6.58.N54A | S | A | S | S | L | A | S |
| 184.6.58.N54Q | S | A | S | S | L | A | S |
| 184.6.1.NS D30E | S | A | S | F | L | Y | S |

| Clone # | L3 | | | | | | | | |
|---|---|---|---|---|---|---|---|---|---|
| | 89 | 90 | 91 | 92 | 93 | 94 | 95 | 96 | 97 |
| 184.6 | Q | Q | S | Y | T | T | P | P | T |
| 184.6.1 | Q | Q | S | T | G | H | P | Q | T |
| 184.6.58 | Q | Q | G | A | G | N | P | Y | T |
| 184.6.62 | Q | Q | T | Y | T | T | S | L | T |
| 184.6.21 | Q | Q | S | Y | T | T | P | L | T |
| 184.6.49 | Q | Q | S | A | A | D | P | Y | T |
| 184.6.51 | Q | Q | S | Y | T | T | P | P | T |
| 184.6.52 | Q | Q | T | Y | S | A | Q | P | T |
| 184.6.92 | Q | Q | S | Y | S | H | Q | S | T |
| 184.6.1.N54S | Q | Q | S | T | G | H | P | Q | T |
| 184.6.1.N54G | Q | Q | S | T | G | H | P | Q | T |
| 184.6.1.N54A | Q | Q | S | T | G | H | P | Q | T |
| 184.6.1.N54Q | Q | Q | S | T | G | H | P | Q | T |
| 184.6.58.N54S | Q | Q | G | A | G | N | P | Y | T |
| 184.6.58.N54G | Q | Q | G | A | G | N | P | Y | T |
| 184.6.58.N54A | Q | Q | G | A | G | N | P | Y | T |
| 184.6.58.N54Q | Q | Q | G | A | G | N | P | Y | T |
| 184.6.1.NS D30E | Q | Q | S | T | G | H | P | Q | T |

*FIG. 1C*

Clone 184.6.1.N54S

VH
EVQLVESGGGLVQPGGSLRLSCAASGFTFTSTGISWVRQAPGKGLEWV
GRIYPTSGSTNYADSVKGRFTISADTSKNTAYLQMNSLRAEDTAVYYCAR
ARTYGIYDLYVDYTEYVMDYWGQGTLV   (SEQ ID NO: 132)

VL
DIQMTQSPSSLSASVGDRVTITCRASQDVDTSLAWYQQKPGKAPKLLIYSASFLYS
GVPSRFSGSGSGTDFTLTISSLQPEDFATYYCQQSTGHPQTFGQGTKVEIKR   (SEQ ID NO:133)

Clone 184.6.58

VH
EVQLVESGGGLVQPGGSLRLSCAASGFTFTSTGISWVRQAPGKGLEWV
ARIYPTNGSTNYADSVKGRFTISADTSKNTAYLQMNSLRAEDTAVYYCAR
ARTYGIYDLYVDYTEYVMDYWGQGTLV   (SEQ ID NO:134)

VL
DIQMTQSPSSLSASVGDRVTITCRASQDVDISLAWYQQKPGKAPKLLIYSASFLYS
GVPSRFSGSGSGTDFTLTISSLQPEDFATYYCQQGAGNPYTFGQGTKVEIKR   (SEQ ID NO:135)

Clone 184.6.62
VH
EVQLVESGGGLVQPGGSLRLSCAASGFTFSTTGISWVRQAPGKGLEWV
ARIYPLYGSTHYADSVKGRFTISADTSKNTAYLQMNSLRAEDTAVYYCAR
ARTYGIYDLYVDYTEYVMDYWGQGTLV   (SEQ ID NO:136)

VL
DIQMTQSPSSLSASVGDRVTITCRASQDVSTAVAWYQQKPGKAPKLLIYSASFLYS
GVPSRFSGSGSGTDFTLTISSLQPEDFATYYCQQTYTTSLTFGQGTKVEIKR   (SEQ ID NO:137)

Clone 184.6.1.NS D30E
VH
EVQLVESGGGLVQPGGSLRLSCAASGFTFTSTGISWVRQAPGKGLEWV
GRIYPTSGSTNYADSVKGRFTISADTSKNTAYLQMNSLRAEDTAVYYCAR
ARTYGIYDLYVDYTEYVMDYWGQGTLV   (SEQ ID NO:138)

VL
DIQMTQSPSSLSASVGDRVTITCRASQDVETSLAWYQQKPGKAPKLLIYSASFLYS
GVPSRFSGSGSGTDFTLTISSLQPEDFATYYCQQSTGHPQTFGQGTKVEIKR   (SEQ ID NO:139)

*FIG. 2A*

Clone 1G6

HVR-H1: GYSFTDYNMY (SEQ ID NO:164)

HVR-H2: WIGYIEPYNGGTSYNQKFKG (SEQ ID NO:167)

HVR-H3: ASPNYYDSSPFAY (SEQ ID NO:170)

HVR-L1: SASSSVSYMH (SEQ ID NO:155)

HVR-L2: TWIYDTSILAS (SEQ ID NO:158)

HVR-L3: QQWTSNPLT (SEQ ID NO:161)

Clone 6G1

HVR-H1: GYVFTHYNMY (SEQ ID NO:165)

HVR-H2: WIGYIEPYNGGTSYNQKFKG (SEQ ID NO:168)

HVR-H3: ARGQGPDFDV (SEQ ID NO:171)

HVR-L1: SASSSVSYMH (SEQ ID NO:156)

HVR-L2: RWIYDTSKLAS (SEQ ID NO:159)

HVR-L3: QQWSSYPPT (SEQ ID NO:162)

Clone 15B2

HVR-H1: GYAFTSYNMY (SEQ ID NO:166)

HVR-H2: WIGYIDPYIGGTSYNQKFKG (SEQ ID NO:169)

HVR-H3: ARWGDYDVGAMDY (SEQ ID NO:172)

HVR-L1: LASQTIGTWLA (SEQ ID NO:157)

HVR-L2: LLIYAATSLAD (SEQ ID NO:160)

HVR-L3: QQLYSPPWT (SEQ ID NO:163)

*FIG. 2B*

| | | | |
|---|---|---|---|
| I | | | |
| A | QVQLVQSGAEVKKPGASVKVSCKASGYTFT | -H1- | WVRQAPGQGLEWMG |
| B | QVQLVQSGAEVKKPGASVKVSCKAS | -H1- | WVRQAPGQGLEWM |
| C | QVQLVQSGAEVKKPGASVKVSCKAS | -H1- | WVRQAPGQGLEWM |
| D | QVQLVQSGAEVKKPGASVKVSCKAS | -H1- | WVRQAPGQGLEWM |
| II | | | |
| A | QVQLQESGPGLVKPSQTLSLTCTVSGGSVS | -H1- | WIRQPPGKGLEWIG |
| B | QVQLQESGPGLVKPSQTLSLTCTVS | -H1- | WIRQPPGKGLEWI |
| C | QVQLQESGPGLVKPSQTLSLTCTVS | -H1- | WIRQPPGKGLEWI |
| D | QVQLQESGPGLVKPSQTLSLTCTVS | -H1- | WIRQPPGKGLEWI |
| III | | | |
| A | EVQLVESGGGLVQPGGSLRLSCAASGFTFS | -H1- | WVRQAPGKGLEWVS |
| B | EVQLVESGGGLVQPGGSLRLSCAAS | -H1- | WVRQAPGKGLEWV |
| C | EVQLVESGGGLVQPGGSLRLSCAAS | -H1- | WVRQAPGKGLEWV |
| D | EVQLVESGGGLVQPGGSLRLSCAAS | -H1- | WVRQAPGKGLEWV |
| Acceptor | | | |
| A | EVQLVESGGGLVQPGGSLRLSCAASGFNIK | -H1- | WVRQAPGKGLEWVS |
| B | EVQLVESGGGLVQPGGSLRLSCAAS | -H1- | WVRQAPGKGLEWV |
| C | EVQLVESGGGLVQPGGSLRLSCAAS | -H1- | WVRQAPGKGLEWV |
| Second Acceptor | | | |
| A | EVQLVESGGGLVQPGGSLRLSCAASGFNIK | -H1- | WVRQAPGKGLEWVS |
| B | EVQLVESGGGLVQPGGSLRLSCAAS | -H1- | WVRQAPGKGLEWV |
| C | EVQLVESGGGLVQPGGSLRLSCAAS | -H1- | WVRQAPGKGLEWV |
| D | EVQLVESGGGLVQPGGSLRLSCAAS | -H1- | WVRQAPGKGLEWV |

All rows continue with -H2-

FIG. 3A

|   | | | |
|---|---|---|---|
| I | | | |
| A | RVTITADTSTSTAYMELSSLRSEDTAVYYCAR | -H3- | WGQGTLVTVSS SEQ ID NO: 19, 203-205 |
| B | RVTITADTSTSTAYMELSSLRSEDTAVYYCAR | -H3- | WGQGTLVTVSS SEQ ID NO: 20, 206-208 |
| C | RVTITADTSTSTAYMELSSLRSEDTAVYYCA | -H3- | WGQGTLVTVSS SEQ ID NO: 21, 209-211 |
| D | RVTITADTSTSTAYMELSSLRSEDTAVYYC | -H3- | WGQGTLVTVSS SEQ ID NO: 22, 212-214 |
| II | | | |
| A | RVTISVDTSKNQFSLKLSSVTAADTAVYYCAR | -H3- | WGQGTLVTVSS SEQ ID NO: 23, 215-217 |
| B | RVTISVDTSKNQFSLKLSSVTAADTAVYYCAR | -H3- | WGQGTLVTVSS SEQ ID NO: 24, 218-220 |
| C | RVTISVDTSKNQFSLKLSSVTAADTAVYYCA | -H3- | WGQGTLVTVSS SEQ ID NO: 25, 221-223 |
| D | RVTISVDTSKNQFSLKLSSVTAADTAVYYC | -H3- | WGQGTLVTVSS SEQ ID NO: 26, 224-226 |
| III | | | |
| A | RFTISRDNSKNTLYLQMNSLRAEDTAVYYCAR | -H3- | WGQGTLVTVSS SEQ ID NO: 27, 227-229 |
| B | RFTISRDNSKNTLYLQMNSLRAEDTAVYYCAR | -H3- | WGQGTLVTVSS SEQ ID NO: 28, 230-232 |
| C | RFTISRDNSKNTLYLQMNSLRAEDTAVYYCA | -H3- | WGQGTLVTVSS SEQ ID NO: 29, 233-235 |
| D | RFTISRDNSKNTLYLQMNSLRAEDTAVYYC | -H3- | WGQGTLVTVSS SEQ ID NO: 30, 236-238 |
| Acceptor | | | |
| A | RFTISADTSKNTAYLQMNSLRAEDTAVYYCSR | -H3- | WGQGTLVTVSS SEQ ID NO: 31, 239-241 |
| B | RFTISADTSKNTAYLQMNSLRAEDTAVYYCSR | -H3- | WGQGTLVTVSS SEQ ID NO: 32, 242-244 |
| C | RFTISADTSKNTAYLQMNSLRAEDTAVYYCS | -H3- | WGQGTLVTVSS SEQ ID NO: 33, 245-247 |
| Second Acceptor | | | |
| A | RFTISADTSKNTAYLQMNSLRAEDTAVYYCAR | -H3- | WGQGTLVTVSS SEQ ID NO: 34, 248-250 |
| B | RFTISADTSKNTAYLQMNSLRAEDTAVYYCAR | -H3- | WGQGTLVTVSS SEQ ID NO: 35, 251-253 |
| C | RFTISADTSKNTAYLQMNSLRAEDTAVYYCA | -H3- | WGQGTLVTVSS SEQ ID NO: 36, 254-256 |
| D | RFTISADTSKNTAYLQMNSLRAEDTAVYYC | -H3- | WGQGTLVTVSS SEQ ID NO: 37, 257-259 |

FIG. 3B

Framework Sequences of huMAb4D5-8 Light Chain

LC-FR1   $^1$Asp Ile Gln Met Thr Gln Ser Pro Ser Ser Leu Ser Ala Ser Val Gly Asp Arg Val Thr Ile Thr Cys$^{23}$   (SEQ ID NO: 42)

LC-FR2   $^{35}$Trp Tyr Gln Gln Lys Pro Gly Lys Ala Pro Lys Leu Leu Ile Tyr$^{49}$ (SEQ ID NO: 43)

LC-FR3   $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 44)

LC-FR4   $^{98}$Phe Gly Gln Gly Thr Lys Val Glu Ile Lys$^{107}$ (SEQ ID NO: 45)

Framework Sequences of huMAb4D5-8 Heavy Chain

HC-FR1   $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 46)

HC-FR2   $^{36}$Trp Val Arg Gln Ala Pro Gly Lys Gly Leu Glu Trp Val$^{48}$ (SEQ ID NO: 47)

HC-FR3   $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO: 175)

HC-FR4   $^{103}$Trp Gly Gln Gly Thr Leu Val Thr Val Ser Ser$^{113}$ (SEQ ID NO: 176)

*FIG. 5*

Framework Sequences of huMAb4D5-8 Light Chain Modified at Position 66 (Underlined)

LC-FR1   $^1$Asp Ile Gln Met Thr Gln Ser Pro Ser Ser Leu Ser Ala Ser Val Gly Asp Arg Val Thr Ile Thr Cys$^{23}$ (SEQ ID NO: 42)

LC-FR2   $^{35}$Trp Tyr Gln Gln Lys Pro Gly Lys Ala Pro Lys Leu Leu Ile Tyr$^{49}$ (SEQ ID NO: 43)

LC-FR3   $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO: 177)

LC-FR4   $^{98}$Phe Gly Gln Gly Thr Lys Val Glu Ile Lys$^{107}$ (SEQ ID NO: 45)

Framework Sequences of huMAb4D5-8 Heavy Chain Modified at Postions 71, 73 and 78 (Underlined)

HC-FR1   $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 46)

HC-FR2   $^{36}$Trp Val Arg Gln Ala Pro Gly Lys Gly Leu Glu Trp Val$^{48}$ (SEQ ID NO: 47)

HC-FR3   $^{66}$Arg Phe Thr Ile Ser <u>Arg</u> Asp <u>Asn</u> Ser Lys Asn Thr <u>Leu</u> Tyr Leu Gln Met Asn83 Ser83a Leu83b Arg83c Ala Glu Asp Thr Ala Val Tyr Tyr Cys$^{92}$ (SEQ ID NO: 178)

HC-FR4   $^{103}$Trp Gly Gln Gly Thr Leu Val Thr Val Ser Ser$^{113}$ (SEQ ID NO: 176)

*FIG. 6*

```
         164       178
FGFR3    LAVPAANTVRFRCPA    Peptide 3
FGFR1    HAVPAAKTVKFKCPS 269       283
FGFR3    SDVEFHCKVYSDAQP    Peptide 11
FGFR1    SNVEFMCKVYSDPQP
```

U.S. 8,710,189 B2

SEQUENCE LISTING

```
<160> NUMBER OF SEQ ID NOS: 271

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Thr Ser Thr Gly Ile Ser
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Arg Ile Tyr Pro Thr Asn Gly Ser Thr Asn Tyr Ala Asp Ser Val
1               5                   10                  15

Lys Gly

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                               peptide

<400> SEQUENCE: 4

Arg Ala Ser Gln Asp Val Ser Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ala Ser Phe Leu Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Ser Tyr Thr Thr Pro Pro Thr
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Phe Thr Phe Thr Ser Thr Gly Ile Ser
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Arg Ile Tyr Pro Thr Asn Gly Ser Thr Asn Tyr Ala Asp Ser Val
1               5                   10                  15

Lys Gly

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Thr Tyr Gly Ile Tyr Asp Leu Tyr Val Asp Tyr Thr Glu Tyr
1               5                   10                  15

Val Met Asp Tyr
```

```
<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Gln Asp Val Asp Thr Ser Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Ala Ser Phe Leu Tyr Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Ser Thr Gly His Pro Gln Thr
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Thr Phe Thr Ser Thr Gly Ile Ser
1               5                   10

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Arg Ile Tyr Pro Thr Asn Gly Ser Thr Asn Tyr Ala Asp Ser Val
1               5                   10                  15

Lys Gly

<210> SEQ ID NO 15
<211> LENGTH: 20
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 15

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ala Ser Gln Asp Val Asp Ile Ser Leu Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ala Ser Ser Leu Ala Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln Gly Ala Gly Asn Pro Tyr Thr
1               5

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser
            20                  25                  30

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 25
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 25

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 26
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 29
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

```
<210> SEQ ID NO 30
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Asn Ile Lys
            20                  25                  30

<210> SEQ ID NO 35
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 37
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 38
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 39
<211> LENGTH: 23
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 39

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 40
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Tyr Gln Gln Lys Pro Gly Lys Ala Pro Lys Leu Leu Ile Tyr
1               5                   10                  15

<210> SEQ ID NO 44
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 44

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Phe Gly Gln Gly Thr Lys Val Glu Ile Lys
1               5                   10

<210> SEQ ID NO 46
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Val Arg Gln Ala Pro Gly Lys Gly Leu Glu Trp Val
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Phe Thr Phe Ser Thr Thr Gly Ile Ser
1               5                   10

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 49

Gly Arg Ile Tyr Pro Leu Tyr Gly Ser Thr His Tyr Ala Asp Ser Val
1               5                   10                  15

Lys Gly

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ala Ser Gln Asp Val Ser Thr Ala Val Ala
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Ala Ser Phe Leu Tyr Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Gln Thr Tyr Thr Thr Ser Leu Thr
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Phe Thr Phe Thr Ser Thr Gly Ile Ser
1               5                   10
```

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Arg Ile Tyr Pro Tyr Asp Asp Ser Phe Tyr Tyr Ala Asp Ser Val
1               5                   10                  15

Lys Gly

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ala Ser Gln Asp Val Ser Thr Ala Val Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Ala Ser Phe Leu Tyr Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln Ser Tyr Thr Thr Pro Leu Thr
1               5

<210> SEQ ID NO 60
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 60

Gly Phe Thr Phe Thr Ser Thr Gly Ile Ser
1               5                   10

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Arg Ile Tyr Pro Thr Asn Gly Ser Thr Asn Tyr Ala Asp Ser Val
1               5                   10                  15

Lys Gly

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ala Ser Gln Val Ile Asp Ile Ser Leu Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Ala Ser Thr Leu Ala Ser
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65
```

```
Gln Gln Ser Ala Ala Asp Pro Tyr Thr
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Phe Ser Phe Thr Gly Thr Gly Ile Ser
1               5                   10

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ser Ile Tyr Pro Tyr Phe Ala Thr Lys Asn Tyr Ala Asp Ser Val
1               5                   10                  15

Lys Gly

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ala Ser Gln Asp Val Ser Thr Ala Val Ala
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Ala Ser Phe Leu Tyr Ser
1               5
```

```
<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gln Ser Tyr Thr Thr Pro Pro Thr
1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Phe Thr Phe Tyr Thr Thr Gly Ile Ser
1               5                   10

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Arg Ile Tyr Pro Ala Phe Gly Ser Ser Ile Tyr Ala Asp Ser Val
1               5                   10                  15

Lys Gly

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ala Ser Gln Asp Val Ser Thr Ala Val Ala
1               5                   10

<210> SEQ ID NO 76
<211> LENGTH: 7
<212> TYPE: PRT
<213> ORGANISM: Artificial Sequence
<220> FEATURE:
```

<223> OTHER INFORMATION: Description of Artificial Sequence: Synthetic
     peptide

<400> SEQUENCE: 76

Ser Ala Ser Phe Leu Tyr Ser
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 77

Gln Gln Thr Tyr Ser Ala Gln Pro Thr
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 78

Gly Phe Ser Phe Trp Ser Thr Gly Ile Ser
1               5                   10

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 79

Gly Arg Ile Tyr Pro Ser Ser Ala Thr Thr Asn Tyr Ala Asp Ser Val
1               5                   10                  15

Lys Gly

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 80

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 81

-continued

Arg Ala Ser Gln Asp Val Ser Thr Ala Val Ala
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Ala Ser Phe Leu Tyr Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Gln Ser Tyr Ser His Gln Ser Thr
1               5

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Phe Thr Phe Thr Ser Thr Gly Ile Ser
1               5                   10

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Arg Ile Tyr Pro Thr Ser Gly Ser Thr Asn Tyr Ala Asp Ser Val
1               5                   10                  15

Lys Gly

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 87

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ala Ser Gln Asp Val Asp Thr Ser Leu Ala
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Ala Ser Phe Leu Tyr Ser
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gln Ser Thr Gly His Pro Gln Thr
1               5

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Phe Thr Phe Thr Ser Thr Gly Ile Ser
1               5                   10

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Arg Ile Tyr Pro Thr Gly Gly Ser Thr Asn Tyr Ala Asp Ser Val
1               5                   10                  15

Lys Gly

<210> SEQ ID NO 92
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92
```

```
Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Ala Ser Gln Asp Val Asp Thr Ser Leu Ala
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Ala Ser Phe Leu Tyr Ser
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Ser Thr Gly His Pro Gln Thr
1               5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Phe Thr Phe Thr Ser Thr Gly Ile Ser
1               5                   10

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Arg Ile Tyr Pro Thr Ala Gly Ser Thr Asn Tyr Ala Asp Ser Val
1               5                   10                  15

Lys Gly
```

```
<210> SEQ ID NO 98
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Ser Gln Asp Val Asp Thr Ser Leu Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Ala Ser Phe Leu Tyr Ser
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Ser Thr Gly His Pro Gln Thr
1               5

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Phe Thr Phe Thr Ser Thr Gly Ile Ser
1               5                   10

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 103

Gly Arg Ile Tyr Pro Thr Gln Gly Ser Thr Asn Tyr Ala Asp Ser Val
1               5                   10                  15

Lys Gly

<210> SEQ ID NO 104
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ala Ser Gln Asp Val Asp Thr Ser Leu Ala
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Ala Ser Phe Leu Tyr Ser
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gln Ser Thr Gly His Pro Gln Thr
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Phe Thr Phe Thr Ser Thr Gly Ile Ser
1               5                   10
```

<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Arg Ile Tyr Pro Thr Ser Gly Ser Thr Asn Tyr Ala Asp Ser Val
1               5                   10                  15

Lys Gly

<210> SEQ ID NO 110
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ala Ser Gln Val Val Asp Thr Ser Leu Ala
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Ala Ser Ser Leu Ala Ser
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Gln Gly Ala Gly Asn Pro Tyr Thr
1               5

<210> SEQ ID NO 114
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 114

Gly Phe Thr Phe Thr Ser Thr Gly Ile Ser
1               5                   10

<210> SEQ ID NO 115
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Arg Ile Tyr Pro Thr Gly Gly Ser Thr Asn Tyr Ala Asp Ser Val
1               5                   10                  15

Lys Gly

<210> SEQ ID NO 116
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Ala Ser Gln Val Val Asp Thr Ser Leu Ala
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ser Ala Ser Ser Leu Ala Ser
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 119

Gln Gln Gly Ala Gly Asn Pro Tyr Thr
1               5

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Phe Thr Phe Thr Ser Thr Gly Ile Ser
1               5                   10

<210> SEQ ID NO 121
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Arg Ile Tyr Pro Thr Ala Gly Ser Thr Asn Tyr Ala Asp Ser Val
1               5                   10                  15

Lys Gly

<210> SEQ ID NO 122
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Ala Ser Gln Val Val Asp Thr Ser Leu Ala
1               5                   10

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Ala Ser Ser Leu Ala Ser
1               5
```

```
<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Gln Gly Ala Gly Asn Pro Tyr Thr
1               5

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Phe Thr Phe Thr Ser Thr Gly Ile Ser
1               5                   10

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Arg Ile Tyr Pro Thr Gln Gly Ser Thr Asn Tyr Ala Asp Ser Val
1               5                   10                  15

Lys Gly

<210> SEQ ID NO 128
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Arg Ala Ser Gln Val Val Asp Thr Ser Leu Ala
1               5                   10

<210> SEQ ID NO 130
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 130

Ser Ala Ser Ser Leu Ala Ser
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gln Gln Gly Ala Gly Asn Pro Tyr Thr
1               5

<210> SEQ ID NO 132
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Gly Ile Ser Trp Val Arg Gln Ala Pro Gly Lys Gly Leu Glu Trp Val
        35                  40                  45

Gly Arg Ile Tyr Pro Thr Ser Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Arg Thr Tyr Gly Ile Tyr Asp Leu Tyr Val Asp Tyr Thr
            100                 105                 110

Glu Tyr Val Met Asp Tyr Trp Gly Gln Gly Thr Leu Val
        115                 120                 125

<210> SEQ ID NO 133
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ser
            20                  25                  30

Leu Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Thr Gly His Pro Gln
                 85                  90                  95

Thr Phe Gly Gln Gly Thr Lys Val Glu Ile Lys Arg
            100                 105

<210> SEQ ID NO 134
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Thr Ser Thr
             20                  25                  30

Gly Ile Ser Trp Val Arg Gln Ala Pro Gly Lys Gly Leu Glu Trp Val
         35                  40                  45

Ala Arg Ile Tyr Pro Thr Asn Gly Ser Thr Asn Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ala Arg Thr Tyr Gly Ile Tyr Asp Leu Tyr Val Asp Tyr Thr
            100                 105                 110

Glu Tyr Val Met Asp Tyr Trp Gly Gln Gly Thr Leu Val
        115                 120                 125

<210> SEQ ID NO 135
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Val Asp Ile Ser
             20                  25                  30

Leu Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ala Gly Asn Pro Tyr
                 85                  90                  95

Thr Phe Gly Gln Gly Thr Lys Val Glu Ile Lys Arg
            100                 105

<210> SEQ ID NO 136
<211> LENGTH: 125
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Thr
            20                  25                  30

Gly Ile Ser Trp Val Arg Gln Ala Pro Gly Lys Gly Leu Glu Trp Val
        35                  40                  45

Ala Arg Ile Tyr Pro Leu Tyr Gly Ser Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Arg Thr Tyr Gly Ile Tyr Asp Leu Tyr Val Asp Tyr Thr
            100                 105                 110

Glu Tyr Val Met Asp Tyr Trp Gly Gln Gly Thr Leu Val
        115                 120                 125

<210> SEQ ID NO 137
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Thr Ser Leu
                85                  90                  95

Thr Phe Gly Gln Gly Thr Lys Val Glu Ile Lys Arg
            100                 105

<210> SEQ ID NO 138
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30
```

```
Gly Ile Ser Trp Val Arg Gln Ala Pro Gly Lys Gly Leu Glu Trp Val
            35                  40                  45

Gly Arg Ile Tyr Pro Thr Ser Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Arg Thr Tyr Gly Ile Tyr Asp Leu Tyr Val Asp Tyr Thr
            100                 105                 110

Glu Tyr Val Met Asp Tyr Trp Gly Gln Gly Thr Leu Val
        115                 120                 125
```

<210> SEQ ID NO 139
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 139

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Glu Thr Ser
            20                  25                  30

Leu Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Gly His Pro Gln
                85                  90                  95

Thr Phe Gly Gln Gly Thr Lys Val Glu Ile Lys Arg
            100                 105
```

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

```
Arg Ala Ser Gln Asp Val Glu Thr Ser Leu Ala
1               5                   10
```

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

```
Ser Ala Ser Phe Leu Tyr Ser
1               5
```

```
<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Gln Ser Thr Gly His Pro Gln Thr
1               5

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Phe Thr Phe Thr Ser Thr Gly Ile Ser
1               5                   10

<210> SEQ ID NO 144
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Arg Ile Tyr Pro Thr Ser Gly Ser Thr Asn Tyr Ala Asp Ser Val
1               5                   10                  15

Lys Gly

<210> SEQ ID NO 145
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Arg Thr Tyr Gly Ile Tyr Asp Leu Tyr Val Asp Tyr Thr Glu Tyr
1               5                   10                  15

Val Met Asp Tyr
            20

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Val or Asp
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (7)..(7)
<223> OTHER INFORMATION: Asp, Glu or Ser
```

```
<220> FEATURE:
<221> NAME/KEY: MOD_RES
<222> LOCATION: (8)..(8)
<223> OTHER INFORMATION: Thr or Ile
<220> FEATURE:
<221> NAME/KEY: MOD_RES
<222> LOCATION: (9)..(9)
<223> OTHER INFORMATION: Ala or Ser
<220> FEATURE:
<221> NAME/KEY: MOD_RES
<222> LOCATION: (10)..(10)
<223> OTHER INFORMATION: Val or Leu

<400> SEQUENCE: 146

Arg Ala Ser Gln Xaa Xaa Xaa Xaa Xaa Xaa Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Gly
<220> FEATURE:
<221> NAME/KEY: MOD_RES
<222> LOCATION: (6)..(6)
<223> OTHER INFORMATION: Ala or Tyr

<400> SEQUENCE: 147

Xaa Ala Ser Phe Leu Xaa Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Ser or Thr
<220> FEATURE:
<221> NAME/KEY: MOD_RES
<222> LOCATION: (4)..(4)
<223> OTHER INFORMATION: Thr, Tyr or Ala
<220> FEATURE:
<221> NAME/KEY: MOD_RES
<222> LOCATION: (5)..(5)
<223> OTHER INFORMATION: Gly, Ser, Thr or Ala
<220> FEATURE:
<221> NAME/KEY: MOD_RES
<222> LOCATION: (6)..(6)
<223> OTHER INFORMATION: Ala, His, Asp, Thr or Asn
<220> FEATURE:
<221> NAME/KEY: MOD_RES
<222> LOCATION: (7)..(7)
<223> OTHER INFORMATION: Gln, Pro or Ser
<220> FEATURE:
<221> NAME/KEY: MOD_RES
<222> LOCATION: (8)..(8)
<223> OTHER INFORMATION: Ser, Tyr, Leu, Pro or Gln

<400> SEQUENCE: 148

Gln Gln Xaa Xaa Xaa Xaa Xaa Xaa Thr
1               5

<210> SEQ ID NO 149
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Trp, Tyr, Ser or Thr
<220> FEATURE:
<221> NAME/KEY: MOD_RES
<222> LOCATION: (6)..(6)
<223> OTHER INFORMATION: Ser, Gly or Thr

<400> SEQUENCE: 149

Gly Phe Xaa Phe Xaa Xaa Thr Gly Ile Ser
1               5                   10

<210> SEQ ID NO 150
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Tyr, Ala, Leu, Ser or Thr
<220> FEATURE:
<221> NAME/KEY: MOD_RES
<222> LOCATION: (7)..(7)
<223> OTHER INFORMATION: Ala, Gln, Asp, Gly, Tyr, Ser, Asn or Phe
<220> FEATURE:
<221> NAME/KEY: MOD_RES
<222> LOCATION: (8)..(8)
<223> OTHER INFORMATION: Ala, Asp or Gly
<220> FEATURE:
<221> NAME/KEY: MOD_RES
<222> LOCATION: (9)..(9)
<223> OTHER INFORMATION: Thr or Ser
<220> FEATURE:
<221> NAME/KEY: MOD_RES
<222> LOCATION: (10)..(10)
<223> OTHER INFORMATION: Lys, Phe, Thr or Ser
<220> FEATURE:
<221> NAME/KEY: MOD_RES
<222> LOCATION: (11)..(11)
<223> OTHER INFORMATION: Tyr, His, Asn or Ile

<400> SEQUENCE: 150

Gly Arg Ile Tyr Pro Xaa Xaa Xaa Xaa Xaa Xaa Tyr Ala Asp Ser Val
1               5                   10                  15

Lys Gly

<210> SEQ ID NO 151
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Arg Thr Tyr Gly Ile Tyr Asp Leu Tyr Val Asp Tyr Thr Glu Tyr
1               5                   10                  15

Val Met Asp Tyr
            20
```

```
<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Val or Asp
<220> FEATURE:
<221> NAME/KEY: MOD_RES
<222> LOCATION: (7)..(7)
<223> OTHER INFORMATION: Asp, Glu or Ser
<220> FEATURE:
<221> NAME/KEY: MOD_RES
<222> LOCATION: (8)..(8)
<223> OTHER INFORMATION: Thr or Ile
<220> FEATURE:
<221> NAME/KEY: MOD_RES
<222> LOCATION: (9)..(9)
<223> OTHER INFORMATION: Ala or Ser

<400> SEQUENCE: 152

Arg Ala Ser Gln Xaa Val Xaa Xaa Xaa Val Ala
1               5                   10

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser, Gly or Thr
<220> FEATURE:
<221> NAME/KEY: MOD_RES
<222> LOCATION: (4)..(4)
<223> OTHER INFORMATION: Tyr, Thr or Ala
<220> FEATURE:
<221> NAME/KEY: MOD_RES
<222> LOCATION: (5)..(5)
<223> OTHER INFORMATION: Thr or Gly
<220> FEATURE:
<221> NAME/KEY: MOD_RES
<222> LOCATION: (6)..(6)
<223> OTHER INFORMATION: Thr, His or Asn
<220> FEATURE:
<221> NAME/KEY: MOD_RES
<222> LOCATION: (7)..(7)
<223> OTHER INFORMATION: Pro or Ser
<220> FEATURE:
<221> NAME/KEY: MOD_RES
<222> LOCATION: (8)..(8)
<223> OTHER INFORMATION: Pro, Gln, Tyr or Leu

<400> SEQUENCE: 153

Gln Gln Xaa Xaa Xaa Xaa Xaa Xaa Thr
1               5

<210> SEQ ID NO 154
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
```

<223> OTHER INFORMATION: Thr or Leu
<220> FEATURE:
<221> NAME/KEY: MOD_RES
<222> LOCATION: (7)..(7)
<223> OTHER INFORMATION: Asn, Tyr, Ser, Gly, Ala or Gln
<220> FEATURE:
<221> NAME/KEY: MOD_RES
<222> LOCATION: (11)..(11)
<223> OTHER INFORMATION: Asn or His

<400> SEQUENCE: 154

Gly Arg Ile Tyr Pro Xaa Xaa Gly Ser Thr Xaa Tyr Ala Asp Ser Val
1               5                  10                  15

Lys Gly

<210> SEQ ID NO 155
<211> LENGTH: 10
<212> TYPE: PRT
<213> ORGANISM: Mus musculus

<400> SEQUENCE: 155

Ser Ala Ser Ser Ser Val Ser Tyr Met His
1               5                  10

<210> SEQ ID NO 156
<211> LENGTH: 10
<212> TYPE: PRT
<213> ORGANISM: Mus musculus

<400> SEQUENCE: 156

Ser Ala Ser Ser Ser Val Ser Tyr Met His
1               5                  10

<210> SEQ ID NO 157
<211> LENGTH: 11
<212> TYPE: PRT
<213> ORGANISM: Mus musculus

<400> SEQUENCE: 157

Leu Ala Ser Gln Thr Ile Gly Thr Trp Leu Ala
1               5                  10

<210> SEQ ID NO 158
<211> LENGTH: 11
<212> TYPE: PRT
<213> ORGANISM: Mus musculus

<400> SEQUENCE: 158

Thr Trp Ile Tyr Asp Thr Ser Ile Leu Ala Ser
1               5                  10

<210> SEQ ID NO 159
<211> LENGTH: 11
<212> TYPE: PRT
<213> ORGANISM: Mus musculus

<400> SEQUENCE: 159

Arg Trp Ile Tyr Asp Thr Ser Lys Leu Ala Ser
1               5                  10

<210> SEQ ID NO 160
<211> LENGTH: 11
<212> TYPE: PRT
<213> ORGANISM: Mus musculus

<400> SEQUENCE: 160

```
Leu Leu Ile Tyr Ala Ala Thr Ser Leu Ala Asp
1               5                   10

<210> SEQ ID NO 161
<211> LENGTH: 9
<212> TYPE: PRT
<213> ORGANISM: Mus musculus

<400> SEQUENCE: 161

Gln Gln Trp Thr Ser Asn Pro Leu Thr
1               5

<210> SEQ ID NO 162
<211> LENGTH: 9
<212> TYPE: PRT
<213> ORGANISM: Mus musculus

<400> SEQUENCE: 162

Gln Gln Trp Ser Ser Tyr Pro Pro Thr
1               5

<210> SEQ ID NO 163
<211> LENGTH: 9
<212> TYPE: PRT
<213> ORGANISM: Mus musculus

<400> SEQUENCE: 163

Gln Gln Leu Tyr Ser Pro Pro Trp Thr
1               5

<210> SEQ ID NO 164
<211> LENGTH: 10
<212> TYPE: PRT
<213> ORGANISM: Mus musculus

<400> SEQUENCE: 164

Gly Tyr Ser Phe Thr Asp Tyr Asn Met Tyr
1               5                   10

<210> SEQ ID NO 165
<211> LENGTH: 10
<212> TYPE: PRT
<213> ORGANISM: Mus musculus

<400> SEQUENCE: 165

Gly Tyr Val Phe Thr His Tyr Asn Met Tyr
1               5                   10

<210> SEQ ID NO 166
<211> LENGTH: 10
<212> TYPE: PRT
<213> ORGANISM: Mus musculus

<400> SEQUENCE: 166

Gly Tyr Ala Phe Thr Ser Tyr Asn Met Tyr
1               5                   10

<210> SEQ ID NO 167
<211> LENGTH: 20
<212> TYPE: PRT
<213> ORGANISM: Mus musculus

<400> SEQUENCE: 167

Trp Ile Gly Tyr Ile Glu Pro Tyr Asn Gly Gly Thr Ser Tyr Asn Gln
1               5                   10                  15
```

```
Lys Phe Lys Gly
        20

<210> SEQ ID NO 168
<211> LENGTH: 20
<212> TYPE: PRT
<213> ORGANISM: Mus musculus

<400> SEQUENCE: 168

Trp Ile Gly Tyr Ile Glu Pro Tyr Asn Gly Gly Thr Ser Tyr Asn Gln
1               5                   10                  15

Lys Phe Lys Gly
        20

<210> SEQ ID NO 169
<211> LENGTH: 20
<212> TYPE: PRT
<213> ORGANISM: Mus musculus

<400> SEQUENCE: 169

Trp Ile Gly Tyr Ile Asp Pro Tyr Ile Gly Gly Thr Ser Tyr Asn Gln
1               5                   10                  15

Lys Phe Lys Gly
        20

<210> SEQ ID NO 170
<211> LENGTH: 13
<212> TYPE: PRT
<213> ORGANISM: Mus musculus

<400> SEQUENCE: 170

Ala Ser Pro Asn Tyr Tyr Asp Ser Ser Pro Phe Ala Tyr
1               5                   10

<210> SEQ ID NO 171
<211> LENGTH: 10
<212> TYPE: PRT
<213> ORGANISM: Mus musculus

<400> SEQUENCE: 171

Ala Arg Gly Gln Gly Pro Asp Phe Asp Val
1               5                   10

<210> SEQ ID NO 172
<211> LENGTH: 13
<212> TYPE: PRT
<213> ORGANISM: Mus musculus

<400> SEQUENCE: 172

Ala Arg Trp Gly Asp Tyr Asp Val Gly Ala Met Asp Tyr
1               5                   10

<210> SEQ ID NO 173
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 174
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 175
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Trp Gly Gln Gly Thr Leu Val Thr Val Ser Ser
1               5                   10

```
<210> SEQ ID NO 177
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 178
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 179
<211> LENGTH: 15
<212> TYPE: PRT
<213> ORGANISM: Homo sapiens

<400> SEQUENCE: 179

Leu Ala Val Pro Ala Ala Asn Thr Val Arg Phe Arg Cys Pro Ala
1               5                   10                  15

<210> SEQ ID NO 180
<211> LENGTH: 15
<212> TYPE: PRT
<213> ORGANISM: Homo sapiens

<400> SEQUENCE: 180

Ser Asp Val Glu Phe His Cys Lys Val Tyr Ser Asp Ala Gln Pro
1               5                   10                  15

<210> SEQ ID NO 181
<211> LENGTH: 15
<212> TYPE: PRT
<213> ORGANISM: Homo sapiens

<400> SEQUENCE: 181

His Ala Val Pro Ala Ala Lys Thr Val Lys Phe Lys Cys Pro Ser
1               5                   10                  15

<210> SEQ ID NO 182
<211> LENGTH: 15
<212> TYPE: PRT
<213> ORGANISM: Homo sapiens

<400> SEQUENCE: 182

Ser Asn Val Glu Phe Met Cys Lys Val Tyr Ser Asp Pro Gln Pro
1               5                   10                  15

<210> SEQ ID NO 183
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asp Ile Cys Leu Pro Arg Trp Gly Cys Leu Trp
1               5                   10

<210> SEQ ID NO 184
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Trp Val Arg Gln Ala Pro Gly Lys Gly Leu Glu Trp Val
1               5                   10

<210> SEQ ID NO 186
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Trp Gly Gln Gly Thr Leu Val Thr Val Ser Ser
1               5                   10

<210> SEQ ID NO 188
<211> LENGTH: 23
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Trp Tyr Gln Gln Lys Pro Gly Lys Ala Pro Lys Leu Leu Ile Tyr
1               5                   10                  15

<210> SEQ ID NO 190
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Phe Gly Gln Gly Thr Lys Val Glu Ile Lys
1               5                   10

<210> SEQ ID NO 192
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gatccccgca tcaagctgcg gcatcattca agagatgatg ccgcagcttg atgcttttt      60 ggaaa                                                                65

<210> SEQ ID NO 193
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193

```
gatcccctgc acaacctcga ctactattca agagatagta gtcgaggttg tgcattttt     60 ggaaa                                                                 65

<210> SEQ ID NO 194
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gatccccaac ctcgactact acaagattca agagatcttg tagtagtcga ggttttttt      60 ggaaa                                                                 65

<210> SEQ ID NO 195
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gtcagatatc gtkctsacmc artctccwgc                                      30

<210> SEQ ID NO 196
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gatcgacgta cgctgagatc carytgcarc artctgg                              37

<210> SEQ ID NO 197
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
gtcagatatc gtgctgacmc artctcc                                         27

<210> SEQ ID NO 198
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gatcgacgta cgctgagatc carytgcarc artctgg                              37

<210> SEQ ID NO 199
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 199
gtacgatatc cagatgacmc artctcc                                       27

<210> SEQ ID NO 200
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
gatcgacgta cgctgagatc carytgcarc artctgg                            37

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
tttdakytcc agcttggtac c                                             21

<210> SEQ ID NO 202
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
acagtgggcc cttggtggag gctgmrgaga cdgtgashrd rgt                     43

<210> SEQ ID NO 203
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Trp Val Arg Gln Ala Pro Gly Gln Gly Leu Glu Trp Met Gly
1               5                   10

<210> SEQ ID NO 204
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 205
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 205

Trp Gly Gln Gly Thr Leu Val Thr Val Ser Ser
1               5                   10

<210> SEQ ID NO 206
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Trp Val Arg Gln Ala Pro Gly Gln Gly Leu Glu Trp Met
1               5                   10

<210> SEQ ID NO 207
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Trp Gly Gln Gly Thr Leu Val Thr Val Ser Ser
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Trp Val Arg Gln Ala Pro Gly Gln Gly Leu Glu Trp Met
1               5                   10

<210> SEQ ID NO 210
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Arg Val Thr Ile Thr Ala Asp Thr Ser Thr Ser Thr Ala Tyr Met Glu
```

```
                1               5                  10                 15
Leu Ser Ser Leu Arg Ser Glu Asp Thr Ala Val Tyr Tyr Cys Ala
                20                  25                  30

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Trp Gly Gln Gly Thr Leu Val Thr Val Ser Ser
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Trp Val Arg Gln Ala Pro Gly Gln Gly Leu Glu Trp Met
1               5                   10

<210> SEQ ID NO 213
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys
                20                  25                  30

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Trp Gly Gln Gly Thr Leu Val Thr Val Ser Ser
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Trp Ile Arg Gln Pro Pro Gly Lys Gly Leu Glu Trp Ile Gly
1               5                   10

<210> SEQ ID NO 216
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Trp Gly Gln Gly Thr Leu Val Thr Val Ser Ser
1               5                   10

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Trp Ile Arg Gln Pro Pro Gly Lys Gly Leu Glu Trp Ile
1               5                   10

<210> SEQ ID NO 219
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Trp Gly Gln Gly Thr Leu Val Thr Val Ser Ser
1               5                   10

<210> SEQ ID NO 221
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 221

Trp Ile Arg Gln Pro Pro Gly Lys Gly Leu Glu Trp Ile
1               5                   10

<210> SEQ ID NO 222
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Trp Gly Gln Gly Thr Leu Val Thr Val Ser Ser
1               5                   10

<210> SEQ ID NO 224
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Trp Ile Arg Gln Pro Pro Gly Lys Gly Leu Glu Trp Ile
1               5                   10

<210> SEQ ID NO 225
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 226
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226
```

Trp Gly Gln Gly Thr Leu Val Thr Val Ser Ser
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Trp Val Arg Gln Ala Pro Gly Lys Gly Leu Glu Trp Val Ser
1               5                   10

<210> SEQ ID NO 228
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 229
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Trp Gly Gln Gly Thr Leu Val Thr Val Ser Ser
1               5                   10

<210> SEQ ID NO 230
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Trp Val Arg Gln Ala Pro Gly Lys Gly Leu Glu Trp Val
1               5                   10

<210> SEQ ID NO 231
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 232
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Trp Gly Gln Gly Thr Leu Val Thr Val Ser Ser
1               5                   10

<210> SEQ ID NO 233
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Trp Val Arg Gln Ala Pro Gly Lys Gly Leu Glu Trp Val
1               5                   10

<210> SEQ ID NO 234
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
                20                  25                  30

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Trp Gly Gln Gly Thr Leu Val Thr Val Ser Ser
1               5                   10

<210> SEQ ID NO 236
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Trp Val Arg Gln Ala Pro Gly Lys Gly Leu Glu Trp Val
1               5                   10

<210> SEQ ID NO 237
<211> LENGTH: 30
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 237

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys
            20                  25                  30

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Trp Gly Gln Gly Thr Leu Val Thr Val Ser Ser
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Trp Val Arg Gln Ala Pro Gly Lys Gly Leu Glu Trp Val Ser
1               5                   10

<210> SEQ ID NO 240
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Arg Phe Thr Ile Ser Ala Asp Thr Ser Lys Asn Thr Ala Tyr Leu Gln
1               5                   10                  15
Met Asn Ser Leu Arg Ala Glu Asp Thr Ala Val Tyr Tyr Cys Ser Arg
            20                  25                  30

<210> SEQ ID NO 241
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Trp Gly Gln Gly Thr Leu Val Thr Val Ser Ser
1               5                   10

<210> SEQ ID NO 242
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

```
Trp Val Arg Gln Ala Pro Gly Lys Gly Leu Glu Trp Val
1               5                   10
```

<210> SEQ ID NO 243
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

```
Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30
```

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Trp Gly Gln Gly Thr Leu Val Thr Val Ser Ser
1               5                   10
```

<210> SEQ ID NO 245
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

```
Trp Val Arg Gln Ala Pro Gly Lys Gly Leu Glu Trp Val
1               5                   10
```

<210> SEQ ID NO 246
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

```
Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser
            20                  25                  30
```

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

```
Trp Gly Gln Gly Thr Leu Val Thr Val Ser Ser
1               5                   10
```

```
<210> SEQ ID NO 248
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Trp Val Arg Gln Ala Pro Gly Lys Gly Leu Glu Trp Val Ser
1               5                   10

<210> SEQ ID NO 249
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Trp Gly Gln Gly Thr Leu Val Thr Val Ser Ser
1               5                   10

<210> SEQ ID NO 251
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Trp Val Arg Gln Ala Pro Gly Lys Gly Leu Glu Trp Val
1               5                   10

<210> SEQ ID NO 252
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 253
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 253

Trp Gly Gln Gly Thr Leu Val Thr Val Ser Ser
1               5                   10

<210> SEQ ID NO 254
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Trp Val Arg Gln Ala Pro Gly Lys Gly Leu Glu Trp Val
1               5                   10

<210> SEQ ID NO 255
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Trp Gly Gln Gly Thr Leu Val Thr Val Ser Ser
1               5                   10

<210> SEQ ID NO 257
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Trp Val Arg Gln Ala Pro Gly Lys Gly Leu Glu Trp Val
1               5                   10

<210> SEQ ID NO 258
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Arg Phe Thr Ile Ser Ala Asp Thr Ser Lys Asn Thr Ala Tyr Leu Gln
```

```
                1               5                  10                  15
Met Asn Ser Leu Arg Ala Glu Asp Thr Ala Val Tyr Tyr Cys
                20                  25                  30

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Trp Gly Gln Gly Thr Leu Val Thr Val Ser Ser
1               5                  10

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Trp Tyr Gln Gln Lys Pro Gly Lys Ala Pro Lys Leu Leu Ile Tyr
1               5                  10                  15

<210> SEQ ID NO 261
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gly Val Pro Ser Arg Phe Ser Gly Ser Gly Ser Gly Thr Asp Phe Thr
1               5                  10                  15

Leu Thr Ile Ser Ser Leu Gln Pro Glu Asp Phe Ala Thr Tyr Tyr Cys
                20                  25                  30

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Phe Gly Gln Gly Thr Lys Val Glu Ile Lys
1               5                  10

<210> SEQ ID NO 263
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Trp Tyr Leu Gln Lys Pro Gly Gln Ser Pro Gln Leu Leu Ile Tyr
1               5                  10                  15

<210> SEQ ID NO 264
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Phe Gly Gln Gly Thr Lys Val Glu Ile Lys
1               5                   10

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Trp Tyr Gln Gln Lys Pro Gly Gln Ala Pro Arg Leu Leu Ile Tyr
1               5                   10                  15

<210> SEQ ID NO 267
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Phe Gly Gln Gly Thr Lys Val Glu Ile Lys
1               5                   10

<210> SEQ ID NO 269
<211> LENGTH: 15
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 269

Trp Tyr Gln Gln Lys Pro Gly Gln Pro Pro Lys Leu Leu Ile Tyr
1               5                   10                  15

<210> SEQ ID NO 270
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
                20                  25                  30

<210> SEQ ID NO 271
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Phe Gly Gln Gly Thr Lys Val Glu Ile Lys
1               5                   10
```

ANTI-FGFR3 ANTIBODIES AND METHODS USING SAME

CROSS-REFERENCE TO RELATED APPLICATIONS

This application is a divisional application of U.S. patent application Ser. No. 12/731,100, filed Mar. 24, 2010 and issued as U.S. Pat. No. 8,410,250, claiming priority under 35 USC 119(e) to provisional application No. 61/163,222, filed Mar. 25, 2009, the contents of which are incorporated herein by reference.

SEQUENCE LISTING

This application contains a Sequence Listing which submitted via EFS-Web and hereby incorporated by reference in its entirety. Said ASCII copy, created on Oct. 16, 2012, is named P4294R1D1US and is 86,879 bytes in size.

FIELD OF THE INVENTION

The present invention relates generally to the field of molecular biology. More specifically, the invention concerns anti-FGFR3 antibodies, and uses of same.

BACKGROUND OF THE INVENTION

Fibroblast growth factors (FGFs) and their receptors (FGFRs) play critical roles during embryonic development, tissue homeostasis and metabolism (1-3). In humans, there are 22 FGFs (FGF1-14, FGF16-23) and four FGF receptors with tyrosine kinase domain (FGFR1-4). FGFRs consist of an extracellular ligand binding region, with two or three immunoglobulin-like domains (IgD1-3), a single-pass transmembrane region, and a cytoplasmic, split tyrosine kinase domain. FGFR1, 2 and 3 each have two major alternatively spliced isoforms, designated IIIb and IIIc. These isoforms differ by about 50 amino acids in the second half of IgD3, and have distinct tissue distribution and ligand specificity. In general, the IIIb isoform is found in epithelial cells, whereas IIIc is expressed in mesenchymal cells. Upon binding FGF in concert with heparan sulfate proteoglycans, FGFRs dimerize and become phosphorylated at specific tyrosine residues. This facilitates the recruitment of critical adaptor proteins, such as FGFR substrate 2 α (FRS2α), leading to activation of multiple signaling cascades, including the mitogen-activated protein kinase (MAPK) and PI3K-AKT pathways (1, 3, 4). Consequently, FGFs and their cognate receptors regulate a broad array of cellular processes, including proliferation, differentiation, migration and survival, in a context-dependent manner.

Aberrantly activated FGFRs have been implicated in specific human malignancies (1, 5). In particular, the t(4;14) (p16.3;q32) chromosomal translocation occurs in about 15-20% of multiple myeloma patients, leading to overexpression of FGFR3 and correlates with shorter overall survival (6-9). FGFR3 is implicated also in conferring chemoresistance to myeloma cell lines in culture (10), consistent with the poor clinical response of t(4;14)+ patients to conventional chemotherapy (8). Overexpression of mutationally activated FGFR3 is sufficient to induce oncogenic transformation in hematopoietic cells and fibroblasts (11-14, 15), transgenic mouse models (16), and murine bone marrow transplantation models (16, 17). Accordingly, FGFR3 has been proposed as a potential therapeutic target in multiple myeloma. Indeed, several small-molecule inhibitors targeting FGFRs, although not selective for FGFR3 and having cross-inhibitory activity toward certain other kinases, have demonstrated cytotoxicity against FGFR3-positive myeloma cells in culture and in mouse models (18-22).

FGFR3 overexpression has been documented also in a high fraction of bladder cancers (23, 24). Furthermore, somatic activating mutations in FGFR3 have been identified in 60-70% of papillary and 16-20% of muscle-invasive bladder carcinomas (24, 25). In cell culture experiments, RNA interference (11, 26) or an FGFR3 single-chain Fv antibody fragment inhibited bladder cancer cell proliferation (27). A recent study demonstrated that an FGFR3 antibody-toxin conjugate attenuates xenograft growth of a bladder cancer cell line through FGFR3-mediated toxin delivery into tumors (28). However, it remains unclear whether FGFR3 signaling is indeed an oncogenic driver of in vivo growth of bladder tumors. Moreover, the therapeutic potential for targeting FGFR3 in bladder cancer has not been defined on the basis of in vivo models. Publications relating to FGFR3 and anti-FGFR3 antibodies include U.S. Patent Publication no. 2005/0147612; Rauchenberger et al, J Biol Chem 278 (40):38194-38205 (2003); WO2006/048877; Martinez-Torrecuadrada et al, (2008) Mol Cancer Ther 7(4): 862-873; WO2007/144893; Trudel et al. (2006) 107(10): 4039-4046; Martinez-Torrecuadrada et al (2005) Clin Cancer Res 11 (17): 6280-6290; Gomez-Roman et al (2005) Clin Cancer Res 11:459-465; Direnzo, R et al (2007) Proceedings of AACR Annual Meeting, Abstract No. 2080; WO2010/002862. Crystal structures of FGFR3:anti-FGFR3 antibody are disclosed in co-pending, co-owned U.S. patent application Ser. No. 12/661,852 filed Mar. 24, 2010.

It is clear that there continues to be a need for agents that have clinical attributes that are optimal for development as therapeutic agents. The invention described herein meets this need and provides other benefits.

All references cited herein, including patent applications and publications, are incorporated by reference in their entirety.

SUMMARY OF THE INVENTION

The invention is based in part on the identification of a variety of FGFR3 binding agents (such as antibodies, and fragments thereof). FGFR3 presents an important and advantageous therapeutic target, and the invention provides compositions and methods based on binding of the agents to FGFR3. FGFR3 binding agents of the invention, as described herein, provide important therapeutic and diagnostic agents for use in targeting pathological conditions associated with expression and/or activity of the FGFR3 signaling pathways. Accordingly, the invention provides methods, compositions, kits, and articles of manufacture related to FGFR3 binding.

The present invention provides antibodies that bind to FGFR3. In one aspect, the invention features an isolated antibody that binds an FGFR3. In some embodiments, the antibody binds a FGFR3 IIIb isoform and/or a FGFR3 IIIc isoform. In some embodiments, the antibody binds a mutated FGFR3 (e.g., one or more of FGFR3 IIIb R248C, S249C, G372C, Y375C, K652E, and/or one or more of FGFR3 IIIc R248C, S249C, G370C, Y373C, K650E). In some embodiments, the antibody binds monomeric FGFR3 (e.g., monomeric FGFR3 IIIb and/or IIIc isoforms). In some embodiments, the antibody promotes formation of monomeric FGFR3, such as by stabilizing the monomeric FGFR3 form relative to the dimeric FGFR3 form.

In one aspect, the invention provides an isolated anti-FGFR3 antibody, wherein a full length IgG form of the antibody binds human FGFR3 with a Kd of $1 \times 10^{-7}$ or stronger. As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. Any of a number of assays known in the art, including those described herein, can be used to obtain binding affinity measurements, including, for example, Biacore, radioimmunoassay (RIA), and ELISA. In some embodiments, the full length IgG form of the antibody binds human FGFR3 with a Kd of $1 \times 10^{-8}$ or stronger, with a Kd of $1 \times 10^{-9}$ or stronger, or with a Kd of $1 \times 10^{-10}$ or stronger.

Generally, the anti-FGFR3 antibodies of the present invention are antagonist antibodies. Thus, in one aspect, the anti-FGFR3 antibodies inhibit FGFR3 activity (e.g., FGFR3-IIIb and/or FGFR3-IIIc activity). In some embodiments, the anti-FGFR3 antibody (generally in bivalent form) does not possess substantial FGFR3 agonist function. In some embodiments, the anti-FGFR3 antagonist antibody (generally in bivalent form) possesses little or no FGFR3 agonist function. In one embodiment, an antibody of the invention (generally in bivalent form) does not exhibit an FGFR3 agonist activity level that is above background level that is of statistical significance.

In one aspect, binding of the antibody to a FGFR3 may inhibit dimerization of the receptor with another unit of the receptor, whereby activation of the receptor is inhibited (due, at least in part, to a lack of receptor dimerization). Inhibition can be direct or indirect.

In one aspect, the invention provides anti-FGFR3 antibodies that do not possess substantial apoptotic activity (e.g., does not induce apoptosis of a cell, e.g., a transitional cell carcinoma cell or a multiple myeloma cell, such as a multiple myeloma cell comprising a FGFR3 translocation, such as a t(4;14) translocation). In some embodiments, the anti-FGFR3 antibody possesses little or no apoptotic function. In some embodiment, the FGFR3 antibodies do not exhibit apoptotic function that is above background level that is of statistical significance.

In one aspect, the invention provides anti-FGFR3 antibodies that do not induce substantial FGFR3 down-regulation. In some embodiments, the anti-FGFR3 antibody induces little or no receptor down-regulation. In some embodiment, the FGFR3 antibodies do not induce receptor down-regulation that is above background level that is of statistical significance.

In one aspect, the invention provides anti-FGFR3 antibodies that possess effector function. In one embodiment, the effector function comprises antibody-dependent cell-mediated cytotoxicity (ADCC). In one embodiment, the anti-FGFR3 antibody (in some embodiments, a naked anti-FGFR3 antibody) is capable of killing a cell, in some embodiments, a multiple myeloma cells (e.g., multiple myeloma cells comprising a translocation, e.g., a t(4;14) translocation). In some embodiments, the anti-FGFR3 antibody is capable of killing a cell that expresses about 10,000 FGFR3 molecules per cell or more (such as about 11,000, about 12,000, about 13,000, about 14,000, about 15,000, about 16,000, about 17,000, about 18,000 or more FGFR3 molecules per cell). In other embodiments, the cell expresses about 2000, about 3000, about 4000, about 5000, about 6000, about 7000, about 8000, or more FGFR3 molecules per cell.

In one aspect, the anti-FGFR3 antibody of the invention inhibits constitutive FGFR3 activity. In some embodiments, constitutive FGFR3 activity is ligand-dependent FGFR3 constitutive activity. In some embodiments, constitutive FGFR3 activity is ligand-independent constitutive FGFR3 activity.

In one aspect, the anti-FGFR3 antibody inhibits FGFR3 comprising a mutation corresponding to FGFR3-IIIb$^{R248C}$. As used herein the term "comprising a mutation corresponding to FGFR3-IIIb$^{R248C}$" is understood to encompass FGFR3-IIIb$^{R248C}$ and FGFR3-IIIc$^{R248C}$, as well as additional FGFR3 forms comprising an R to C mutation at a position corresponding to FGFR3-IIIb R248. One of ordinary skill in the art understands how to align FGFR3 sequences in order identify corresponding residues between respective FGFR3 sequences, e.g., aligning a FGFR3-IIIc sequence with a FGFR3-IIIb sequence to identify the position in FGFR3 corresponding R248 position in FGFR3-IIIb. In some embodiments, the anti-FGFR3 antibody inhibits FGFR3-IIIb$^{R248C}$ and/or FGFR3-IIIc$^{R248C}$.

In one aspect, the anti-FGFR3 antibodies inhibit FGFR3 comprising a mutation corresponding to FGFR3-IIIb$^{K652E}$. For convenience, the term "comprising a mutation corresponding to FGFR3-IIIb$^{K652E}$" is understood to encompass FGFR3-IIIb$^{K652E}$ and FGFR3-IIIc$^{K650E}$, as well as additional FGFR3 forms comprising an K to E mutation at a position corresponding to FGFR3-IIIb K652. One of ordinary skill in the art understands how to align FGFR3 sequences in order identify corresponding residues between respective FGFR3 sequences, e.g., aligning a FGFR3-IIIc sequence with a FGFR3-IIIb sequence to identify the position in FGFR3 corresponding K652 position in FGFR3-IIIb. In some embodiments, the anti-FGFR3 antibody inhibits FGFR3-IIIb$^{K652E}$ and/or FGFR3-IIIc$^{K650E}$.

In one aspect, the anti-FGFR3 antibodies inhibit FGFR3 comprising a mutation corresponding to FGFR3-IIIb$^{S249C}$. For convenience, the term "comprising a mutation corresponding to FGFR3-IIIb$^{S249C}$" is understood to encompass FGFR3-IIIb$^{S249C}$ and FGFR3-IIIc$^{S249C}$, as well as additional FGFR3 forms comprising an S to C mutation at a position corresponding to FGFR3-IIIb S249. In some embodiments, the anti-FGFR3 antibody inhibits FGFR3-IIIb$^{S249C}$ and/or FGFR3-IIIc$^{S249C}$.

In one aspect, the anti-FGFR3 antibodies inhibit FGFR3 comprising a mutation corresponding to FGFR3-IIIb$^{G372C}$. For convenience, the term "comprising a mutation corresponding to FGFR3-IIIb$^{G372C}$" is understood to encompass FGFR3-IIIb$^{G372C}$ and FGFR3-IIIc$^{G370C}$, as well as additional FGFR3 forms comprising a G to C mutation at a position corresponding to FGFR3-IIIb G372. In some embodiments, the anti-FGFR3 antibody inhibits FGFR3-IIIb$^{G372C}$ and/or FGFR3-IIIc$^{G370C}$.

In one aspect, the anti-FGFR3 antibodies inhibit FGFR3 comprising a mutation corresponding to FGFR3-IIIb$^{Y375C}$. For convenience, the term "comprising a mutation corresponding to FGFR3-IIIb$^{Y375C}$" is understood to encompass FGFR3-IIIb$^{Y375C}$ and FGFR3-IIIc$^{Y373C}$, as well as additional FGFR3 forms comprising an S to C mutation at a position corresponding to FGFR3-IIIb S249. In some embodiments, the anti-FGFR3 antibody inhibits FGFR3-IIIb$^{Y375C}$ and/or FGFR3-IIIc$^{Y373C}$. In one aspect, the anti-FGFR3 antibodies inhibit (a) FGFR3-IIIb$^{K652E}$ and (b) one or more of FGFR3-IIIc$^{R248C}$, FGFR3-IIIb$^{Y375C}$, FGFR3-IIIb$^{S249C}$, and FGFR3IIIb$^{G372C}$.

In one aspect, the anti-FGFR3 antibodies inhibit (a) FGFR3-IIIc$^{K650E}$ and (b) one or more of FGFR3-IIIc$^{R248C}$, FGFR3-IIIc$^{Y373C}$, FGFR3-IIIc$^{S249C}$, and FGFR3IIIc$^{G370C}$.

In one aspect, the anti-FGFR3 antibodies inhibit (a) FGFR3-IIIb$^{R248C}$ and (b) one or more of FGFR3-IIIb$^{K652E}$, FGFR3-IIIb$^{Y375C}$, FGFR3-IIIb$^{S249C}$, and FGFR3-IIIb$^{G372C}$.

In one aspect, the anti-FGFR3 antibodies inhibit (a) FGFR3-IIIc$^{R248C}$ and (b) one or more of FGFR3-IIIc$^{K650E}$, FGFR3-IIIc$^{Y373C}$, FGFR3-IIIc$^{S249C}$, and FGFR3-IIIc$^{G370C}$.

In one aspect, the anti-FGFR3 antibodies inhibit (a) FGFR3-IIIb$^{G372C}$ and (b) one or more of FGFR3-IIIb$^{K652E}$, FGFR3-IIIb$^{Y375C}$, FGFR3-IIIb$^{S249C}$, and FGFR3-IIIb$^{R248C}$.

In one aspect, the anti-FGFR3 antibodies inhibit (a) FGFR3-IIIc$^{G370C}$ and (b) one or more of FGFR3-IIIc$^{K650E}$, FGFR3-IIIc$^{Y373C}$, FGFR3-IIIc$^{S249C}$, and FGFR3-IIIc$^{R248C}$.

In one aspect, the anti-FGFR3 antibodies inhibit FGFR3-IIIb$^{R248C}$, FGFR3-IIIb$^{K652E}$, FGFR3-IIIb$^{Y375C}$, FGFR3-IIIb$^{S249C}$, and FGFR3-IIIb$^{G372C}$.

In one aspect, the anti-FGFR3 antibodies inhibit FGFR3-IIIc$^{R248C}$, FGFR3-IIIc$^{K650E}$, FGFR3-IIIc$^{Y373C}$, FGFR3-IIIc$^{S249C}$, and FGFR3-IIIc$^{G370C}$.

In one aspect, the invention provides an isolated anti-FGFR3 antibody comprising:

(a) at least one, two, three, four, or five hypervariable region (HVR) sequences selected from:

(i) HVR-L1 comprising sequence A1-A11, wherein A1-A11 is RASQDVDTSLA (SEQ ID NO:87), (ii) HVR-L2 comprising sequence B1-B7, wherein B1-B7 is SASFLYS (SEQ ID NO:88), (iii) HVR-L3 comprising sequence C1-C9, wherein C1-C9 is QQSTGHPQT (SEQ ID NO:89), (iv)) HVR-H1 comprising sequence D1-D10, wherein D1-D10 is GFTFTSTGIS (SEQ ID NO:84), (v) HVR-H2 comprising sequence E1-E18, wherein E1-E18 is GRIYPTSGSTNYADSVKG (SEQ ID NO:85), and (vi) HVR-H3 comprising sequence F1-F20, wherein F1-F20 is ARTYGIYDLYVDYTEYVMDY (SEQ ID NO:86); and (b) at least one variant HVR, where the variant HVR sequence comprises modification of at least one residue (at least two residues, at least three or more residues) of the sequence depicted in SEQ ID NOS:1-18, 48-131 and 140-145. The modification desirably is a substitution, insertion, or deletion.

In some embodiments, a HVR-L1 variant comprises 1-6 (1, 2, 3, 4, 5, or 6) substitutions in any combination of the following positions: A5 (V or D), A6 (V or I), A7 (D, E or S), A8 (T or I), A9 (A or S) and A10 (V or L). In some embodiments, a HVR-L2 variant comprises 1-2 (1 or 2) substitutions in any combination of the following positions: B1 (S or G), B4 (F or S or T) and B6 (A or Y). In some embodiments, a HVR-L3 variant comprises 1-6 (1, 2, 3, 4, 5, or 6) substitutions in any combination of the following positions: C3 (G or S or T), C4 (T or Y or A), C5 (G or S or T or A), C6 (A or H or D or T or N), C7 (Q or P or S), and C8 (S or Y or L or P or Q). In some embodiment, a HVR-L1 variant comprises 1-3 (1, 2, or 3) substitutions in any combination of the following positions: D3 (S or T), D5 (W or Y or S or T), D6 (S or G or T). In some embodiment, a HVR-H2 variant comprises 1-6 (1, 2, 3, 4, 5, or 6) substitutions in any combination of the following positions: E2 (R or S), E6 (Y or A or L or S or T), E7 (A or Q or D or G or Y or S or N or F), E8 (A or D or G), E9 (T or S), E10 (K or F or T or S), E11 (Y or H or N or I).

In one aspect, the invention provides an isolated anti-FGFR3 antibody comprising:

(a) at least one, two, three, four, or five hypervariable region (HVR) sequences selected from:

(i) HVR-L1 comprising sequence RASQX$_1$X$_2$X$_3$X$_4$X$_5$X$_6$A, wherein X$_1$ is V or D, X$_2$ is V or I, X$_3$ is D, E or S, X$_4$ is T or I, X$_5$ is A or S, and X$_6$ is V or L (SEQ ID NO:146), (ii) HVR-L2 comprising sequence X$_1$ASFLX$_2$S wherein X$_1$ is S or G and X$_2$ is A or Y (SEQ ID NO:147), (iii) HVR-L3 comprising sequence QQX$_1$X$_2$X$_3$X$_4$X$_5$X$_6$T, wherein X$_1$ is G, S or T, X$_2$ is T, Y or A, X$_3$ is G, S, T, or A, X$_4$ is A, H, D, T, or N, X$_5$ is Q, P or S, X$_6$ is S, Y, L, P or Q (SEQ ID NO:148), (iv)) HVR-H1 comprising sequence GFX$_1$FX$_2$X$_3$TGIS, wherein X$_1$ is S or T, X$_2$ is W, Y, S or T, X$_3$ is S, G, or T (SEQ ID NO:149), (v) HVR-H2 comprising sequence GRIYPX$_1$X$_2$X$_3$X$_4$X$_5$X$_6$YADSVKG, wherein X$_1$ is Y, A, L, S, or T, X$_2$ is A, Q, D, G, Y, S, N or F, X$_3$ is A, D, or G, X$_4$ is T or S, X$_5$ is K, F, T, or S, X$_6$ is Y, H, N or I (SEQ ID NO:150), and (vi) HVR-H3 comprising sequence ARTYGIYDLYVDYTEYVMDY (SEQ ID NO:151).

In some embodiments, HVR-L1 comprises sequence RASQX$_1$VX$_2$X$_3$X$_4$VA, wherein X$_1$ is V or D, X$_2$ is D, E or S, X$_3$ is T or I, X$_4$ is A or S (SEQ ID NO:152). In some embodiments, HVR-L3 comprises sequence QQX$_1$X$_2$X$_3$X$_4$X$_5$X$_6$T, wherein X$_1$ is S, G, or T, X$_2$ is Y, T, or A, X$_3$ is T or G, X$_4$ is T, H or N, X$_5$ is P or S, X$_6$ is P, Q, Y, or L (SEQ ID NO:153). In some embodiments, HVR-H2 comprises sequence GRIYPX$_1$X$_2$GSTX$_3$YADSVKG, wherein X$_1$ is T or L, X$_2$ is N, Y, S, G, A, or Q; X$_3$ is N or H (SEQ ID NO:154).

In another aspect, the invention features an isolated anti-FGFR3 antibody that comprises one, two, three, four, five, or six HVRs, where each HVR comprises, consists, or consists essentially of a sequence selected from SEQ ID NOS:1-18, 48-131 and 140-145, and where SEQ ID NO:1, 7, 13, 48, 54, 60, 66, 72, 78, 84, 90, 96, 102, 108, 114, 120, 126 or 143 corresponds to an HVR-H1, SEQ ID NO:2, 8, 14, 49, 55, 61, 67, 73, 79, 85, 91, 97, 103, 109, 115, 121, 127 or 144 corresponds to an HVR-H2, SEQ ID NO:3, 9, 15, 50, 56, 62, 68, 74, 80, 86, 92, 98, 104, 110, 116, 122, 128 or 145 corresponds to an HVR-H3, SEQ ID NO:4, 10, 16, 51, 57, 63, 69, 75, 81, 87, 93, 99, 105, 111, 117, 123, 129 or 140 corresponds to an HVR-L1, SEQ ID NO:5, 11, 17, 52, 58, 64, 70, 76, 82, 88, 94, 100, 106, 112, 118, 124, 130 or 141 corresponds to an HVR-L2, and SEQ ID NO:6, 12, 18, 53, 59, 65, 71, 77, 83, 89, 95, 101, 107, 113, 119, 125, 131 or 142 corresponds to an HVR-L3.

In one aspect, the invention provides an anti-FGFR3 antibody comprising a HVR-H1 comprising the sequence of SEQ ID NO:1, 7, 13, 48, 54, 60, 66, 72, 78, 84, 90, 96, 102, 108, 114, 120, 126 or 143.

In one aspect, the invention provides an anti-FGFR3 antibody comprising a HVR-H2 comprising the sequence of SEQ ID NO:2, 8, 14, 49, 55, 61, 67, 73, 79, 85, 91, 97, 103, 109, 115, 121, 127 or 144.

In one aspect, the invention provides an anti-FGFR3 antibody comprising a HVR-H3 comprising the sequence of SEQ ID NO:3, 9, 15, 50, 56, 62, 68, 74, 80, 86, 92, 98, 104, 110, 116, 122, 128 or 145.

In one aspect, the invention provides an anti-FGFR3 antibody comprising a HVR-L1 region comprising the sequence of SEQ ID NO:4, 10, 16, 51, 57, 63, 69, 75, 81, 87, 93, 99, 105, 111, 117, 123, 129 or 140.

In one aspect, the invention provides an anti-FGFR3 antibody comprising a HVR-L2 region comprising the sequence of SEQ ID NO:5, 11, 17, 52, 58, 64, 70, 76, 82, 88, 94, 100, 106, 112, 118, 124, 130 or 141.

In one aspect, the invention provides an anti-FGFR3 antibody comprising a HVR-L3 region comprising the sequence of SEQ ID NO:6, 12, 18, 53, 59, 65, 71, 77, 83, 89, 95, 101, 107, 113, 119, 125, 131 or 142.

In one aspect, an anti-FGFR3 antibody comprises a heavy chain variable region comprising HVR-H1, HVR-H2, HVR-H3, wherein each, in order, comprises SEQ ID NO:1, 2, 3, and/or a light chain variable region comprising HVR-L1, HVR-L2, and HVR-L3, where each, in order, contains SEQ ID NO: 4, 5, 6.

In another aspect, an-anti-FGFR3 antibody comprises a heavy chain variable region comprising HVR-H1, HVR-H2, HVR-H3, wherein each, in order, comprises SEQ ID NO:7, 8, 9, and/or a light chain variable region comprising HVR-L1, HVR-L2, and HVR-L3, where each, in order, comprises SEQ ID NO: 10, 11, 12.

In another aspect, an anti-FGFR3 antibody comprises a heavy chain variable region comprising HVR-H1, HVR-H2, HVR-H3, where each, in order, comprises SEQ ID NO:13, 14, 15, and/or a light chain variable region comprising HVR-L1, HVR-L2, and HVR-L3, where each, in order, comprises SEQ ID NO:16, 17, 18.

In another aspect, an anti-FGFR3 antibody comprises a heavy chain variable region comprising HVR-H1, HVR-H2, HVR-H3, where each, in order, comprises SEQ ID NO: 48, 49, 50, and/or a light chain variable region HVR-L1, HVR-L2, and HVR-L3, where each, in order, comprises SEQ ID NO: 51, 52, 53.

In another aspect, an anti-FGFR3 antibody comprises a heavy chain variable region comprising HVR-H1, HVR-H2, HVR-H3, where each, in order, comprises SEQ ID NO: 54, 55, 56, and/or a light chain variable region comprising HVR-L1, HVR-L2, and HVR-L3, where each, in order, comprises SEQ ID NO: 57, 58, 59.

In another aspect, an anti-FGFR3 antibody comprises a heavy chain variable region comprising HVR-H1, HVR-H2, HVR-H3, where each, in order, comprises SEQ ID NO:60, 61, 62, 63, and/or a light chain variable region comprising HVR-L1, HVR-L2, and HVR-L3, where each, in order, comprises SEQ ID NO: 63, 64, 65.

In another aspect, an anti-FGFR3 antibody comprises a heavy chain variable region comprising HVR-H1, HVR-H2, HVR-H3, where each, in order, comprises SEQ ID NO:66, 67, 68, and/or a light chain variable region comprising HVR-L1, HVR-L2, and HVR-L3, where each, in order, comprises SEQ ID NO: 69, 70, 71.

In another aspect, an anti-FGFR3 antibody comprises a heavy chain variable region comprising HVR-H1, HVR-H2, HVR-H3, where each, in order, comprises SEQ ID NO:72, 73, 74, and/or a light chain variable region comprising HVR-L1, HVR-L2, and HVR-L3, where each, in order, comprises SEQ ID NO: 75, 76, 77.

In another aspect, an anti-FGFR3 antibody comprises a heavy chain variable region comprising HVR-H1, HVR-H2, HVR-H3, where each, in order, comprises SEQ ID NO:78, 79 80, and/or a light chain variable region comprising HVR-L1, HVR-L2, and HVR-L3, where each, in order, comprises SEQ ID NO:81, 82, 83.

In another aspect, an anti-FGFR3 antibody comprises a heavy chain variable region comprising HVR-H1, HVR-H2, HVR-H3, where each, in order, comprises SEQ ID NO: 84, 85, 86, and/or a light chain variable region comprising HVR-L1, HVR-L2, and HVR-L3, where each, in order, comprises SEQ ID NO:87, 88, 89.

In another aspect, an anti-FGFR3 antibody comprises a heavy chain variable region comprising HVR-H1, HVR-H2, HVR-H3, where each, in order, comprises SEQ ID NO: 90, 91, 92, and/or a light chain variable region comprising HVR-L1, HVR-L2, and HVR-L3, where each, in order, comprises SEQ ID NO:93, 94, 95.

In another aspect, an anti-FGFR3 antibody comprises a heavy chain variable region comprising HVR-H1, HVR-H2, HVR-H3, where each, in order, comprises SEQ ID NO: 96, 97, 98, and/or a light chain variable region comprising HVR-L1, HVR-L2, and HVR-L3, where each, in order, comprises SEQ ID NO: 99, 100, 101.

In another aspect, an anti-FGFR3 antibody comprises a heavy chain variable region comprising HVR-H1, HVR-H2, HVR-H3, where each, in order, comprises SEQ ID NO: 102, 103, 104, and/or a light chain variable region comprising HVR-L1, HVR-L2, and HVR-L3, where each, in order, comprises SEQ ID NO: 105, 106, 107.

In another aspect, an anti-FGFR3 antibody comprises a heavy chain variable region comprising HVR-H1, HVR-H2, HVR-H3, where each, in order, comprises SEQ ID NO:108, 109, 110, and/or a light chain variable region comprising HVR-L1, HVR-L2, and HVR-L3, where each, in order, comprises SEQ ID NO: 111, 112, 113.

In another aspect, an anti-FGFR3 antibody comprises a heavy chain variable region comprising HVR-H1, HVR-H2, HVR-H3, where each, in order, comprises SEQ ID NO:114, 115, 116, and/or a light chain variable region comprising HVR-L1, HVR-L2, and HVR-L3, where each, in order, comprises SEQ ID NO:117, 118, 119.

In another aspect, an anti-FGFR3 antibody comprises a heavy chain variable region comprising HVR-H1, HVR-H2, HVR-H3, where each, in order, comprises SEQ ID NO:120, 121, 122, and/or a light chain variable region comprising HVR-L1, HVR-L2, and HVR-L3, where each, in order, comprises SEQ ID NO: 123, 124, 125.

In another aspect, an anti-FGFR3 antibody comprises a heavy chain variable region comprising HVR-H1, HVR-H2, HVR-H3, where each, in order, comprises SEQ ID NO:126, 127, 128, and/or a light chain variable region comprising HVR-L1, HVR-L2, and HVR-L3, where each, in order, comprises SEQ ID NO:129, 130, 131.

In another aspect, an anti-FGFR3 antibody comprises a heavy chain variable region comprising HVR-H1, HVR-H2, HVR-H3, where each, in order, comprises SEQ ID NO:143, 144, 145, and/or a light chain variable region comprising HVR-L1, HVR-L2, and HVR-L3, where each, in order, comprises SEQ ID NO:140, 141, 142.

The amino acid sequences of SEQ ID NOs:1-18, 48-131 and 140-145 are numbered with respect to individual HVR (i.e., H1, H2 or H3) as indicated in FIG. 1, the numbering being consistent with the Kabat numbering system as described below.

In another aspect, an anti-FGFR3 antibody comprises comprises a heavy chain variable region comprising SEQ ID NO:132 and a light chain variable region.

In another aspect, an anti-FGFR3 antibody comprises a light chain variable region comprising SEQ ID NO: 133, and a heavy chain variable region.

In another aspect, an anti-FGFR3 antibody comprises a heavy chain variable region comprising SEQ ID NO:132 and a light chain variable region comprising SEQ ID NO:133.

In another aspect, an anti-FGFR3 antibody comprises a heavy chain variable region comprising SEQ ID NO:134 and a light chain variable region.

In another aspect, an anti-FGFR3 antibody comprises a light chain variable region comprising SEQ ID NO: 135, and a heavy chain variable region.

In another aspect, an anti-FGFR3 antibody comprises a light chain variable region comprising SEQ ID NO: 139, and a heavy chain variable region.

In another aspect, an anti-FGFR3 antibody comprises a heavy chain variable region comprising SEQ ID NO:134 and a light chain variable region comprising SEQ ID NO:135.

In another aspect, an anti-FGFR3 antibody comprises a heavy chain variable region comprising SEQ ID NO:136 and a light chain variable region.

In another aspect, an anti-FGFR3 antibody comprises a light chain variable region comprising SEQ ID NO: 137, and a heavy chain variable region.

In another aspect, an anti-FGFR3 antibody comprises a heavy chain variable region comprising SEQ ID NO:136 and a light chain variable region comprising SEQ ID NO:137.

In another aspect, an anti-FGFR3 antibody comprises a heavy chain variable region comprising SEQ ID NO:138 and a light chain variable region.

In another aspect, an anti-FGFR3 antibody comprises a light chain variable region comprising SEQ ID NO: 139, and a heavy chain variable region.

In another aspect, an anti-FGFR3 antibody comprises a heavy chain variable region comprising SEQ ID NO:138 and a light chain variable region comprising SEQ ID NO:139.

In one aspect, the invention provides an anti-FGFR3 antibody comprising: at least one, two, three, four, five, and/or six hypervariable region (HVR) sequences selected from the group consisting of:

```
(a) HVR-L1 comprising sequence
                                            (SEQ ID NO: 155)
SASSSVSYMH, (SEQ ID NO: 156)
SASSSVSYMH or (SEQ ID NO: 157)
LASQTIGTWLA, (b) HVR-L2 comprising sequence
                                            (SEQ ID NO: 158)
TWIYDTSILAS, (SEQ ID NO: 159)
RWIYDTSKLAS, or (SEQ ID NO: 160)
LLIYAATSLAD, (c) HVR-L3 comprising sequence
                                            (SEQ ID NO: 161)
QQWTSNPLT, (SEQ ID NO: 162)
QQWSSYPPT, or (SEQ ID NO: 163)
QQLYSPPWT, (d) HVR-H1 comprising sequence
                                            (SEQ ID NO: 164)
GYSFTDYNMY, (SEQ ID NO: 165)
GYVFTHYNMY, or (SEQ ID NO: 166)
GYAFTSYNMY, (e) HVR-H2 comprising sequence
                                            (SEQ ID NO: 167)
WIGYIEPYNGGTSYNQKFKG, (SEQ ID NO: 168)
WIGYIEPYNGGTSYNQKFKG, or (SEQ ID NO: 169)
WIGYIDPYIGGTSYNQKFKG, and (f) HVR-H3 comprising sequence
                                            (SEQ ID NO: 170)
ASPNYYDSSPFAY, (SEQ ID NO: 171)
ARGQGPDFDV, or (SEQ ID NO: 172)
ARWGDYDVGAMDY.
```

In one aspect, the invention provides an anti-FGFR3 antibody comprising: at least one, two, three, four, five, and/or six hypervariable region (HVR) sequences selected from the group consisting of:

```
(a) HVR-L1 comprising sequence
                                            (SEQ ID NO: 155)
SASSSVSYMH, (b) HVR-L2 comprising sequence
                                            (SEQ ID NO: 158)
TWIYDTSILAS, (c) HVR-L3 comprising sequence
                                            (SEQ ID NO: 161)
QQWTSNPLT, (d) HVR-H1 comprising sequence
                                            (SEQ ID NO: 164)
GYSFTDYNMY, (e) HVR-H2 comprising sequence
                                            (SEQ ID NO: 167)
WIGYIEPYNGGTSYNQKFKG, and (f) HVR-H3 comprising sequence
                                            (SEQ ID NO: 170)
ASPNYYDSSPFAY.
```

In one aspect, the invention provides an anti-FGFR3 antibody comprising: at least one, two, three, four, five, and/or six hypervariable region (HVR) sequences selected from the group consisting of:

```
(a) HVR-L1 comprising sequence
                                            (SEQ ID NO: 156)
SASSSVSYMH, (b) HVR-L2 comprising sequence
                                            (SEQ ID NO: 159)
RWIYDTSKLAS, (c) HVR-L3 comprising sequence
                                            (SEQ ID NO: 162)
QQWSSYPPT, (d) HVR-H1 comprising sequence
                                            (SEQ ID NO: 165)
GYVFTHYNMY, (e) HVR-H2 comprising sequence
                                            (SEQ ID NO: 168)
WIGYIEPYNGGTSYNQKFKG, and (f) HVR-H3 comprising sequence
                                            (SEQ ID NO: 171)
ARGQGPDFDV.
```

In one aspect, the invention provides an anti-FGFR3 antibody comprising: at least one, two, three, four, five, and/or six hypervariable region (HVR) sequences selected from the group consisting of:

(a) HVR-L1 comprising sequence LASQTIGTWLA, (SEQ ID NO: 157)

(b) HVR-L2 comprising sequence LLIYAATSLAD, (SEQ ID NO: 160)

(c) HVR-L3 comprising sequence QQLYSPPWT, (SEQ ID NO: 163)

(d) HVR-H1 comprising sequence GYAFTSYNMY, (SEQ ID NO: 166)

(e) HVR-H2 comprising sequence WIGYIDPYIGGTSYNQKFKG, and (SEQ ID NO: 169)

(f) HVR-H3 comprising sequence ARWGDYDVGAMDY. (SEQ ID NO: 172)

In one aspect, the invention provides an anti-FGFR3 antibody comprising (a) a light chain comprising (i) HVR-L1 comprising sequence SASSSVSYMH (SEQ ID NO:155); (ii) HVR-L2 comprising sequence TWIYDTSILAS (SEQ ID NO:158); and (iii) HVR-L3 comprising sequence QQWSSYPPT (SEQ ID NO:162); and/or (b) a heavy chain comprising (i) HVR-H1 comprising sequence GYVFTHYNMY (SEQ ID NO:165); (ii) HVR-H2 comprising sequence WIGYIEPYNGGTSYNQKFKG (SEQ ID NO:168); and (iii) HVR-H3 comprising sequence ARGQGPDFDV (SEQ ID NO:171).

In one aspect, the invention provides an anti-FGFR3 antibody comprising (a) a light chain comprising (i) HVR-L1 comprising sequence LASQTIGTWLA (SEQ ID NO:157); (ii) HVR-L2 comprising sequence LLIYAATSLAD (SEQ ID NO:160); and (iii) HVR-L3 comprising sequence QQLYSPPWT (SEQ ID NO:163); and/or (b) a heavy chain comprising (i) HVR-H1 comprising sequence GYAFTSYNMY (SEQ ID NO:166); (ii) HVR-H2 comprising sequence WIGYIDPYIGGTSYNQKFKG (SEQ ID NO:169); and (iii) HVR-H3 comprising sequence ARWGDYDVGAMDY (SEQ ID NO:172). Some embodiments of antibodies of the invention comprise a light chain variable domain of humanized 4D5 antibody (huMAb4D5-8) (HERCEPTIN®, Genentech, Inc., South San Francisco, Calif., USA) (also referred to in U.S. Pat. No. 6,407,213 and Lee et al., J. Mol. Biol. (2004), 340 (5):1073-1093) as depicted in SEQ ID NO:173 below.

(SEQ ID NO: 173)
1 Asp Ile Gln Met Thr Gln Ser Pro Ser Ser Leu Ser Ala Ser Val Gly Asp

Arg Val Thr Ile Thr Cys <u>Arg Ala Ser Gln Asp Val</u> Asn <u>Thr Ala Val Ala</u>

Trp Tyr Gln Gln Lys Pro Gly Lys Ala Pro Lys Leu Leu Ile Tyr <u>Ser Ala</u>

<u>Ser Phe Leu Tyr Ser</u> Gly Val Pro Ser Arg Phe Ser Gly Ser *Arg* Ser Gly

Thr Asp Phe Thr Leu Thr Ile Ser Ser Leu Gln Pro Glu Asp Phe Ala Thr

Tyr Tyr Cys <u>Gln Gln</u> His <u>Tyr Thr Thr Pro Pro Thr</u> Phe Gly Gln Gly Thr

Lys Val Glu Ile Lys 107
(HVR residues are underlined)

QQWTSNPLT (SEQ ID NO:161); and/or (b) a heavy chain comprising (i) HVR-H1 comprising sequence GYSFTDYNMY (SEQ ID NO:164); (ii) HVR-H2 comprising sequence WIGYIEPYNGGTSYNQKFKG (SEQ ID NO:167); and (iii) HVR-H3 comprising sequence ASPNYYDSSPFAY (SEQ ID NO:170).

In one aspect, the invention provides an anti-FGFR3 antibody comprising (a) a light chain comprising (i) HVR-L1 comprising sequence SASSSVSYMH (SEQ ID NO:156); (ii) HVR-L2 comprising sequence RWIYDTSKLAS (SEQ ID NO:159); and (iii) HVR-L3 comprising sequence In one embodiment, the huMAb4D5-8 light chain variable domain sequence is modified at one or more of positions 30, 66, and 91 (Asn, Arg, and His as indicated in bold/italics above, respectively). In a particular embodiment, the modified huMAb4D5-8 sequence comprises Ser in position 30, Gly in position 66, and/or Ser in position 91. Accordingly, in one embodiment, an antibody of the invention comprises a light chain variable domain comprising the sequence depicted in SEQ ID NO:174 below:

(SEQ ID NO: 174)
1 Asp Ile Gln Met Thr Gln Ser Pro Ser Ser Leu Ser Ala Ser Val Gly Asp

Arg Val Thr Ile Thr Cys <u>Arg Ala Ser Gln Asp Val</u> *Ser* <u>Thr Ala Val Ala</u>

Trp Tyr Gln Gln Lys Pro Gly Lys Ala Pro Lys Leu Leu Ile Tyr <u>Ser Ala</u>

<u>Ser Phe Leu Tyr Ser</u> Gly Val Pro Ser Arg Phe Ser Gly Ser *Gly* Ser Gly

Thr Asp Phe Thr Leu Thr Ile Ser Ser Leu Gln Pro Glu Asp Phe Ala Thr

Tyr Tyr Cys <u>Gln Gln</u> *Ser* <u>Tyr Thr Thr Pro Pro Thr</u> Phe Gly Gln Gly Thr

Lys Val Glu Ile Lys 107
(HVR residues are underlined)

Substituted residues with respect to huMAb4D5-8 are indicated in bold/italics.

Antibodies of the invention can comprise any suitable framework variable domain sequence, provided binding activity to FGFR3 is substantially retained. For example, in some embodiments, antibodies of the invention comprise a human subgroup III heavy chain framework consensus sequence. In one embodiment of these antibodies, the framework consensus sequence comprises a substitution at position 71, 73, and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-1093). In one embodiment, these antibodies further comprise a human κI light chain framework consensus sequence. In a particular embodiment, these antibodies comprise light chain HVR sequences of huMAb4D5-8 as described in U.S. Pat. Nos. 6,407,213 & 5,821,337.) In one embodiment, these antibodies comprise light chain variable domain sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-1093).

In one embodiment, an antibody of the invention comprises a heavy chain variable domain, wherein the framework sequence comprises the sequence of SEQ ID NOS:19 and 203-205, 20 and 206-208, 21 and 209-211, 22 and 212-214, 23 and 215-217, 24 and 218-220, 25 and 221-223, 26 and 224-226, 27 and 227-229, 28 and 230-232, 29 and 233-235, 30 and 236-238, 31 and 239-241, 32 and 242-244, 33 and 245-247, 34 and 248-250, 35 and 251-253, 36 and 254-256, and/or 37 and 257-259, and HVR H1, H2, and H3 sequences are SEQ ID NOS:13, 14 and/or 15, respectively. In another embodiment, the framework sequence comprises the sequence of SEQ ID NOS: 19 and 203-205, 20 and 206-208, 21 and 209-211, 22 and 212-214, 23 and 215-217, 24 and 218-220, 25 and 221-223, 26 and 224-226, 27 and 227-229, 28 and 230-232, 29 and 233-235, 30 and 236-238, 31 and 239-241, 32 and 242-244, 33 and 245-247, 34 and 248-250, 35 and 251-253, 36 and 254-256, and/or 37 and 257-259, and HVR H1, H2, and H3 sequences are SEQ ID NOS:48, 49 and/or 50, respectively. In yet another embodiment, the framework sequence comprises the sequence of SEQ ID NOS: 19 and 203-205, 20 and 206-208, 21 and 209-211, 22 and 212-214, 23 and 215-217, 24 and 218-220, 25 and 221-223, 26 and 224-226, 27 and 227-229, 28 and 230-232, 29 and 233-235, 30 and 236-238, 31 and 239-241, 32 and 242-244, 33 and 245-247, 34 and 248-250, 35 and 251-253, 36 and 254-256, and/or 37 and 257-259, and HVR H1, H2, and H3 sequences are SEQ ID NOS:84, 85, and/or 86, respectively. In a further embodiment, the framework sequence comprises the sequence of SEQ ID NOS: 19 and 203-205, 20 and 206-208, 21 and 209-211, 22 and 212-214, 23 and 215-217, 24 and 218-220, 25 and 221-223, 26 and 224-226, 27 and 227-229, 28 and 230-232, 29 and 233-235, 30 and 236-238, 31 and 239-241, 32 and 242-244, 33 and 245-247, 34 and 248-250, 35 and 251-253, 36 and 254-256, and/or 37 and 257-259, and HVR H1, H2, and H3 sequences are SEQ ID NOS:108, 109, and/or 110, respectively.

In a particular embodiment, an antibody of the invention comprises a light chain variable domain, wherein the framework sequence comprises the sequence of SEQ ID NOS:38 and 260-262, 39 and 263-265, 40 and 266-268, and/or 41 and 269-271, and HVR L1, L2, and L3 sequences are SEQ ID NOS:16, 17, and/or 18, respectively. In another embodiment, an antibody of the invention comprises a light chain variable domain, wherein the framework sequence comprises the sequence of SEQ ID NOS: 38 and 260-262, 39 and 263-265, 40 and 266-268, and/or 41 and 269-271, and HVR L1, L2, and L3 sequences are SEQ ID NOS:51, 52 and/or 53, respectively. In an additional embodiment, an antibody of the invention comprises a light chain variable domain, wherein the framework sequence comprises the sequence of SEQ ID NOS: 38 and 260-262, 39 and 263-265, 40 and 266-268, and/or 41 and 269-271, and HVR L1, L2, and L3 sequences are SEQ ID NOS:87, 88 and/or 89, respectively. In yet another embodiment, an antibody of the invention comprises a light chain variable domain, wherein the framework sequence comprises the sequence of SEQ ID NOS: 38 and 260-262, 39 and 263-265, 40 and 266-268, and/or 41 and 269-271, and HVR L1, L2, and L3 sequences are SEQ ID NOS:111, 112, and/or 113, respectively.

In another aspect, an antibody of the invention comprises a heavy chain variable domain comprising the sequence of SEQ ID NO:132 and/or a light chain variable domain comprising the sequence of SEQ ID NO:133. In another aspect, an antibody of the invention comprises a heavy chain variable domain comprising the sequence of SEQ ID NO:134 and/or a light chain variable domain comprising the sequence of SEQ ID NO:135. In another aspect, an antibody of the invention comprises a heavy chain variable domain comprising the sequence of SEQ ID NO:136 and/or a light chain variable domain comprising the sequence of SEQ ID NO:137. In another aspect, an antibody of the invention comprises a heavy chain variable domain comprising the sequence of SEQ ID NO:138 and/or a light chain variable domain comprising the sequence of SEQ ID NO:139.

In one aspect, the invention provides an anti-FGFR3 antibody that binds a polypeptide comprising, consisting essentially of or consisting of the following amino acid sequence: LAVPAANTVRFRCPA (SEQ ID NO:179) and/or SDVEFHCKVYSDAQP (SEQ ID NO:180).

In some embodiments, the antibody binds a polypeptide comprising, consisting essentially of or consisting of amino acid numbers 164-178 and/or 269-283 of the mature human FGFR3 amino acid sequence.

In one embodiment, an anti-FGFR3 antibody of the invention specifically binds an amino acid sequence having at least 50%, 60%, 70%, 80%, 90%, 95%, 98% sequence identity or similarity with the sequence LAVPAANTVRFRCPA (SEQ ID NO:179) and/or SDVEFHCKVYSDAQP (SEQ ID NO:180).

In one aspect, the anti-FGFR3 antibody of the present invention binds to at least one, two, three, four, or any number up to all of residues 154, 155, 158, 159, 161, 162, 163, 164, 165, 166, 167, 168, 169, 170, 171, 172, 173, 174, 175, 177, 202, 205, 207, 210, 212, 214, 216, 217, 241, 246, 247, 248, 278, 279, 280, 281, 282, 283, 314, 315, 316, 317 and/or 318 of FGFR3111b polypeptide, or equivalent residues of FGFR3 IIIc polypeptide. One of ordinary skill in the art understands how to align FGFR3 sequences in order identify corresponding residues between respective FGFR3 sequences. Combinations of two or more residues can include any of residues 154, 155, 158, 159, 161, 162, 163, 164, 165, 166, 167, 168, 169, 170, 171, 172, 173, 174, 175, 177, 202, 205, 207, 210, 212, 214, 216, 217, 241, 246, 247, 248, 278, 279, 280, 281, 282, 283, 314, 315, 316, 317 and/or 318 of FGFR3 IIIb polypeptide, or equivalent residues of FGFR3 IIIc polypeptide. In some embodiments, the anti-FGFR3 antibody binds to at least one, two, three, four, or any number up to all of residues 158, 159, 169, 170, 171, 173, 175, 205, 207, and/or 315 of FGFR3 IIIb polypeptide, or equivalent residues of FGFR3IIIc polypeptide. In some embodiments, the anti- FGFR3 antibody binds to at least one, two three, four, or any number up to all of residues 158, 170, 171, 173, 175, and/or 315 of FGFR3 IIIb polypeptide, or equivalent residues of FGFR3 IIIc polypeptide.

In one aspect, the invention provides an anti-FGFR3 antibody that competes with any of the above-mentioned antibodies for binding to FGFR3. In one aspect, the invention provides an anti-FGFR3 antibody that binds to the same or a similar epitope on FGFR3 as any of the above-mentioned antibodies.

As is known in the art, and as described in greater detail hereinbelow, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below).

In some embodiments, the antibody is a monoclonal antibody. In other embodiments, the antibody is a polyclonal antibody. In some embodiments, the antibody is selected from the group consisting of a chimeric antibody, an affinity matured antibody, a humanized antibody, and a human antibody. In certain embodiments, the antibody is an antibody fragment. In some embodiments, the antibody is a Fab, Fab', Fab'-SH, F(ab')$_2$, or scFv.

In some embodiment, the FGFR3 antibody is a one-armed antibody (i.e., the heavy chain variable domain and the light chain variable domain form a single antigen binding arm) comprising an Fc region, wherein the Fc region comprises a first and a second Fc polypeptide, wherein the first and second Fc polypeptides are present in a complex and form a Fc region that increases stability of said antibody fragment compared to a Fab molecule comprising said antigen binding arm. See, e.g., WO2006/015371.

In one embodiment, the antibody is a chimeric antibody, for example, an antibody comprising antigen binding sequences from a non-human donor grafted to a heterologous non-human, human, or humanized sequence (e.g., framework and/or constant domain sequences). In one embodiment, the non-human donor is a mouse. In a further embodiment, an antigen binding sequence is synthetic, e.g., obtained by mutagenesis (e.g., phage display screening, etc.). In a particular embodiment, a chimeric antibody of the invention has murine V regions and a human C region. In one embodiment, the murine light chain V region is fused to a human kappa light chain. In another embodiment, the murine heavy chain V region is fused to a human IgG1 C region.

Humanized antibodies of the invention include those that have amino acid substitutions in the framework region (FR) and affinity maturation variants with changes in the grafted CDRs. The substituted amino acids in the CDR or FR are not limited to those present in the donor or recipient antibody. In other embodiments, the antibodies of the invention further comprise changes in amino acid residues in the Fc region that lead to improved effector function including enhanced CDC and/or ADCC function and B-cell killing. Other antibodies of the invention include those having specific changes that improve stability. In other embodiments, the antibodies of the invention comprise changes in amino acid residues in the Fc region that lead to decreased effector function, e.g., decreased CDC and/or ADCC function and/or decreased B-cell killing. In some embodiments, the antibodies of the invention are characterized by decreased binding (such as absence of binding) to human complement factor C1q and/or human Fc receptor on natural killer (NK) cells. In some embodiments, the antibodies of the invention are characterized by decreased binding (such as the absence of binding) to human FcγRI, FcγRIIA, and/or FcγRIIIA. In some embodiments, the antibodies of the invention are of the IgG class (e.g., IgG1 or IgG4) and comprise at least one mutation in E233, L234, G236, D265, D270, N297, E318, K320, K322, A327, A330, P331, and/or P329 (numbering according to the EU index). In some embodiments, the antibodies comprise the mutations L234A/L235A or D265A/N297A.

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation. In one aspect, the invention provides FGFR3 binding polypeptides comprising any of the antigen binding sequences provided herein, wherein the FGFR3 binding polypeptides specifically bind to a FGFR3, e.g., a human and/or cyno and/or mouse FGFR3.

The antibodies of the invention bind (such as specifically bind) FGFR3 (e.g. FGFR3-IIIb and/or FGFR3-IIIc), and in some embodiments, may modulate (e.g. inhibit) one or more aspects of FGFR3 signaling (such as FGFR3 phosphorylation) and/or disruption of any biologically relevant FGFR3 and/or FGFR3 ligand biological pathway, and/or treatment and/or prevention of a tumor, cell proliferative disorder or a cancer; and/or treatment or prevention of a disorder associated with FGFR3 expression and/or activity (such as increased FGFR3 expression and/or activity). In some embodiments, the FGFR3 antibody specifically binds to a polypeptide consisting of or consisting essentially of a FGFR3 (e.g., a human or mouse FGFR3). In some embodiments, the antibody specifically binds FGFR3 with a Kd of $1 \times 10^{-7}$ M or stronger.

In some embodiments, the anti-FGFR3 antibody of the invention is not an anti-FGFR3 antibody described in U.S. Patent Publication no. 2005/0147612 (e.g., antibody MSPRO2, MSPRO12, MSPRO59, MSPRO11, MSPRO21, MSPRO24, MSPRO26, MSPRO28, MSPRO29, MSPRO43, MSPRO55), antibody described in Rauchenberger et al, J Biol Chem 278 (40):38194-38205 (2003); an antibody described in PCT Publication No. WO2006/048877 (e.g., antibody PRO-001), an antibody described in Martinez-Torrecuadrada et al, Mol Cancer Ther (2008) 7(4): 862-873 (e.g., scFvaFGFR33C), an antibody described in Direnzo, R et al (2007) Proceedings of AACR Annual Meeting, Abstract No. 2080 (e.g., D11), or an antibody described in WO 2010/002862 (e.g., antibodies 15D8, 27H2, 4E7, 2G4, 20B4).

In one aspect, the invention provides compositions comprising one or more antibodies of the invention and a carrier. In one embodiment, the carrier is pharmaceutically acceptable.

In another aspect, the invention provides nucleic acids encoding a FGFR3 antibody of the invention.

In yet another aspect, the invention provides vectors comprising a nucleic acid of the invention.

In a further aspect, the invention provides compositions comprising one or more nucleic acids of the invention and a carrier. In one embodiment, the carrier is pharmaceutically acceptable.

In one aspect, the invention provides host cells comprising a nucleic acid or a vector of the invention. A vector can be of any type, for example, a recombinant vector such as an expression vector. Any of a variety of host cells can be used. In one embodiment, a host cell is a prokaryotic cell, for example, E. coli. In another embodiment, a host cell is a eukaryotic cell, for example a mammalian cell such as Chinese Hamster Ovary (CHO) cell.

In a further aspect, the invention provides methods of making an antibody of the invention. For example, the invention provides methods of making an anti-FGFR3 antibody (which, as defined herein includes full length antibody and fragments thereof), said method comprising expressing in a suitable host cell a recombinant vector of the invention encoding the antibody, and recovering the antibody. In some embodiments, the method comprises culturing a host cell comprising nucleic acid encoding the antibody so that the nucleic acid is expressed. In some embodiments, the method further comprises recovering the antibody from the host cell culture. In some embodiments, the antibody is recovered from the host cell culture medium. In some embodiments, the method further comprises combining the recovered antibody with a pharmaceutically acceptable carrier, excipient, or carrier to prepare a pharmaceutical formulation comprising the humanized antibody.

In one aspect, the invention provides an article of manufacture comprising a container; and a composition contained within the container, wherein the composition comprises one or more FGFR3 antibodies of the invention. In one embodiment, the composition comprises a nucleic acid of the invention. In another embodiment, a composition comprising an antibody further comprises a carrier, which in some embodiments is pharmaceutically acceptable. In one embodiment, an article of manufacture of the invention further comprises instructions for administering the composition (e.g., the antibody) to an individual (such as instructions for any of the methods described herein).

In another aspect, the invention provides a kit comprising a first container comprising a composition comprising one or more anti-FGFR3 antibodies of the invention; and a second container comprising a buffer. In one embodiment, the buffer is pharmaceutically acceptable. In one embodiment, a composition comprising an antibody further comprises a carrier, which in some embodiments is pharmaceutically acceptable. In another embodiment, a kit further comprises instructions for administering the composition (e.g., the antibody) to an individual.

In a further aspect, the invention provides an anti-FGFR3 antibody of the invention for use as a medicament.

In a further aspect, the invention provides an anti-FGFR3 antibody of the invention for use in treating or preventing a disorder, such as a pathological condition associated with FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer.

In a further aspect, the invention provides an anti-FGFR3 antibody of the invention for use in treating or preventing a disorder such as a skeletal disorder. In some embodiments, the disorder is achondroplasia, hypochondroplasia, dwarfism, thantophoric dysplasia (TD; clinical forms TD1 and TDII), or craniosynostosis syndrome.

In a further aspect, the invention provides an anti-FGFR3 antibody of the invention for use in reducing cell proliferation.

In a further aspect, the invention provides an anti-FGFR3 antibody of the invention for use in killing a cell. In some embodiments, the cell is a multiple myeloma cell. In some embodiments, the cell is killed by ADCC. In some embodiments, the antibody is a naked antibody. In some embodiments, the cell over-expresses FGFR3.

In a further aspect, the invention provides an anti-FGFR3 antibody of the invention for use in depleting cells, such as multiple myeloma cells. In some embodiments, the cell is killed by ADCC. In some embodiments, the antibody is a naked antibody. In some embodiments, the cell over-expresses FGFR3.

In a further aspect, the invention provides use of an anti-FGFR3 antibody of the invention in the preparation of a medicament for the therapeutic and/or prophylactic treatment of a disorder, such as a pathological condition associated with FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In one aspect, the invention provides use of a nucleic acid of the invention in the preparation of a medicament for the therapeutic and/or prophylactic treatment of a disorder, such as a pathological condition associated with FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In another aspect, the invention provides use of an expression vector of the invention in the preparation of a medicament for the therapeutic and/or prophylactic treatment of a disorder, such as a pathological condition associated with FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In yet another aspect, the invention provides use of a host cell of the invention in the preparation of a medicament for the therapeutic and/or prophylactic treatment of a disorder, such as a pathological condition associated with FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In a further aspect, the invention provides use of an article of manufacture of the invention in the preparation of a medicament for the therapeutic and/or prophylactic treatment of a disorder, such as a pathological condition associated with FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In one aspect, the invention also provides use of a kit of the invention in the preparation of a medicament for the therapeutic and/or prophylactic treatment of a disorder, such as a pathological condition associated with FGFR3 activation and/or expression (in some embodiments, over-expression). In some embodiments, the disorder is a cancer, a tumor, and/or a cell proliferative disorder. In some embodiments, the cancer, a tumor, and/or a cell proliferative disorder is multiple myeloma or bladder cancer (e.g., transitional cell carcinoma), breast cancer or liver cancer. In some embodiments, the disorder is a skeletal disorder, e.g., achondroplasia, hypochondroplasia, dwarfism, thantophoric dysplasia (TD; clinical forms TD1 and TDII), or craniosynostosis syndrome.

In a further aspect, the invention provides use of an anti-FGFR3 antibody of the invention in the preparation of a medicament for inhibition of cell proliferation. In a further aspect, the invention provides use of an anti-FGFR3 antibody of the invention in the preparation of a medicament for cell killing. In some embodiments, the cell is a multiple myeloma cell. In some embodiments, the cell is killed by ADCC. In some embodiments, the antibody is a naked antibody. In some embodiments, the cell over-expresses FGFR3.

In a further aspect, the invention provides use of an anti-FGFR3 antibody of the invention in the preparation of a medicament for depleting cells, such as multiple myeloma cells. In some embodiments, the cell is killed by ADCC. In some embodiments, the antibody is a naked antibody. In some embodiments, the cell over-expresses FGFR3.

The invention provides methods and compositions useful for modulating disorders associated with expression and/or signaling of FGFR3, such as increased expression and/or signaling or undesired expression and/or signaling.

Methods of the invention can be used to affect any suitable pathological state. Exemplary disorders are described herein, and include a cancer selected from the group consisting of non-small cell lung cancer, ovarian cancer, thyroid cancer, testicular cancer, endometrial cancer, head and neck cancer, brain cancer (e.g., neuroblastoma or meningioma), skin cancer (e.g., melanoma, basal cell carcinoma, or squamous cell carcinoma), bladder cancer (e.g., transitional cell carcinoma), breast carcinoma, gastric cancer, colorectal cancer (CRC), hepatocellular carcinoma, cervical cancer, lung cancer, pancreatic cancer, prostate cancer, and hematologic malignancies (e.g., T-cell acute lymphoblastic leukemia (T-ALL), B-cell acute lymphoblastic leukemia (B-ALL), acute myelogenous leukemia (AML), B-cell malignancies, Hodgkin lymphoma, and multiple myeloma). In some embodiments, the disorder is invasive transitional cell carcinoma. In some embodiments, the disorder is multiple myeloma. Additional exemplary disorders include skeletal disorders, such as achondroplasia, hypochondroplasia, dwarfism, thantophoric dysplasia (TD; clinical forms TD1 and TDII), or craniosynostosis syndrome.

In certain embodiments, the cancer expresses FGFR3, amplified FGFR3, translocated FGFR3, and/or mutated FGFR3. In certain embodiments, the cancer expresses activated FGFR3. In certain embodiments, the cancer expresses translocated FGFR3 (e.g., a t(4;14) translocation). In certain embodiments, the cancer expresses constitutive FGFR3. In some embodiments, the constitutive FGFR3 comprises a mutation in the tyrosine kinase domain and/or the juxtamembrane domain and/or a ligand-binding domain. In certain embodiments, the cancer expresses ligand-independent FGFR3. In some embodiments, the cancer expresses ligand-dependent FGFR3.

In some embodiments, the cancer expresses FGFR3 comprising a mutation corresponding to FGFR3-IIIb$^{S248C}$. In some embodiments, the cancer expressed FGFR3-IIIb$^{S248C}$ and/or FGFR3-IIIc$^{S248C}$.

In some embodiments, the cancer expresses FGFR3 comprising a mutation corresponding to FGFR3-IIIb$^{K652E}$. In some embodiments, the cancer expressed FGFR3-IIIb$^{K652E}$ and/or FGFR3-IIIc$^{K650E}$.

FGFR3 comprising a mutation corresponding to FGFR3-IIIb$^{S249C}$. In some embodiments, the cancer expresses FGFR3-IIIb$^{S249C}$ and/or FGFR3-IIIc$^{S249C}$.

In one aspect, the cancer expresses FGFR3 comprising a mutation corresponding to FGFR3-IIIb$^{G372C}$. In some embodiments, the cancer expresses FGFR3-IIIb$^{G372C}$ and/or FGFR3-IIIc$^{G370C}$.

In one aspect, the cancer expresses FGFR3 comprising a mutation corresponding to FGFR3-IIIb$^{Y375C}$. In some embodiments, the cancer expresses FGFR3-IIIb$^{Y375C}$ and/or FGFR3-IIIc$^{Y373C}$.

In some embodiments, the cancer expresses (a) FGFR3-IIIb$^{K652E}$ and (b) one or more of FGFR3-IIIb$^{R248C}$, FGFR3-IIIb$^{Y375C}$, FGFR3-IIIb$^{S249C}$, and FGFR3IIIb$^{G372C}$.

In some embodiments, the cancer expresses (a) FGFR3-IIIb$^{R248C}$ and (b) one or more of FGFR3-IIIb$^{K652E}$, FGFR3-IIIb$^{Y375C}$, FGFR3-IIIb$^{S249C}$, and FGFR3-IIIb$^{G372C}$.

In some embodiments, the cancer expresses (a) FGFR3-IIIb$^{G372C}$ and (b) one or more of FGFR3-IIIb$^{K652E}$, FGFR3-IIIb$^{Y375C}$, FGFR3-IIIb$^{S249C}$, and FGFR3-IIIb$^{R248C}$.

In some embodiments, the cancer expresses FGFR3-IIIb$^{R248C}$, FGFR3-IIIb$^{K652E}$, FGFR3-IIIb$^{Y375C}$, FGFR3-IIIb$^{S249C}$, and FGFR3-IIIb$^{G372C}$.

In certain embodiments, the cancer expresses increased levels of phospho-FGFR3, phospho-FRS2 and/or phospho-MAPK relative to a control sample (e.g., a sample of normal tissue) or level.

In some embodiments, the cancer expresses (e.g., on the cell surface) about 10,000 FGFR3 molecules per cell or more (such as 11,000, 12,000, 13,000, 14,000, 15,000, 16,000, 17,000, 18,000 or more FGFR3 receptors). In some embodiments, the cancer expresses about 13000 FGFR3 molecules. In other embodiments, the cancer expresses about 5000, 6000, 7000, 8000, or more FGFR3 molecules. In some embodiments, the cancer expresses less than about 4000, 3000, 2000, 1000, or fewer FGFR3 molecules. In some embodiments, the cancer expresses less than about 1000 FGFR3 molecules.

In one embodiment, a cell that is targeted in a method of the invention is a cancer cell. For example, a cancer cell can be one selected from the group consisting of a breast cancer cell, a colorectal cancer cell, a lung cancer cell (e.g., a non-small cell lung cancer cell), a thyroid cancer cell, a multiple myeloma cell, a testicular cancer cell, a papillary carcinoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell (e.g., a transitional cell carcinoma cell), a gastric carcinoma cell, a head and neck squamous carcinoma cell, a melanoma cell, a leukemia cell, a multiple myeloma cell (e.g. a multiple myeloma cell comprising a t(4:14) FGFR3 translocation) and a colon adenoma cell. In one embodiment, a cell that is targeted in a method of the invention is a hyperproliferative and/or hyperplastic cell. In another embodiment, a cell that is targeted in a method of the invention is a dysplastic cell. In yet another embodiment, a cell that is targeted in a method of the invention is a metastatic cell.

In one aspect, the invention provides methods for inhibiting cell proliferation in a subject, the method comprising administering to the subject an effective amount of an anti-FGFR3 antibody to reduce cell proliferation.

In one aspect, the invention provides methods for killing a cell in a subject, the method comprising administering to the subject an effective amount of an anti-FGFR3 antibody to kill a cell. In some embodiments, the cell is a multiple myeloma cell. In some embodiments, the cell is killed by ADCC. In some embodiments, the antibody is a naked antibody. In some embodiments, the cell over-expresses FGFR3.

In one aspect, the invention provides methods for depleting cells (such as multiple myeloma cells) in a subject, the method comprising administering to the subject an effective amount of an anti-FGFR3 antibody to kill a cell. In some embodiments, the cell is killed by ADCC. In some embodiments, the antibody is a naked antibody. In some embodiments, the cell over-expresses FGFR3.

In one aspect, the invention provides methods for treating or preventing a skeletal disorder. In some embodiments, the disorder is achondroplasia, hypochondroplasia, dwarfism, thantophoric dysplasia (TD; clinical forms TD1 and TDII), or craniosynostosis syndrome.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

In one aspect, the invention provides methods comprising administration of an effective amount of an anti-FGFR3 antibody in combination with an effective amount of another therapeutic agent (such as an anti-angiogenesis agent, another antibody, a chemotherapeutic agent, a cytotoxic agent, an immunosuppressive agent, a prodrug, a cytokine, cytotoxic radiotherapy, a corticosteroid, an anti-emetic, a cancer vaccine, an analgesic, or a growth inhibitory agent). For example, anti-FGFR3 antibodies are used in combinations with an anti-cancer agent or an anti-angiogenic agent to treat various neoplastic or non-neoplastic conditions. In particular examples, the anti-FGFR3 antibodies are used in combination with velcade, revlimid, tamoxifen, letrozole, exemestane, anastrozole, irinotecan, cetuximab, fulvestrant, vinorelbine, bevacizumab, vincristine, cisplatin, gemcitabine, methotrexate, vinblastine, carboplatin, paclitaxel, docetaxel, pemeterxed, 5-fluorouracil, doxorubicin, bortezomib, lenalidomide, dexamethasone, melphalin, prednisone, vincristine, and/or thalidomide.

Depending on the specific cancer indication to be treated, the combination therapy of the invention can be combined with additional therapeutic agents, such as chemotherapeutic agents, or additional therapies such as radiotherapy or surgery. Many known chemotherapeutic agents can be used in the combination therapy of the invention. Preferably those chemotherapeutic agents that are standard for the treatment of the specific indications will be used. Dosage or frequency of each therapeutic agent to be used in the combination is preferably the same as, or less than, the dosage or frequency of the corresponding agent when used without the other agent(s).

In another aspect, the invention provides any of the anti-FGFR3 antibodies described herein, wherein the anti-FGFR3 antibody comprises a detectable label.

In another aspect, the invention provides a complex of any of the anti-FGFR3 antibodies described herein and FGFR3. In some embodiments, the complex is in vivo or in vitro. In some embodiments, the complex comprises a cancer cell. In some embodiments, the anti-FGFR3 antibody is detectably labeled.

BRIEF DESCRIPTION OF THE DRAWINGS

FIGS. 1A, 1B and 1C: Heavy chain and light chain HVR loop sequences of anti-FGFR3 antibodies. The figures show the heavy chain HVR sequences, H1, H2, and H3, and light chain HVR sequences, L1, L2, and L3. Sequence numbering is as follows:

Figure 4:
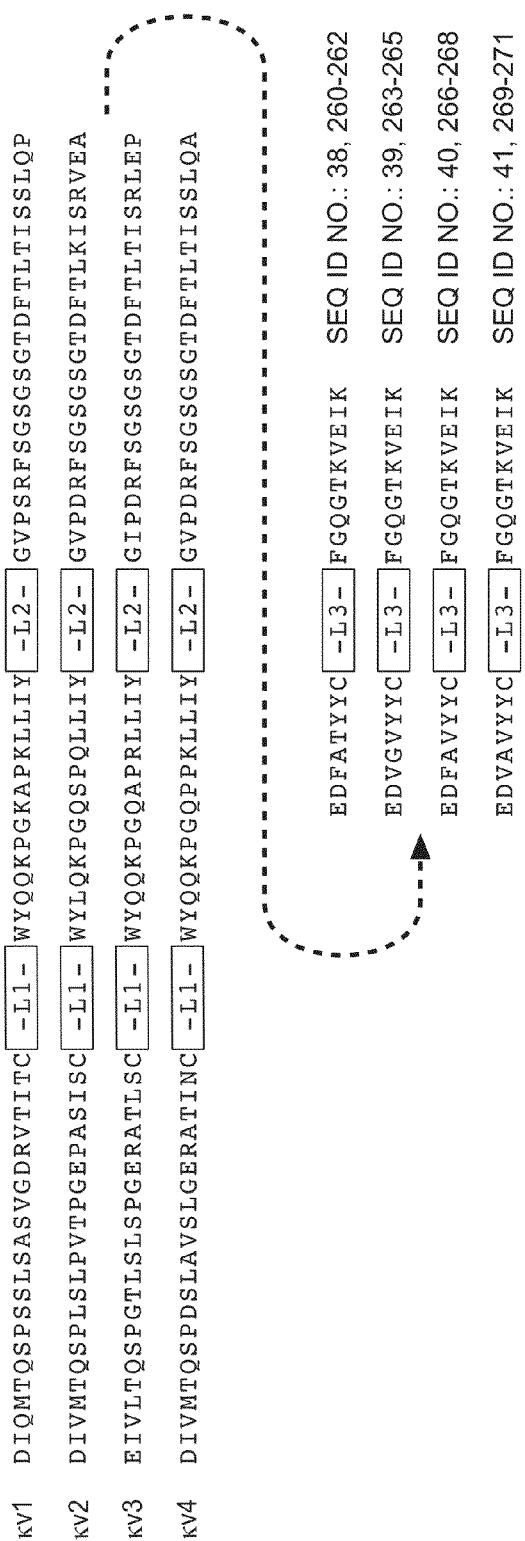

Clone 184.6 (HVR-H1 is SEQ ID NO:1; HVR-H2 is SEQ ID NO:2; HVR-H3 is SEQ ID NO:3; HVR-L1 is SEQ ID NO:4; HVR-L2 is SEQ ID NO:5; HVR-L3 is SEQ ID NO:6);

Clone 184.6.1 (HVR-H1 is SEQ ID NO:7; HVR-H2 is SEQ ID NO:8; HVR-H3 is SEQ ID NO:9; HVR-L1 is SEQ ID NO:10; HVR-L2 is SEQ ID NO:11; HVR-L3 is SEQ ID NO:12)

Clone 184.6.58 (HVR-H1 is SEQ ID NO:13; HVR-H2 is SEQ ID NO:14; HVR-H3 is SEQ ID NO:15; HVR-L1 is SEQ ID NO:16; HVR-L2 is SEQ ID NO:17; HVR-L3 is SEQ ID NO:18)

Clone 184.6.62 (HVR-H1 is SEQ ID NO:48; HVR-H2 is SEQ ID NO:49; HVR-H3 is SEQ ID NO:50; HVR-L1 is SEQ ID NO:51; HVR-L2 is SEQ ID NO:52; HVR-L3 is SEQ ID NO:53)

Clone 184.6.21 (HVR-H1 is SEQ ID NO:54; HVR-H2 is SEQ ID NO:55; HVR-H3 is SEQ ID NO:56; HVR-L1 is SEQ ID NO:57; HVR-L2 is SEQ ID NO:58; HVR-L3 is SEQ ID NO:59)

Clone 184.6.49 (HVR-H1 is SEQ ID NO:60; HVR-H2 is SEQ ID NO:61; HVR-H3 is SEQ ID NO:62; HVR-L1 is SEQ ID NO:63; HVR-L2 is SEQ ID NO:64; HVR-L3 is SEQ ID NO:65)

Clone 184.6.51 (HVR-H1 is SEQ ID NO:66; HVR-H2 is SEQ ID NO:67; HVR-H3 is SEQ ID NO:68; HVR-L1 is SEQ ID NO:69; HVR-L2 is SEQ ID NO:70; HVR-L3 is SEQ ID NO:71)

Clone 184.6.52 (HVR-H1 is SEQ ID NO:72; HVR-H2 is SEQ ID NO:73; HVR-H3 is SEQ ID NO:74; HVR-L1 is SEQ ID NO:75; HVR-L2 is SEQ ID NO:76; HVR-L3 is SEQ ID NO:77)

Clone 184.6.92 (HVR-H1 is SEQ ID NO:78; HVR-H2 is SEQ ID NO:79; HVR-H3 is SEQ ID NO:80; HVR-L1 is SEQ ID NO:81; HVR-L2 is SEQ ID NO:82; HVR-L3 is SEQ ID NO:83)

Clone 184.6.1.N54S (HVR-H1 is SEQ ID NO:84; HVR-H2 is SEQ ID NO:85; HVR-H3 is SEQ ID NO:86; HVR-L1 is SEQ ID NO:87; HVR-L2 is SEQ ID NO:88; HVR-L3 is SEQ ID NO:89)

Clone 184.6.1.N54G (HVR-H1 is SEQ ID NO:90; HVR-H2 is SEQ ID NO:91; HVR-H3 is SEQ ID NO:92; HVR-L1 is SEQ ID NO:93; HVR-L2 is SEQ ID NO:94; HVR-L3 is SEQ ID NO:95)

Clone 184.6.1.N54A (HVR-H1 is SEQ ID NO:96; HVR-H2 is SEQ ID NO:97; HVR-H3 is SEQ ID NO:98; HVR-L1 is SEQ ID NO:99; HVR-L2 is SEQ ID NO:100; HVR-L3 is SEQ ID NO:101)

Clone 184.6.1.N54Q (HVR-H1 is SEQ ID NO:102; HVR-H2 is SEQ ID NO:103; HVR-H3 is SEQ ID NO:104; HVR-L1 is SEQ ID NO:105; HVR-L2 is SEQ ID NO:106; HVR-L3 is SEQ ID NO:107)

Clone 184.6.58.N54S (HVR-H1 is SEQ ID NO:108; HVR-H2 is SEQ ID NO:109; HVR-H3 is SEQ ID NO:110; HVR-L1 is SEQ ID NO:111; HVR-L2 is SEQ ID NO:112; HVR-L3 is SEQ ID NO:113)

Clone 184.6.58.N54G (HVR-H1 is SEQ ID NO:114; HVR-H2 is SEQ ID NO:115; HVR-H3 is SEQ ID NO:116; HVR-L1 is SEQ ID NO:117; HVR-L2 is SEQ ID NO:118; HVR-L3 is SEQ ID NO:119)

Clone 184.6.58.N54A (HVR-H1 is SEQ ID NO:120; HVR-H2 is SEQ ID NO:121; HVR-H3 is SEQ ID NO:122; HVR-L1 is SEQ ID NO:123; HVR-L2 is SEQ ID NO:124; HVR-L3 is SEQ ID NO:125)

Clone 184.6.58.N54Q (HVR-H1 is SEQ ID NO:126; HVR-H2 is SEQ ID NO:127; HVR-H3 is SEQ ID NO:128; HVR-L1 is SEQ ID NO:129; HVR-L2 is SEQ ID NO:130; HVR-L3 is SEQ ID NO:131).

Clone 184.6.1.NS D30E (HVR-H1 is SEQ ID NO:143; HVR-H2 is SEQ ID NO:144; HVR-H3 is SEQ ID NO:145; HVR-L1 is SEQ ID NO:140; HVR-L2 is SEQ ID NO:141; HVR-L3 is SEQ ID NO:142).

Amino acid positions are numbered according to the Kabat numbering system as described below.

FIGS. 2A and 2B: depict (A) the amino acid sequences of the heavy chain variable regions and light chain variable regions of anti-FGFR3 antibodies 184.6.1.N54S, 184.6.58, and 184.6.62; and (B) the hypervariable regions of anti-FGFR3 antibodies 1G6, 6G1, and 15B2.

FIGS. 3A, 3B, and 4: depict exemplary acceptor human consensus framework sequences for use in practicing the instant invention with sequence identifiers as follows:

Variable Heavy (VH) Consensus Frameworks (FIG. 3a, 3b)

human VH subgroup I consensus framework minus Kabat CDRs (SEQ ID NOS:19 and 203-205)
human VH subgroup I consensus framework minus extended hypervariable regions (SEQ ID NOS:20 and 206-208, 21 and 209-211, 22 and 212-214)
human VH subgroup II consensus framework minus Kabat CDRs (SEQ ID NOS:23 and 215-217)
human VH subgroup II consensus framework minus extended hypervariable regions (SEQ ID NOS:24 and 218-220, 25 and 221-223, 26 and 224-226)
human VH subgroup II consensus framework minus extended
human VH subgroup III consensus framework minus Kabat CDRs (SEQ ID NOS:27 and 227-229)
human VH subgroup III consensus framework minus extended hypervariable regions (SEQ ID NOS:28 and 230-232, 29 and 233-235, 30 and 236-238)
human VH acceptor framework minus Kabat CDRs (SEQ ID NOS:31 and 239-241)
human VH acceptor framework minus extended hypervariable regions (SEQ ID NOS:32 and 242-244, 33 and 2245-247)
human VH acceptor 2 framework minus Kabat CDRs (SEQ ID NOS:34 and 248-250)
human VH acceptor 2 framework minus extended hypervariable regions (SEQ ID NOS:35 and 251-253, 36 and 254-256, 37 and 257-259)

Variable Light (VL) Consensus Frameworks (FIG. 4)

human VL kappa subgroup I consensus framework (SEQ ID NO:38 and 260-262)
human VL kappa subgroup II consensus framework (SEQ ID NO:39 and 263-265)
human VL kappa subgroup III consensus framework (SEQ ID NO:40 and 266-268)
human VL kappa subgroup IV consensus framework (SEQ ID NO:41 and 269-271)

FIG. 5: depicts framework region sequences of huMAb4D5-8 light (SEQ ID NOS:42-45) and heavy chains (SEQ ID NOS:46, 47, 175, 176). Numbers in superscript/bold indicate amino acid positions according to Kabat.

FIG. 6: depicts modified/variant framework region sequences of huMAb4D5-8 light (SEQ ID NOS:42, 43, 177, 45) and heavy chains (SEQ ID NOS:46, 47, 178, and 176). Numbers in superscript/bold indicate amino acid positions according to Kabat.

FIG. 7: FGFR3 knockdown in bladder cancer cell RT112 inhibits proliferation and induces G1 cell cycle arrest in vitro, and suppresses tumor growth in vivo. Three different FGFR3 shRNAs were cloned into a Tet-inducible expression vector. RT112 cells stably expressing FGFR3 shRNAs or a control shRNA were established with puromycin selection. (A) Representative blots showing FGFR3 expression in selected clones treated with or without doxycycline (Dox, 0, 0.1 and 1 μg/ml, left to right). (B) [$^3$H]-thymidine incorporation by RT112 stable cells. RT112 stable clones were cultured with or without 1 μg/ml doxycycline for 3 days prior to 16 hour-incubation with [$^3$H]-thymidine (1 μCi per well). Counts of incorporated [$^3$H]-thymidine were normalized to that from cells without doxycycline induction. Error bars represent SEM. (C) DNA fluorescence flow cytometry histograms of RT112 stable cells. RT112 clones expressing control shRNA or FGFR3 shRNA4 were cultured with or without 1 μg/ml doxycycline for 72 hours, and the nuclei were stained with propidium iodide (PI). Similar results were obtained for FGFR3 shRNA2 and 6 (FIG. 16). (D) The growth of RT112 cells expressing control shRNA (n=9 per treatment group) or FGFR3 shRNA4 (n=11 per treatment group) in mice. Mice were given 5% sucrose alone or supplemented with 1 mg/ml doxycycline, and tumor size was measured twice a week. Error bars represent SEM. Similar results were obtained for FGFR3 shRNA2 and 6 (FIG. 16). Lower panel: Expression of FGFR3 protein in tumor lysates extracted from control shRNA or FGFR3 shRNA4 stable cell xenograft tissues.

FIG. 8: R3M ab blocks FGF/FGFR3 interaction. (A) Selective binding of human FGFR3 by R3Mab. Human FGFR1-4 Fc chimeric proteins were immobilized and incubated with increasing amount of R3Mab. Specific binding was detected using an anti-human Fab antibody. (B-C) Blocking of FGF1 binding to human FGFR3-IIIb (B) or Inc (C) by R3Mab. Specific binding was detected by using a biotinylated FGF1-specific polyclonal antibody. (D-E) Blocking of FGF9 binding to human FGFR3-IIIb (D) or IIIc (E) by R3Mab. Specific binding was detected by using a biotinylated FGF9-specific polyclonal antibody. Error bars represent standard error of the mean (SEM) and are sometimes smaller than symbols.

FIG. 9: R3M ab inhibits Ba/F3 cell proliferation driven by wild type and mutated FGFR3. (A) Inhibitory effect of R3Mab on the viability of Ba/F3 cells expressing wild type human FGFR3-IIIb. Cells were cultured in medium without FGF1 (no FGF1), or in the presence of 10 ng/ml FGF1 plus 10 μg/ml heparin alone (FGF1), or in combination with a control antibody (Control) or R3Mab. Cell viability was assessed with CellTiter-Glo (Promega) after 72 hr incubation with antibodies. (B) Inhibition of FGFR3 and MAPK phosphorylation by R3Mab in Ba/F3-FGFR3—IIIb$^{WT}$ stable cells. Cells were treated with 15 ng/ml FGF1 and 10 μg/ml heparin (+) or heparin alone (−) for 10 minutes, following pre-incubation with a Control Ab (Ctrl), decreasing amount of R3Mab (1, 0,2, 0.04 μg/ml respectively) in PBS, or PBS alone (Mock) for 3 hours. Lysates were immunoblotted to assess phosphorylation of FGFR3 and p44/42 MAPK with antibodies to pFGFR$^{Y653/654}$ and pMAPK$^{Thr202/Tyr204}$ respectively. (C) Schematic representation of FGFR3 mutation hot spots and frequency in bladder cancer (sequence numbering depicted is based on the FGFR3 IIIb isoform amino acid sequence) based on published data (32). TM, transmembrane domain; TK1 and TK2, tyrosine kinase domain 1 and 2. (D-H) Inhibitory effect of R3Mab on the viability of Ba/F3 cells expressing cancer-associated FGFR3 mutants. G372C is derived from IIIc isoform, and the rest are derived from IIIb isoform. Sequence numbering for all mutants is based on the FGFR3 IIIb isoform amino acid sequence (including the G372C mutant, which would be numbered G370C based on the FGFR3 IIIc isoform amino acid sequence). Cell viability was assessed after 72 hour incubation with antibodies as described in (A). Error bars represent SEM.

FIG. 10: Epitope mapping for R3Mab and crystal structure of the complex between R3Mab Fab fragment and IgD2-D3 of human FGFR3-IIIb. (A) Epitope determined by the binding of 13 peptides spanning IgD2-D3 of human FGFR3 to R3Mab. Each biotinylated peptide was captured onto streptavidin-coated microtiter well and incubated with R3Mab. Specifically bound R3Mab was detected using a goat anti-human IgG antibody. (B) Sequence alignment of human FGFR3 peptides 3 (LAVPAANTVRFRCPA (SEQ ID NO:179) and 11 (SDVEFHCKVYSDAQP (SEQ ID NO:180) with extracellular segments of human FGFR1 (peptide 3: HAVPAAKTVKFKCPS (SEQ ID NO:181); peptide 11: SNVEFMCKVYSDPQP (SEQ ID NO:182)). FGFR1 residues engaged in the primary FGF2-FGFR1 interaction, heparin binding, and receptor-receptor association are shown in bold, italics, and underlined font, respectively. Functional assignment of FGFR1 residues is based on Plotnikov et al (34). (C) Structure of R3Mab Fab (shown in ribbon-helix, light chain grey, heavy chain black) in complex with human FGFR3 IgD2-D3 (shown in molecular surface, white). Receptor residues involved in ligand binding and dimerization are colored in grey/crosshatched and dark grey respectively based on Plotnikov et al (34). (D) The close-up of the crystal structure shows that CDR-H3 and —H2 from the Fab constitute the major interaction sites with IgD2 and IgD3 of FGFR3. (E) Superposition of FGFR3-IIIc-FGF1 complex (PDB code 1RY7) with FGFR3-IIIb-Fab complex. FGFR3-IIIc and FGF1 are colored in grey and dark grey respectively. FGFR3-IIIb is shown in white and the Fab is shown in light grey for light chain, dark grey for heavy chain. IgD2 was used as the anchor for superposition. Note the well-superposed IgD2 from both structures and the new conformation adopted by IgD3 of FGFR3-IIIb when bound by R3Mab. (F) Another representation of the superposition of FGFR3-IIIc-FGF1 complex (PDB code 1RY7) with FGFR3-IIIb-Fab complex. FGFR3-IIIc and FGF1 are shown as molecular surfaces that are grey/mesh texture and dark grey/dotted texture, respectively. FGFR3-IIIb is shown in white and the Fab is shown in grey for light chain, black for heavy chain. IgD2 was used as the anchor for superposition. Note the well-superposed IgD2 from both structures and the new conformation adopted by IgD3 of FGFR3-IIIb when bound by R3Mab.

FIG. 11: R3M ab inhibits proliferation, clonal growth and FGFR3 signaling in bladder cancer cells expressing wild type or mutated FGFR3$^{S249C}$. (A) Inhibition of [$^3$H]-thymidine incorporation by R3Mab in bladder cancer cell line RT112. Error bars represent SEM. (B) Blocking of FGF1-activated FGFR3 signaling by R3Mab (15 μg/ml) in bladder cancer cell line RT112 as compared to treatment medium alone (Mock) or a control antibody (Ctrl). Cell lysates were immunoprecipitated with anti-FGFR3 antibody and assessed for FGFR3 phosphorylation with an anti-phospho-tyrosine antibody (4G10). Lysates were immunoblotted to detect phosphorylation of AKT (pAKT$^{S473}$) and p44/42 MAPK (pMAPK$^{Thr202/Tyr204}$). (C) Inhibition of clonal growth by R3Mab (10 μg/ml) in bladder cancer cell line UMUC-14 (harboring FGFR3$^{S249C}$) as compared to treatment medium alone (Mock) or a control antibody (Ctrl). (D) Quantitation of the study in (C) reporting the number of colonies larger than 120 μm in diameter per well from a replicate of 12 wells. Error bars represent SEM. P<3.4×10$^{-9}$ versus Mock or Ctrl. (E) Inhibition of FGFR3 phosphorylation in UMUC-14 cells by R3Mab (15 μg/ml). FGFR3 phosphorylation was analyzed as in (B). Note constitutive phosphorylation of FGFR3 in this cell line.

FIG. 12: R3M ab decreases steady-state level of disulfide-linked FGFR3$^{S249C}$ dimer by driving the dimer-monomer equilibrium toward monomeric state. (A) Effect of R3Mab on FGFR3$^{S249C}$ dimer in UMUC-14 cells. Cells were incubated with R3Mab (15 μg/ml) or a control antibody (Ctrl) for 3 hours, and whole cell lysates were analyzed by immunoblot under non-reducing and reducing conditions. (B) Effect of free-sulfhydryl blocker DTNB on FGFR3$^{S249C}$ dimer-monomer equilibrium in UMUC-14 cells. UMUC-14 cells were treated with increasing concentration of DTNB for 3 hours, and cell lysates were analyzed as in (A). (C) Effect of R3Mab on purified recombinant FGFR3$^{S249C}$ dimer in vitro. FGFR3$^{S249C}$ dimer composed of IgD2-D3 was purified through size-exclusion column, and incubated with PBS (Mock), a control antibody (Ctrl), or R3Mab at 37° C. Samples were collected at indicated time for immunoblot analysis under non-reducing conditions. FGFR3 dimer-monomer was detected using anti-FGFR3 hybridoma antibody 6G1 (A-C).

FIG. 13: R3M ab inhibits xenograft growth of bladder cancer cells and allograft growth of Ba/F3-FGFR3$^{S249C}$ (A) Effect of R3Mab on the growth of pre-established RT112 bladder cancer xenografts compared with vehicle control. n=10 per group. (B) Inhibition of FGFR3 signaling in RT112 tumor tissues by R3Mab. In a separate experiment, RT112 xenograft tumors that were treated with 15 mg/kg of a control antibody (Ctrl) or R3Mab for 48 hours or 72 hours were collected (n=3 per group), homogenized and analyzed for FRS2α and MAPK activation by immunoblot. (C) Effect of R3Mab on the growth of pre-established Ba/F3-FGFR3$^{S249C}$ allografts. n=10 per group. (D) Effect of R3Mab on the growth of pre-established UMUC-14 bladder cancer xenografts, n=10 per group. (E) Effect of R3Mab on FGFR3$^{S249C}$ dimer and signaling in UMUC-14 tumor tissues. UMUC-14 xenograft tumors that were treated with 30 mg/kg of a control antibody (Ctrl) or R3Mab for 24 hours or 72 hours were collected (n=3 per group), homogenized, and analyzed for FGFR3$^{S249C}$ dimer-monomer as well as MAPK activation by immunoblot. FGFR3 dimer-monomer was detected using an anti-FGFR3 rabbit polyclonal antibody sc9007 to avoid interference from mouse IgG in tumor lysates. Error bars represent SEM.

FIG. 14: ADCC contributes to the anti-tumor efficacy of R3Mab in t(4;14) positive multiple myeloma models. (A-B) Effect of R3Mab on the growth of pre-established OPM2 (A) and KMS11 (B) myeloma xenografts. n=10 per group. (C—F) Cytolysis of myeloma cell lines OPM2 (C) and KMS11 (D), or bladder cancer cell lines RT112 (E) and UMUC-14 (F) induced by R3Mab in cell culture. Myeloma or bladder cancer cells were incubated with freshly isolated human PBMC in the presence of R3Mab or a control antibody. Cytotoxicity was determined by measuring LDH released in the supernatant. (G-H) Effect of R3Mab or its DANA mutant on the growth of pre-established OPM2 (G) and KMS11 (H) myeloma xenografts. n=10 per group. Error bars represent SEM and are sometimes smaller than symbols.

FIG. 15: Knockdown of FGFR3 with siRNA inhibits cell proliferation of bladder cancer cell lines. Six to seven different FGFR3 siRNAs and three non-specific control siRNAs were designed and synthesized in Genentech. Bladder cancer cell lines RT112 (A), SW780 (B), RT4 (C) and UMUC-14 (D) were plated into 96-well plate (3000 cells per well) and allowed to attach overnight, and transiently transfected with 25 nM siRNA in complex with RNAiMax (Invitrogen). 72 hr post-transfection, [$^3$H]-thymidine (1 μCi per well) was added to the culture (A, C, and D) for another 16 hour incubation. Incorporated [$^3$H]-thymidine was quantitated with TopCount. Data were normalized to that from cells transfected with RNAiMax alone (Mock). Error bars represent SEM. Lower panel: Representative blots showing FGFR3 expression in siRNA transfected cells. (B) Cell viability was measured with CellTiter-Glo (Promega) 96 hours after transfection. Error bars represent SEM.

FIG. 16: FGFR3 knockdown in bladder cancer cell line RT112 induces G1 cell cycle arrest in vitro, and suppresses tumor growth in vivo. Three different FGFR3RNAs were designed and cloned into a Tet-inducible shRNA expression retroviral vector. RT112 stable clones expressing FGFR3 shRNAs or control shRNA were established with puromycin selection. (A) DNA fluorescence flow cytometry histograms of propidium iodide (PI)-stained nuclei obtained from RT112 stable cells expressing FGFR3 shRNA2 or shRNA6 following treatment with or without 1 μg/ml doxycycline for 72 hours. (B) The growth of RT112 stable cells expressing FGFR3 shRNA2-4 (n=11 per treatment group) or FGFR3shRNA6-16 (n=10 per treatment group) in nu/nu mice. Tumor bearing mice received 5% sucrose only (solid circle) or 5% sucrose plus 1 mg/ml doxycycline (solid square), and tumors were measured with calipers twice a week. Error bars represent SEM.

Figure 17:
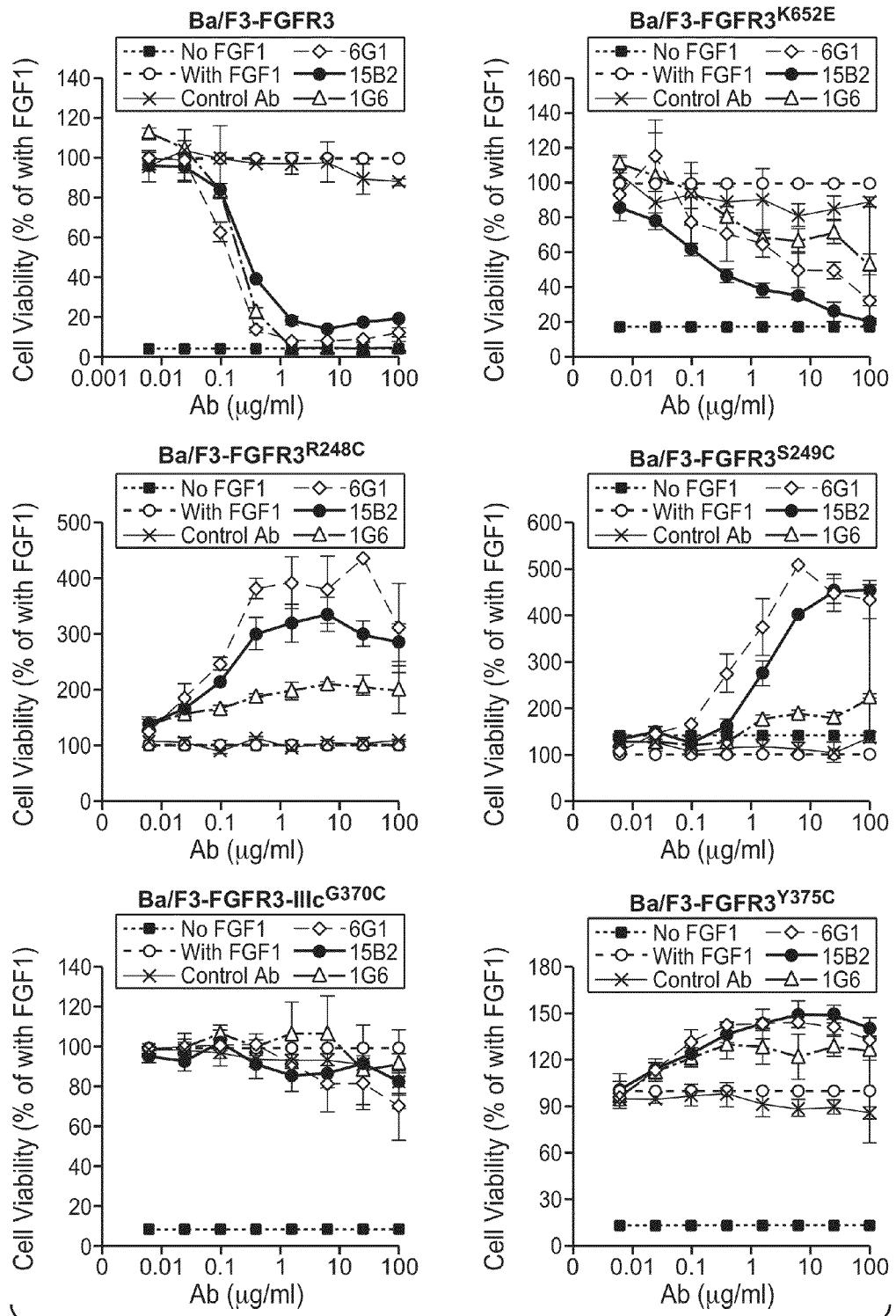

FIG. 17: Effect of anti-FGFR3 hybridoma antibodies 16G, 6G1 and 15B2 on Ba/F3 cell proliferation driven by wild type and mutated FGFR3. Anti-FGFR3 hybridoma antibodies were generated by immunizing BALB/c mice with human FGFR3-IIIb/Fc or human FGFR3-IIIc/Fc chimera. Fused hybridoma cells were selected using hypoxanthin-aminopterin-thymidine selection in Medium D from the ClonaCell® hybridoma selection kit (StemCell Technologies, Inc., Vancouver, BC, Canada). Hybridoma antibodies were sequentially screened for their ability to bind to FGFR3-IIIb and FGFR3-IIIc by ELISA and to recognize cell surface FGFR3 by FACS. Selected hybridomas were then cloned by limiting dilution. 16G, 6G1 and 15B2 are clones used to assess the effect on the proliferation of Ba/F3 cells expressing wild type or mutated FGFR3 similarly as described in FIG. 9A. Error bars represent SEM.

Figure 18A:
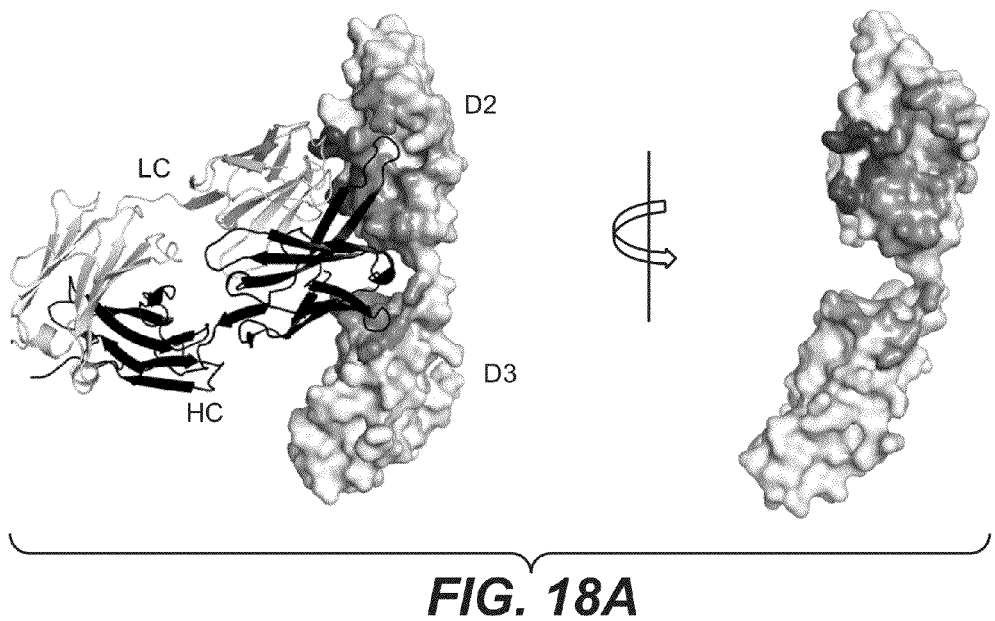
Figure 18B:
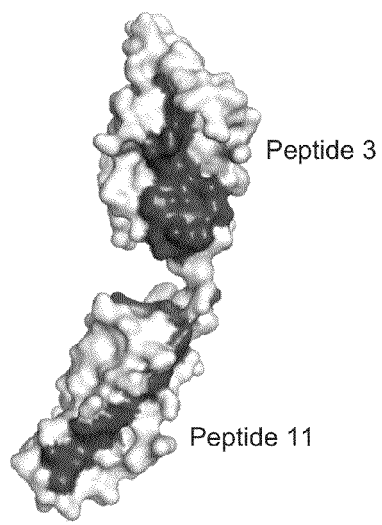

FIG. 18: Comparison of R3Mab epitopes determined by peptide mapping and crystal structure analysis. (A) Epitope revealed by the structure of the R3Mab Fab fragment in complex with the extracellular IgD2-D3 segment of human FGFR3. FGFR3 residues contacted by Fab heavy chain and light chain are colored in black and grey, respectively. (B) Location of peptides 3 and 11 on FGFR3.

FIG. 19: R3M ab inhibits proliferation and FGFR3 signaling in bladder cancer cells containing wild type or mutated FGFR3$^{S249C}$. (A) Inhibition of cell viability by R3Mab in bladder cancer cell line RT4. Cell viability was assessed with CellTiter-Glo (Promega) after 96 hr incubation with the antibody. Error bars represent SEM. (B) Blocking of FGF1-activated FGFR3 signaling by R3Mab (15 ug/ml) in bladder cancer cell line RT4. (C) Inhibition of [$^{31}$-1]-thymidine incorporation by R3Mab in bladder cancer cell line RCC-97-7 (containing FGFR3$^{S249C}$). Error bars represent SEM. (D) Inhibition of FGFR3 phosphorylation in TCC-97-7 cells by R3Mab (15 ug/ml). (E) Decrease of FGFR3$^{S249C}$ dimer in TCC-97-7 cells after 3 hours incubation with R3Mab (15 ug/ml) compared with a control antibody (Ctrl).

Figure 20A:
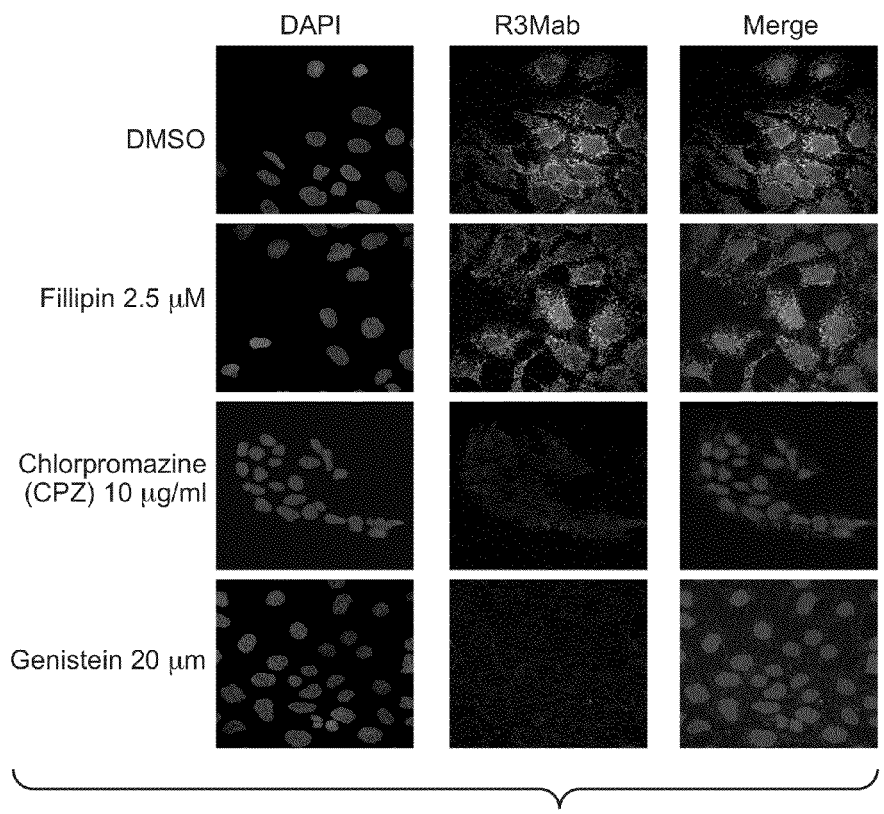
Figure 20B:
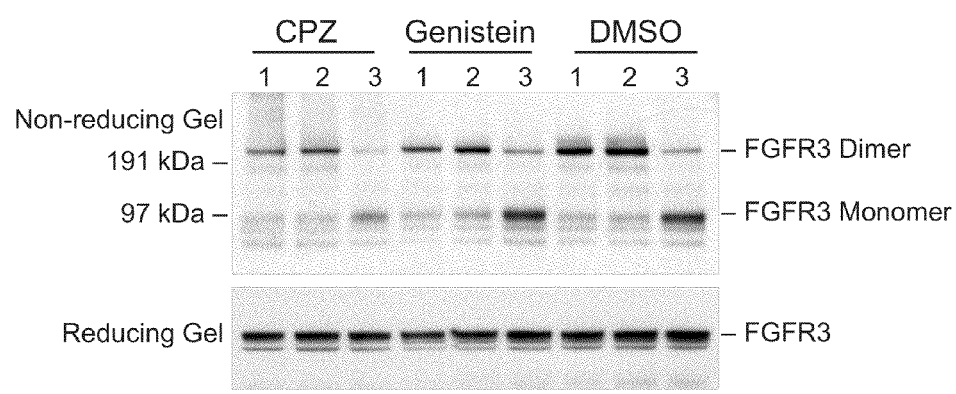

FIG. 20: Effect of endocytosis inhibitors on the internalization of R3Mab and FGFR3$^{S249C}$ dimer in UMUC-14 cells. (A) Effect of endocytosis inhibitors on the internalization of R3Mab. UMUC-14 cells, pre-treated with various endocytosis inhibitor or DMSO for 1 hour at 37° C., were incubated with R3Mab (15 ug/ml) for 3 hours at 37° C. to allow internalization. A low pH wash was used to remove cell surface R3Mab to visualize internalized antibody. Cells were fixed and stained with Alexa 488-labeled anti-human IgG. Image was taken using confocal microscopy. (B) Effect of endocytosis inhibitors on FGFR3$^{S249C}$ dimer in UMUC-14 cells treated with R3Mab. UMUC-14 cells, pre-treated with various endocytosis inhibitor or DMSO for 1 hour at 37° C., were incubated with mock (Lane 1), a control antibody (Lane 2), or R3Mab (15 ug/ml, Lane 3) for 3 hours at 37° C. Cell lysates were analyzed for FGFR3 protein under non-reducing or reducing conditions by immunoblot. Note that chlorpromazine (inhibitor of clathrin-mediated endocytosis) and genistein (pan-inhibitor of endocytosis) blocked R3Mab internalization, but had no effect on R3Mab-induced decrease of FGFR3$^{S249C}$ dimer.

Figure 21:
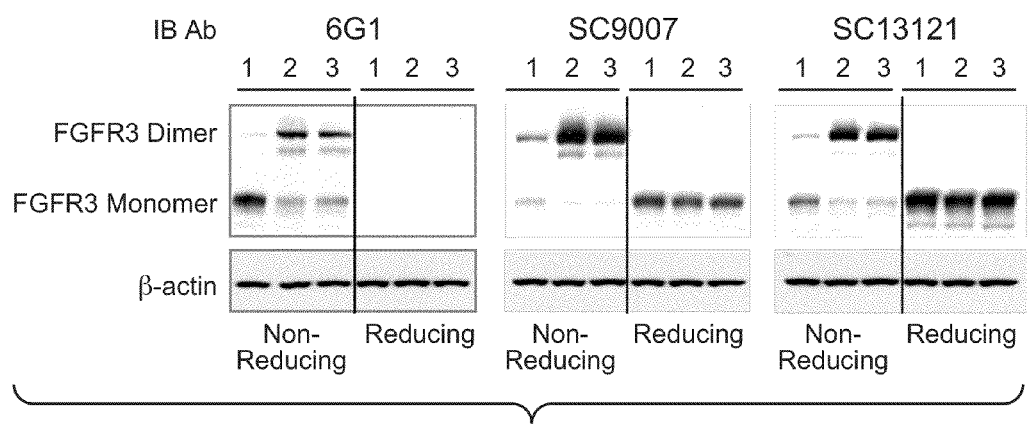

FIG. 21: Detection sensitivity of different anti-FGFR3 antibodies toward monomeric and dimeric FGFR3$^{S249C}$ under non-reducing conditions. UMUC-14 cells were lysed after treatment with R3Mab (Lane 1), a control IgG1 (Lane 2), or PBS (Lane 3) for 3 hours, and cell lysates were subject to immunoblot analyses under reducing or non-reducing conditions. Note that 6G1 (murine hybridoma antibody generated at Genentech) detected both FGFR3$^{S249C}$ dimer and monomer, whereas sc9007 (rabbit polyclonal antibody, Santa Cruz Biotechnology) or sc13121 (murine hybridoma antibody, Santa Cruz Biotechnology) preferentially detected the dimeric FGFR3$^{S249C}$ FIG. 22: Effect of R3Mab on the proliferation of t(4;14)+ multiple myeloma cells. (A) Inhibitory effect of R3Mab on [$^3$H]-thymidine incorporation by UTMC-2 cells. UTMC-2 cells were grown in medium containing R3Mab or a control antibody in the presence of 25 ng/ml FGF9 and 5 ug/ml heparin or heparin alone (No FGF9). After 6 days incubation, [$^3$H]-thymidine was added for 16 hr incubation. Data were normalized to that from cells grown in the absence of FGF9 and antibody. (B-C) Effect of R3Mab on [$^3$H]-thymidine incorporation by OPM2 (B) and KMS11 (C) cells. Cells grown in 1.5% FBS medium were treated with R3Mab or a control antibody for 6 days. Data were normalized to that from untreated cells. Error bars represent SEM.

Figure 23A:
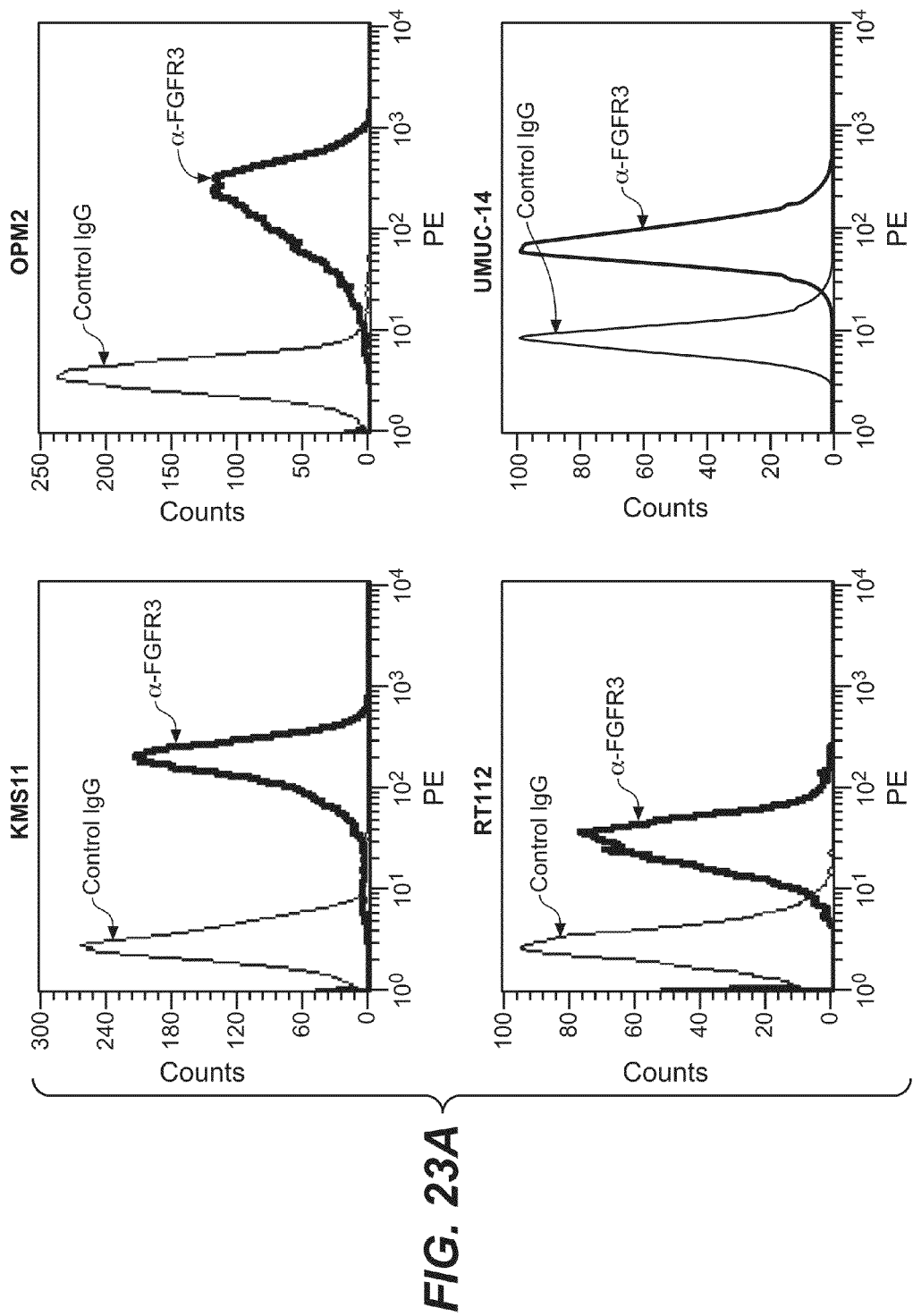
Figure 23B:
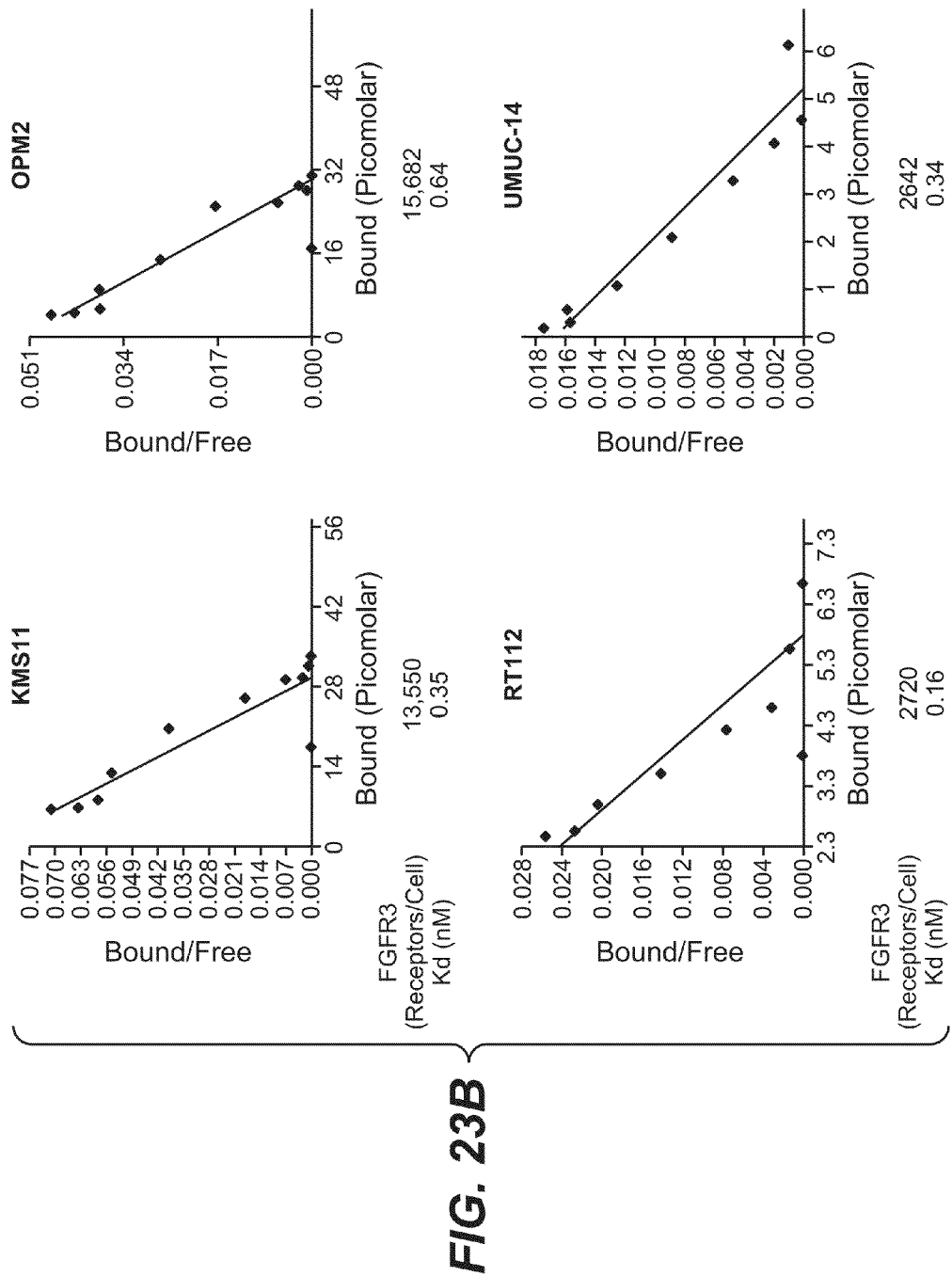

FIG. 23: Cell surface expression levels of FGFR3 in myeloma and bladder cancer cells. (A) Cell surface FGFR3 expression in myeloma cells and bladder cancer cells assessed by FACS analysis. Cells were stained with phycoerythin-conjugated mouse mAb against human FGFR3 (FAB766P, R&D Systems) or phycoerythin-conjugated isotype control mouse IgG1(BD Pharmingen). (B) Scatchard analysis of FGFR3 density in myeloma cells and bladder cancer cells. R3Mab was radioiodinated, and incubated with cells in suspension with excess unlabeled antibody. After incubation at RT for 2 hours, cells were pelleted by centrifugation and washed twice. Specifically bound $^{125}I$ was determined. Receptor density and binding affinity (Kd) represent the mean from two binding experiments.

Figure 24A:
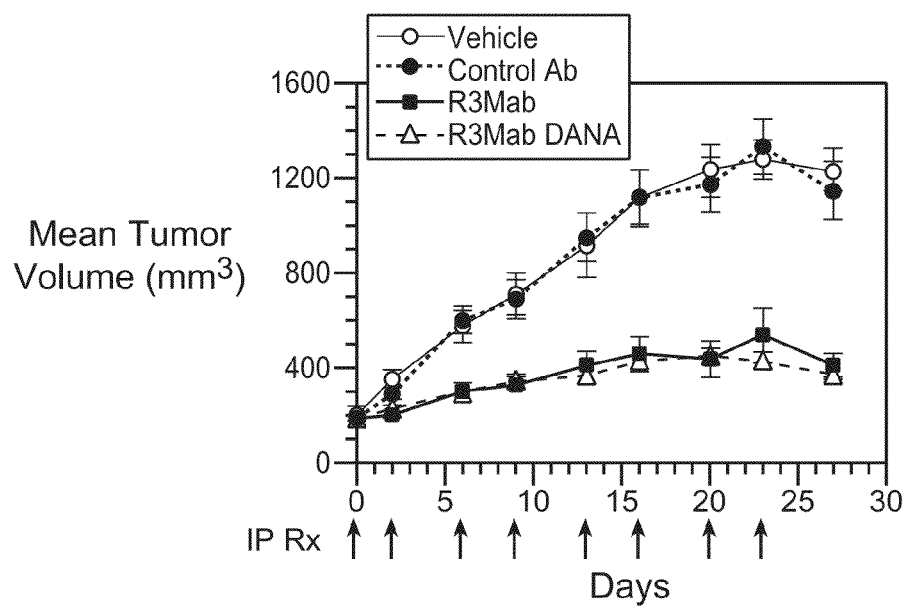
Figure 24B:
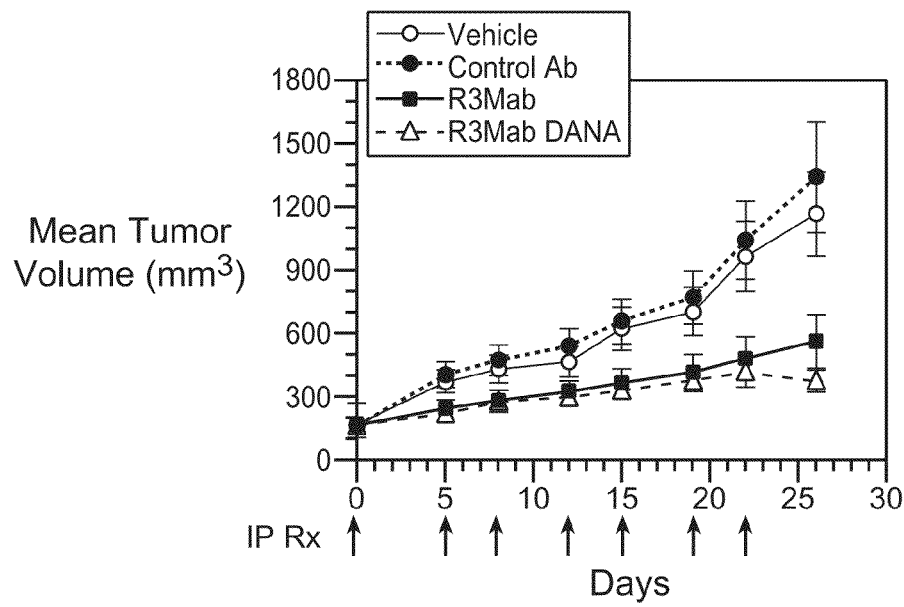

FIG. 24: Effect of R3Mab or its DANA mutant on xenograft growth of bladder carcinoma cells. (A) Effect of R3Mab and its DANA mutant (50 mg/kg each) on the growth of pre-established RT112 tumors. (B) Effect of R3Mab and its DANA mutant (50 mg/kg each) on the growth of pre-established UMUC-14 tumors. Error bars represent SEM.

DETAILED DESCRIPTION OF THE INVENTION

The invention herein provides anti-FGFR3 antibodies that are useful for, e.g., treatment or prevention of disease states associated with expression and/or activity of FGFR3, such as increased expression and/or activity or undesired expression and/or activity. In some embodiments, the antibodies of the invention are used to treat a tumor, a cancer, and/or a cell proliferative disorder.

In another aspect, the anti-FGFR3 antibodies of the invention find utility as reagents for detection and/or isolation of FGFR3, such as detection of FGFR3 in various tissues and cell type.

The invention further provides methods of making and using anti-FGFR3 antibodies, and polynucleotides encoding anti-FGFR3 antibodies.

General Techniques

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE (sodium dodecyl sulfate polyacrylamide gel electrophoresis) under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the nucleic acid (for example, an antibody encoding nucleic acid) where, for example, the nucleic acid molecule is in a chromosomal location different from that of natural cells.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Desirably the Kd is $1\times10^{-7}$, $1\times10^{-8}$, $5\times10^{-8}$, $1\times10^{-9}$, $3\times10^{-9}$, $5\times10^{-9}$, or even $1\times10^{-10}$ or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol. 293: 865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 μM or 26 μM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 μg/ml (~0.2 μM) before injection at a flow rate of 5W/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. In some embodiments, the following modifications are used for the surface Plasmon resonance assay method: antibody is immobilized to CM5 biosensor chips to achieve approximately 400 RU, and for kinetic measurements, two-fold serial dilutions of target protein (e.g., FGFR3-IIIb or -IIIc) (starting from 67 nM) are injected in PBST buffer at 25° C. with a flow rate of about 30 ul/minute. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol. 293: 865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 μg/ml (~0.2 uM) before injection at a flow rate of 5 μl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. In some embodiments, the following modifications are used for the surface Plasmon resonance assay method: antibody is immobilized to CM5 biosensor chips to achieve approximately 400 RU, and for kinetic measurements, two-fold serial dilutions of target protein (e.g., FGFR3-IIIb or -IIIc) (starting from 67 nM) are injected in PBST buffer at 25° C. with a flow rate of about 30 ul/minute. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) J. Mol. Biol. 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table A below. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in, e.g., WO2007/001851. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In some embodiments, two or more amino acid sequences are at least 50%, 60%, 70%, 80%, or 90% identical. In some embodiments, two or more amino acid sequences are at least 95%, 97%, 98%, 99%, or even 100% identical. Unless specifically stated otherwise, all % amino acid sequence identity values used herein are obtained as described in the immediately preceding paragraph using the ALIGN-2 computer program.

The term "FGFR3," as used herein, refers, unless specifically or contextually indicated otherwise, to any native or variant (whether native or synthetic) FGFR3 polypeptide (e.g., FGFR3-IIIb isoform or FGFR3-IIIc isoform). The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type FGFR3" generally refers to a polypeptide comprising an amino acid sequence of a naturally occurring FGFR3 protein. The term "wild type FGFR3 sequence" generally refers to an amino acid sequence found in a naturally occurring FGFR3.

The term "FGFR3 ligand," (interchangeably termed "FGF") as used herein, refers, unless specifically or contextually indicated otherwise, to any native or variant (whether native or synthetic) FGFR3 ligand (for example, FGF1, FGF2, FGF4, FGF8, FGF9, FGF17, FGF18, FGF23) polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type FGFR3 ligand" generally refers to a polypeptide comprising an amino acid sequence of a naturally occurring FGFR3 ligand protein. The term "wild type FGFR3 ligand sequence" generally refers to an amino acid sequence found in a naturally occurring FGFR3 ligand.

"FGFR3 activation" refers to activation, or phosphorylation, of the FGFR3 receptor. Generally, FGFR3 activation results in signal transduction (e.g. that caused by an intracellular kinase domain of a FGFR3 receptor phosphorylating tyrosine residues in FGFR3 or a substrate polypeptide). FGFR3 activation may be mediated by FGFR ligand binding to a FGFR3 receptor of interest. FGFR3 ligand (e.g., such as FGF1 or FGF9) binding to FGFR3 may activate a kinase domain of FGFR3 and thereby result in phosphorylation of tyrosine residues in the FGFR3 and/or phosphorylation of tyrosine residues in additional substrate polypeptides(s).

The term "constitutive" as used herein, as for example applied to receptor kinase activity, refers to continuous signaling activity of a receptor that is not dependent on the presence of a ligand or other activating molecules. Depending on the nature of the receptor, all of the activity may be constitutive or the activity of the receptor may be further activated by the binding of other molecules (e.g. ligands). Cellular events that lead to activation of receptors are well known among those of ordinary skill in the art. For example, activation may include oligomerization, e.g., dimerization, trimerization, etc., into higher order receptor complexes. Complexes may comprise a single species of protein, i.e., a homomeric complex. Alternatively, complexes may comprise at least two different protein species, i.e., a heteromeric complex. Complex formation may be caused by, for example, overexpression of normal or mutant forms of receptor on the surface of a cell. Complex formation may also be caused by a specific mutation or mutations in a receptor.

The term "ligand-independent" as used herein, as for example applied to receptor signaling activity, refers to signaling activity that is not dependent on the presence of a ligand. A receptor having ligand-independent kinase activity will not necessarily preclude the binding of ligand to that receptor to produce additional activation of the kinase activity.

The term "ligand-dependent" as used herein, as for example applied to receptor signaling activity, refers to signaling activity that is dependent on the presence of a ligand.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

A "tyrosine kinase inhibitor" is a molecule which inhibits to some extent tyrosine kinase activity of a tyrosine kinase such as a FGFR3 receptor.

A cancer or biological sample which "displays FGFR3 expression, amplification, or activation" is one which, in a diagnostic test, expresses (including overexpresses) FGFR3, has amplified FGFR3 gene, and/or otherwise demonstrates activation or phosphorylation of a FGFR3.

A cancer or biological sample which "displays FGFR3 activation" is one which, in a diagnostic test, demonstrates activation or phosphorylation of FGFR3. Such activation can be determined directly (e.g. by measuring FGFR3 phosphorylation by ELISA) or indirectly.

A cancer or biological sample which "displays constitutive FGFR3 activation" is one which, in a diagnostic test, demonstrates constitutive activation or phosphorylation of a FGFR3. Such activation can be determined directly (e.g. by measuring c-FGFR3 phosphorylation by ELISA) or indirectly.

A cancer or biological sample which "displays FGFR3 amplification" is one which, in a diagnostic test, has amplified FGFR3 gene.

A cancer or biological sample which "displays FGFR3 translocation" is one which, in a diagnostic test, has translocated FGFR3 gene. An example of a FGFR3 translocation is the t(4;14) translocation, which occurs in some multiple myeloma tumors.

A "phospho-ELISA assay" herein is an assay in which phosphorylation of one or more FGFR3, substrate or downstream signaling molecules is evaluated in an enzyme-linked immunosorbent assay (ELISA) using a reagent, usually an antibody, to detect phosphorylated FGFR3, substrate, or downstream signaling molecule. In some embodiments, an antibody which detects phosphorylated FGFR3 or pMAPK is used. The assay may be performed on cell lysates, preferably from fresh or frozen biological samples.

A cancer or biological sample which "displays ligand-independent FGFR3 activation" is one which, in a diagnostic test, demonstrates ligand-independent activation or phosphorylation of a FGFR3. Such activation can be determined directly (e.g. by measuring FGFR3 phosphorylation by ELISA) or indirectly.

A cancer or biological sample which "displays ligand-dependent FGFR3 activation" is one which, in a diagnostic test, demonstrates ligand-dependent activation or phosphorylation of a FGFR3. Such activation can be determined directly (e.g. by measuring FGFR3 phosphorylation by ELISA) or indirectly.

A cancer or biological sample which "displays ligand-independent FGFR3 activation" is one which, in a diagnostic test, demonstrates ligand-independent activation or phosphorylation of a FGFR3. Such activation can be determined directly (e.g. by measuring FGFR3 phosphorylation by ELISA) or indirectly.

A cancer cell with "FGFR3 overexpression or amplification" is one which has significantly higher levels of a FGFR3 protein or gene compared to a noncancerous cell of the same tissue type. Such overexpression may be caused by gene amplification or by increased transcription or translation. FGFR3 overexpression or amplification may be determined in a diagnostic or prognostic assay by evaluating increased levels of the FGFR3 protein present on the surface of a cell (e.g. via an immunohistochemistry assay; IHC). Alternatively, or additionally, one may measure levels of FGFR3-encoding nucleic acid in the cell, e.g. via fluorescent in situ hybridization (FISH; see WO98/45479 published October, 1998), southern blotting, or polymerase chain reaction (PCR) techniques, such as quantitative real time PCR (qRT-PCR). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

The term "mutation", as used herein, means a difference in the amino acid or nucleic acid sequence of a particular protein or nucleic acid (gene, RNA) relative to the wild-type protein or nucleic acid, respectively. A mutated protein or nucleic acid can be expressed from or found on one allele (heterozygous) or both alleles (homozygous) of a gene, and may be somatic or germ line. In the instant invention, mutations are generally somatic. Mutations include sequence rearrangements such as insertions, deletions, and point mutations (including single nucleotide/amino acid polymorphisms).

To "inhibit" is to decrease or reduce an activity, function, and/or amount as compared to a reference.

An agent possesses "agonist activity or function" when an agent mimics at least one of the functional activities of a polypeptide of interest (e.g., FGFR ligand, such as FGF1 or FGF9).

An "agonist antibody", as used herein, is an antibody which mimics at least one of the functional activities of a polypeptide of interest (e.g., FGFR ligand, such as FGF1 or FGF9).

Protein "expression" refers to conversion of the information encoded in a gene into messenger RNA (mRNA) and then to the protein.

Herein, a sample or cell that "expresses" a protein of interest (such as a FGF receptor or FGF receptor ligand) is one in which mRNA encoding the protein, or the protein, including fragments thereof, is determined to be present in the sample or cell.

An "immunoconjugate" (interchangeably referred to as "antibody-drug conjugate," or "ADC") means an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. The Fc sequence of an immunoglobulin generally comprises two constant domains, a CH2 domain and a CH3 domain, and optionally comprises a CH4 domain. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

By "Fc polypeptide" herein is meant one of the polypeptides that make up an Fc region. An Fc polypeptide may be obtained from any suitable immunoglobulin, such as IgG$_1$, IgG$_2$, IgG$_3$, or IgG$_4$ subtypes, IgA, IgE, IgD or IgM. In some embodiments, an Fc polypeptide comprises part or all of a wild type hinge sequence (generally at its N terminus). In some embodiments, an Fc polypeptide does not comprise a functional or wild type hinge sequence.

A "blocking" antibody or an antibody "antagonist" is one which inhibits or reduces biological activity of the antigen it binds. Preferred blocking antibodies or antagonist antibodies completely inhibit the biological activity of the antigen.

A "naked antibody" is an antibody that is not conjugated to a heterologous molecule, such as a cytotoxic moiety or radiolabel.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule (e.g., Ghetie et al., *Ann. Rev. Immunol.* 18:739-766 (2000), Table 1). Antibodies with substitutions in an Fc region thereof and increased serum half-lives are also described in WO00/42072, WO 02/060919; Shields et al., *J. Biol. Chem.* 276: 6591-6604 (2001); Hinton, *J. Biol. Chem.* 279:6213-6216 (2004)). In another embodiment, the serum half-life can also be increased, for example, by attaching other polypeptide sequences. For example, antibodies or other polypeptides useful in the methods of the invention can be attached to serum albumin or a portion of serum albumin that binds to the FcRn receptor or a serum albumin binding peptide so that serum albumin binds to the antibody or polypeptide, e.g., such polypeptide sequences are disclosed in WO01/45746. In one preferred embodiment, the serum albumin peptide to be attached comprises an amino acid sequence of DICLPRWG-CLW (SEQ ID NO:183). In another embodiment, the half-life of a Fab is increased by these methods. See also, Dennis et al. *J. Biol. Chem.* 277:35035-35043 (2002) for serum albumin binding peptide sequences.

By "fragment" is meant a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment may contain 10, 20, 30, 40, 50, 60, 70, 80, 90, or 100, 200, 300, 400, 500, 600, or more nucleotides or 10, 20, 30, 40, 50, 60, 70, 80, 90, 100, 120, 140, 160, 180, 190, 200 amino acids or more.

The phrase "little to no agonist function" with respect to an antibody of the invention, as used herein, means the antibody does not elicit a biologically meaningful amount of agonist activity, e.g., upon administration to a subject. As would be understood in the art, amount of an activity may be determined quantitatively or qualitatively, so long as a comparison between an antibody of the invention and a reference counterpart can be done. The activity can be measured or detected according to any assay or technique known in the art, including, e.g., those described herein. The amount of activity for an antibody of the invention and its reference counterpart can be determined in parallel or in separate runs. In some embodiments, a bivalent antibody of the invention does not possess substantial agonist function.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured using techniques known in the art, for instance, by cell viability assays, FACS analysis or DNA electrophoresis, and more specifically by binding of annexin V, fragmentation of DNA, cell shrinkage, dilation of endoplasmatic reticulum, cell fragmentation, and/or formation of membrane vesicles (called apoptotic bodies).

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized, and/or affinity matured.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known. "Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region," "HVR," or "HV," when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). Humanized antibody as used herein is a subset of chimeric antibodies.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al., Proc Nat. Acad. Sci, USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., PNAS (USA) 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulates homeostasis of immunoglobulins. WO 00/42072 (Presta) describes antibody variants with improved or diminished binding to FcRs. The content of that patent publication is specifically incorporated herein by reference. See, also, Shields et al., *J. Biol. Chem.* 9(2): 6591-6604 (2001).

Methods of measuring binding to FcRn are known (see, e.g., Ghetie 1997, Hinton 2004). Binding to human FcRn in vivo and serum half life of human FcRn high affinity binding polypeptides can be assayed, e.g, in transgenic mice or transfected human cell lines expressing human FcRn, or in primates administered with the Fc variant polypeptides.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551B1 and WO 99/51642. The contents of those patent publications are specifically incorporated herein by reference. See, also, Idusogie et al., *J. Immunol.* 164:4178-4184 (2000).

The term "Fc region-comprising polypeptide" refers to a polypeptide, such as an antibody or immunoadhesin, which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two, or one of positions 71H, 73H, and 78H; for instance, the amino acid residues at those positions may be 71A, 73T, and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences: EVQLVESGGGLVQPGGSL-RLSCAAS (SEQ ID NO:184)-H1-WVRQAPGKGLEWV (SEQ ID NO:185)-H2-RFTISRDNSKNTLYLQMNSL-RAEDTAVYYC (SEQ ID NO:186)-H3-WGQGTLVTVSS (SEQ ID NO:187).

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

DIQMTQSPSSLSASVGDRVTITC- (SEQ ID NO: 188)

L1-WYQQKPGKAPKLLIY- (SEQ ID NO: 189)

L2-GVPSRFSGSGSGTDFTLTISSLQPEDFATYYC- (SEQ ID NO: 190)

L3-FGQGTKVEIK. (SEQ ID NO: 191)

As used herein, "antibody mutant" or "antibody variant" refers to an amino acid sequence variant of an antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; carcinoma, blastoma, and sarcoma.

"Treatment" refers to both therapeutic treatment and prophylactic or preventative measures. Those in need of treatment include those already having a benign, pre-cancerous, or non-metastatic tumor as well as those in which the occurrence or recurrence of cancer is to be prevented.

The term "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, I, or II cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer and multiple myeloma.

The term "pre-cancerous" refers to a condition or a growth that typically precedes or develops into a cancer. A "pre-cancerous" growth will have cells that are characterized by abnormal cell cycle regulation, proliferation, or differentiation, which can be determined by markers of cell cycle regulation, cellular proliferation, or differentiation.

By "dysplasia" is meant any abnormal growth or development of tissue, organ, or cells. Preferably, the dysplasia is high grade or precancerous.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass.

Both stimulatory and inhibitory molecular pathways within the tumor cell regulate this behavior, and interactions between the tumor cell and host cells in the distant site are also significant.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

By "primary tumor" or "primary cancer" is meant the original cancer and not a metastatic lesion located in another tissue, organ, or location in the subject's body.

By "benign tumor" or "benign cancer" is meant a tumor that remains localized at the site of origin and does not have the capacity to infiltrate, invade, or metastasize to a distant site.

By "tumor burden" is meant the number of cancer cells, the size of a tumor, or the amount of cancer in the body. Tumor burden is also referred to as tumor load.

By "tumor number" is meant the number of tumors.

By "subject" is meant a mammal, including, but not limited to, a human or non-human mammal, such as a bovine, equine, canine, ovine, or feline. Preferably, the subject is a human.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib. Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$, $Re^{186}$), chemotherapeutic agents, and toxins such as enzymatically active toxins of bacterial, fungal, plant or animal origin, or fragments thereof A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1 I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimeterxate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; VELCADE bortezomib; REVLIMID lenalidomide; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON• toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

A "biological sample" (interchangeably termed "sample" or "tissue or cell sample") encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the individual. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g., a thin slice of tissue or cells cut from a tissue sample. It is understood that multiple sections of tissue samples may be taken and subjected to analysis according to the present invention. In some embodiments, the same section of tissue sample is analyzed at both morphological and molecular levels, or is analyzed with respect to both protein and nucleic acid.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

Compositions and Methods of the Invention

This invention encompasses compositions, including pharmaceutical compositions, comprising an anti-FGFR3 antibody; and polynucleotides comprising sequences encoding an anti-FGFR3 antibody. As used herein, compositions comprise one or more antibodies that bind to FGFR3, and/or one or more polynucleotides comprising sequences encoding one or more antibodies that bind to FGFR3. These compositions may further comprise suitable carriers, such as pharmaceutically acceptable excipients including buffers, which are well known in the art.

The invention also encompasses isolated antibody and polynucleotide embodiments. The invention also encompasses substantially pure antibody and polynucleotide embodiments.

The invention also encompasses method of treating a disorder, e.g. multiple myeloma or transitional stage carcinoma (e.g., invasive transitional stage carcinoma) using an anti-FGFR3 antibody (as described herein or as known in the art).

Compositions

The anti-FGFR3 antibodies of the invention are preferably monoclonal. Also encompassed within the scope of the invention are Fab, Fab', Fab'-SH and F(ab')$_2$ fragments of the anti-FGFR3 antibodies provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-FGFR3 monoclonal antibodies of the invention can be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to FGFR3 may be raised in animals by multiple subcutaneous (sc) or intraperitoneal (ip) injections of FGFR3 and an adjuvant. FGFR3 may be prepared using methods well-known in the art, some of which are further described herein. For example, recombinant production of human and mouse FGFR3 is described below. In one embodiment, animals are immunized with a FGFR3 fused to the Fc portion of an immunoglobulin heavy chain. In a preferred embodiment, animals are immunized with a FGFR3-IgG1 fusion protein. Animals ordinarily are immunized against immunogenic conjugates or derivatives of FGFR3 with monophosphoryl lipid A (MPL)/trehalose dicrynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for anti-FGFR3 titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications, pp.* 51-63 (Marcel Dekker, Inc., New York, 1987)).

Culture medium in which hybridoma cells are growing is assayed for production of monoclonal antibodies directed against FGFR3. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The anti-FGFR3 antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-FGFR3 antibodies of the invention can be obtained by designing a suitable antigen screening procedure to select for the phage clone of interest followed by construction of a full length anti-FGFR3 antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g., as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g., as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-FGFR3 clones is desired, the individual is immunized with FGFR3 to generate an antibody response, and spleen cells and/or circulating B cells other peripheral blood lymphocytes (PBLs) are recovered for library construction. In a preferred embodiment, a human antibody gene fragment library biased in favor of anti-FGFR3 clones is obtained by generating an anti-FGFR3 antibody response in transgenic mice carrying a functional human immunoglobulin gene array (and lacking a functional endogenous antibody production system) such that FGFR3 immunization gives rise to B cells producing human antibodies against FGFR3. The generation of human antibody-producing transgenic mice is described below.

Additional enrichment for anti-FGFR3 reactive cell populations can be obtained by using a suitable screening procedure to isolate B cells expressing FGFR3-specific membrane bound antibody, e.g., by cell separation with FGFR3 affinity chromatography or adsorption of cells to fluorochrome-labeled FGFR3 followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which FGFR3 is not antigenic. For libraries incorporating in vitro antibody gene construction, stem cells are harvested from the individual to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (*USA*), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci.* (*USA*), 86: 5728-5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128:119-126 (1993), or in vivo by combinatorial infection, e.g., the loxP system described in Waterhouse et al., *Nucl. Acids Res.*, 21:2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g., as described in Barbas et al., *Proc. Natl. Acad. Sci. USA*, 88:7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20:3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutations can be introduced at random in vitro by using error-prone polymerase (reported in Leung et al., *Technique*, 1:11-15 (1989)) in the method of Hawkins et al., *J. Mol. Biol.*, 226: 889-896 (1992) or in the method of Gram et al., *Proc. Natl. Acad. Sci. USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 96/07754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10:779-783 (1992). This technique allows the production of antibodies and antibody fragments with affinities in the $10^{-9}$ M range.

FGFR3 nucleic acid and amino acid sequences are known in the art. Nucleic acid sequence encoding the FGFR3 can be designed using the amino acid sequence of the desired region of FGFR3. As is well-known in the art, there are two major splice isoforms of FGFR3, FGFR3 IIIb and FGFR3 IIIc. FGFR3 sequences are well-known in the art and may include the sequence of UniProKB/Swiss-Prot accession number P22607 (FGFR3 IIIc) or P22607_2 (FGFR3 IIIb). FGFR3 mutations have been identified and are well-known in the art and include the following mutations (with reference to the sequences shown in UniProKB/Swiss-Prot accession number P22607 (FGFR3 IIIc) or P22607_2 (FGFR3 IIIb):

| FGFR3-IIIb | FGFR3 IIIc |
|---|---|
| R248C | R248C |
| S249C | S249C |
| G372C | G370C |
| Y375C | Y373C |
| G382R | G380R |
| K652E | K650E |

Nucleic acids encoding FGFR3 can be prepared by a variety of methods known in the art. These methods include, but are not limited to, chemical synthesis by any of the methods described in Engels et al., *Agnew. Chem. Int. Ed. Engl.*, 28: 716-734 (1989), such as the triester, phosphite, phosphoramidite and H-phosphonate methods. In one embodiment, codons preferred by the expression host cell are used in the design of the FGFR3 encoding DNA. Alternatively, DNA encoding the FGFR3 can be isolated from a genomic or cDNA library.

Following construction of the DNA molecule encoding the FGFR3, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells. Suitable vectors for expression in prokaryotic and eukaryotic host cells are known in the art and some are further described herein. Eukaryotic organisms, such as yeasts, or cells derived from multicellular organisms, such as mammals, may be used.

Optionally, the DNA encoding the FGFR3 is operably linked to a secretory leader sequence resulting in secretion of the expression product by the host cell into the culture medium. Examples of secretory leader sequences include stII, ecotin, lamB, herpes GD, 1pp, alkaline phosphatase, invertase, and alpha factor. Also suitable for use herein is the 36 amino acid leader sequence of protein A (Abrahmsen et al., *EMBO J.*, 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell. Methods for transfection are well known in the art, and some are further described herein.

Transformation means introducing DNA into an organism so that the DNA is replicable, either as an extrachromosomal element or by chromosomal integrant. Depending on the host cell used, transformation is done using standard techniques appropriate to such cells. Methods for transformation are well known in the art, and some are further described herein.

Prokaryotic host cells used to produce the FGFR3 can be cultured as described generally in Sambrook et al., supra.

The mammalian host cells used to produce the FGFR3 can be cultured in a variety of media, which is well known in the art and some of which is described herein.

The host cells referred to in this disclosure encompass cells in in vitro culture as well as cells that are within a host animal.

Purification of FGFR3 may be accomplished using art-recognized methods, some of which are described herein.

The purified FGFR3 can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Attachment of the FGFR3 protein to the matrix can be accomplished by the methods described in *Methods in Enzymology*, vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, FGFR3 can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized FGFR3 under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA*, 88: 7978-7982 (1991), or by alkali, e.g. as described in Marks et al., *J. Mol. Biol.*, 222: 581-597 (1991), or by FGFR3 antigen competition, e.g. in a procedure similar to the antigen competition method of Clackson et al., *Nature*, 352: 624-628 (1991). Phages can be enriched 20-1.000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for FGFR3. However, random mutation of a selected antibody (e.g. as performed in some of the affinity maturation techniques described above) is likely to give rise to many mutants, most binding to antigen, and a few with higher affinity. With limiting FGFR3, rare high affinity phage could be competed out. To retain all the higher affinity mutants, phages can be incubated with excess biotinylated FGFR3, but with the biotinylated FGFR3 at a concentration of lower molarity than the target molar affinity constant for FGFR3. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

FGFR3 clones may be activity selected. In one embodiment, the invention provides FGFR3 antibodies that block the binding between a FGFR3 receptor and its ligand (such as FGF1 and/or FGF9). Fv clones corresponding to such FGFR3 antibodies can be selected by (1) isolating FGFR3 clones from a phage library as described above, and optionally amplifying the isolated population of phage clones by growing up the population in a suitable bacterial host; (2) selecting FGFR3 and a second protein against which blocking and non-blocking activity, respectively, is desired; (3) adsorbing the anti-FGFR3 phage clones to immobilized FGFR3; (4) using an excess of the second protein to elute any undesired clones that recognize FGFR3-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the hybridoma-derived monoclonal antibodies or phage display Fv clones of the invention is readily isolated and sequenced using conventional procedures (e.g., by using oligonucleotide primers designed to specifically amplify the heavy and light chain coding regions of interest from hybridoma or phage DNA template). Once isolated, the DNA can be placed into expression vectors, which are then transfected into host cells such as $E.$ $coli$ cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., $Curr.$ $Opinion$ $in$ $Immunol.,$ 5: 256 (1993) and Pluckthun, $Immunol.$ $Revs,$ 130:151 (1992).

DNA encoding the Fv clones of the invention can be combined with known DNA sequences encoding heavy chain and/or light chain constant regions (e.g., the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-FGFR3 antibody derived from a hybridoma of the invention can also be modified, for example, by substituting the coding sequence for human heavy- and light-chain constant domains in place of homologous murine sequences derived from the hybridoma clone (e.g., as in the method of Morrison et al., $Proc.$ $Natl.$ $Acad.$ $Sci.$ $USA,$ 81:6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from $E.$ $coli,$ thus allowing the facile production of large amounts of these fragments. Antibody fragments can be isolated from the antibody phage libraries discussed above. Alternatively, Fab'-SH fragments can be directly recovered from $E.$ $coli$ and chemically coupled to form $F(ab')_2$ fragments (Carter et al., Bio/Technology 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv) (see, e.g., WO 93/16185; U.S. Pat. Nos. 5,571,894 and 5,587,458). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody," e.g., as described, for example, in U.S. Pat. No. 5,641,870. Such linear antibody fragments may be monospecific or bispecific.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) $Nature$ 321:522-525; Riechmann et al. (1988) $Nature$ 332:323-327; Verhoeyen et al. (1988) $Science$ 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA,* 89:4285; Presta et al. (1993) *J. Immunol.,* 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-FGFR3 antibodies of the invention can be constructed by combining Fv clone variable domain sequence(s) selected from human-derived phage display libraries with known human constant domain sequences(s) as described above. Alternatively, human monoclonal anti-FGFR3 antibodies of the invention can be made by the hybridoma method. Human myeloma and mouse-human heteromyeloma cell lines for the production of human monoclonal antibodies have been described, for example, by Kozbor *J. Immunol.,* 133:3001 (1984); Brodeur et al., *Monoclonal Antibody Production Techniques and Applications,* pp. 51-63 (Marcel Dekker, Inc., New York, 1987); and Boerner et al., *J. Immunol.,* 147:86 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90: 2551 (1993); Jakobovits et al., *Nature,* 362: 255 (1993); Bruggermann et al., *Year in Immunol.,* 7:33 (1993).

Gene shuffling can also be used to derive human antibodies from non-human, e.g., rodent, antibodies, where the human antibody has similar affinities and specificities to the starting non-human antibody. According to this method, which is also called "epitope imprinting," either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal, preferably human or humanized, antibodies that have binding specificities for at least two different antigens. In the present case, one of the binding specificities is for FGFR3 and the other is for any other antigen. Exemplary bispecific antibodies may bind to two different epitopes of the FGFR3. Bispecific antibodies may also be used to localize cytotoxic agents to cells which express FGFR3. These antibodies possess an FGFR3-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature,* 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.,* 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336: 1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8,knockout CHO cells (Yamane-Ohnuki et al. Biotech. Bioeng. 87: 614 (2004)).

Another type of variant is an amino acid substitution variant. These variants have at least one amino acid (at leat two, at leat three, at least 4 or more) residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions." If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: Cys, Ser, Thr, Asn, Gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, e.g., in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter *Nature* 322:738-40 (1988); U.S. Pat. Nos. 5,648,260; 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al., *J. Immunol.* 164: 4178-4184 (2000).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Screening for Antibodies with Desired Properties

The antibodies of the present invention can be characterized for their physical/chemical properties and biological functions by various assays known in the art (some of which are disclosed herein). In some embodiments, antibodies are characterized for any one or more of reduction or blocking of FGF (such as FGF1 and/or FGF9) binding, reduction or blocking of FGFR3 activation, reduction or blocking of FGFR3 downstream molecular signaling, disruption or blocking of FGFR3 binding to a ligand (e.g., FGF1, FGF9), reduction or blocking of FGFR3 dimerization, promotion of formation of monomeric FGFR3, binding to monomeric FGFR3, and/or treatment and/or prevention of a tumor, cell proliferative disorder or a cancer; and/or treatment or prevention of a disorder associated with FGFR3 expression and/or activity (such as increased FGFR3 expression and/or activity). In some embodiments, the antibodies are screened for increased FGFR3 activation, increased FGFR3 downstream molecule signaling, apoptotic activity, FGFR3 down-regulation, and effector function (e.g., ADCC activity).

The purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibodies produced herein are analyzed for their biological activity. In some embodiments, the antibodies of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Illustrative antigen binding and other assay are provided below in the Examples section.

If an anti-FGFR3 antibody that inhibits cell growth is desired, the candidate antibody can be tested in in vitro and/or in vivo assays that measure inhibition of cell growth. If an anti-FGFR3 antibody that does or does not promote apoptosis is desired, the candidate antibody can be tested in assays that measure apoptosis. Methods for examining growth and/or proliferation of a cancer cell, or determining apoptosis of a cancer cell are well known in the art and some are described and exemplified herein. Exemplary methods for determining cell growth and/or proliferation and/or apoptosis include, for example, BrdU incorporation assay, MTT, [3H]-thymidine incorporation (e.g., TopCount assay (PerkinElmer)), cell viability assays (e.g., CellTiter-Glo (Promega)), DNA fragmentation assays, caspase activation assays, tryptan blue exclusion, chromatin morphology assays and the like.

In one embodiment, the present invention contemplates an antibody that possesses effector functions. In certain embodiments, the Fc activities of the antibody are measured. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu Rev. Immunol 9:457-92 (1991). An example of an in vitro assay to assess ADCC activity of a molecule of interest is described in U.S. Pat. Nos. 5,500,362 or 5,821,337. An assay to detect ADCC activity is also exemplified herein. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g., as described in Gazzano-Santoro et al., J. Immunol. Methods 202:163 (1996), may be performed. FcRn binding and in vivo clearance/half life determinations can also be performed using methods known in the art, e.g., those described in the Examples section.

If an anti-FGFR3 antibody that binds monomeric FGFR3 is desired, the candidate antibody can be tested in assays (such as in vitro assays) that measure binding to monomeric FGFR3 and promotion of the formation of monomeric FGFR3. Such assays are known in the art and some assays are described and exemplified herein.

If an anti-FGFR3 antibody that inhibits FGFR3 dimerization is desired, the candidate antibody can be tested in dimerization assays, e.g., as described and exemplified herein.

In some embodiments, the FGFR3 agonist function of the candidate antibody is determined. Methods for assessing agonist function or activity of FGFR3 antibodies are known in the art and some are also described and exemplified herein.

In some embodiments, ability of an FGFR3 antibody to promote FGFR3 receptor down-regulation is determined, e.g., using methods described and exemplified herein. In one embodiment, FGFR3 antibody is incubated with suitable test cells, e.g., bladder cancer cell lines (e.g., RT112), and after a suitable period of time, cell lysates are harvested and examined for total FGFR3 levels. FACS analysis may also be used to examine surface FGFR3 receptor levels following incubation with candidate FGFR3 antibodies Vectors, Host Cells, and Recombinant Methods For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:

i. Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al., (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA, and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB- strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli*λ 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275: 17106-17113; Arie et al., (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some *E. coli* protease-deficient strains are available and described in, for example, Joly et al., (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41kD cell wall protein from *Staphylococcus aureas* which binds with a high affinity to the Fc region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention also provides immunoconjugates (interchangeably termed "antibody-drug conjugates" or "ADC"), comprising any of the anti-FGFR3 antibodies described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e., drugs to kill or inhibit tumor cells in the treatment of cancer (Syrigos and Epenetos (1999) Anticancer Research 19:605-614; Niculescu-Duvaz and Springer (1997) Adv. Drg. Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al., (2000) Bioorganic & Med. Chem. Letters 10:1025-1028; Mandler et al., (2002) Bioconjugate Chem. 13:786-791), maytansinoids (EP 1391213; Liu et al., (1996) Proc. Natl. Acad. Sci. USA 93:8618-8623), and calicheamicin (Lode et al., (1998) Cancer Res. 58:2928; Hinman et al., (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al., (2000) Eur. Jour. Nucl. Med. 27(7):766-77; Wiseman et al., (2002) Blood 99(12):4336-42; Witzig et al., (2002) J. Clin. Oncol. 20(10):2453-63; Witzig et al., (2002) J. Clin. Oncol. 20(15):3262-69). Although ZEVA- LIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,6937,62; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al., (2003) Nature Biotechnology 21(7):778-784) and are under therapeutic development.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC 1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and dolastatins

In some embodiments, the immunoconjugate comprises an antibody of the invention conjugated to dolastatins or dolastatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al., (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., (1989) J. Am. Chem. Soc. 111:5463-5465; Pettit et al., (1998) Anti-Cancer Drug Design 13:243-277; Pettit, G. R., et al., Synthesis, 1996, 719-725; and Pettit et al., (1996) J. Chem. Soc. Perkin Trans. 1 5:859-863. See also Doronina (2003) Nat. Biotechnol. 21(7):778-784; "Monomethylvaline Compounds Capable of Conjugation to Ligands," U.S. Ser. No. 10/983, 340, filed Nov. 5, 2004, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712, 374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other cytotoxic agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc$^{99m}$ or I$^{123}$, Re$^{186}$, Re$^{188}$ and In$^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab-(L-D)_p \quad\quad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands," U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

Methods Using Anti-FGFR3 Antibodies

The present invention features the use of an FGFR3 antibody as part of a specific treatment regimen intended to provide a beneficial effect from the activity of this therapeutic agent. The present invention is particularly useful in treating cancers of various types at various stages.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from the original site and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade, and cancer cells are described as being well-differentiated (low grade), moderately-differentiated, poorly-differentiated, or undifferentiated (high grade). Well-differentiated cells are quite normal appearing and resemble the normal cells from which they originated. Undifferentiated cells are cells that have become so abnormal that it is no longer possible to determine the origin of the cells.

Cancer staging systems describe how far the cancer has spread anatomically and attempt to put patients with similar prognosis and treatment in the same staging group. Several tests may be performed to help stage cancer including biopsy and certain imaging tests such as a chest x-ray, mammogram, bone scan, CT scan, and MRI scan. Blood tests and a clinical evaluation are also used to evaluate a patient's overall health and detect whether the cancer has spread to certain organs.

To stage cancer, the American Joint Committee on Cancer first places the cancer, particularly solid tumors, in a letter category using the TNM classification system. Cancers are designated the letter T (tumor size), N (palpable nodes), and/or M (metastases). T1, T2, T3, and T4 describe the increasing size of the primary lesion; N0, N1, N2, N3 indicates progressively advancing node involvement; and M0 and M1 reflect the absence or presence of distant metastases.

In the second staging method, also known as the Overall Stage Grouping or Roman Numeral Staging, cancers are divided into stages 0 to IV, incorporating the size of primary lesions as well as the presence of nodal spread and of distant metastases. In this system, cases are grouped into four stages denoted by Roman numerals I through IV, or are classified as "recurrent." For some cancers, stage 0 is referred to as "in situ" or "T is," such as ductal carcinoma in situ or lobular carcinoma in situ for breast cancers. High grade adenomas can also be classified as stage 0. In general, stage I cancers are small localized cancers that are usually curable, while stage IV usually represents inoperable or metastatic cancer. Stage II and III cancers are usually locally advanced and/or exhibit involvement of local lymph nodes. In general, the higher stage numbers indicate more extensive disease, including greater tumor size and/or spread of the cancer to nearby lymph nodes and/or organs adjacent to the primary tumor. These stages are defined precisely, but the definition is different for each kind of cancer and is known to the skilled artisan.

Many cancer registries, such as the NCI's Surveillance, Epidemiology, and End Results Program (SEER), use summary staging. This system is used for all types of cancer. It groups cancer cases into five main categories:

In situ is early cancer that is present only in the layer of cells in which it began.

Localized is cancer that is limited to the organ in which it began, without evidence of spread.

Regional is cancer that has spread beyond the original (primary) site to nearby lymph nodes or organs and tissues.

Distant is cancer that has spread from the primary site to distant organs or distant lymph nodes.

Unknown is used to describe cases for which there is not enough information to indicate a stage.

In addition, it is common for cancer to return months or years after the primary tumor has been removed. Cancer that recurs after all visible tumor has been eradicated, is called recurrent disease. Disease that recurs in the area of the primary tumor is locally recurrent, and disease that recurs as metastases is referred to as a distant recurrence.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia) or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further divided into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors. Other examples of tumors are described in the Definitions section.

In some embodiments, the patient herein is subjected to a diagnostic test e.g., prior to and/or during and/or after therapy. Generally, if a diagnostic test is performed, a sample may be obtained from a patient in need of therapy. Where the subject has cancer, the sample may be a tumor sample, or other biological sample, such as a biological fluid, including, without limitation, blood, urine, saliva, ascites fluid, or derivatives such as blood serum and blood plasma, and the like.

The biological sample herein may be a fixed sample, e.g. a formalin fixed, paraffin-embedded (FFPE) sample, or a frozen sample.

Various methods for determining expression of mRNA or protein include, but are not limited to, gene expression profiling, polymerase chain reaction (PCR) including quantitative real time PCR (qRT-PCR), microarray analysis, serial analysis of gene expression (SAGE), MassARRAY, Gene Expression Analysis by Massively Parallel Signature Sequencing (MPSS), proteomics, immunohistochemistry (IHC), etc. Preferably mRNA is quantified. Such mRNA analysis is preferably performed using the technique of polymerase chain reaction (PCR), or by microarray analysis. Where PCR is employed, a preferred form of PCR is quantitative real time PCR (qRT-PCR). In one embodiment, expression of one or more of the above noted genes is deemed positive expression if it is at the median or above, e.g. compared to other samples of the same tumor-type. The median expression level can be determined essentially contemporaneously with measuring gene expression, or may have been determined previously.

The steps of a representative protocol for profiling gene expression using fixed, paraffin-embedded tissues as the RNA source, including mRNA isolation, purification, primer extension and amplification are given in various published journal articles (for example: Godfrey et al. *J. Molec. Diagnostics* 2: 84-91 (2000); Specht et al., *Am. J. Pathol.* 158: 419-29 (2001)). Briefly, a representative process starts with cutting about 10 microgram thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by PCR. Finally, the data are analyzed to identify the best treatment option(s) available to the patient on the basis of the characteristic gene expression pattern identified in the tumor sample examined.

Detection of gene or protein expression may be determined directly or indirectly.

One may determine expression or translocation or amplification of FGFR3 in the cancer (directly or indirectly). Various diagnostic/prognostic assays are available for this. In one embodiment, FGFR3 overexpression may be analyzed by IHC. Parafin embedded tissue sections from a tumor biopsy may be subjected to the IHC assay and accorded a FGFR3 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

In some embodiments, those tumors with 0 or 1+ scores for FGFR3 overexpression assessment may be characterized as not overexpressing FGFR3, whereas those tumors with 2+ or 3+ scores may be characterized as overexpressing FGFR3.

In some embodiments, tumors overexpressing FGFR3 may be rated by immunohistochemical scores corresponding to the number of copies of FGFR3 molecules expressed per cell, and can been determined biochemically:

0=0-90 copies/cell,
1+=at least about 100 copies/cell,
2+=at least about 1000 copies/cell,
3+=at least about 10,000 copies/cell.

Alternatively, or additionally, FISH assays may be carried out on formalin-fixed, paraffin-embedded tumor tissue to determine the presence or and/or extent (if any) of FGFR3 amplification or translocation in the tumor.

FGFR3 activation may be determined directly (e.g., by phospho-ELISA testing, or other means of detecting phosphorylated receptor) or indirectly (e.g., by detection of activated downstream signaling pathway components, detection of receptor dimers (e.g., homodimers, heterodimers), detection of gene expression profiles and the like.

Similarly, constitutive FGFR3 and/or ligand-independent or ligand-dependent FGFR3 may be detected directly or indirectly (e.g., by detection of receptor mutations correlated with constitutive activity, by detection of receptor amplification correlated with constitutive activity and the like).

Methods for detection of nucleic acid mutations are well known in the art. Often, though not necessarily, a target nucleic acid in a sample is amplified to provide the desired amount of material for determination of whether a mutation is present. Amplification techniques are well known in the art. For example, the amplified product may or may not encompass all of the nucleic acid sequence encoding the protein of interest, so long as the amplified product comprises the particular amino acid/nucleic acid sequence position where the mutation is suspected to be.

In one example, presence of a mutation can be determined by contacting nucleic acid from a sample with a nucleic acid probe that is capable of specifically hybridizing to nucleic acid encoding a mutated nucleic acid, and detecting said hybridization. In one embodiment, the probe is detectably labeled, for example with a radioisotope ($^3$H, $^{32}$P, $^{33}$P etc), a fluorescent agent (rhodamine, fluorescene etc.) or a chromogenic agent. In some embodiments, the probe is an antisense oligomer, for example PNA, morpholino-phosphoramidates, LNA or 2'-alkoxyalkoxy. The probe may be from about 8 nucleotides to about 100 nucleotides, or about 10 to about 75, or about 15 to about 50, or about 20 to about 30. In another aspect, nucleic acid probes of the invention are provided in a kit for identifying FGFR3 mutations in a sample, said kit comprising an oligonucleotide that specifically hybridizes to or adjacent to a site of mutation in the nucleic acid encoding FGFR3. The kit may further comprise instructions for treating patients having tumors that contain FGFR3 mutations with a FGFR3 antagonist based on the result of a hybridization test using the kit.

Mutations can also be detected by comparing the electrophoretic mobility of an amplified nucleic acid to the electrophoretic mobility of corresponding nucleic acid encoding wild-type FGFR3. A difference in the mobility indicates the presence of a mutation in the amplified nucleic acid sequence. Electrophoretic mobility may be determined by any appropriate molecular separation technique, for example on a polyacrylamide gel.

Nucleic acids may also be analyzed for detection of mutations using Enzymatic Mutation Detection (EMD) (Del Tito et al, Clinical Chemistry 44:731-739, 1998). EMD uses the bacteriophage resolvase $T_4$ endonuclease VII, which scans along double-stranded DNA until it detects and cleaves structural distortions caused by base pair mismatches resulting from nucleic acid alterations such as point mutations, insertions and deletions. Detection of two short fragments formed by resolvase cleavage, for example by gel eletrophoresis, indicates the presence of a mutation. Benefits of the EMD method are a single protocol to identify point mutations, deletions, and insertions assayed directly from amplification reactions, eliminating the need for sample purification, shortening the hybridization time, and increasing the signal-to-noise ratio. Mixed samples containing up to a 20-fold excess of normal nucleic acids and fragments up to 4 kb in size can been assayed. However, EMD scanning does not identify particular base changes that occur in mutation positive samples, therefore often requiring additional sequencing procedures to identify the specific mutation if necessary. CEL I enzyme can be used similarly to resolvase T$_4$ endonuclease VII, as demonstrated in U.S. Pat. No. 5,869,245.

Another simple kit for detecting mutations is a reverse hybridization test strip similar to Haemochromatosis StripAssay™(Viennalabs world wide web bamburghmarrsh.com/pdf/4220.pdf) for detection of multiple mutations in HFE, TFR2 and FPN1 genes causing Haemochromatosis. Such an assay is based on sequence specific hybridization following amplification by PCR. For single mutation assays, a microplate-based detection system may be applied, whereas for multi-mutation assays, test strips may be used as "macro-arrays". Kits may include ready-to use reagents for sample prep, amplification and mutation detection. Multiplex amplification protocols provide convenience and allow testing of samples with very limited volumes. Using the straightforward StripAssay format, testing for twenty and more mutations may be completed in less than five hours without costly equipment. DNA is isolated from a sample and the target nucleic acid is amplified in vitro (e.g., by PCR) and biotin-labelled, generally in a single ("multiplex") amplification reaction. The amplification products are then selectively hybridized to oligonucleotide probes (wild-type and mutant specific) immobilized on a solid support such as a test strip in which the probes are immobilized as parallel lines or bands. Bound biotinylated amplicons are detected using streptavidin-alkaline phosphatase and color substrates. Such an assay can detect all or any subset of the mutations of the invention. With respect to a particular mutant probe band, one of three signaling patterns are possible: (i) a band only for wild-type probe which indicates normal nucleic acid sequence, (ii) bands for both wild-type and a mutant probe which indicates heterozygous genotype, and (iii) band only for the mutant probe which indicates homozygous mutant genotype. Accordingly, in one aspect, the invention provides a method of detecting mutations of the invention comprising isolating and/or amplifying a target FGFR3 nucleic acid sequence from a sample, such that the amplification product comprises a ligand, contacting the amplification product with a probe which comprises a detectable binding partner to the ligand and the probe is capable of specifically hydribizing to a mutation of the invention, and then detecting the hybridization of said probe to said amplification product. In one embodiment, the ligand is biotin and the binding partner comprises avidin or streptavidin. In one embodiment, the binding partner comprises steptavidin-alkaline which is detectable with color substrates. In one embodiment, the probes are immobilized for example on a test strip wherein probes complementary to different mutations are separated from one another. Alternatively, the amplified nucleic acid is labelled with a radioisotope in which case the probe need not comprise a detectable label.

Alterations of a wild-type gene encompass all forms of mutations such as insertions, inversions, deletions, and/or point mutations. In one embodiment, the mutations are somatic. Somatic mutations are those which occur only in certain tissues, e.g., in the tumor tissue, and are not inherited in the germ line. Germ line mutations can be found in any of a body's tissues.

A sample comprising a target nucleic acid can be obtained by methods well known in the art, and that are appropriate for the particular type and location of the tumor. Tissue biopsy is often used to obtain a representative piece of tumor tissue. Alternatively, tumor cells can be obtained indirectly in the form of tissues/fluids that are known or thought to contain the tumor cells of interest. For instance, samples of lung cancer lesions may be obtained by resection, bronchoscopy, fine needle aspiration, bronchial brushings, or from sputum, pleural fluid or blood. Mutant genes or gene products can be detected from tumor or from other body samples such as urine, sputum or serum. The same techniques discussed above for detection of mutant target genes or gene products in tumor samples can be applied to other body samples. Cancer cells are sloughed off from tumors and appear in such body samples. By screening such body samples, a simple early diagnosis can be achieved for diseases such as cancer. In addition, the progress of therapy can be monitored more easily by testing such body samples for mutant target genes or gene products.

Means for enriching a tissue preparation for tumor cells are known in the art. For example, the tissue may be isolated from paraffin or cryostat sections. Cancer cells may also be separated from normal cells by flow cytometry or laser capture microdissection. These, as well as other techniques for separating tumor from normal cells, are well known in the art. If the tumor tissue is highly contaminated with normal cells, detection of mutations may be more difficult, although techniques for minimizing contamination and/or false positive/negative results are known, some of which are described hereinbelow. For example, a sample may also be assessed for the presence of a biomarker (including a mutation) known to be associated with a tumor cell of interest but not a corresponding normal cell, or vice versa.

Detection of point mutations in target nucleic acids may be accomplished by molecular cloning of the target nucleic acids and sequencing the nucleic acids using techniques well known in the art. Alternatively, amplification techniques such as the polymerase chain reaction (PCR) can be used to amplify target nucleic acid sequences directly from a genomic DNA preparation from the tumor tissue. The nucleic acid sequence of the amplified sequences can then be determined and mutations identified therefrom. Amplification techniques are well known in the art, e.g., polymerase chain reaction as described in Saiki et al., Science 239:487, 1988; U.S. Pat. Nos. 4,683,203 and 4,683,195.

It should be noted that design and selection of appropriate primers are well established techniques in the art.

The ligase chain reaction, which is known in the art, can also be used to amplify target nucleic acid sequences. See, e.g., Wu et al., Genomics, Vol. 4, pp. 560-569 (1989). In addition, a technique known as allele specific PCR can also be used. See, e.g., Ruano and Kidd, Nucleic Acids Research, Vol. 17, p. 8392, 1989. According to this technique, primers are used which hybridize at their 3' ends to a particular target nucleic acid mutation. If the particular mutation is not present, an amplification product is not observed. Amplification Refractory Mutation System (ARMS) can also be used, as disclosed in European Patent Application Publication No. 0332435, and in Newton et al., Nucleic Acids Research, Vol. 17, p. 7, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Single stranded conformation polymorphism (SSCP) analysis can also be used to detect base change variants of an allele. See, e.g. Orita et al., Proc. Natl. Acad. Sci. USA Vol. 86, pp. 2766-2770, 1989, and Genomics, Vol. 5, pp. 874-879, 1989. Other techniques for detecting insertions and deletions as known in the art can also be used.

Alteration of wild-type genes can also be detected on the basis of the alteration of a wild-type expression product of the gene. Such expression products include both mRNA as well as the protein product. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR).

Mismatches are hybridized nucleic acid duplexes which are not 100% complementary. The lack of total complementarity may be due to deletions, insertions, inversions, substitutions or frameshift mutations. Mismatch detection can be used to detect point mutations in a target nucleic acid. While these techniques can be less sensitive than sequencing, they are simpler to perform on a large number of tissue samples. An example of a mismatch cleavage technique is the RNase protection method, which is described in detail in Winter et al., Proc. Natl. Acad. Sci. USA, Vol. 82, p. 7575, 1985, and Meyers et al., Science, Vol. 230, p. 1242, 1985. For example, a method of the invention may involve the use of a labeled riboprobe which is complementary to the human wild-type target nucleic acid. The riboprobe and target nucleic acid derived from the tissue sample are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid mRNA or gene, but can a portion of the target nucleic acid, provided it encompasses the position suspected of being mutated. If the riboprobe comprises only a segment of the target nucleic acid mRNA or gene, it may be desirable to use a number of these probes to screen the whole target nucleic acid sequence for mismatches if desired.

In a similar manner, DNA probes can be used to detect mismatches, for example through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the target nucleic acid mRNA or DNA which might contain a mutation can be amplified before hybridization. Changes in target nucleic acid DNA can also be detected using Southern hybridization, especially if the changes are gross rearrangements, such as deletions and insertions.

Target nucleic acid DNA sequences which have been amplified may also be screened using allele-specific probes. These probes are nucleic acid oligomers, each of which contains a region of the target nucleic acid gene harboring a known mutation. For example, one oligomer may be about 30 nucleotides in length, corresponding to a portion of the target gene sequence. By use of a battery of such allele-specific probes, target nucleic acid amplification products can be screened to identify the presence of a previously identified mutation in the target gene. Hybridization of allele-specific probes with amplified target nucleic acid sequences can be performed, for example, on a nylon filter. Hybridization to a particular probe under stringent hybridization conditions indicates the presence of the same mutation in the tumor tissue as in the allele-specific probe.

Alteration of wild-type target genes can also be detected by screening for alteration of the corresponding wild-type protein. For example, monoclonal antibodies immunoreactive with a target gene product can be used to screen a tissue, for example an antibody that is known to bind to a particular mutated position of the gene product (protein). For example, an antibody that is used may be one that binds to a deleted exon or that binds to a conformational epitope comprising a deleted portion of the target protein. Lack of cognate antigen would indicate a mutation. Antibodies specific for products of mutant alleles could also be used to detect mutant gene product. Antibodies may be identified from phage display libraries. Such immunological assays can be done in any convenient format known in the art. These include Western blots, immunohistochemical assays and ELISA assays. Any means for detecting an altered protein can be used to detect alteration of wild-type target genes.

Primer pairs are useful for determination of the nucleotide sequence of a target nucleic acid using nucleic acid amplification techniques such as the polymerase chain reaction. The pairs of single stranded DNA primers can be annealed to sequences within or surrounding the target nucleic acid sequence in order to prime amplification of the target sequence. Allele-specific primers can also be used. Such primers anneal only to particular mutant target sequence, and thus will only amplify a product in the presence of the mutant target sequence as a template. In order to facilitate subsequent cloning of amplified sequences, primers may have restriction enzyme site sequences appended to their ends. Such enzymes and sites are well known in the art. The primers themselves can be synthesized using techniques which are well known in the art. Generally, the primers can be made using oligonucleotide synthesizing machines which are commercially available. Design of particular primers is well within the skill of the art.

Nucleic acid probes are useful for a number of purposes. They can be used in Southern hybridization to genomic DNA and in the RNase protection method for detecting point mutations already discussed above. The probes can be used to detect target nucleic acid amplification products. They may also be used to detect mismatches with the wild type gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See Novack et al., Proc. Natl. Acad. Sci. USA, Vol. 83, p. 586, 1986. Generally, the probes are complementary to sequences outside of the kinase domain. An entire battery of nucleic acid probes may be used to compose a kit for detecting mutations in target nucleic acids. The kit allows for hybridization to a large region of a target sequence of interest. The probes may overlap with each other or be contiguous.

If a riboprobe is used to detect mismatches with mRNA, it is generally complementary to the mRNA of the target gene. The riboprobe thus is an antisense probe in that it does not code for the corresponding gene product because it is complementary to the sense strand. The riboprobe generally will be labeled with a radioactive, colorimetric, or fluorometric material, which can be accomplished by any means known in the art. If the riboprobe is used to detect mismatches with DNA it can be of either polarity, sense or anti-sense. Similarly, DNA probes also may be used to detect mismatches.

In some instances, the cancer does or does not overexpress FGFR3. Receptor overexpression may be determined in a diagnostic or prognostic assay by evaluating increased levels of the receptor protein present on the surface of a cell (e.g. via an immunohistochemistry assay; IHC). Alternatively, or additionally, one may measure levels of receptor-encoding nucleic acid in the cell, e.g. via fluorescent in situ hybridization (FISH; see WO98/45479 published October, 1998), southern blotting, or polymerase chain reaction (PCR) techniques, such as real time quantitative PCR(RT-PCR). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Chemotherapeutic Agents

The combination therapy of the invention can further comprise one or more chemotherapeutic agent(s). The combined administration includes coadministration or concurrent administration, using separate formulations or a single pharmaceutical formulation, and consecutive administration in either order, wherein preferably there is a time period while both (or all) active agents simultaneously exert their biological activities.

The chemotherapeutic agent, if administered, is usually administered at dosages known therefor, or optionally lowered due to combined action of the drugs or negative side effects attributable to administration of the antimetabolite chemotherapeutic agent. Preparation and dosing schedules for such chemotherapeutic agents may be used according to manufacturers' instructions or as determined empirically by the skilled practitioner.

Various chemotherapeutic agents that can be combined are disclosed herein.

In some embodiments, chemotherapeutic agents to be combined are selected from the group consisting of lenalidomide (REVLIMID), proteosome inhibitors (such as bortezomib (VELCADE) and PS342), bora taxoid (including docetaxel and paclitaxel), vinca (such as vinorelbine or vinblastine), platinum compound (such as carboplatin or cisplatin), aromatase inhibitor (such as letrozole, anastrazole, or exemestane), anti-estrogen (e.g. fulvestrant or tamoxifen), etoposide, thiotepa, cyclophosphamide, pemeterxed, methotrexate, liposomal doxorubicin, pegylated liposomal doxorubicin, capecitabine, gemcitabine, melthalin, doxorubicin, vincristine, COX-2 inhibitor (for instance, celecoxib), or steroid (e.g., dexamethasone and prednisone). In some embodiments (e.g., embodiments involving treatment of t(4;14)+ multiple myeloma, dexamethasone and lenalidomide, or dexamethasone, or bortezomib, or vincristine, doxorubicin and dexamethason, or thalidomide and dexamethasone, or liposomal doxorubicin, vincristine and dexamethasone, or lenalidomide and dexamethasone, or bortezomib and dexamethasone, or bortezomib, doxorubicin, and dexamethasone are combined. In some embodiments (e.g., embodiments involving bladder cancer), gemcitabine and cisplatin, or a taxane (e.g., paclitaxel, docetaxel), or pemeterxed, or methotrexate, vinblastine, doxorubicin and cisplatin, or carboplatin, or mitomycin C in combination with 5-Fluorouracil, or cisplatin, or cisplatin and 5-Fluorouracil are combined.

Formulations, Dosages and Administrations

The therapeutic agents used in the invention will be formulated, dosed, and administered in a fashion consistent with good medical practice. Factors for consideration in this context include the particular disorder being treated, the particular subject being treated, the clinical condition of the individual patient, the cause of the disorder, the site of delivery of the agent, the method of administration, the scheduling of administration, the drug-drug interaction of the agents to be combined, and other factors known to medical practitioners.

Therapeutic formulations are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The therapeutic agents of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. An ex vivo strategy can also be used for therapeutic applications. Ex vivo strategies involve transfecting or transducing cells obtained from the subject with a polynucleotide encoding a FGFR3 antagonist. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

For example, if the FGFR3 antagonist is an antibody, the antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

In another example, the FGFR3 antagonist compound is administered locally, e.g., by direct injections, when the disorder or location of the tumor permits, and the injections can be repeated periodically. The FGFR3 antagonist can also be delivered systemically to the subject or directly to the tumor cells, e.g., to a tumor or a tumor bed following surgical excision of the tumor, in order to prevent or reduce local recurrence or metastasis.

Administration of the therapeutic agents in combination typically is carried out over a defined time period (usually minutes, hours, days or weeks depending upon the combination selected). Combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner.

The therapeutic agent can be administered by the same route or by different routes. For example, the anti-FGFR3 antibody in the combination may be administered by intravenous injection while a chemotherapeutic agent in the combination may be administered orally. Alternatively, for example, both of the therapeutic agents may be administered orally, or both therapeutic agents may be administered by intravenous injection, depending on the specific therapeutic agents. The sequence in which the therapeutic agents are administered also varies depending on the specific agents.

Depending on the type and severity of the disease, about 1 µg/kg to 100 mg/kg of each therapeutic agent is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until the cancer is treated, as measured by the methods described above. However, other dosage regimens may be useful.

The present application contemplates administration of the FGFR3 antibody by gene therapy. See, for example, WO96/07321 published Mar. 14, 1996 concerning the use of gene therapy to generate intracellular antibodies.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition(s) effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein, wherein the composition comprises a further cytotoxic agent. The article of manufacture in this embodiment of the invention may further comprise a package insert indicating that the first and second antibody compositions can be used to treat a particular condition, e.g., cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Materials and Methods

Cell Lines and Cell Culture

The cell line RT4 was obtained from American Type Cell Culture Collection. Cell lines RT112, OPM2 and Ba/F3 were purchased from German Collection of Microorganisms and Cell Cultures (DSMZ, (Germany)). Multiple myeloma cell line KMS11 was kindly provided by Dr. Takemi Otsuki at Kawasaki Medical School (Japan). Bladder cancer cell line TCC-97-7 was a generous gift from Dr. Margaret Knowles at St James's University Hospital (Leeds, UK). UMUC-14 cell line was obtained from Dr. H. B. Grossman (currently at University of Texas M.D. Anderson Cancer Center, Tex.). The cells were maintained with RPMI medium supplemented with 10% fetal bovine serum (FBS) (Sigma), 100 U/ml penicillin, 0.1 mg/ml streptomycin and L-glutamine under conditions of 5% $CO_2$ at 37° C.

FGFR3$^{S249C}$ Dimerization Studies

UMUC-14 cells were grown in cysteine-free medium, treated with R3Mab or DTNB for 3 hr, and cell lysates were subject to immunoblot analysis under reducing or non-reducing conditions. For in vitro dimerization studies, FGFR3-IIIb$^{S249C}$ (residues 143-374) was cloned into pAcGP67A vector and expressed in T.ni Pro cells. The recombinant protein was purified through Ni-NTA column followed by Superdex 5200 column. Dimeric FGFR3$^{S249C}$ was eluted in 25 mM Tris (pH 7.5) and 300 mM NaCl. R3Mab (1 μM) was incubated with FGFR3$^{S249C}$ dimer (0.1 μM) at 37° C. under the following conditions: 100 mM KH$_2$PO4 (pH 7.5), 25 μM DTT, 1 mM EDTA and 0.75 mg/ml BSA. Aliquots of the reaction were taken at indicated time points and the reaction was stopped by adding sample buffer without β-mercaptoethanol. Dimer-monomer was analyzed by immunoblot.

Xenograft Studies

All studies were approved by Genentech's Institutional Animal Care and Use Committee. Female nu/nu mice or CB17 severe combined immunodeficiency (SCID) mice, 6-8 weeks of age, were purchased from Charles River Laboratory (Hollister, Calif.). Female athymic nude mice were obtained from the National Cancer Institute-Frederick Cancer Center. Mice were maintained under specific pathogen-free conditions. RT112 shRNA stable cells (7×10$^6$), RT112 (7×10$^6$), Ba/F3-FGFR3$^{S249C}$ (5×10$^6$), OPM2 (15×10$^6$), or KMS11 cells (20×10$^6$) were implanted subcutaneously into the flank of mice in a volume of 0.2 ml in HBSS/matrigel (1:1 v/v, BD Biosciences). UMUC-14 cells (5×10$^6$) were implanted without matrigel. Tumors were measured twice weekly using a caliper, and tumor volume was calculated using the formula: V=0.5 a×b$^2$, where a and b are the length and width of the tumor, respectively. When the mean tumor volume reached 150-200 mm$^3$, mice were randomized into groups of 10 and were treated twice weekly with intraperitoneal (i.p) injection of R3Mab (0.3-50 mg/kg), or a control human IgG1 diluted in HBSS. Control animals were given vehicle (HBSS) alone.

Statistics

Pooled data are expressed as mean+/−SEM. Unpaired Student's t tests (2-tailed) were used for comparison between two groups. A value of P<0.05 was considered statistically significant in all experiments.

Generation of FGFR3 shRNA Stable Cells

Three independent FGFR3 shRNA were cloned into pHUSH vector as described (1). The sequence for FGFR3 shRNAs used in the studies is as follows: shRNA2: 5'GATC-CCCGCATCAAGCTGCGGCATCATTCAA-GAGATGATGCCGCAGCTTGATGCTTTTT TGGAAA (SEQ ID NO:192); shRNA4: 5'-GATCCCCTGCACAAC-CTCGACTACTA TTCAAGAGATAGTAGTCGAGGTTGTG-CATTTTTTGGAAA-3' (SEQ ID NO:193); shRNA6: 5'-GATCCCCAACCTCGACTACTACAAGAT-TCAAGAGATCTTGTAGTAGTCGAGGTTTTTTTT GGAAA-3' (SEQ ID NO:194). All constructs were confirmed by sequencing. EGFP control shRNA was described in our previous study (50). The shRNA containing retrovirus was produced by co-transfecting GP2-293 packaging cells (Clontech Laboratories, Mountain View, Calif.) with VSV-G (Clontech Laboratories) and pHUSH-FGFR3 shRNA constructs, and viral supernatants were harvested 72 hr after transfection, and cleared of cell debris by centrifugation for transduction experiment.

RT112 cells were maintained in RPMI 1640 medium containing tetracycline-free FBS (Clontech Laboratories), and transduced with retroviral supernatant in the presence of 4 μg/ml polybrene. 72 hours after infection, 2 μg/ml puromycin (Clontech Laboratories) was added to the medium to select stable clones expressing shRNA. Stable cells were isolated, treated with 0.1 or 1 μg/ml doxycycline (Clontech Laboratories) for 4 days, and inducible knockdown of FGFR3 protein expression was assessed by Western blotting analysis. Cell cycle analyses were performed as described (51).

Selecting Phage Antibodies Specific for FGFR3

Human phage antibody libraries with synthetic diversities in the selected complementary determining regions (H1, H2, H3, L3), mimicking the natural diversity of human IgG repertoire were used for panning. The Fab fragments were displayed bivalently on the surface of M13 bacteriophage particles (52). His-tagged IgD2-D3 of human FGFR3-IIIb and IIIc were used as antigens. 96-well MaxiSorp immunoplates (Nunc) were coated overnight at 4° C. with FGFR3-IIIb-His protein or FGFR3-IIIC-His protein (10 μg/ml) and blocked for 1 hour with PBST buffer (PBS with 0.05% Tween 20) supplemented with 1% BSA. The antibody phage libraries were added and incubated overnight at room temperature (RT). The plates were washed with PBST buffer and bound phage were eluted with 50 mM HCl and 500 mM NaCl for 30 minutes and neutralized with equal volume of 1M Tris base. Recovered phages were amplified in E. coli XL-1 blue cells. During subsequent selection rounds, the incubation time of the phage antibodies was decreased to 2 hours and the stringency of plate washing was gradually increased (53). Unique and specific phage antibodies that bind to both IIIb and IIIc isoforms of FGFR3 were identified by phage ELISA and DNA sequencing. Out of 400 clones screened, four were selected to reformat to full length IgGs by cloning VL and VH regions of individual clones into LPG3 and LPG4 vectors, respectively, transiently expressed in mammalian cells, and purified with protein A columns (54). Clone 184.6 was selected for affinity maturation.

For affinity maturation, phagemid displaying monovalent Fab on the surface of M13 bacteriophage (52) served as the library template for grafting light chain (VL) and heavy chain (VH) variable domains of the phage Ab. Stop codons was incorporated in CDR-L3. A soft randomization strategy was adopted for affinity maturation as described (53). Two different combinations of CDR loops, H1/H2/L3, H3/L3, or L1/L2/L3 were selected for randomization. For selecting affinity-matured clones, phage libraries were sorted against FGFR3 IIIb or IIIc-His protein, subjected to plate sorting for the first round and followed by four rounds of solution phase sorting as described (52). After five rounds of panning, a high-throughput single-point competitive phage ELISA was used to rapidly screen for high-affinity clones as described (55). Clones with low ratio of the absorbance at 450 nm in the presence of 10 nM FGFR3-His to that in the absence of FGFR3-His were chosen for further characterization.

Clones 184.6.1, 184.6.21, 184.6.49, 184.6.51, 184.6.58, 184.6.62 and 184.6.92 significantly reduced viability of Ba/F3-FGFR3-IIIb, Ba/F3-FGFR3-IIIc and Ba/F3-FGFR3-S249C cell lines, and clone 184.6.52 significantly reduced the viability of the Ba/F3-FGFR3-S249C cell line. The increased inhibitory activity ranged from about 50-fold (clone 184.6.52) to about 100-fold (clones 184.6.1, 184.6.21, 184.6.49, 184.6.51, 184.6.58, 184.6.62 and 184.6.92) greater than parent clone 184.6, depending on the cell line assayed. Binding kinetics of clones 184.6.1, 184.6.58, and 184.6.62 to FGFR3-IIIb and FGFR3-IIIc were determined using BIAcore as follows:

|  | FGFR3-IIIb KD (M) | FGFR3-IIIc KD (M) |
| --- | --- | --- |
| 184.6 | 3.80E−08 | 1.10E−07 |
| 184.6.1 | 2.64E−10 | 1.44E−09 |

| | FGFR3-IIIb KD (M) | FGFR3-IIIc KD (M) |
|---|---|---|
| 184.6.58 | 1.90E−10 | 8.80E−10 |
| 184.6.62 | 1.20E−10 | 2.24E−09 |

Clones 184.6.1, 184.6.58, and 184.6.62 also showed improved inhibition of FGFR3 downstream signaling in Ba/F3-FGFR3 cells, RT112 cells and OPM2 cells.

Clone 184.6.1 was selected. A sequence modification, N54S, was introduced into HVR H2 at residue 54, to improve manufacturability, creating clone 184.6.1N54S. Clones 184.6.1 and 184.6.1N54S displayed comparable binding kinetics (measured in Biacore assays) and comparable activity in the Ba/F3 cell viability assay. Additional HVR H2 variants were generated: N54S was introduced in clone 184.6.58, and N54G, N54A, or N54Q were introduced in clone 184.6.1 and 184.6.58. These clones showed comparable activity in the Ba/F3 cell viability assay to parent clones 184.6.1 or 184.6.58.

Another sequence modification, D30E, was introduced into HVR L1 of clone 184.6.1N54S, creating clone 184.6.1NSD30E. Clone 184.6.1NSD30E and clone 184.6.1N54S showed comparable binding kinetics and comparable activity in the BA/F3 cell viability assay to parent clones 184.6.1 or 184.6.58.

Figure 9A:
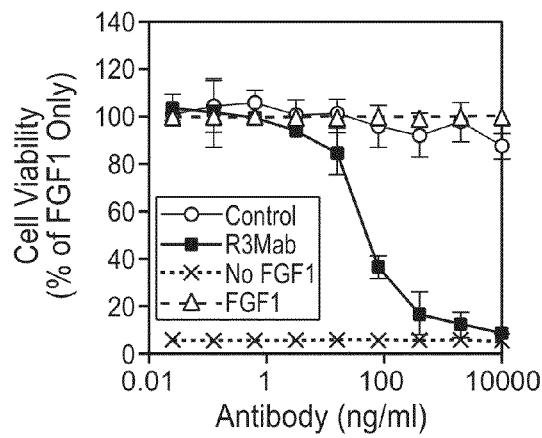
Figure 9B:
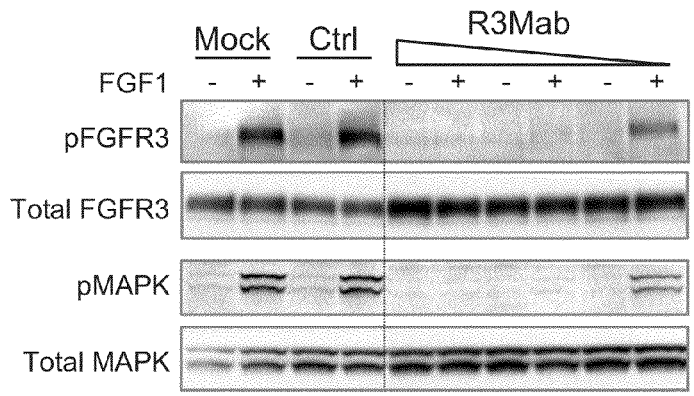

As used herein, "R3Mab" refers to anti-FGFR3 antibody clones 184.6.1N54S, 184.6.1, or 184.6. Clone 184.6.1N54S was used in figures and experiments referencing "R3Mab", except in the experiments leading to the results shown in the following figures (for which the antibody used is shown in parentheses): FIGS. 9B (clone 184.6.1), 10 (clone 184.6), 11A and B (clone 184.6), 13 (clone 184.6.1), 14A (clone 184.6.1), 14B, G, and H (clone 184.6), 19 (clone184.6.1), and 22B and C (clone 184.6.1).

BIAcore/Surface Plasmon Resonance (SRP) Analysis to Determine Antibody Binding Affinities Binding affinities of R3Mab to FGFR3 were measured by Biacore/SRP using a BIAcore™-3000 instrument as described (52) with the following modifications. R3Mab was directly coated on CM5 biosensor chips to achieve approximately 400 response units (RU). For kinetic measurement, two-fold serial dilutions of FGFR3-IIIb or IIIc-His protein (starting from 67 nM) were injected in PBST buffer at 25° C. with a flow rate of 30 µl/minute. Association rates (Kon, per mol/s) and dissociation rates (Koff, per s) were calculated using a simple one-one Langmuir binding model (BIAcore Evaluation Software version 3.2). The equilibrium dissociation constant (Kd, per mol) was calculated as the ratio of Koff/Kon.

Binding affinities of mouse hybridoma antibodies to FGFR3 were measured by Biacore/SRP as follows. Human FGFR3-IIIb or IIIc was coupled onto three different flow cells (FC), FC2, FC3 and FC4, of a BIACORE™ CM5 sensor chip to achieve the response unit (RU) about 50 RU. Immobilization was achieved by random coupling through amino groups using a protocol provided by the manufacturer. Sensorgrams were recorded for binding of hybridoma-derived anti-FGFR3 murine IgG or the Fab fragment to these surfaces at 25° C. by injection of a series of solutions ranging from 250 nM to 0.48 nM in 2-fold increments at a flow rate of 300 min. Between each injection, 10 mM Glycine-HCl pH 1.7 was served as the buffer to regenerate the sensor chip. The signal from the reference cell (FC1) was subtracted from the observed sensorgram at FC2, FC3 and FC4. Kinetic constants were calculated by nonlinear regression fitting of the data according to a 1:1 Langmuir binding model using BIAcore evaluation software (version 3.2) supplied by the manufacturer.

ELISA Binding Studies cDNAs encoding the extracellular domains (ECD) of human FGFR1-IIIb, IIIc, FGFR2-IIIb and IIIc, FGFR3-IIIb and IIIc, and FGFR4 were cloned into pRK-based vector to generate human FGFR-human Fc chimeric proteins. The recombinant proteins were produced by transiently transfecting Chinese hamster ovary (CHO) cells and purified via protein A affinity chromatography. To test binding of antibodies to human FGFRs, Maxisorp 96-well plates (Nunc) were coated overnight at 4° C. with 50 µl of 2 µg/ml of FGFR ECD-human Fc chimeric proteins. After blocking with phosphate-buffered saline (PBS)/3% BSA, FGFR3 antibody was added and incubated at RT for 2 hours. Specifically bound FGFR3 antibody was detected using an HRP-conjugated anti-human Fab and the TMB peroxidase colorigenic substrate (KPL, Gaithersburg, Md.).

To test the effect of antibodies to FGFR3 on FGF/FGFR3 interaction, FGFR3-Fc chimeric proteins were captured on Maxisorp plate coated with anti-human immunoglobulin Fcγ fragment-specific antibody (Jackson Immunoresearch, West Grove, Pa.). After wash, increasing amount of FGFR3 antibody was added to the plate and incubated for 30 minutes. Then, FGF1 or FGF9 and heparin were added for incubation at RT for 2 hours. The plates were washed and incubated for 1 hour with biotinylated FGF1-specific polyclonal antibody (BAF232) or biotinylated FGF9 antibody (BAF273, R&D Systems), followed by detection with streptavidin-HRP and TMB.

Generation of Ba/F3-FGFR3 Stable Cells cDNA encoding full-length human FGFR3 IIIb or IIIc was cloned into pQCXIP vector (Clontech Laboratories, Mountain View, Calif.) to generate pQCXIP-FGFR3-IIIb or IIIc. Specific mutations, i.e., R248C, S249C, G372C, Y375C and K652E, were introduced into the cDNA via QuickChange (Stratagene, La Jolla, Calif.). To generate Ba/F3 stable cells expressing wild type or mutant FGFR3, various pQCXIP-FGFR3 constructs were co-transfected into packaging cells GP2-293 with VSV-G plasmid (Clontech Laboratories). After selection with 2 µg/ml puromycin for two weeks, cells expressing wild type or mutant FGFR3 were stained with Phycoerythrin-conjugated anti-human FGFR3 mAb (FAB766P, R&D Systems), and selected through fluorescence-activated cell sorting (FACS) for functional assays. For cell proliferation assay in 96-well micro-titer plate, the following cell density was used: For cells expressing wild type FGFR3-IIIb and FGFR3-K652E: 5,000 cells/well; for the rest: 10,000 cells/well. Cells were seeded in RPMI 1640 medium supplemented with 10% fetal bovine serum, 10 ng/ml FGF1 plus 10 µg/ml heparin (Sigma-Aldrich, St. Louis, Mo.). R3Mab was added at indicated concentration and mouse hybridoma FGFR3 antibodies were added at 2000 to 0.49 ng/ml (in four-fold serial dilutions) in the FGFR3-IIIb experiment and 5000 to 1.2 ng/ml (in four-fold serial dilutions) in the FGFR3-IIIc experiment. After incubation for 72 hours, cell viability was assessed with CellTiter-Glo (Promega, Madison, Wis.).

Cell Proliferation Assay

For proliferation assays for RT112, RT4 and TCC-97-7 cells, 3000 cells/well were seeded into 96-well micro-titer plate and were allowed to adhere overnight. The medium was then replaced with low serum medium (0.5% FBS) with control or R3Mab at concentrations indicated. Following 4 days incubation, 1 µCi of [Methyl-$^3$H] thymidine (PerkinElmer, Waltham, Mass.) was added to each well, and incubated for additional 16 hours. Cells were transferred to UniFilters using Packard Filtermate Harvester, and [$^3$H]-thymidine incorporated into the genomic DNA of growing cells was measured using TopCount (PerkinElmer). In some cases, cell viability was assessed with CellTiter-Glo (Promega) following incubation with antibodies for 4 days. Values are presented as means+/−SE of quadruplets.

Clonal Growth Assay

The effect of R3Mab on cell clonogenicity was assessed following a previously described protocol (50). In brief, 400 UMUC-14 cells were seeded into 6-well plate in DMEM medium supplemented with 10% fetal bovine serum to allow adhesion overnight. Then R3Mab or control antibody diluted in 0.1% BSA medium was added to a final concentration of 10 µg/ml. Equal volume of 0.1% BSA medium alone (Mock) was used as another control. The cells were incubated for about 12 days until cells in control groups formed sufficiently large colonies. Colonies were stained with 0.5% crystal violet, and the number and size of colonies were quantitated using GelCount (Oxford, UK). The number of colonies larger than 120 µm in diameter was presented as mean+/−SEM (n=12).

Immunoprecipitation and Immunoblotting Analyses

To study the effect of antibodies on FGFR3 signaling, cells were starved in serum-free medium overnight prior to the beginning of treatment. Cells were incubated with either antibodies diluted in 0.1% BSA (w/v), RPMI 1640 medium, or with 0.1% BSA medium alone (Mock). After 3 hours at 37° C., FGF1 (final concentration of 15 ng/ml) and heparin (final concentration of 5-10 µg/ml) were added to half of the samples. As controls, a similar volume of heparin alone was added to the other half of samples. The incubation was continued for 10 min. Supernatants were removed by aspiration, and cells were washed with ice-cold PBS, then lysed in RIPA buffer (Upstate, Charlottesville, Va.) supplemented with 1 mM sodium orthovanadate and Complete protease inhibitor cocktail (Roche Applied Science, Indianapolis, Ind.). The lysates were cleared of insoluble materials by centrifugation.

FGFR3 was immunoprecipitated using a rabbit polyclonal antibody (sc-123, Santa Cruz Biotechnology, Santa Cruz, Calif.) and analyzed by sodium dodecyl-polyacrylamide gel electrophoresis (SDS-PAGE) and Western blot. Phosphorylated FGFR3 was assessed with a monoclonal antibody against phospho-tyrosine (4G10, Upstate). Total FGFR3 was probed with a monoclonal antibody against FGFR3 (sc-13121, Santa Cruz Biotechnology). Phosphorylation and activation of FGFR3 signaling pathway were probed using the following antibodies: anti-FGFR$^{Y653/654}$, anti-FRS2α$^{Y196}$, anti-phospho-p44/42 MAPK$^{T202/Y204}$, anti-total p44/42 MAPK and anti-AKT$^{S473}$ were obtained from Cell Signaling Technology (Danvers, Mass.); and anti-total FRS2α (sc-8318) was purchased from Santa Cruz Biotechnology (Santa Cruz, Calif.). The blots were visualized using a chemiluminescent substrate (ECL Plus, Amersham Pharmacia Biotech, Piscataway, N.J.).

Antibody Epitope Mapping

To determine the epitope of R3Mab, 13 overlapping peptides, each of 15 amino acids in length, were synthesized to cover the extracellular domain of human FGFR3 from residues 138 to 310. The peptides were biotinylated at the C-terminus, and captured on streptavidin plates (Pierce, Rockford, Ill.) overnight. After blocking with PBS/3% BSA, the plates were incubated with R3Mab and detected using an HRP-conjugated anti-human IgG (Jackson Immunoresearch) and the TMB peroxidase colorigenic substrate (KPL, Gaithersburg, Md.).

Mouse anti-human FGFR3 hybridoma antibodies 1G6, 6G1, and 15B2 were tested in ELISA assay to identify their binding epitopes. 1G6, 6G1 and 15B2 bind to human FGFR3 IgD2-IgD3 (both IIIb and Inc isoforms), whereas 5B8 only binds IgD2-IgD3 of human FGFR3-IIIb. In a competition assay, 1G6, 6G1 and 15B2 competed with each other to bind human FGFR3, suggesting that 1G6, 6G1 and 15B2 have overlapping epitopes. None of the hybridoma antibodies competed with phage antibody 184.6, suggesting that the hybridoma antibodies have distinct epitope(s) from 184.6.

Preparation and Molecular Cloning of Mouse Anti-FGFR3 Antibodies 1G6, 6G1, and 15B2

BALB/c mice were immunized 12 times with 2.0 µg of FGFR3-IIIb (rhFGFR3 (IIIB)/Fc Chimera, from R&D Systems, catalog #1264-FR, lot # CYH025011, or with 2.0 µg of FGFR3-IIIc (rhFGFR3 (IIIc)/Fc Chimera, from R&D Systems, catalog #766-FR, lot # CWZ055041, resuspended in monophosphoryl lipid A/trehalose dicorynomycolate adjuvant (Corixa, Hamilton, Mont.) into each hind footpad twice a week. Three days after final boost, popliteal lymph nodes were fused with mouse myeloma cell line P3X63Ag.U.1, via electrofusion (Hybrimune, Cyto Pulse Sciences, Glen Burnie, Md.). Fused hybridoma cells were selected from unfused popliteal node or myeloma cells using hypoxanthin-aminopterin-thymidine (HAT) selection in Medium D from the ClonaCell® hybridoma selection kit (StemCell Technologies, Inc., Vancouver, BC, Canada). Culture supernatants were initially screened for its ability to bind to FGFR3-IIIb and FGFR3-IIIc by ELISA, and hybridomas of interest were subsequently screened for its ability to stain by FACS on transfected FGFR3-IIIb Ba/F cells and control Ba/F, as well as antibody blocking activity. Selected hybridomas were then cloned by limiting dilution.

Total RNA was extracted from hybridoma cells producing the mouse anti human FGFRIII monoclonal antibody 1G6 and 15B2, using RNeasy Mini Kit (Qiagen, Germany). The variable light (VL) and variable heavy (VH) domains were amplified using RT-PCR with the following degenerate primers:

```
1G6:
Light chain (LC) forward:
                                          (SEQ ID NO: 195)
5'-GTCAGATATCGTKCTSACMCARTCTCCWGC-3'

Heavy chain (HC) forward:
                                          (SEQ ID NO: 196)
5'-GATCGACGTACGCTGAGATCCARYTGCARCARTCTGG-3'

6G1:
Light chain (LC) forward:
                                          (SEQ ID NO: 197)
5'-GTCAGATATCGTGCTGACMCARTCTCC-3'

Heavy chain (HC) forward:
                                          (SEQ ID NO: 198)
5'-GATCGACGTACGCTGAGATCCARYTGCARCARTCTGG-3'

15B2:
Light chain (LC) forward:
                                          (SEQ ID NO: 199)
5'-GTACGATATCCAGATGACMCARTCTCC-3'

Heavy chain (HC) forward:
                                          (SEQ ID NO: 200)
5'-GATCGACGTACGCTGAGATCCARYTGCARCARTCTGG-3'
```

Light chain and Heavy chain reverse primer for all three clones are as followed:

```
Light chain reverse:
                                        (SEQ ID NO: 201)
5'-TTTDAKYTCCAGCTTGGTACC-3'

Heavy chain reverse:
                                        (SEQ ID NO: 202)
5'-ACAGTGGGCCCTTGGTGGAGGCTGMRGAGACDGTGASHRDRGT-3'.
```

The forward primers were specific for the N-terminal amino acid sequence of the VL and VH region. The LC and HC reverse primers were designed to anneal to a region in the constant light (CL) and constant heavy domain 1 (CH1), respectively, which are highly conserved across species.

Amplified VL was cloned into a pRK mammalian cell expression vector (Shields et al, (2000) J. Biol. Chem. 276: 659) containing the human kappa constant domain. Amplified VH was inserted to a pRK mammalian cell expression vector encoding the full-length human IgG1 constant domain. The sequence of the heavy and light chains was determined using conventional methods.

Crystallization, Structure Determination and Refinement

The human FGFR3-IIIb ECD (residues 143-374) was cloned into pAcGP67A vector (BD Bioscience, San Jose, Calif.), produced in T.ni Pro cells and purified using Ni-NTA column followed by size exclusion chromatography. The R3Mab Fab was expressed in *E. coli* and purified sequentially over a protein G affinity column, an SP sepharose column and a Superdex 75 column. Fab-FGFR3 complex was generated by incubating the Fab with an excess of FGFR3ECD, and the complex was then deglycosylated and purified over a Superdex-200 sizing column in 20 mM TrisCl pH 7.5 and 200 mM NaCl buffer. The complex-containing fractions were pooled and concentrated to 20 mg/ml and used in crystallization trials. Crystals used in the structure determination were grown at 4° C. from the following condition: 0.1 M sodium cacodylate pH 6.5, 40% MPD and 5% PEG8000 using vapor diffusion method. Data was processed using HKL2000 and Scalepack (56). The structure was solved with molecular replacement using program Phaser (57) and the coordinates of 1RY3 (FGFR3) and 1N8Z (Fab-fragment). The model was completed using program Coot (58) and the structure refined to $R/R_{free}$ of 20.4%/24.3% with program Refmac (59). Coordinates and structure factors were deposited in the Protein Data Bank with accession code 3GRW and are also disclosed in U.S. Ser. No. 61/163,222, filed on Mar. 25, 2009, the contents of which is hereby incorporated by reference.

ADCC Assay

Human PBMCs were isolated by Ficoll gradient centrifugation of heparinized blood, and ADCC was measured using the multiple myeloma cell lines OPM2 or KMS11 or bladder cancer cell lines RT112 or UMUC-14 as target and PBMCs as effector cells at a 1:100 target:effector ratio. The target cells (10,000 cells/well) were treated with R3Mab or with control human IgG1 for 4 hours at 37° C. Cytotoxicity was determined by measuring LDH release using the CytoTox-ONE Homogeneous Membrane Integrity Assay following manufacturer's instructions (Promega, Madison, Wis.). The results are expressed as percentage of specific cytolysis using the formula: Cytotoxicity (%)=[(Experimental lysis−Experimental spontaneous lysis)/(Target maximum lysis−target spontaneous lysis)]×100, where spontaneous lysis is the non-specific cytolysis in the absence of antibody, and target maximum lysis is induced by 1% Triton X-100.

Results

Inducible shRNA Knockdown of FGFR3 Attenuates Bladder Cancer Growth In Vivo

Figure 7A:
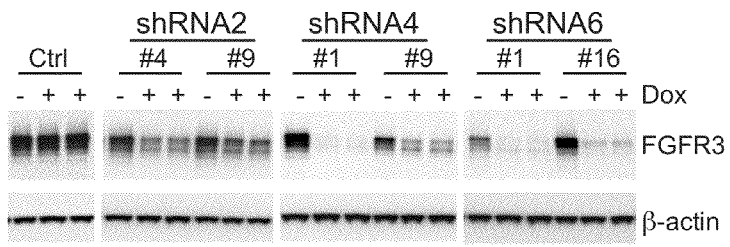
Figure 7B:
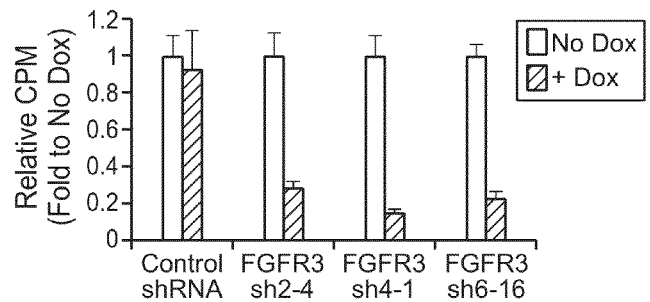
Figure 7C:
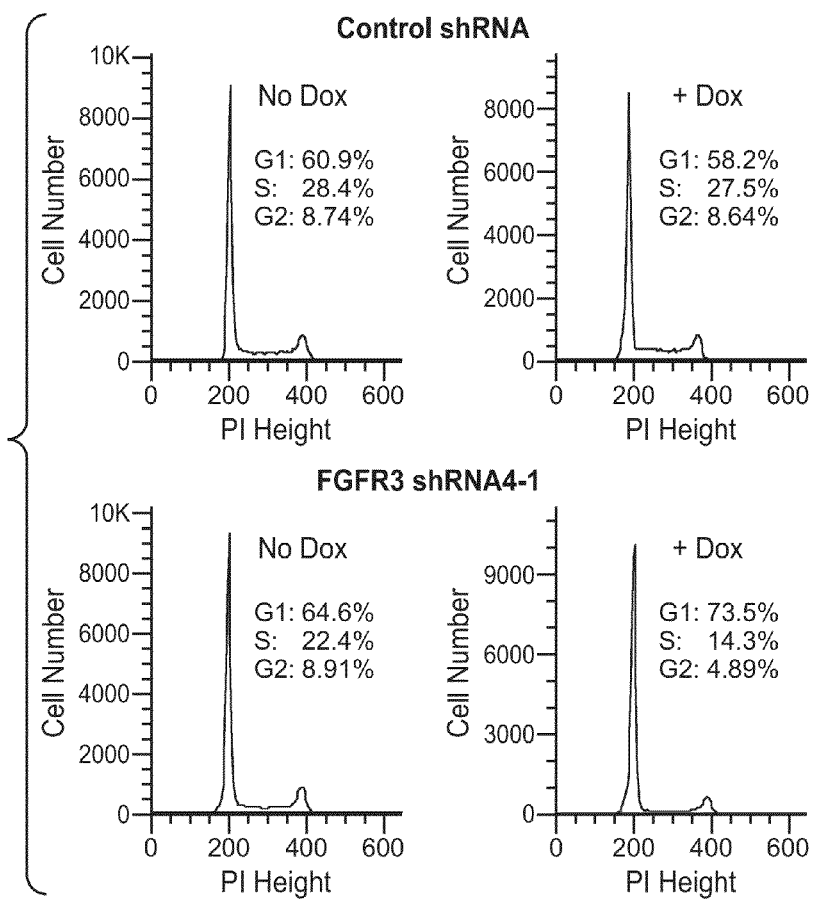
Figure 16A:
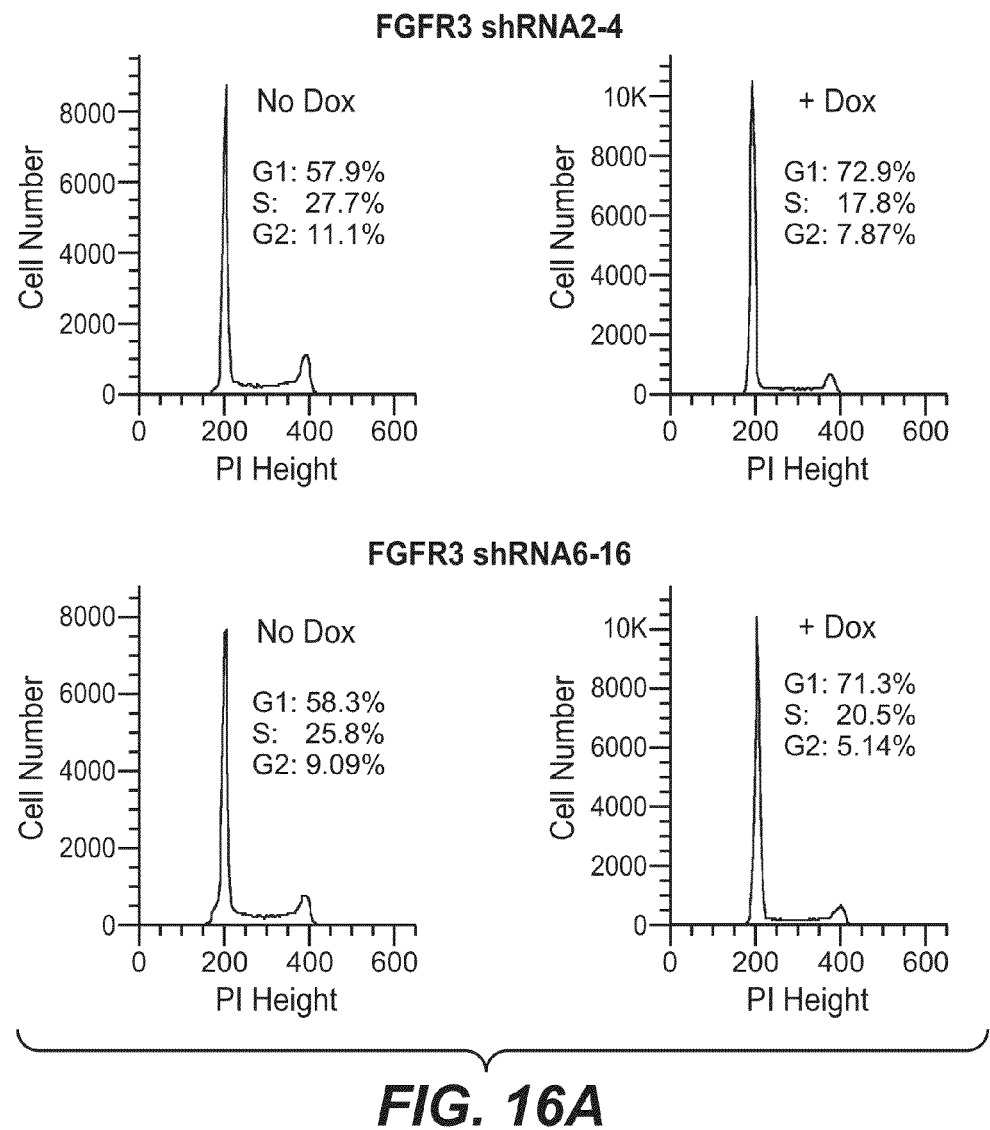

As a prelude to assessing the importance of FGFR3 for bladder tumor growth in vivo, we examined the effect of FGFR3 knockdown in vitro. Several FGFR3 small interfering (si) RNAs effectively downregulated FGFR3 in bladder cancer cell lines expressing either WT (RT112, RT4, SW780) or mutant (UMUC-14, S249C mutation) FGFR3. FGFR3 knockdown in all four cell lines markedly suppressed proliferation in culture (FIG. 15). Next, we generated stable RT112 cell lines expressing doxycycline-inducible FGFR3 shRNA. Induction of three independent FGFR3 shRNAs by doxycycline diminished FGFR3 expression, whereas induction of a control shRNA targeting EGFP had no effect (FIG. 7A). In the absence of exogenous FGF, doxycycline treatment reduced [$^3$H]-thymidine incorporation by cells expressing different FGFR3 shRNAs, but not control shRNA (FIG. 7B), confirming that FGFR3 knockdown inhibits proliferation. Further analysis of exponentially growing RT112 cells revealed that FGFR3 knockdown over a 72 hr treatment with doxycycline markedly and specifically reduced the percentage of cells in the S and G2 phases of the cell cycle, with a concomitant increase of cells in G1 phase (FIG. 7C). Similar effect was observed with two other FGFR3 shRNAs (FIG. 16A). No significant numbers of cells with a sub-diploid DNA content were detected, suggesting no change in apoptosis levels. Hence, the inhibitory effect of FGFR3 knockdown on the proliferation of RT112 cells is mainly due to attenuation of cell cycle progression.

Figure 7D:
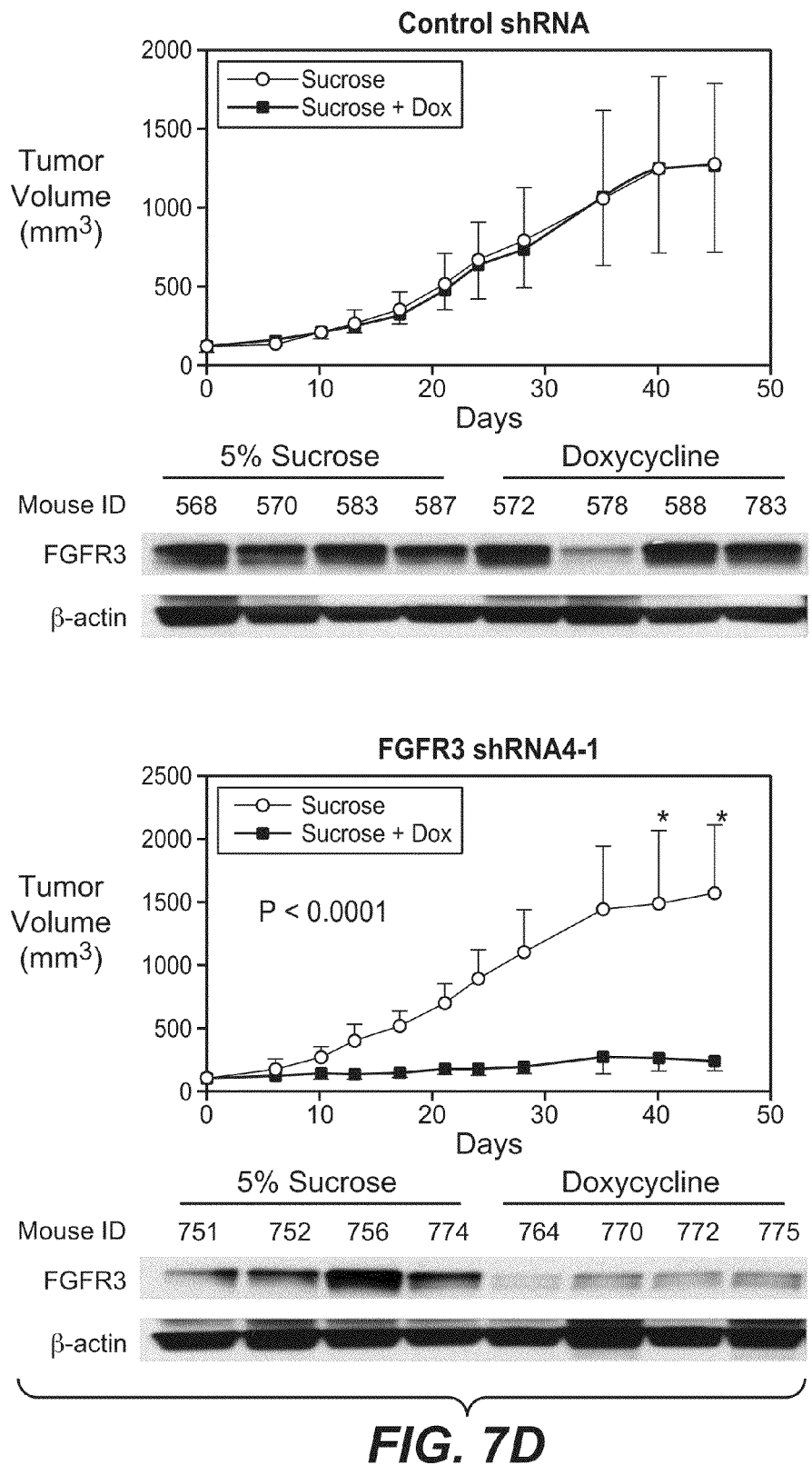
Figure 16B:
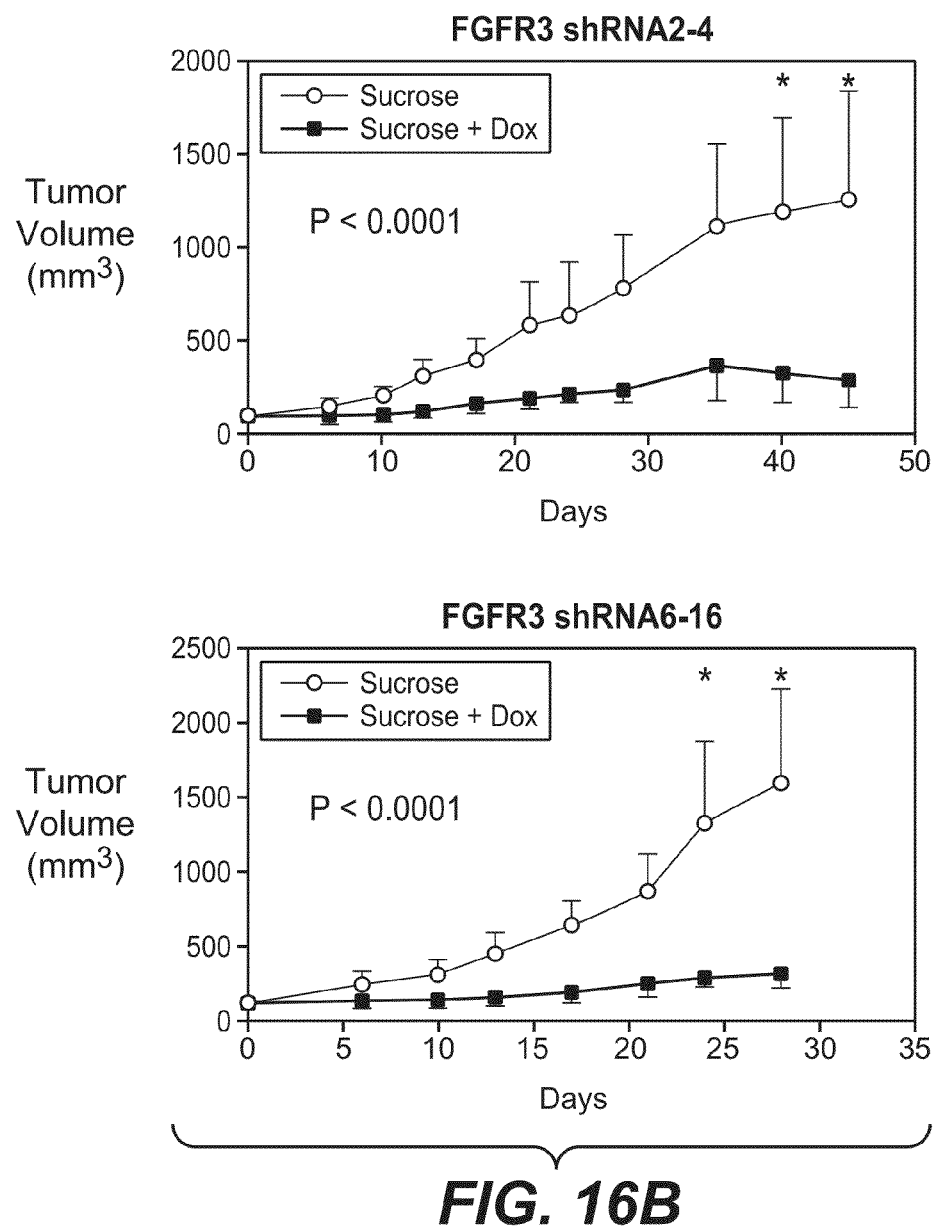

We next evaluated the effect of FGFR3 knockdown on the growth of pre-established RT112 tumor xenografts in mice. FGFR3 knockdown substantially and specifically suppressed tumor growth (FIG. 7D, top panels and FIG. 16B). Analysis of day 45 tumor samples confirmed effective FGFR3 knockdown upon doxycycline induction of FGFR3 shRNA as compared to control shRNA (FIG. 7D, bottom panels). These results demonstrate that FGFR3 is critically important both in vitro and in vivo for the growth of RT112 bladder cancer cells.

Generation of a Blocking Anti-FGFR3 Monoclonal Antibody

Figure 8A:
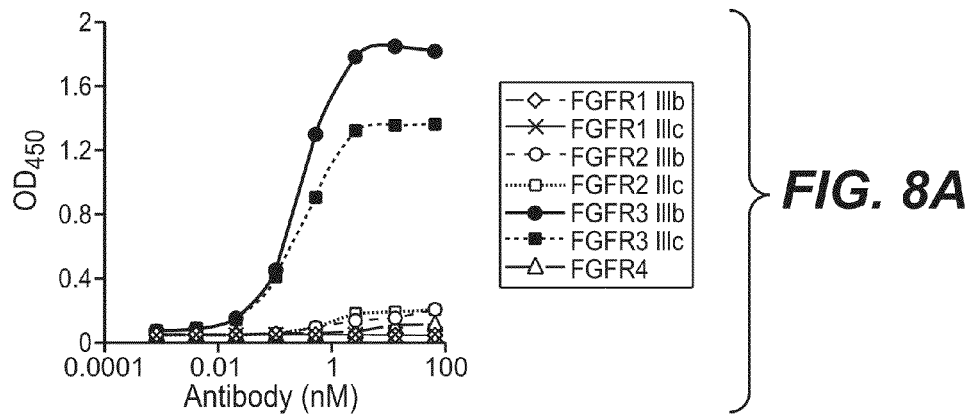

To examine further the importance of FGFR3 in tumor growth and to explore the potential of this receptor as a therapeutic target, we developed an antagonistic anti-FGFR3 monoclonal antibody (dubbed R3Mab) using a phage display approach. We selected this particular antibody based on its ability to block both ligand binding and dimerization by FGFR3, and its unique capacity to inhibit not only WT FGFR3 but also the most prevalent cancer-associated mutants of this receptor (see below). R3Mab targets the extracellular IgD2 and IgD3 domains of FGFR3, which are necessary and sufficient for FGF binding (4). R3Mab bound both the IIIb and IIIc isoforms of human FGFR3, but showed no detectable binding to FGFR1, FGFR2 or FGFR4 (FIG. 8A). Biacore analysis indicated that R3Mab had similar apparent affinity to murine, cynomolgus monkey and human FGFR3-IIIc (data not shown). The affinity of R3Mab to human FGFR3 is shown in Table 2.

TABLE 2

Affinity of R3Mab to human FGFR3 determined by BIAcore analysis.

| Human FGFR3 ECD | R3 Mab captured on chips | | |
|---|---|---|---|
| | kon/(1/Ms) | koff(1/s) | Kd(M) |
| IIIb | 1.80E+06 | 2.00E−04 | 1.11E−10 |
| IIIc | 9.10E+04 | 3.20E−04 | 3.52E−09 |

Figure 8B:
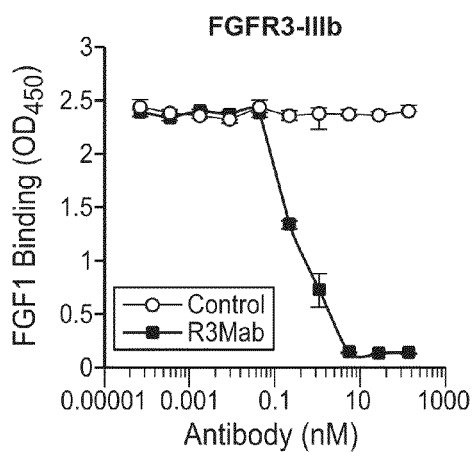
Figure 8C:
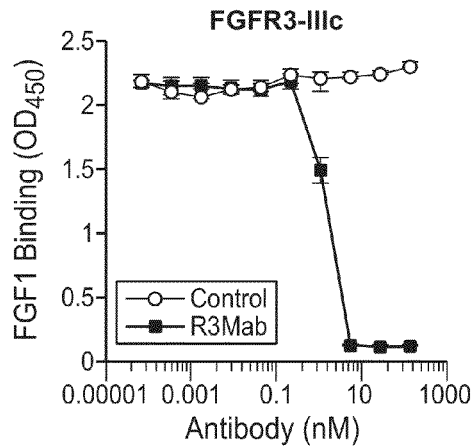
Figure 8D:
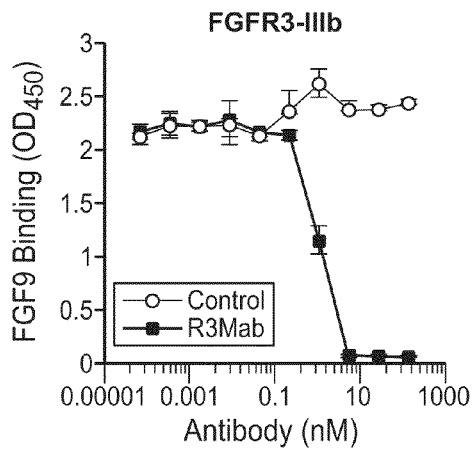
Figure 8E:
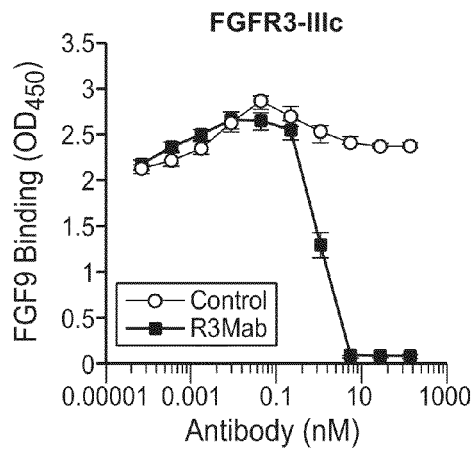

We next tested the ability of R3Mab to block FGFR3 binding to FGF1 and FGF9. R3Mab strongly inhibited binding of FGF1 to FGFR3-IIIb and -IIIc, with half-maximal inhibitory concentrations ($IC_{50}$) of 0.3 nM and 1.7 nM, respectively (FIG. 8B,C). Similarly, R3Mab efficiently blocked FGF9 binding to FGFR3-IIIb and -IIIc, with an $IC_{50}$ of 1.1 nM and 1.3 nM, respectively (FIG. 8D,E).

R3Mab Inhibits WT FGFR3 and its Most Prevalent Cancer-Associated Mutant Variants To examine whether R3Mab inhibits cell proliferation driven by WT or mutant FGFR3, we took advantage of the observation that ectopic FGFR3 expression in murine pro-B cell Ba/F3 confers interleukin (IL)-3-independent, FGF1-dependent proliferation and survival (29). In the absence of FGF1 and IL-3, Ba/F3 cells stably expressing WT FGFR3 were not viable, while FGF1 greatly enhanced their proliferation (FIG. 9A). R3Mab specifically blocked FGF1-stimulated Ba/F3-FGFR3 cell proliferation in a dose-dependent manner (FIG. 9A). We next evaluated the impact of R3Mab on FGFR3 signaling in these cells. FGF1 induced phosphorylation and activation of FGFR3 and concomitant activation of p44/42 MAPK, while R3Mab effectively suppressed the activation of both molecules (FIG. 9B).

Figure 9C:
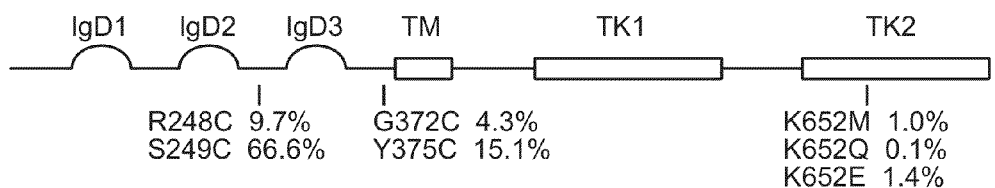
Figure 9D:
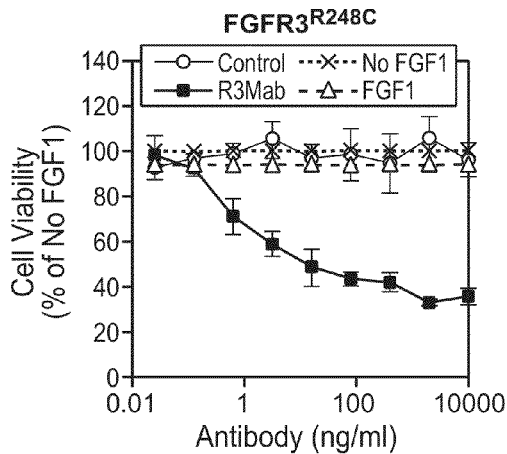
Figure 9E:
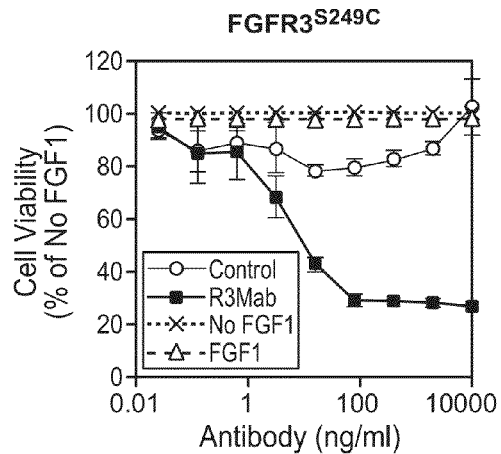
Figure 9F:
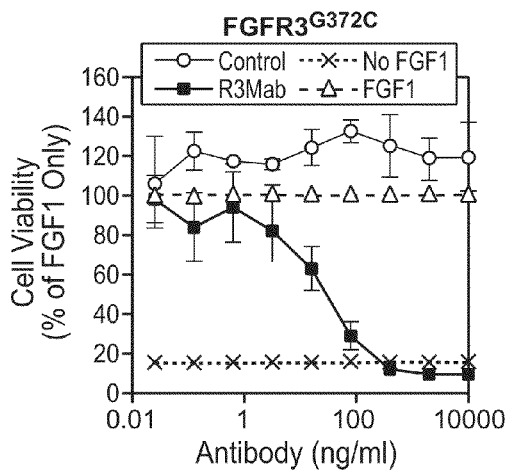
Figure 9G:
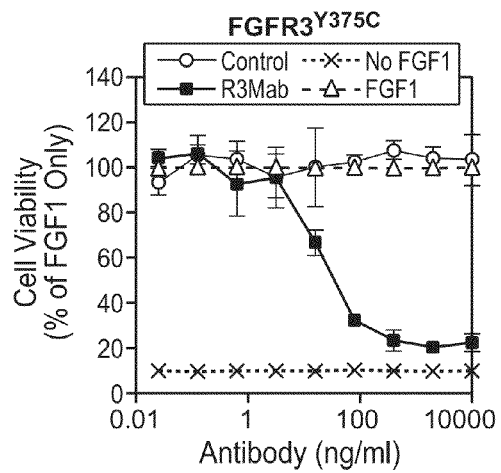
Figure 9H:
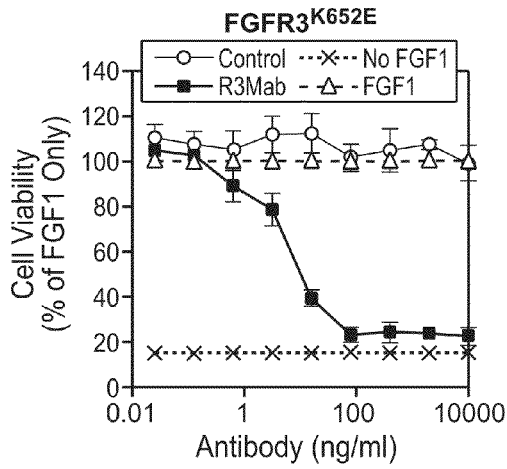

In bladder cancer, somatic activating mutations in FGFR3 cluster within the linker region between IgD2 and IgD3, the extracellular juxtamembrane domain, or the kinase domain (FIG. 9C). The extracellular missense substitutions most often give rise to an unpaired cysteine, leading to ligand-independent dimerization of FGFR3. These mutations cause markedly different levels of constitutive FGFR3 activation, possibly owing to a differential impact on the orientation of the cytoplasmic kinase domain (30, 31). The most frequent mutations are S249C, Y375C, R248C, G372C, and K652E, which together account for 98% of all FGFR3 mutations in bladder cancer (32). We reasoned that an optimal therapeutic agent should block not only the WT FGFR3 protein, which is overexpressed in certain cancers, but also the most prevalent tumor-associated FGFR3 mutants. To assess R3Mab further, we generated Ba/F3 cell lines stably expressing each of the five most common FGFR3 mutant variants. All mutants were expressed at similar levels at the cell surface, and the cysteine mutants dimerized spontaneously without ligand (data not shown). Cell lines expressing different cysteine mutants exhibited a variable growth response to FGF1, consistent with earlier findings (30, 31). As previously reported (33), cells expressing $FGFR3^{R248C}$ displayed constitutive, ligand-independent proliferation, and were not responsive to FGF1 (FIG. 9D). Similarly, the most frequent mutation, $FGFR3^{S249C}$, conferred ligand-independent proliferation (FIG. 9E). Remarkably, R3Mab suppressed constitutive proliferation driven by either mutant (FIG. 9 D,E). Cells expressing the juxtamembrane domain mutations $FGFR3^{G372C}$ (FIG. 9F) or $FGFR3^{Y375C}$ (FIG. 9G) required FGF1 for proliferation, and their growth was completely blocked by R3Mab. Cells expressing $FGFR3^{K652E}$ showed weak ligand-independent proliferation and significant growth in response to FGF1 (33). R3Mab did not affect the weak basal activity of $FGFR3^{K652E}$ (data not shown), but nearly abolished ligand-induced proliferation mediated by this mutant (FIG. 9H). Hence, R3Mab has a unique capacity to inhibit both WT and prevalent cancer-associated mutants of FGFR3. Moreover, R3Mab did not display detectable agonist activity.

As a separate effort, we generated and characterized multiple mouse-anti-human FGFR3 hybridoma antibodies. None of the hybridoma antibodies could inhibit all the cancer-linked FGFR3 mutants we tested (FIG. 17), nor did they share overlapping epitopes with R3Mab.

Moreover, all of the hybridoma antibodies showed agonist activity, strongly stimulating proliferation of cancer-linked FGFR3 mutants R248C and S249C, and showing some stimulation of proliferation of mutants Y375C and G370C. The hybridoma antibodies showed differential levels of antagonist and agonism, depending on the FGFR3 mutant tested, as follows:

|  | 1G6 | 6G1 | 15B2 |
|---|---|---|---|
| FGFR3-IIIb wildtype | inhibition | inhibition | inhibition |
| FGFR3-IIIb R248C | 2X stimulation | 4-5X stimulation | 3-4X stimulation |
| FGFR3-IIIbS249C | 2X stimulation | 4-5X stimulation | 4-5X stimulation |
| FGFR3-IIIb Y375C | 1.2-1.5X stimulation | 1.2-1.5X stimulation | 1.2-1.5X stimulation |
| FGFR3-IIIb K652E | 50% inhibition | 60-70% inhibition | inhibition |
| FGFR3-IIIc | inhibition | inhibition | inhibition |
| FGFR3-IIIc G370C | No effect | 20-30% inhibition | 10-2-% inhibition |

Thus, the hybridoma antibodies showed unpredictable differential effect on Ba/F3 cells cell proliferation driven by various FGFR3 mutants.

Characterization of Mouse-Anti-Human FGFR3 Hybridoma Antibodies

Mouse anti-human FGFR3 hybridoma antibodies were further characterized as follows:

(1) In an assay to test ability of anti-FGFR3 murine hybridoma antibodies to inhibit FGF1 binding to human FGFR3-IIIb and IIIc isoforms, antibodies 1G6, 6G1 and 15B2 were able to block binding of FGF1 to human FGFR3-IIIb and IIIc isoforms in a dose-dependent manner. When tested across an antibody concentration range of about 2000 to 0.49 ng/ml, antibodies 1G6, 6G1 and 15B2 blocked FGF1 binding to FGFR3-IIIb with IC50 values of 0.69, 0.87 and 0.72 nM. When tested across an antibody concentration range of about 5000 to 1.2 ng/ml, antibodies 1G6, 6G1 and 15B2 blocked FGF1 binding to FGFR3-IIIc with IC50 values of 0.57, 3.4 and 0.7 nM, respectively.

(2) In an assay to test ability of anti-FGFR3 murine hybridoma antibodies to inhibit FGF9 binding to human FGFR3-IIIb and Inc isoforms, antibodies 1G6, 6G1 and 15B2 efficiently blocked binding of FGF1 to human FGFR3-IIIb and Inc isoforms in a dose-dependent manner. When tested across an antibody concentration range of about 2000 to 0.49 ng/m, antibodies 1G6, 6G1 and 15B2 blocked FGF9 binding to FGFR3-IIIb with IC50 values of 0.13, 0.16, and 0.07 nM, respectively. When tested across an antibody concentration range of about 5000 to 1.2 ng/ml, antibodies 1G6, 6G1 and 15B2 blocked FGF9 binding to FGFR3-IIIc with IC50 values of 0.13, 0.11, and 0.07 nM, respectively.

(3) The binding affinity of full-length anti-FGFR3 murine hybridoma antibodies 1G6, 6G1 and 15B2 was determined using Biacore analysis. The results of this analysis are shown in Table3.

TABLE 3

| Antibody | FGFR3-IIIB | | | FGFR3-IIIC | | |
|---|---|---|---|---|---|---|
| | kon ($10^5$ $M^{-1}s^{-1}$) | koff ($10^{-4}s^{-1}$) | Kd (nM) | kon ($10^5$ $M^{-1}s^{-1}$) | koff ($10^{-4}s^{-1}$) | Kd (nM) |
| 1G6 mIgG | 2.2 | 3.1 | 1.4 | 2.2 | 2.8 | 1.3 |
| 6G1 mIgG | 2.7 | 3.8 | 1.4 | 2.6 | 3.2 | 1.2 |
| 15B2 mIgG | 4.1 | 29 | 7.1 | 3.5 | 39 | 11.1 |

(4) In an assay to test ability of anti-FGFR3 murine hybridoma antibodies to inhibit Ba/F3 cell proliferation driven by human FGFR3-IIIb or IIIc, antibodies 1G6, 6G1 and 15B2 were able to block Ba/F3 cell proliferation driven by human FGFR3-IIIb or Inc in a dose-dependent manner. When tested across an antibody concentration range of about 0.01 to 100 ug/ml, antibodies 1G6, 6G1 and 15B2 blocked Ba/F3 cell proliferation driven by FGFR3-IIIb with IC50 values of 3-5 nM, 3 nM, and 6-8 nM, respectively, and blocked Ba/F3 cell proliferation driven by FGFR3-IIIc with IC50 values of 10-35 nM, 24 nM, and 60 nM, respectively.

(5) In an assay to test ability of anti-FGFR3 murine hybridoma antibodies to inhibit FGF1-induced signaling in Ba/F3 cells expressing human FGFR3-IIIb, antibodies 1G6, 6G1 and 15B2 were able to block FGF1-induced signaling in Ba/F3 cells expressing human FGFR3-IIIb in a dose-dependent manner when tested across an antibody concentration range of about 0.25 to 6.75 ug/ml. 25 ng/ml of FGF1 was used in this experiment. In the absence of FGF1, antibody treatment had no effect on FGFR3 activation.

(6) In an assay to test ability of anti-FGFR3 murine hybridoma antibodies to inhibit FGF1-induced signaling in Ba/F3 cells expressing human FGFR3-IIIc, antibodies 1G6, 6G1 and 15B2 were able to block FGF1-induced signaling in Ba/F3 cells expressing human FGFR3-IIIc in a dose-dependent manner when tested across an antibody concentration range of about 0.25 to 6.75 ug/ml. 25 ng/ml of FGF1 was used in this experiment. In the absence of FGF1, antibody treatment had no effect on FGFR3 activation.

Structural Basis for the Interaction of R3Mab with FGFR3

Figures 10A, 10B:
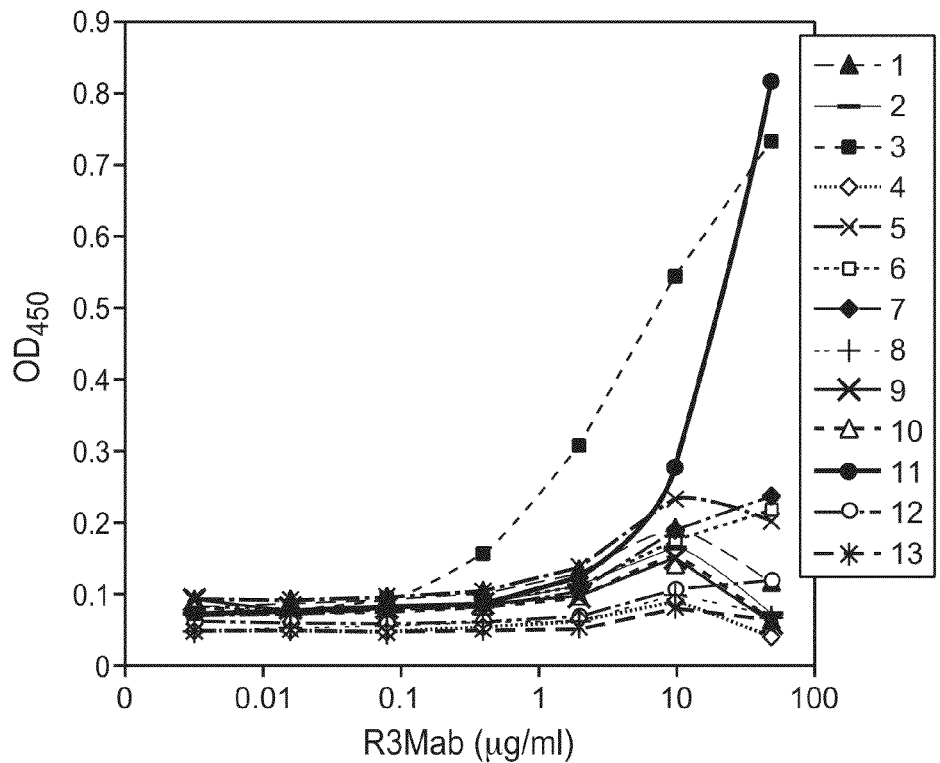

To gain insight into R3Mab's mode of interaction with FGFR3, we synthesized a panel of 13 overlapping peptides spanning the FGFR3-IIIb IgD2 and D3 regions and tested their binding to R3Mab. Peptides 3 (residues 164-178) and 11 (residues 269-283) showed specific binding to R3Mab, with peptide 3 having a stronger interaction (FIG. 10A), indicating that the corresponding regions on FGFR3 are critical for recognition by R3Mab. Previous crystallographic studies of FGFR1 in complex with FGF2 identified critical receptor residues engaged in direct binding to FGF and heparin as well as in receptor dimerization (34). Alignment of FGFR3 peptides 3 and 11 with the functionally important sites in FGFR1 revealed that these peptides encompass corresponding FGFR1 residues essential for direct FGF2 binding, receptor dimerization, as well as interaction with heparin (FIG. 10B). These data indicate that the epitope of R3Mab on FGFR3 overlaps with receptor residues engaged in ligand association and receptor-receptor interaction.

Figure 10C:
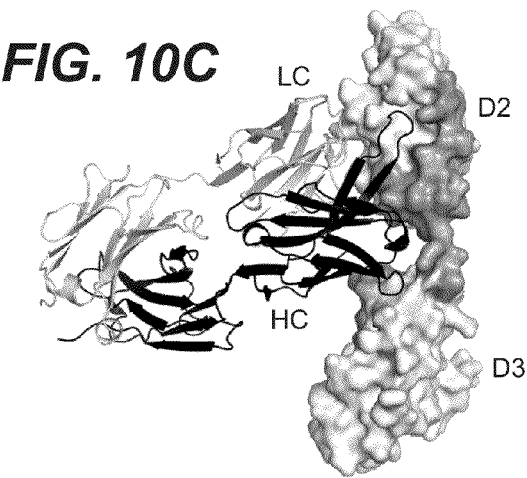
Figure 10D:
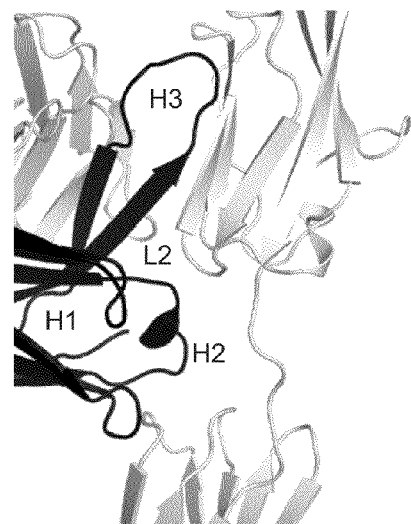

We next crystallized the complex between the Fab fragment of R3Mab and the extracellular IgD2-D3 region of human FGFR3-IIIb, and determined the X-ray structure at 2.1 Å resolution (FIG. 10C, D; Table 4). In this complex, approximately 1400 Å2 and 1500 Å2 of solvent-accessible surface areas are buried on FGFR3 and the Fab, respectively. About 80% of the buried interface involves IgD2, while the remainder entails the linker and IgD3 regions. On the Fab side of the complex, about 40% of the buried interface involve complementarity-determining region (CDR)—H3, 20% CDR-H2, 20% CDR-L2, and minor contributions are from other CDRs and framework residues. Notably, amino acids (AAs) from CDR-H3 form two β-strands, which extend the β-sheet of IgD2 (FIG. 10D). The Fab interacts with AAs that constitute the FGF binding site of FGFR3 as well as residues that form the receptor dimerization interface, as previously identified in various dimeric FGF:FGFR complexes (e.g., PDB code 1CVS, (34); and FIG. 10C, areas in grey/crosshatched and dark grey). The interaction interfaces identified by crystallography were fully consistent with the peptide-based data (FIG. 18 A, B). Together, these results reveal how R3Mab inhibits ligand binding, and further suggest that binding of R3Mab to FGFR3 may prevent receptor dimerization. FGFR3 amino acids that contact R3Mab are shown in Table 5. Crystallographic coordinates for this structure are deposited in the Protein Data Bank with accession code 3GRW.

TABLE 4

Summary of crystallographic analysis

| Data collection | FGFR3-IIIb: R3Mab Fab |
|---|---|
| Space group | $P2_12_12_1$ |
| Cell parameters | a = 58.5, b = 99.3, c = 143.7 |
| Resolution (Å) | 25-2.1 |
| $R_{sym}{}^a$ | 0.098 $(0.663)^b$ |
| Number of observations | 288498 |
| Unique reflections | 49851 |
| Completeness (%) | 99.9 $(100.0)^b$ |
| Refinement | |
| Resolution (Å) | 20-2.1 |
| Number of reflections | 46714 |
| Final $R^c$, $R_{free}$ (F > 0) | 0.187, 0.224 |
| Number of non-H atoms | 5270 |
| Number of Amino Acids | 650 |
| Sulfate | 1 |
| Sugar | 1 |
| Solvent atoms | 274 |
| Rmsd bonds (Å) | 0.011 |
| Rmsd angles (°) | 1.4 |

$^a R_{sym} = \Sigma |I - <I>|/\Sigma I \cdot <I>$ is the average intensity of symmetry related observations of a unique reflection.
$^b$Numbers in parentheses refer to the highest resolution shell.
$^c R = \Sigma |F_o - F_c|/\Sigma F_o \cdot R_{free}$ is calculated as R, but for 5% of the reflections excluded from all refinement.

TABLE 5

Residues in FGFR3 that are in contact with R3Mab Residue
Buried surface of residue in the interface THR 154 0.10
ARG 155 16.50
ARG 158 105.40
MET 159 6.00
LYS 161 52.50
LYS 162 1.70
LEU 163 12.30
LEU 164 55.10
ALA 165 10.10
VAL 166 10.60
PRO 167 45.50
ALA 168 22.60
ALA 169 63.60
ASN 170 75.40
THR 171 83.00
VAL 172 1.70
ARG 173 91.70
PHE 174 1.50
ARG 175 95.60
PRO 177 15.90
GLY 202 2.10

TABLE 5-continued

Residues in FGFR3 that are in contact with R3Mab Residue
Buried surface of residue in the interface

|  |
| --- |
| LYS 205 63.40 |
| ARG 207 67.60 |
| GLN 210 31.60 |
| SER 212 0.40 |
| VAL 214 26.40 |
| GLU 216 48.90 |
| SER 217 1.80 |
| TYR 241 15.90 |
| LEU 246 3.10 |
| GLU 247 1.80 |
| ARG 248 46.90 |
| TYR 278 32.20 |
| SER 279 1.80 |
| ASP 280 19.80 |
| ALA 281 3.00 |
| GLN 282 24.80 |
| PRO 283 0.50 |
| SER 314 1.20 |
| GLU 315 82.60 |
| SER 316 33.20 |
| VAL 317 56.60 |
| GLU 318 51.50 |

Figure 10E:
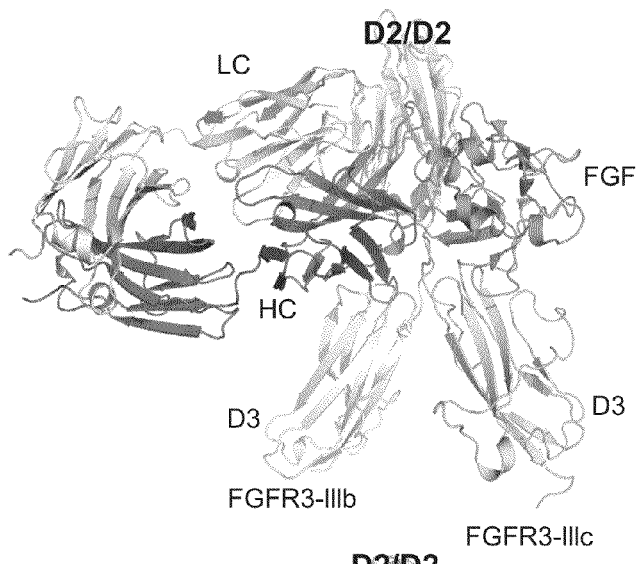
Figure 10F:
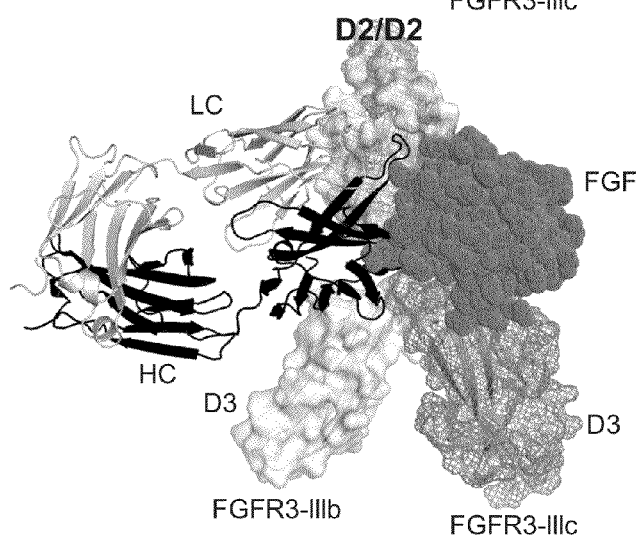

We compared the R3Mab-FGFR3 structure with a previously published structure of FGFR3-IIIc in complex with FGF1 (4, 35) (FIG. 10E, 10F). Superposition of the antibody-receptor and ligand-receptor complexes revealed that there are no major conformational differences within the individual receptor domains, except in the region that distinguishes FGFR3-IIIc from FGFR3-IIIb; however, the orientation of IgD3 relative to IgD2 was drastically different (FIG. 10E, white and grey; FIG. 10F, white and grey-mesh). Since the relative positions of IgD2 and IgD3 are critical for ligand binding, the alternate conformation adopted by IgD3 upon R3Mab binding may provide an additional mechanism to prevent ligand interaction with FGFR3.

R3Mab Inhibits Endogenous Wt and Mutant FGFR3 in Bladder Cancer Cells

Figure 11A:
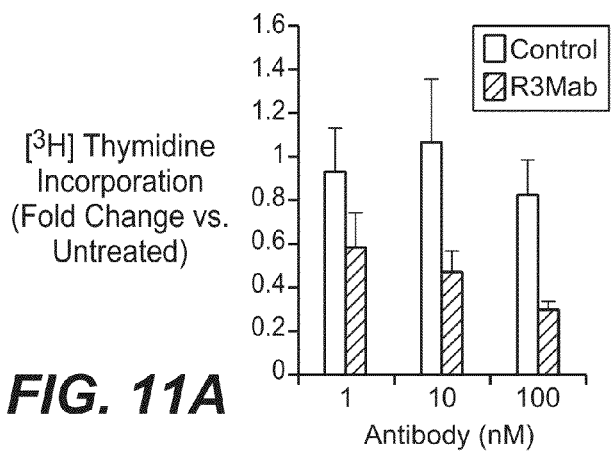
Figure 11B:
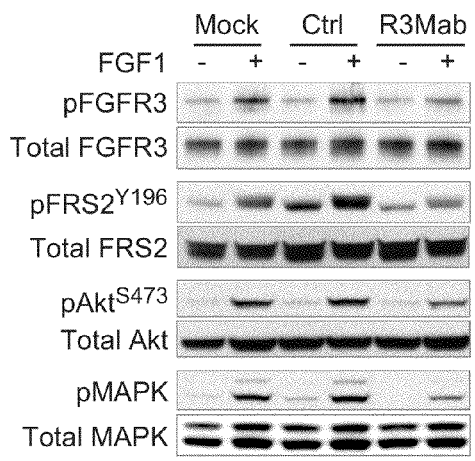
Figure 19A:
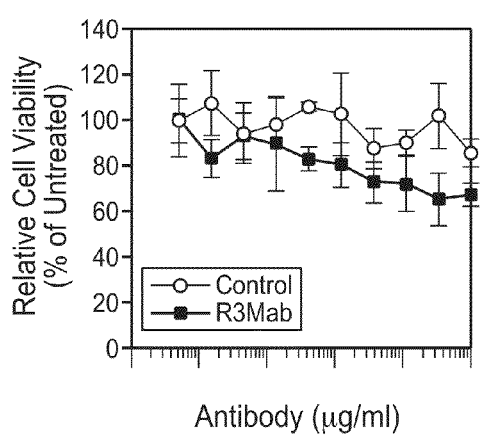
Figure 19B:
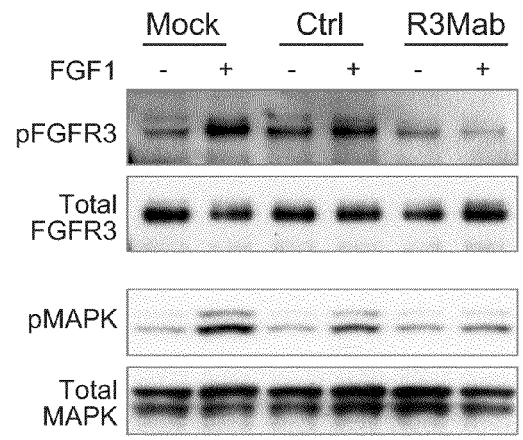

To assess whether R3Mab could suppress FGFR3 function in bladder cancer cells, we first examined RT112 and RT4 cell lines, which express WT FGFR3. R3Mab strongly inhibited [$^3$H]-thymidine incorporation by RT112 cells (FIG. 11A) and exerted a significant, though more moderate suppression of RT4 cell proliferation (FIG. 19A). To investigate R3Mab's effect on FGFR3 activation, we examined the phosphorylation of FGFR3 in RT112 cells. Consistent with the results in Ba/F3-FGFR3 cells (FIG. 9B), R3Mab markedly attenuated FGF1-induced FGFR3 phosphorylation (FIG. 11B). We next examined phosphorylation of FRS2α, AKT, and p44/42 MAPK, three downstream mediators of FGFR3 signaling. FGF1 strongly activated these molecules in RT112 cells, while R3Mab significantly diminished this activation (FIG. 11B). Similarly, R3Mab suppressed FGF1-induced phosphorylation of FGFR3 and MAPK in RT4 cells (FIG. 19B).

Figure 11C:
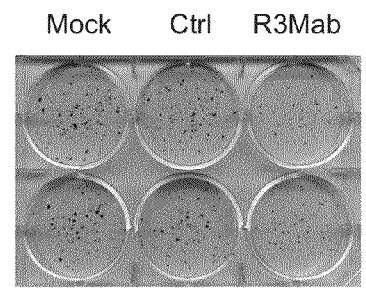
Figure 11D:
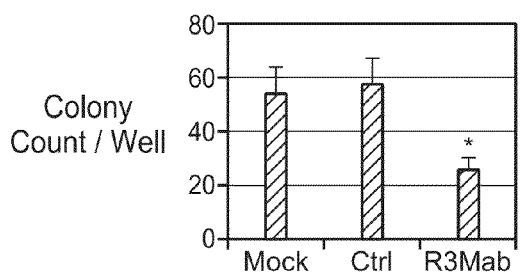
Figure 19C:
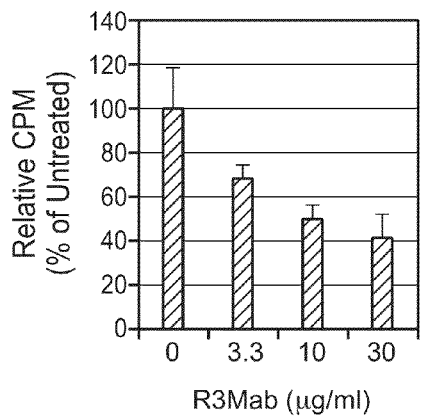

We next investigated whether R3Mab could inhibit activation of endogenous mutant FGFR3 in human bladder cancer cells. S249C is the most frequent FGFR3 mutation in bladder cancer (FIG. 9C). Two available cell lines, UMUC-14 and TCC-97-7, carry a mutated FGFR3$^{S249C}$ allele (Ref. 36 and data not shown). Although R3Mab did not affect the exponential growth of UMUC-14 cells in culture (data not shown), it significantly reduced the clonal growth of these cells (FIG. 11C). Specifically, R3Mab decreased the number of colonies larger than 120 μm in diameter approximately by 77% as compared with control antibody (FIG. 11D). Furthermore, R3Mab inhibited [$^3$H]-thymidine incorporation by TCC-97-7 cells in culture (FIG. 19C).

Figure 11E:
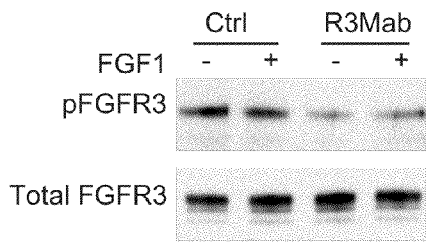
Figure 19D:
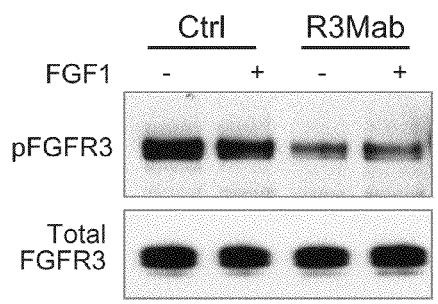

The S249C mutation is reported to result in ligand-independent activation of FGFR3 (26, 30). Indeed, FGFR3$^{S249C}$ was constitutively phosphorylated irrespective of FGF1 treatment in UMUC-14 cells and TCC-97-7 cells, while R3Mab reduced constitutive phosphorylation of FGFR3$^{S249C}$ as compared with control antibody in both cell lines (FIGS. 11E, 19D).

R3Mab inhibits dimer formation by FGFR3$^{S249C}$

Figure 12A:
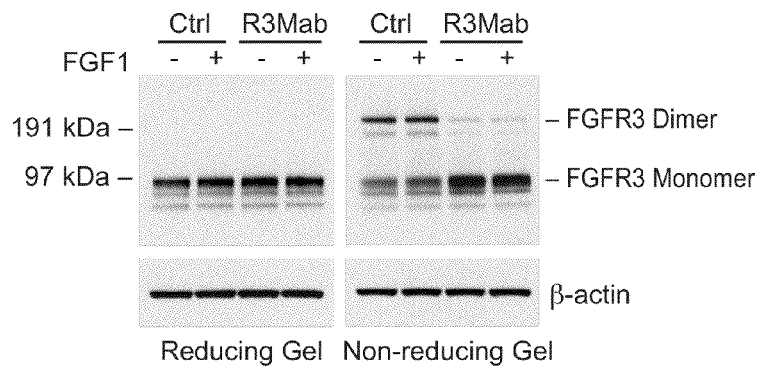
Figure 12B:
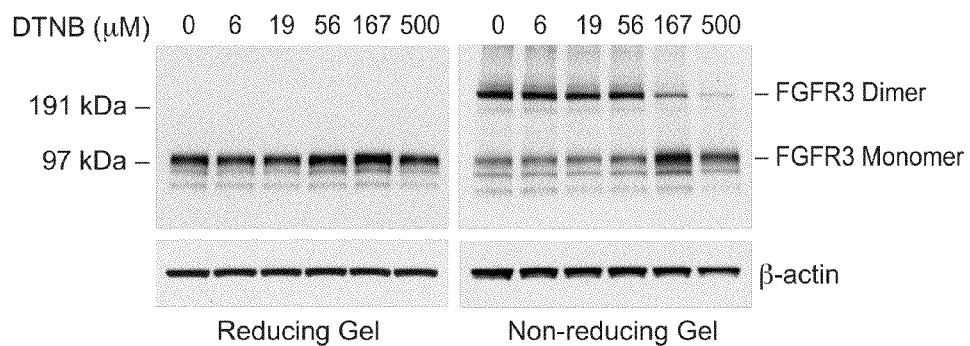
Figure 12C:
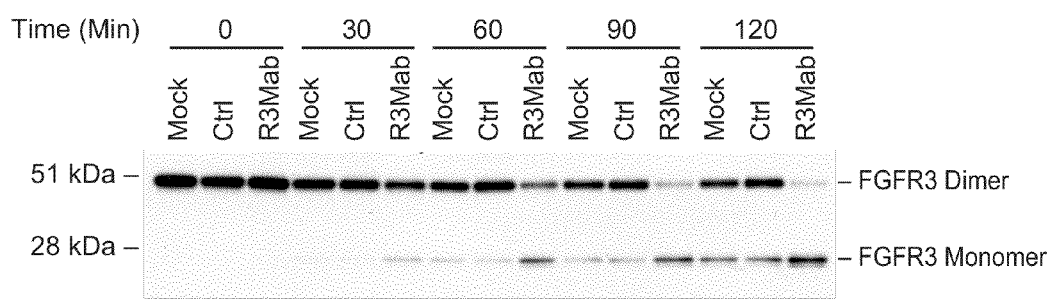
Figure 19E:
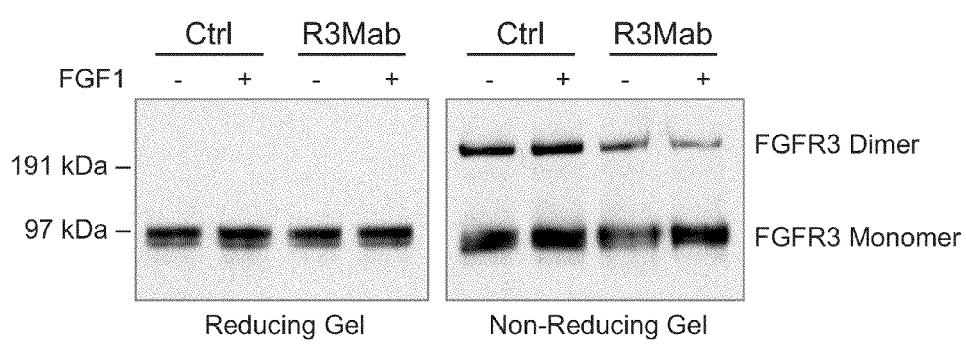

The ability of R3Mab to inhibit constitutive FGFR3$^{S249C}$ signaling and proliferation in bladder cancer cells was surprising, considering that this mutant can undergo disulfide-linked, ligand-independent dimerization (26, 30). To explore how R3Mab inhibits FGFR3$^{S249C}$, we examined the effect of R3Mab on the oligomeric state of this mutant in UMUC-14 cells. Under reducing conditions, FGFR3$^{S249C}$ migrated as a single band of ~97 kDa, consistent with monomeric size (FIG. 12A). Under non-reducing conditions, in cells treated with control antibody a large fraction of FGFR3$^{S249C}$ appeared as a band of ~200 kDa, regardless of FGF1 addition, indicating a constitutive dimeric state (FIG. 12A). R3Mab treatment substantially decreased the amount of dimers, with a concomitant increase in monomers (FIG. 12A). Consistently, R3Mab decreased the level of FGFR3$^{S249C}$ dimers in TCC-97-7 cells irrespective of FGF1 treatment (FIG. 19E).

How does R3Mab decrease the FGFR3$^{S249C}$ dimer levels in bladder cancer cells? One potential explanation is that it may disrupt the FGFR3$^{S249C}$ dimer through antibody-induced FGFR3 internalization and trafficking through endosomes or lysosomes. We tested this possibility by pharmacologically intervening with endocytosis. R3Mab nonetheless decreased the amount of dimer in UMUC-14 cells pre-treated with various endocytosis inhibitors, despite substantial blockade of FGFR3$^{S249C}$ internalization (FIG. 20 A, B). Thus, dimer disruption by R3Mab is independent of endocytosis. Another possible explanation is that cellular FGFR3$^{S249C}$ may exist in a dynamic monomer-dimer equilibrium; accordingly, binding of R3Mab to monomeric FGFR3$^{S249C}$ could prevent dimer formation and thereby shift the equilibrium toward the monomeric state. To examine this possibility, we used the non-cell-permeating agent 5,5 'Dithiobis 2-nitrobenzoic acid (DTNB), which selectively reacts with and blocks free sulfhydryl groups of unpaired cysteines (37). Treatment of UMUC-14 cells with DTNB led to the accumulation of FGFR3$^{S249C}$ monomers at the expense of dimers (FIG. 12B), indicating that FGFR3$^{S249C}$ exists in a dynamic equilibrium between monomers and dimers.

To test whether R3Mab affects this equilibrium, we generated a soluble recombinant protein comprising the IgD2-D3 domains of FGFR3$^{S249C}$ and isolated the dimers by size exclusion chromatography. We incubated the dimers with buffer or antibodies in the presence of a very low concentration of reducing agent (25 μM of DTT), and analyzed the oligomeric state of the receptor by SDS-PAGE under non-reducing conditions. R3Mab significantly accelerated the appearance of a ~25 kDa band representing monomeric FGFR3$^{S249C}$ at the expense of the ~50 kDa dimer, as compared with mock or antibody controls (FIG. 12C); indeed, by 2 hr the decrease in dimers was substantially more complete in the presence of R3Mab. These results indicate that R3Mab shifts the equilibrium between the monomeric and dimeric states of FGFR3$^{S249C}$ in favor of the monomer.

R3Mab does not Promote FGFR3 Down-Regulation

We examined the effect of R3Mab (clone 184.6.1) and anti-FGFR3 hybridoma antibodies on FGFR3 downregulation by analyzing FGFR3 internalization and degradation in FGFR3 antibody-treted cells. Bladder cancer cell lines expressing wild type FGFR3 (RT112) or mutated FGFR3

(S249C in TCC97-7) were treated with R3Mab or hybridoma antibodies 1G6 or 6G1 for 4 to 24 hours, then cell lysates were harvested for western blot analysis of total FGFR3 levels. Treatment with R3Mab did not reduce FGFR3 levels, while treatment with hybridoma mabs 1G6 and 6G1 significantly reduced FGFR3 levels. These results suggested that R3Mab did not promote FGFR3 down-regulation while mabs 1G6 and 6G1 did promote FGFR3 receptor internalization and down regulation. In a separate experiment, surface FGFR3 levels were examined using FACS analysis. After 24 hours of R3Mab (clone 184.6.1) treatment of UMUC-14 cells (containing FGFR3S249C mutation), cell surface FGFR3 levels slightly increased. These results demonstrate that R3Mab treatment did not promote FGFR3 down-regulation.

R3Mab Inhibits Growth and FGFR3 Signaling in Multiple Tumor Models

Figure 13A:
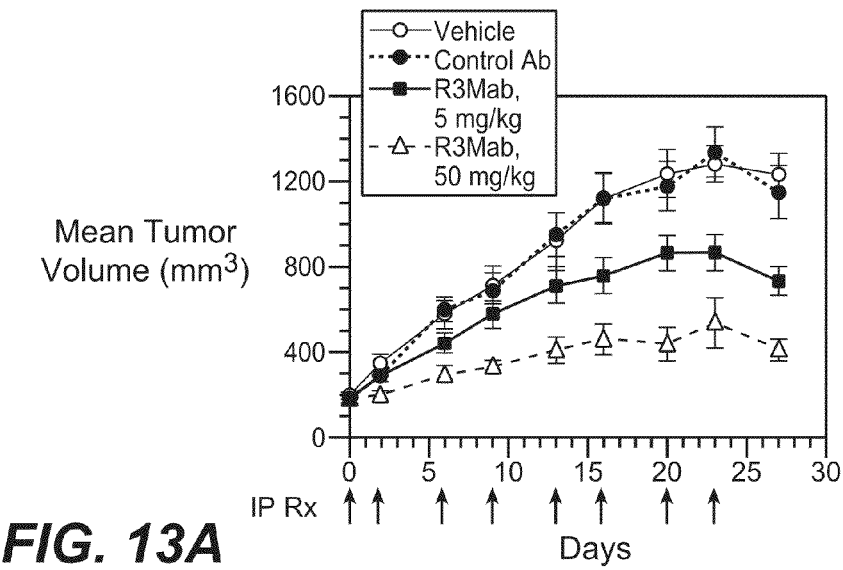
Figure 13B:
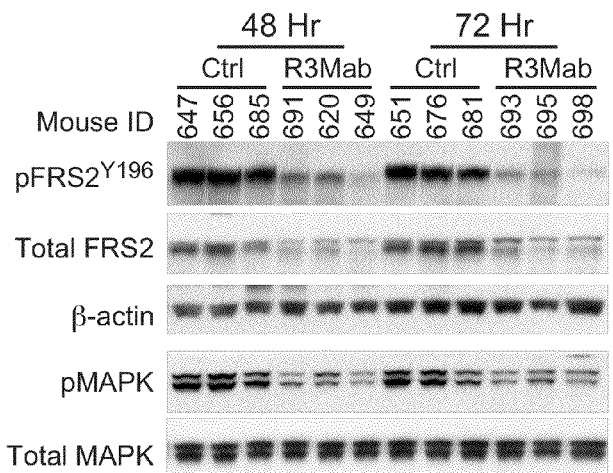

Next, we examined the effect of R3Mab on the growth of bladder cancer cells in vivo. We injected nu/nu mice with RT112 cells (which express WT FGFR3), allowed tumors to grow to a mean volume of ~150 mm$^3$, and dosed the animals twice weekly with vehicle or R3Mab. Compared with vehicle control at day 27, R3Mab treatment at 5 or 50 mg/kg suppressed tumor growth by about 41% or 73% respectively (FIG. 13A). Analysis of tumor lysates collected 48 hr or 72 hr after treatment showed that R3Mab markedly decreased the level of phosphorylated FRS2α (FIG. 13B). Intriguingly, total FRS2α protein levels were also lower in R3Mab-treated tumors, suggesting that FGFR3 inhibition may further lead to downregulation of FRS2α. R3Mab also lowered the amount of phosphorylated MAPK in tumors, without affecting total MAPK levels (FIG. 13B). Thus, R3Mab inhibits growth of RT112 tumor xenografts in conjunction with blocking signaling by WT FGFR3.

Figure 13C:
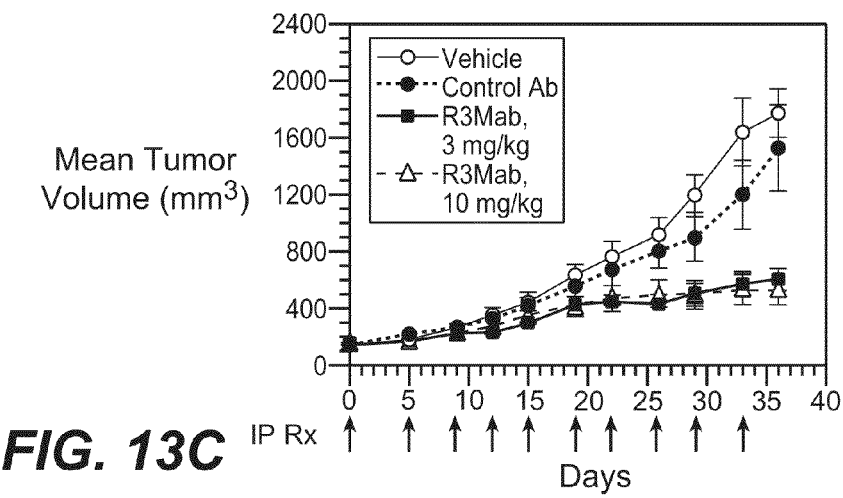
Figure 13D:
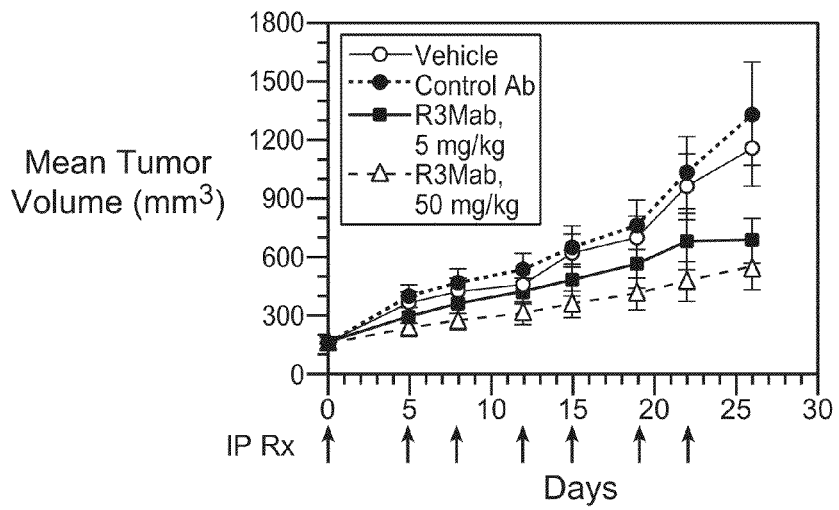
Figure 13E:
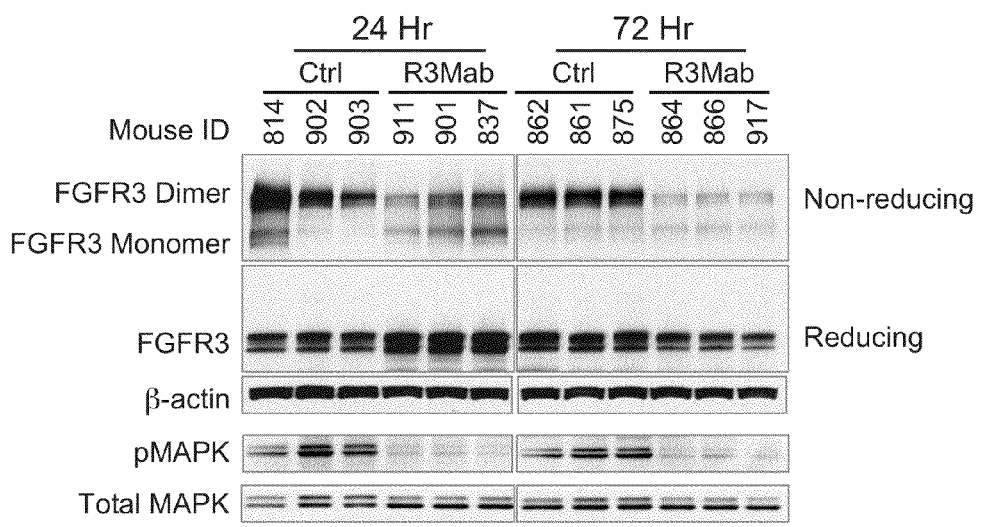

We next investigated the effect of R3Mab on growth of xenografts expressing mutant FGFR3. R3Mab treatment profoundly attenuated the progression of Ba/F3-FGFR3$^{S249C}$ tumors (FIG. 13C). Moreover, R3Mab significantly inhibited growth of UMUC-14 bladder carcinoma xenografts (FIG. 13D). To evaluate whether R3Mab impacts FGFR3$^{S249C}$ activation in vivo, we assessed the level of FGFR3$^{S249C}$ dimer in tumor lysates collected 24 hr or 72 hr after treatment. Under non-reducing conditions, the amount of FGFR3$^{S249C}$ dimer was substantially lower in R3Mab treated tumors as compared with control group, whereas total FGFR3$^{S249C}$ levels, as judged by the amount detected under reducing conditions, showed little change (FIG. 13E). No apparent accumulation of FGFR3$^{S249C}$ monomer was observed in tumor lysates, in contrast to the results in cell culture (FIG. 13E vs. 12A). This could be due to the weak detection sensitivity for monomeric FGFR3 under non-reducing conditions by the rabbit polyclonal anti-FGFR3 antibody used in this study (FIG. 21). Importantly, R3Mab also significantly inhibited the phosphorylation and activation of MAPK in UMUC-14 tumors (FIG. 13E), suggesting that R3Mab inhibits the activity of FGFR3$^{S249C}$ in vivo. We did not observe any significant weight loss or other gross abnormalities in any the in vivo studies. Furthermore, in a safety study conducted in mice, R3Mab, which binds with similar affinity to both human and murine FGFR3, did not exert any discernable toxicity in any organs, including bladder (data not shown). Together, these data indicate that multiple exposures to R3Mab are well tolerated in mouse.

Anti-Tumor Activity of R3Mab in Multiple Myeloma Xenograft Models Involves ADCC

Figure 22A:
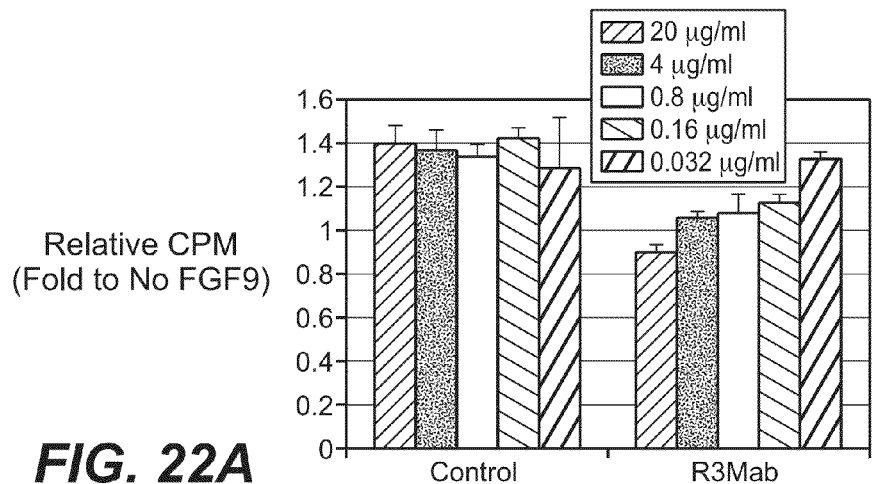
Figure 22B:
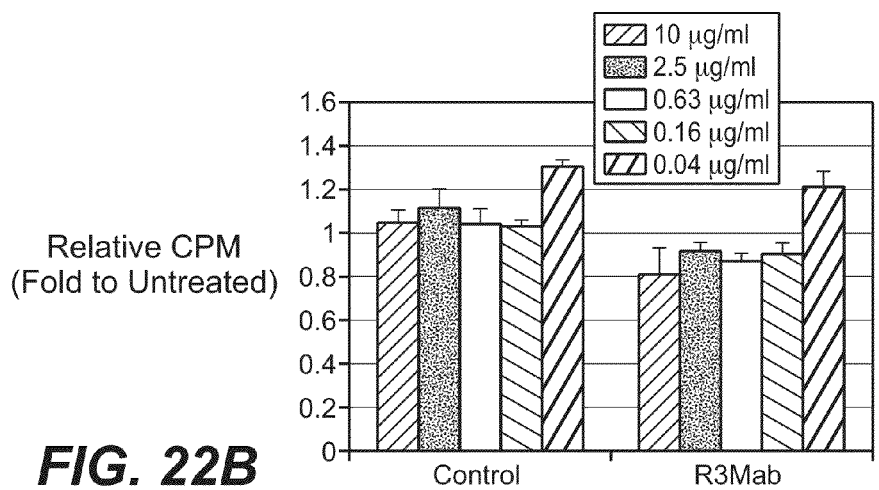
Figure 22C:
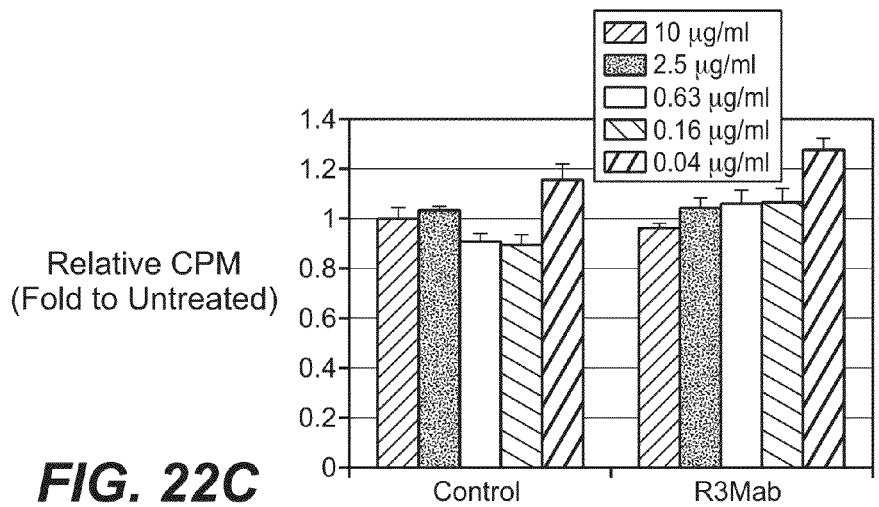

To assess whether R3Mab might harbor therapeutic potential for multiple myeloma, we first tested the effect of R3Mab on the proliferation and survival of three t(4;14)+ cell lines in culture. UTMC-2 cells carry WT FGFR3, while OPM2 and KMS11 harbor a K650E and Y373C substitution, respectively (7). In culture, R3Mab abrogated FGF9-induced proliferation of UTMC-2 cells completely (FIG. 22A). R3Mab modestly inhibited the growth of OPM2 cells, but had no apparent effect on the proliferation of KMS11 cells (FIG. 22B, C). Since UTMC-2 cells do not form tumors in mice, we evaluated the efficacy of R3Mab against OPM2 and KMS11 tumors. R3Mab almost completely abolished xenograft tumor growth of both cell lines (FIG. 14 A, B).

Figure 14A:
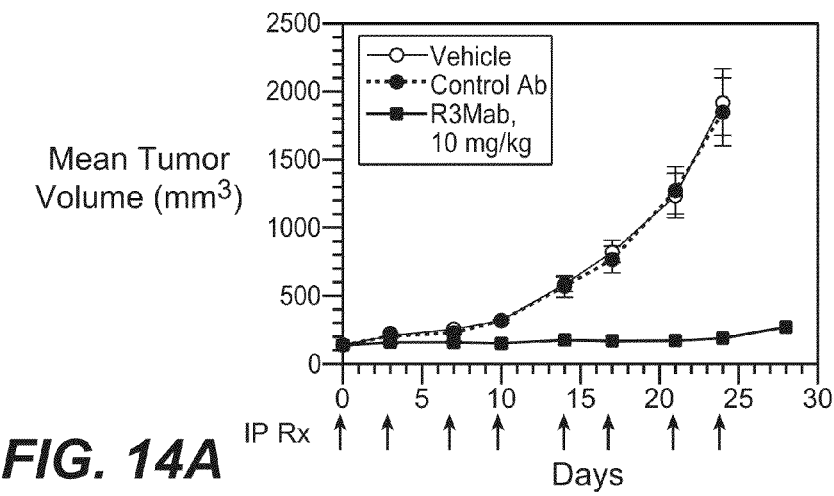
Figure 14B:
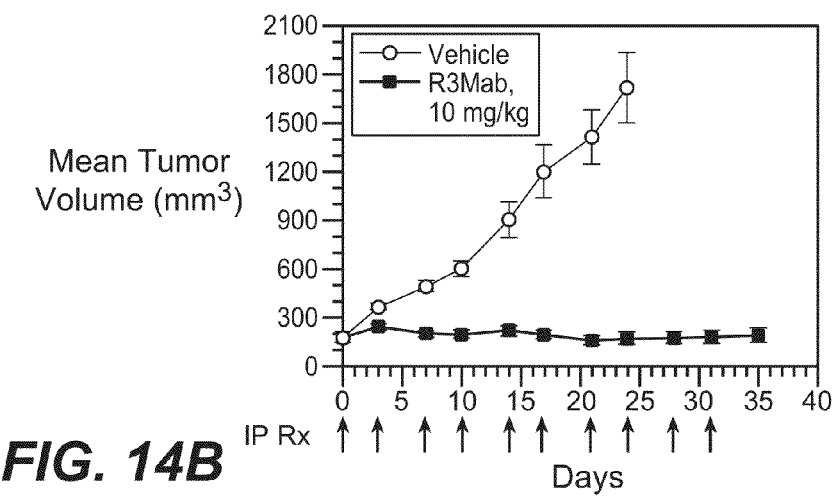
Figure 14C:
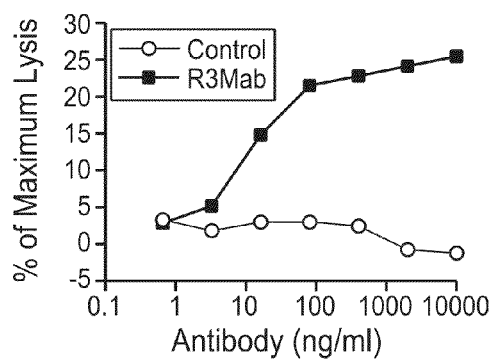
Figure 14D:
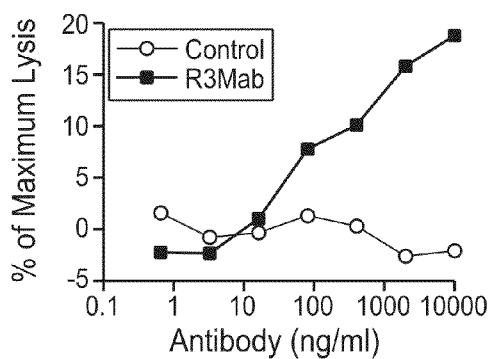
Figure 14E:
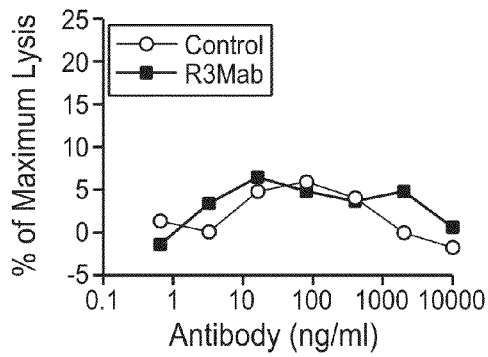
Figure 14F:
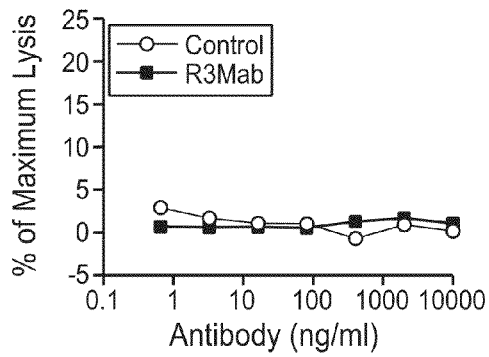

The marked difference in activity of R3Mab against OPM2 and KMS11 tumor cells in vitro and in vivo suggested the possibility that R3Mab may be capable of supporting Fc-mediated immune effector functions against these FGFR3-overexpressing tumors. Both cell lines express high levels of CD55 and CD59 (data not shown), two inhibitors of the complement pathway; accordingly, no complement-dependent cytotoxicity was observed (data not shown). We then focused on ADCC. ADCC occurs when an antibody binds to its antigen on a target cell, and via its Fc region, engages Fcγ receptors (FcγR5) expressed on immune effector cells (38). To test ADCC in vitro, we incubated KMS11 or OPM2 cells with freshly isolated human peripheral blood mononuclear cells (PBMC) in the presence of R3Mab or control antibody. R3Mab mediated significant PBMC cytolytic activity against both myeloma cell lines (FIG. 14C, D). By contrast, R3Mab did not support cytolysis of bladder cancer RT112 or UMUC-14 cells (FIG. 14E, F). As measured by Scatchard analysis, the multiple myeloma cells express substantially more cell-surface FGFR3 than the bladder carcinoma cell lines (~5-6 fold more receptors per cell; FIG. 23 A, B).

Figure 14G:
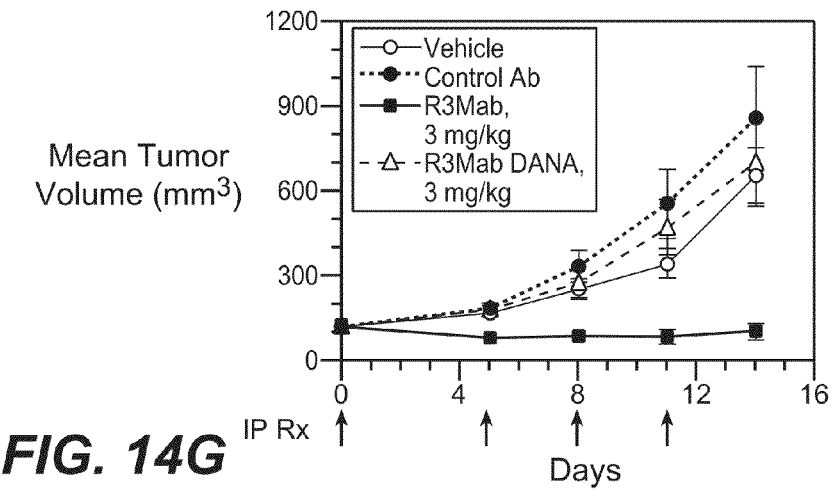
Figure 14H:
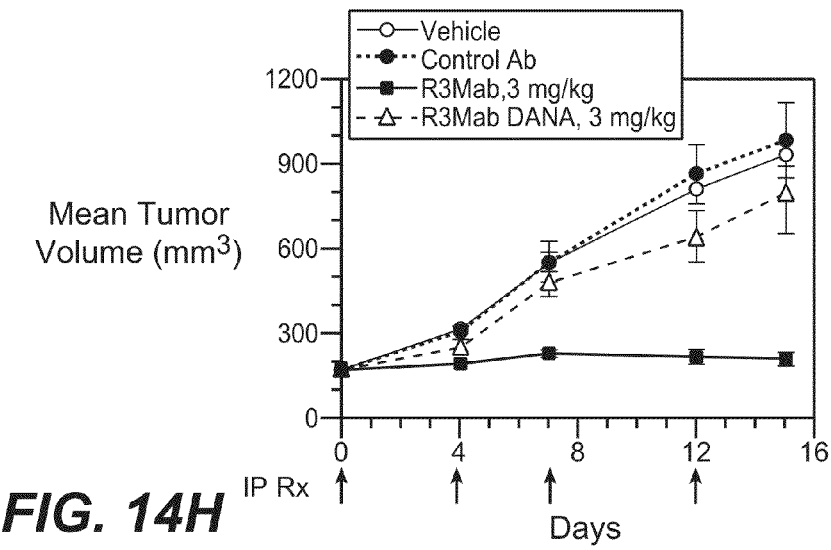
Figure 15A:
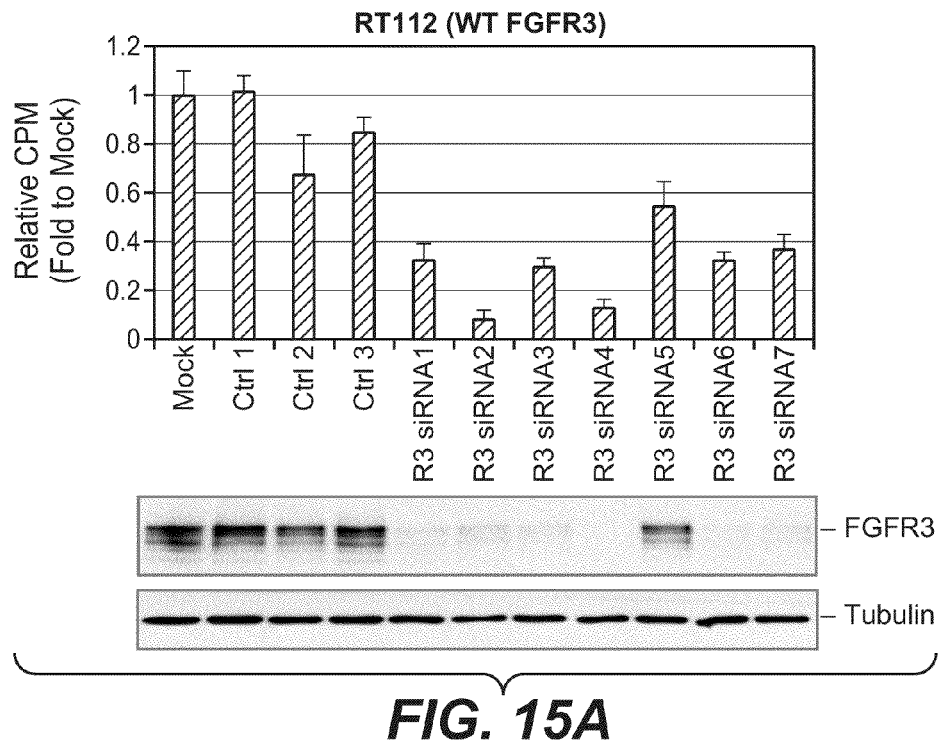
Figure 15B:
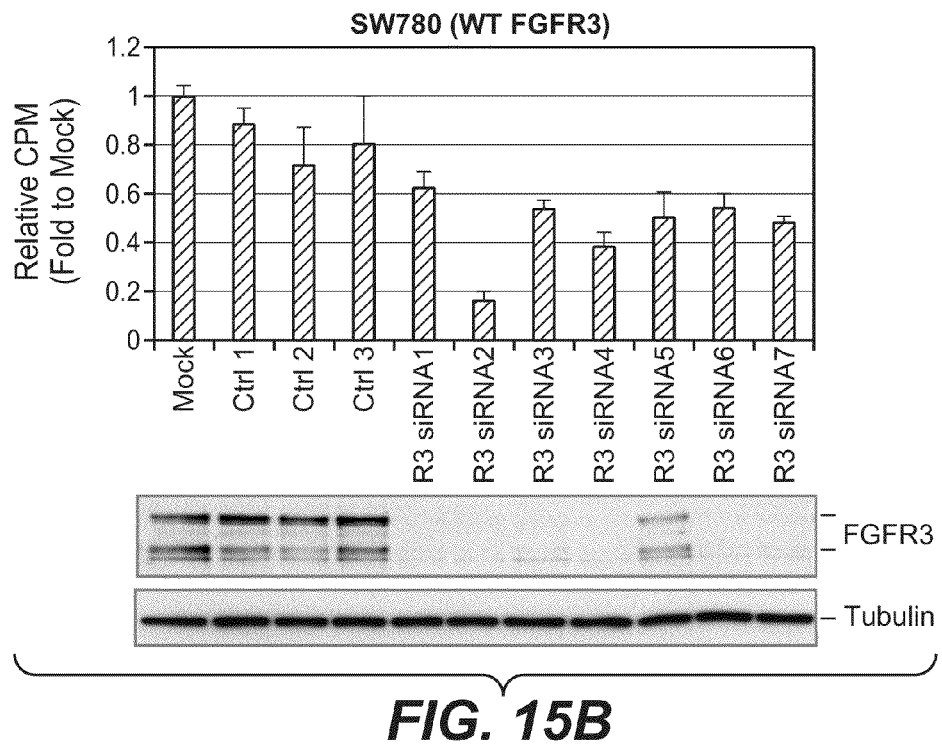
Figure 15C:
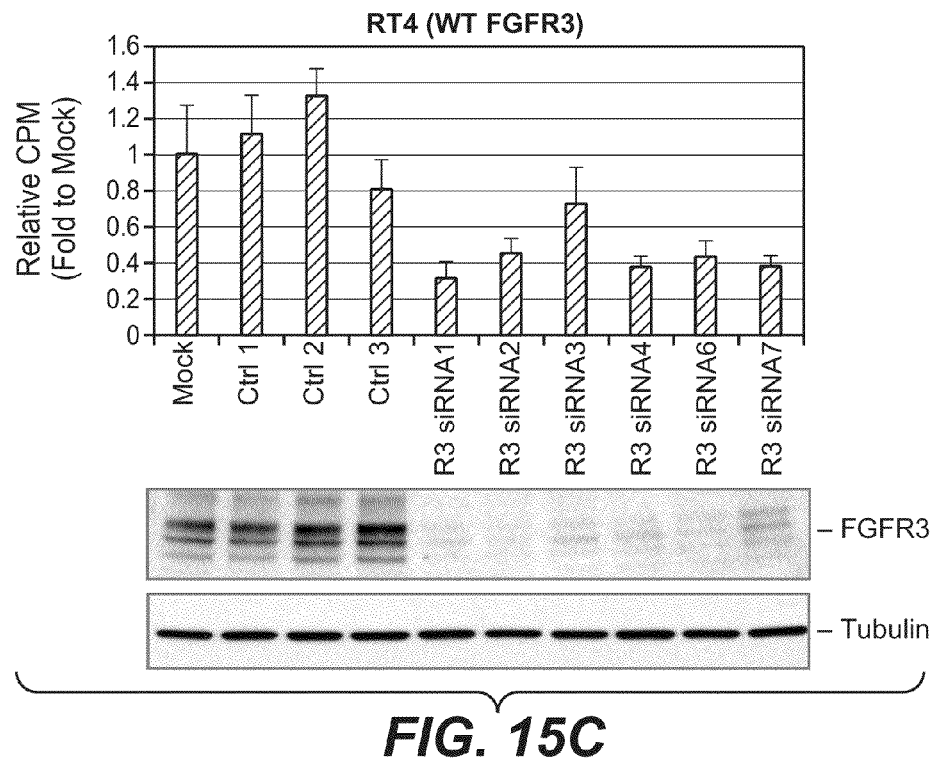
Figure 15D:
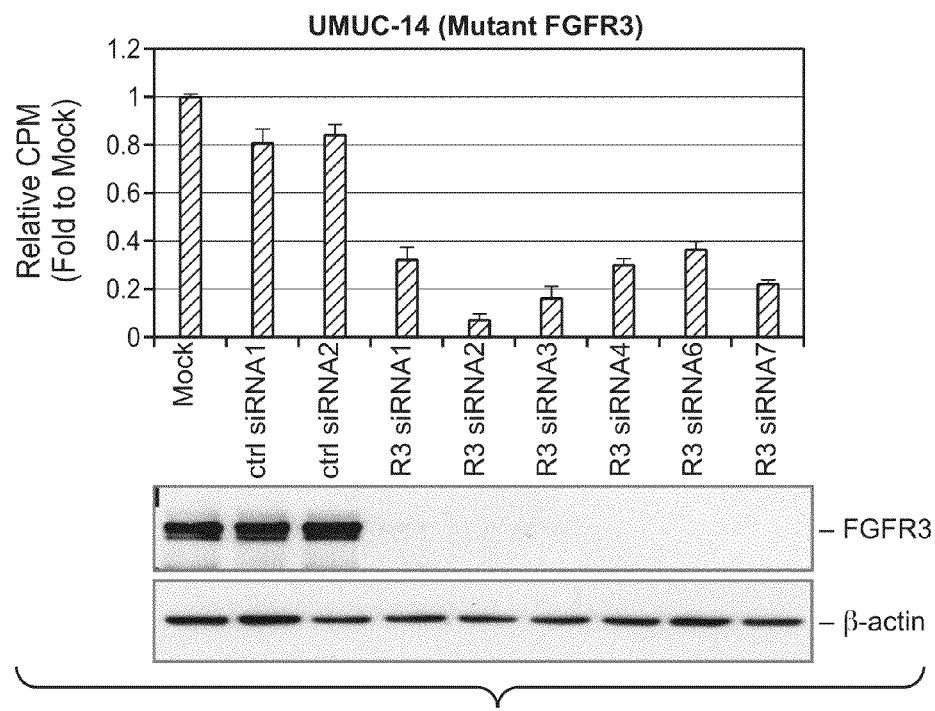

To address the contribution of ADCC to the activity of R3Mab in vivo, we introduced the previously characterized D265A/N297A (DANA) mutation into the antibody's Fc domain. This dual substitution in the Fc domain of an antibody abolishes its binding to FcγRs (39), preventing recruitment of immune effector cells. The DANA mutation did not alter R3Mab binding to FGFR3 or inhibition of FGFR3 activity in vitro, nor did it change the pharmacokinetics of R3Mab in mice (data not shown); however, it substantially abolished in vivo activity against OPM2 or KMS11 xenografts (FIG. 14G, H). By contrast, the DANA mutation did not alter the anti-tumor activity of R3Mab towards RT112 and UMUC-14 bladder cancer xenografts (FIG. 24 A, B). Together, these results suggest that Fc-dependent ADCC plays an important role in the efficacy of R3Mab against OPM2 and KMS11 multiple myeloma xenografts.

Additional Xenograft Studies

R3Mab (clone 184.6.1N54S) was further characterized as follows:

(a) R3Mab was tested for in vivo efficacy using a tumor xenograft model based on a liver cancer cell line (Huh7) essentially as described above. When tested at an antibody concentration of 5 mg/kg and 30 mg/kg, R3Mab significantly inhibited tumor growth in vivo. Tumor growth was inhibited about 50% compared to tumor growth in control animals.

(b) R3Mab was tested for in vivo efficacy using a tumor xenograft model based on a breast cancer cell line (Cal-51) which expressed FGFR3 essentially as described above. Results from this efficacy study showed that the R3Mab antibody was capable of inhibiting tumors in vivo when tested at antibody concentration range of about 1 mg/kg to 100 mg/kgs. Tumor growth was inhibited about 30% compared to tumor growth in control animals.

Discussion

The association of FGFR3 overexpression with poor prognosis in t(4;14)+ multiple myeloma patients and the transforming activity of activated FGFR3 in several experimental models have established FGFR3 as an important oncogenic driver and hence a potential therapeutic target in this hematologic malignancy. By contrast, despite reports of a high frequency of mutation and/or overexpression of FGFR3 in bladder carcinoma (24, 25, 40), a critical role for FGFR3 signaling in this epithelial malignancy has not been established in vivo. Moreover, the therapeutic potential of FGFR3 inhibition in bladder cancer has yet to be defined. Here we show that genetic or pharmacological intervention with FGFR3 inhibits growth of several human bladder cancer xenografts in mice. These results demonstrate that FGFR3 function is critical for tumor growth in this setting, underscoring the potential importance of this receptor as an oncogenic driver and therapeutic target in bladder cancer. Blockade of FGFR3 function inhibited growth of xenografts expressing either WT or mutant FGFR3 alike, suggesting that both forms of the receptor may contribute significantly to bladder tumor progression. Albeit much less frequently than in bladder cancer, FGFR3 mutations or overexpression have been identified in other solid tumor malignancies, including cervical carcinoma (40), hepatocellular carcinoma (41) and non-small cell lung cancer (42, 43), suggesting a potential contribution of FGFR3 to additional types of epithelial cancer.

The apparent involvement of FGFR3 in diverse malignancies identifies this receptor as an intriguing candidate for targeted therapy. While small molecule compounds that can inhibit FGFR3 kinase activity have been described (18-22, 44), the close homology of the kinase domains within the FGFR family has hampered the development of FGFR3-selective inhibitors. The lack of selectivity of the reported inhibitors makes it difficult to discern the relative contribution of FGFR3 to the biology of specific cancer types; further, it may carry safety liabilities, capping maximal dose levels and thus limiting optimal inhibition of FGFR3. Therefore, to achieve selective and specific targeting of FGFR3, we turned to an antibody-based strategy. We reasoned that an optimal therapeutic antibody should be capable of blocking not only the WT but also the prevailing cancer-linked mutants of FGFR3. Furthermore, given that dimerization of FGFR3 is critical for its activation, an antibody that not only blocks ligand binding but also interferes with receptor dimerization could be superior. Additional desirable properties would include the ability to support Fc-mediated effector function and the long serum half-life conferred by the natural framework of a full-length antibody. We focused our screening and engineering efforts to identify an antibody molecule that combines all of these features, leading to the generation of R3Mab. Binding studies demonstrated the ability of R3Mab to compete with FGF ligands for interaction with both the IIIb and IIIc isoforms of FGFR3. Further experiments with transfected BaF/3 cell lines confirmed the remarkable ability of R3Mab to block both WT and prevalent cancer-associated FGFR3 mutants. In addition, R3Mab exerted significant anti-tumor activity in several xenograft models of bladder cancer expressing either WT FGFR3 or $FGFR3^{S249C}$, which is the most common mutant of the receptor in this disease. Pharmacodynamic studies suggested that the anti-tumor activity R3Mab in these models is based on inhibition of FGFR3 signaling, evident by diminished phosphorylation of its downstream mediators FRS2α and MAPK. These data further reinforce the conclusion that FGFR3 is required for bladder tumor progression, as demonstrated by our FGFR3 shRNA studies.

FGFR3 mutations in bladder cancer represent one of the most frequent oncogenic alterations of a protein kinase in solid tumor malignancies, reminiscent of the common mutation of B-Raf in melanoma (45). Most of the activating mutations in FGFR3 give rise to an unpaired cysteine, leading to ligand-independent receptor dimerization and to various degrees of constitutive activation. A previous study using a monovalent anti-FGFR3Fab fragment indicated differential inhibitory activity against specific FGFR3 mutants (46); however, the molecular basis for this variable effect was not investigated. Compared with monovalent antibody fragments, bivalent antibodies have the capacity to induce the clustering of antigens, and in the case of receptor tyrosine kinases, may cause receptor oligomerization and activation. Despite its full-length, bivalent configuration, R3Mab displayed universal inhibition of WT FGFR3 and of a wide spectrum of FGFR3 mutants, including variants that are ligand-dependent ($FGFR3^{G372C}$, $FGFR3^{Y375C}$), constitutively active ($FGFR3^{R248C}$, $FGFR3^{S249C}$), or both ($FGFR3^{K652E}$). These results raise the question: How does R3Mab antagonize both WT and various FGFR3 mutants, including disulfide-linked variants?

Based on sequence alignment with FGFR1, the peptide epitope recognized by R3Mab overlaps with FGFR3 residues involved in binding to ligand and heparin, as well as receptor dimerization. This conclusion was confirmed by crystallographic studies of the complex between R3Mab and the extracellular regions of FGFR3. The X-ray structure revealed that the antibody binds to regions of IgD2 and IgD3 that are critical for ligand-receptor interaction as well as receptor-receptor contact. Thus, R3Mab may block WT FGFR3 both by competing for ligand binding and by preventing receptor dimerization. R3Mab may employ a similar mechanism to inhibit $FGFR3^{K652E}$, which has low constitutive activity, but requires ligand for full activation. Furthermore, R3Mab binding changes the relative orientation of FGFR3 IgD3 with respect to IgD2. This finding raises the formal possibility that the antibody might also inhibit receptor activation by forcing a conformation that is not conducive to signal transduction—a notion that requires further study.

To gain better insight into how R3Mab blocks FGFR3 variants possessing an unpaired cysteine, we analyzed the most common mutant, $FGFR3^{S249C}$, in greater detail. Experiments with the free-sulfhydryl blocker DTNB indicated a dynamic equilibrium between the monomeric and dimeric state of $FGFR3^{S249C}$. Similar equilibrium between oxidized and reduced states modulated by endogenous redox regulators has been reported for NMDA receptors (46). Incubation of bladder cancer cells expressing $FGFR3^{S249C}$ with R3Mab led to a decline in the amount of receptor dimers and a concomitant increase in the level of monomers. Moreover, the purified IgD2-D3 fragment of $FGFR3^{S249C}$ formed dimers in solution; when incubated with R3Mab, the dimers steadily disappeared while monomeric $FGFR3^{S249C}$ accumulated. Taken together with the structural analysis, these results suggest that R3Mab captures monomeric $FGFR3^{S249C}$ and hinders its dimerization. Over time, R3Mab shifts the equilibrium towards the monomeric state, blocking constitutive receptor activity. This mechanism might also explain how R3Mab inhibits other cysteine mutants of FGFR3.

Another important finding of this study was the potent anti-tumor activity of R3Mab against the t(4;14)+ multiple myeloma cell lines OPM2 and KMS11 in vivo. By contrast, R3Mab had modest to minimal impact on proliferation or survival of these cells in culture. OPM2 and KMS11 cells express relatively high cell surface levels of FGFR3 (5-6 fold higher than RT112 and UMUC-14 bladder carcinoma cells).

These higher antigen densities may permit R3Mab to support efficient recruitment of FcγR-bearing immune effector cells and activation of ADCC. Indeed, in the presence of human PBMC, R3Mab mediated cytolysis of OPM2 and KMS11 cells, but not RT112 or UMUC-14 bladder cancer cells. Moreover, the DANA mutant version of R3Mab, which is incapable of FcγR binding, had no effect on KMS11 or OPM2 growth in vivo, but still suppressed growth of RT112 and UMUC-14 tumors similarly to R3Mab. Together, these data indicate that R3Mab has a dual mechanism of anti-tumor activity: (a) In cells expressing lower surface levels of WT or mutant FGFR3, it blocks ligand-dependent or constitutive signaling; (b) In cells expressing relatively high surface FGFR3 levels, it induces ADCC.

Our results also raise some new questions. First, it is unknown why the bladder cancer cell lines tested in this study display variable sensitivity to R3Mab. Such differential response, which is common for targeted therapy, may be a reflection of the distinct genetic make-up of individual tumors. Indeed, Her2-positive breast cancer cells show variable sensitivity to anti-Her2 antibody (48), as do various cancer cells in response to anti-EGFR antibody (49). In this context, development of additional in vivo models for bladder cancer with WT and mutant FGFR3 is urgently needed to assess sensitivity to FGFR3 molecules in animals. Moreover, elucidation of predictive biomarkers may help identify patients who can optimally benefit from FGFR3-targeted therapy. Secondly, because R3Mab did not induce tumor regression in the models we examined, future studies should explore whether R3Mab can cooperate with established therapeutic agents.

In conclusion, our findings implicate both WT and mutant FGFR3 as important for bladder cancer growth, thus expanding the in vivo oncogenic involvement of this receptor from hematologic to epithelial malignancy. Furthermore, our results demonstrate that both WT and mutant FGFR3 can be effectively targeted in tumors with a full-length antibody that combines the ability to block ligand binding, receptor dimerization and signaling, as well as to promote tumor cell lysis by ADCC. These results provide a strong rationale for investigating antibody-based, FGFR3-targeted therapies in diverse malignancies associated with this receptor.

Partial Reference List

1. Eswarakumar, V. P., Lax, I., and Schlessinger, J. 2005. Cellular signaling by fibroblast growth factor receptors. Cytokine Growth Factor Rev 16:139-149.

2. L'Hote, C. G., and Knowles, M. A. 2005. Cell responses to FGFR3 signalling: growth, differentiation and apoptosis. Exp Cell Res 304:417-431.

3. Dailey, L., Ambrosetti, D., Mansukhani, A., and Basilico, C. 2005. Mechanisms underlying differential responses to FGF signaling. Cytokine Growth Factor Rev 16:233-247.

4. Mohammadi, M., Olsen, S. K., and Ibrahimi, O. A. 2005. Structural basis for fibroblast growth factor receptor activation. Cytokine Growth Factor Rev 16:107-137.

5. Grose, R., and Dickson, C. 2005. Fibroblast growth factor signaling in tumorigenesis. Cytokine Growth Factor Rev 16:179-186.

6. Chang, H., Stewart, A. K., Qi, X. Y., Li, Z. H., Yi, Q. L., and Trudel, S. 2005. Immunohistochemistry accurately predicts FGFR3 aberrant expression and t(4;14) in multiple myeloma. Blood 106:353-355.

7. Chesi, M., Nardini, E., Brents, L. A., Schrock, E., Ried, T., Kuehl, W. M., and Bergsagel, P. L. 1997. Frequent translocation t(4;14)(p16.3;q32.3) in multiple myeloma is associated with increased expression and activating mutations of fibroblast growth factor receptor 3. Nat Genet. 16:260-264.

8. Fonseca, R., Blood, E., Rue, M., Harrington, D., Oken, M. M., Kyle, R. A., Dewald, G. W., Van Ness, B., Van Wier, S. A., Henderson, K. J., et al. 2003. Clinical and biologic implications of recurrent genomic aberrations in myeloma. Blood 101:4569-4575.

9. Moreau, P., Facon, T., Leleu, X., Morineau, N., Huyghe, P., Harousseau, J. L., Bataille, R., and Avet-Loiseau, H.2002. Recurrent 14q32 translocations determine the prognosis of multiple myeloma, especially in patients receiving intensive chemotherapy. Blood 100:1579-1583.

10. Pollett, J. B., Trudel, S., Stern, D., L1, Z. H., and Stewart, A. K. 2002. Overexpression of the myeloma-associated oncogene fibroblast growth factor receptor 3 confers dexamethasone resistance. Blood 100:3819-3821.

11. Bernard-Pierrot, I., Brams, A., Dunois-Larde, C., Caillault, A., Diez de Medina, S. G., Cappellen, D., Graff, G., Thiery, J. P., Chopin, D., Ricol, D., et al. 2006. Oncogenic properties of the mutated forms of fibroblast growth factor receptor 3b. Carcinogenesis 27:740-747.

12. Agazie, Y. M., Movilla, N., Ischenko, I., and Hayman, M. J. 2003. The phosphotyrosine phosphatase SHP2 is a critical mediator of transformation induced by the oncogenic fibroblast growth factor receptor 3. Oncogene 22:6909-6918.

13. Ronchetti, D., Greco, A., Compasso, S., Colombo, G., Dell'Era, P., Otsuki, T., Lombardi, L., and Neri, A. 2001. Deregulated FGFR3 mutants in multiple myeloma cell lines with t(4;14): comparative analysis of Y373C, K650E and the novel G384D mutations. Oncogene 20:3553-3562.

14. Chesi, M., Brents, L. A., Ely, S. A., Bais, C., Robbiani, D. F., Mesri, E. A., Kuehl, W. M., and Bergsagel, P. L. 2001. Activated fibroblast growth factor receptor 3 is an oncogene that contributes to tumor progression in multiple myeloma. Blood 97:729-736.

15. Plowright, E. E., L1, Z., Bergsagel, P. L., Chesi, M., Barber, D. L., Branch, D. R., Hawley, R. G., and Stewart, A. K. 2000. Ectopic expression of fibroblast growth factor receptor 3 promotes myeloma cell proliferation and prevents apoptosis. Blood 95:992-998.

16. Chen, J., Williams, I. R., Lee, B. H., Duclos, N., Huntly, B. J., Donoghue, D. J., and Gilliland, D. G. 2005. Constitutively activated FGFR3 mutants signal through PLCgamma-dependent and -independent pathways for hematopoietic transformation. Blood 106:328-337.

17. Li, Z., Zhu, Y. X., Plowright, E. E., Bergsagel, P. L., Chesi, M., Patterson, B., Hawley, T. S., Hawley, R. G., and Stewart, A. K. 2001. The myeloma-associated oncogene fibroblast growth factor receptor 3 is transforming in hematopoietic cells. Blood 97:2413-2419.

18. Trudel, S., Ely, S., Farooqi, Y., Affer, M., Robbiani, D. F., Chesi, M., and Bergsagel, P. L. 2004 Inhibition of fibroblast growth factor receptor 3 induces differentiation and apoptosis in t(4;14) myeloma. Blood 103:3521-3528.

19. Trudel, S., Li, Z. H., Wei, E., Wiesmann, M., Chang, H., Chen, C., Reece, D., Heise, C., and Stewart, A. K. 2005. CHIR-258, a novel, multitargeted tyrosine kinase inhibitor for the potential treatment of t(4;14) multiple myeloma. Blood 105:2941-2948.

20. Chen, J., Lee, B. H., Williams, I. R., Kutok, J. L., Mitsiades, C. S., Duclos, N., Cohen, S., Adelsperger, J., Okabe, R., Coburn, A., et al. 2005. FGFR3 as a therapeutic target of the small molecule inhibitor PKC412 in hematopoietic malignancies. Oncogene 24:8259-8267.

21. Paterson, J. L., L1, Z., Wen, X. Y., Masih-Khan, E., Chang, H., Pollett, J. B., Trudel, S., and Stewart, A. K. 2004.

Preclinical studies of fibroblast growth factor receptor 3 as a therapeutic target in multiple myeloma. Br J Haematol 124:595-603.

22. Grand, E. K., Chase, A. J., Heath, C., Rahemtulla, A., and Cross, N.C. 2004. Targeting FGFR3 in multiple myeloma: inhibition of t(4;14)-positive cells by SU5402 and PD173074. Leukemia 18:962-966.

23. Gomez-Roman, J. J., Saenz, P., Molina, M., Cuevas Gonzalez, J., Escuredo, K., Santa Cruz, S., Junquera, C., Simon, L., Martinez, A., Gutierrez Banos, J. L., et al. 2005. Fibroblast growth factor receptor 3 is overexpressed in urinary tract carcinomas and modulates the neoplastic cell growth. Clin Cancer Res 11:459-465.

24. Tomlinson, D.C., Baldo, O., Hamden, P., and Knowles, M. A. 2007. FGFR3 protein expression and its relationship to mutation status and prognostic variables in bladder cancer. J Pathol 213:91-98.

25. van Rhijn, B. W., Montironi, R., Zwarthoff, E. C., Jobsis, A. C., and van der Kwast, T. H.2002. Frequent FGFR3 mutations in urothelial papilloma. J Pathol 198:245-251.

26. Tomlinson, D.C., Hurst, C.D., and Knowles, M. A. 2007. Knockdown by shRNA identifies S249C mutant FGFR3 as a potential therapeutic target in bladder cancer. Oncogene 26:5889-5899.

27. Martinez-Torrecuadrada, J., Cifuentes, G., Lopez-Serra, P., Saenz, P., Martinez, A., and Casal, J. I. 2005. Targeting the extracellular domain of fibroblast growth factor receptor 3 with human single-chain Fv antibodies inhibits bladder carcinoma cell line proliferation. Clin Cancer Res 11:6280-6290.

28. Martinez-Torrecuadrada, J. L., Cheung, L. H., Lopez-Serra, P., Barderas, R., Canamero, M., Ferreiro, S., Rosenblum, M. G., and Casal, J. I. 2008. Antitumor activity of fibroblast growth factor receptor 3-specific immunotoxins in a xenograft mouse model of bladder carcinoma is mediated by apoptosis. Mol Cancer Ther 7:862-873.

29. Ornitz, D. M., and Leder, P. 1992. Ligand specificity and heparin dependence of fibroblast growth factor receptors 1 and 3. J Biol Chem 267:16305-16311.

30. d'Avis, P. Y., Robertson, S.C., Meyer, A. N., Bardwell, W. M., Webster, M. K., and Donoghue, D. J. 1998. Constitutive activation of fibroblast growth factor receptor 3 by mutations responsible for the lethal skeletal dysplasia thanatophoric dysplasia type I. Cell Growth Differ 9:71-78.

31. Adar, R., Monsonego-Oman, E., David, P., and Yayon, A. 2002. Differential activation of cysteine-substitution mutants of fibroblast growth factor receptor 3 is determined by cysteine localization. J Bone Miner Res 17:860-868.

32. Knowles, M. A. 2008. Novel therapeutic targets in bladder cancer: mutation and expression of FGF receptors. Future Oncol 4:71-83.

33. Naski, M. C., Wang, Q., Xu, J., and Ornitz, D. M. 1996. Graded activation of fibroblast growth factor receptor 3 by mutations causing achondroplasia and thanatophoric dysplasia. Nat Genet. 13:233-237.

34. Plotnikov, A. N., Schlessinger, J., Hubbard, S. R., and Mohammadi, M. 1999. Structural basis for FGF receptor dimerization and activation. Cell 98:641-650.

35. Olsen, S. K., Ibrahimi, O. A., Raucci, A., Zhang, F., Eliseenkova, A. V., Yayon, A., Basilico, C., Linhardt, R. J., Schlessinger, J., and Mohammadi, M. 2004. Insights into the molecular basis for fibroblast growth factor receptor autoinhibition and ligand-binding promiscuity. Proc Natl Acad Sci USA 101:935-940.

36. Jebar, A. H., Hurst, C. D., Tomlinson, D. C., Johnston, C., Taylor, C. F., and Knowles, M. A. 2005. FGFR3 and Ras gene mutations are mutually exclusive genetic events in urothelial cell carcinoma. Oncogene 24:5218-5225.

37. Ellman, G. L. 1959. Tissue sulfhydryl groups. Arch Biochem Biophys 82:70-77.

38. Adams, G. P., and Weiner, L. M. 2005. Monoclonal antibody therapy of cancer. Nat Biotechnol 23:1147-1157.

39. Gong, Q., Ou, Q., Ye, S., Lee, W. P., Cornelius, J., Diehl, L., Lin, W. Y., Hu, Z., Lu, Y., Chen, Y., et al. 2005. Importance of cellular microenvironment and circulatory dynamics in B cell immunotherapy. J Immunol 174:817-826.

40. Cappellen, D., De Oliveira, C., Ricol, D., de Medina, S., Bourdin, J., Sastre-Garau, X., Chopin, D., Thiery, J. P., and Radvanyi, F. 1999. Frequent activating mutations of FGFR3 in human bladder and cervix carcinomas. Nat Genet. 23:18-20.

41. Qiu, W. H., Zhou, B. S., Chu, P. G., Chen, W. G., Chung, C., Shih, J., Hwu, P., Yeh, C., Lopez, R., and Yen, Y. 2005. Over-expression of fibroblast growth factor receptor 3 in human hepatocellular carcinoma. World J Gastroenterol 11:5266-5272.

42. Cortese, R., Hartmann, O., Berlin, K., and Eckhardt, F. 2008. Correlative gene expression and DNA methylation profiling in lung development nominate new biomarkers in lung cancer. Int J Biochem Cell Biol 40:1494-1508.

43. Woenckhaus, M., Klein-Hitpass, L., Grepmeier, U., Merk, J., Pfeifer, M., Wild, P., Bettstetter, M., Wuensch, P., Blaszyk, H., Hartmann, A., et al. 2006. Smoking and cancer-related gene expression in bronchial epithelium and non-small-cell lung cancers. J Pathol 210:192-204.

44. Xin, X., Abrams, T. J., Hollenbach, P. W., Rendahl, K. G., Tang, Y., Oei, Y. A., Embry, M. G., Swinarski, D. E., Garrett, E. N., Pryer, N. K., et al. 2006. CHIR-258 is efficacious in a newly developed fibroblast growth factor receptor 3-expressing orthotopic multiple myeloma model in mice. Clin Cancer Res 12:4908-4915.

45. Davies, H., Bignell, G. R., Cox, C., Stephens, P., Edkins, S., Clegg, S., Teague, J., Woffendin, H., Garnett, M. J., Bottomley, W., et al. 2002. Mutations of the BRAF gene in human cancer. Nature 417:949-954.

46. Trudel, S., Stewart, A. K., Rom, E., Wei, E., Li, Z. H., Kotzer, S., Chumakov, I., Singer, Y., Chang, H., Liang, S. B., et al. 2006. The inhibitory anti-FGFR3 antibody, PRO-001, is cytotoxic to t(4;14) multiple myeloma cells. Blood 107:4039-4046.

47. Gozlan, H., and Ben-Ari, Y. 1995. NMDA receptor redox sites: are they targets for selective neuronal protection? Trends Pharmacol Sci 16:368-374.

48. Hudziak, R. M., Lewis, G. D., Winget, M., Fendly, B. M., Shepard, H. M., and Ullrich, A. 1989. p185HER2 monoclonal antibody has antiproliferative effects in vitro and sensitizes human breast tumor cells to tumor necrosis factor. Mol Cell Biol 9:1165-1172.

49. Masui, H., Kawamoto, T., Sato, J. D., Wolf, B., Sato, G., and Mendelsohn, J. 1984. Growth inhibition of human tumor cells in athymic mice by anti-epidermal growth factor receptor monoclonal antibodies. Cancer Res 44:1002-1007.

50. Pai, R., Dunlap, D., Qing, J., Mohtashemi, I., Hotzel, K., and French, D. M. 2008. Inhibition of fibroblast growth factor 19 reduces tumor growth by modulating beta-catenin signaling. Cancer Res 68:5086-5095.

51. Pegram, M., Hsu, S., Lewis, G., Pietras, R., Beryt, M., Sliwkowski, M., Coombs, D., Baly, D., Kabbinavar, F., and Slamon, D. 1999 Inhibitory effects of combinations of HER-2/neu antibody and chemotherapeutic agents used for treatment of human breast cancers. Oncogene 18:2241-2251.

52. Lee, C.V., Liang, W. C., Dennis, M. S., Eigenbrot, C., Sidhu, S. S., and Fuh, G. 2004. High-affinity human antibodies from phage-displayed synthetic Fab libraries with a single framework scaffold. J Mol Biol 340:1073-1093.

53. Liang, W. C., Dennis, M. S., Stawicki, S., Chanthery, Y., Pan, Q., Chen, Y., Eigenbrot, C., Yin, J., Koch, A. W., Wu, X., et al. 2007. Function blocking antibodies to neuropilin-1 generated from a designed human synthetic antibody phage library. J Mol Biol 366:815-829.

54. Carter, P., Presta, L., Gorman, C. M., Ridgway, J. B., Henner, D., Wong, W. L., Rowland, A. M., Kotts, C., Carver, M. E., and Shepard, H. M. 1992. Humanization of an anti-p185HER2 antibody for human cancer therapy. Proc Natl Acad Sci USA 89:4285-4289.

55. Sidhu, S. S., L1, B., Chen, Y., Fellouse, F. A., Eigenbrot, C., and Fuh, G. 2004. Phage-displayed antibody libraries of synthetic heavy chain complementarity determining regions. J Mol Biol 338:299-310.

56. Otwinowski, Z. a. M., W. 1997. Processing of X-ray diffraction data collected in oscillation mode. Methods in Enzymology 276:307-326.

57. McCoy, A. J., Grosse-Kunstleve, R. W., Storoni, L. C., and Read, R. J. 2005. Likelihood-enhanced fast translation functions. Acta Crystallogr D Biol Crystallogr 61:458-464.

58. Emsley, P., and Cowtan, K. 2004. Coot: model-building tools for molecular graphics. Acta Crystallogr D Biol Crystallogr 60:2126-2132.

59. Murshudov, G. N., Vagin, A. A., and Dodson, E. J. 1997. Refinement of macromolecular structures by the maximum-likelihood method. Acta Crystallogr D Biol Crystallogr 53:240-255.

Although the foregoing invention has been described in some detail by way of illustration and example for purposes of clarity of understanding, the descriptions and examples should not be construed as limiting the scope of the invention.

What is claimed is:

1. An isolated anti-FGFR3 antagonist antibody, wherein the antibody comprises:
   (a) a light chain variable region comprising:
      (i) HVR-L1 comprising the amino acid sequence of SEQ ID NO:48,
      (ii) HVR-L2 comprising the amino acid sequence of SEQ ID NO:49, and
      (iii) HVR-L3 comprising the amino acid sequence of SEQ ID NO:50; and
   (b) a heavy chain variable region comprising:
      (i) HVR-H1 comprising the amino acid sequence of SEQ ID NO:51,
      (ii) HVR-H2 comprising the amino acid sequence of SEQ ID NO:52, and
      (iii) HVR-H3 comprising the amino acid sequence of SEQ ID NO:53, wherein the antibody specifically binds FGFR3.

2. The anti-FGFR3 antagonist antibody of claim 1, wherein the heavy chain variable region comprising SEQ ID NO: 136.

3. The anti-FGFR3 antagonist antibody of claim 1, wherein the light chain variable region comprising SEQ ID NO:137.

4. The anti-FGFR3 antagonist antibody of claim 1, wherein the heavy chain variable region comprising SEQ ID NO:136 and the light chain variable region comprising SEQ ID NO:137.

5. The anti-FGFR3 antagonist antibody of claim 1, wherein the antibody comprises at least a portion of the framework sequence which is a human consensus framework sequence.

6. The anti-FGFR3 antagonist antibody of claim 1, wherein the antibody comprises human κ subgroup consensus framework sequence.

7. The anti-FGFR3 antagonist antibody of claim 1, wherein the antibody comprises heavy chain human subgroup III consensus framework sequence.

8. The anti-FGFR3 antagonist antibody of claim 1, wherein the antibody is a monoclonal antibody.

9. The anti-FGFR3 antagonist antibody of claim 1, wherein the antibody is selected from the group consisting of a chimeric antibody, a humanized antibody, an affinity matured antibody, a human antibody, and a bispecific antibody.

10. The anti-FGFR3 antagonist antibody of claim 1, wherein the antibody is an antibody binding fragment.

* * * * *